US010172905B1

(12) United States Patent
Anderson et al.

(10) Patent No.: US 10,172,905 B1
(45) Date of Patent: Jan. 8, 2019

(54) TREATMENT OF PROTEIN DEGRADATION DISORDERS

(71) Applicants: President and Fellows of Harvard College, Cambridge, MA (US); Dana-Farber Cancer Institute, Inc., Boston, MA (US)

(72) Inventors: Kenneth C. Anderson, Wellesley, MA (US); James E. Bradner, Weston, MA (US); Edward Franklin Greenberg, Cleveland, OH (US); Teru Hideshima, Brookline, MA (US); Nicholas Paul Kwiatkowski, Brookline, MA (US); Ralph Mazitschek, Belmont, MA (US); Stuart L. Schreiber, Boston, MA (US); Jared Shaw, Davis, CA (US); Stephen J. Haggarty, Gloucester, MA (US)

(73) Assignees: President and Fellows of Harvard College, Cambridge, MA (US); Dana-Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 15/401,902

(22) Filed: Jan. 9, 2017

Related U.S. Application Data

(63) Continuation of application No. 14/679,800, filed on Apr. 6, 2015, now Pat. No. 9,572,854, which is a continuation of application No. 11/386,959, filed on Mar. 22, 2006, now Pat. No. 8,999,289.

(60) Provisional application No. 60/664,470, filed on Mar. 22, 2005.

(51) Int. Cl.

| | |
|---|---|
| *A61K 38/05* | (2006.01) |
| *A61K 31/4965* | (2006.01) |
| *A61K 31/69* | (2006.01) |
| *A61K 45/06* | (2006.01) |
| *A61K 49/00* | (2006.01) |
| *G01N 33/50* | (2006.01) |
| *A61K 31/422* | (2006.01) |
| *A61K 38/50* | (2006.01) |
| *A61K 31/35* | (2006.01) |
| *A61K 31/357* | (2006.01) |

(52) U.S. Cl.
CPC .............. *A61K 38/05* (2013.01); *A61K 31/35* (2013.01); *A61K 31/357* (2013.01); *A61K 31/422* (2013.01); *A61K 31/4965* (2013.01); *A61K 31/69* (2013.01); *A61K 38/50* (2013.01); *A61K 45/06* (2013.01); *A61K 49/0008* (2013.01); *G01N 33/5011* (2013.01)

(58) Field of Classification Search
CPC ...... A61K 38/05; A61K 31/35; A61K 31/357; A61K 31/4965; A61K 31/69; A61K 45/06; A61K 49/0008; A61K 38/50; A61K 31/4221; G01N 33/5011
See application file for complete search history.

(56) References Cited

U.S. PATENT DOCUMENTS

| | | | |
|---|---|---|---|
| 4,160,866 A | 7/1979 | Brooks et al. |
| 4,608,390 A | 8/1986 | Summers, Jr. |
| 4,631,211 A | 12/1986 | Houghten |
| 4,639,462 A | 1/1987 | Kramer et al. |
| 4,683,195 A | 7/1987 | Mullis et al. |
| 4,683,202 A | 7/1987 | Mullis |
| 4,820,828 A | 4/1989 | Demers et al. |
| 4,833,080 A | 5/1989 | Brent et al. |
| 4,861,798 A | 8/1989 | Tramposch et al. |
| 5,045,538 A | 9/1991 | Schneider et al. |
| 5,059,698 A | 10/1991 | Schulthess et al. |
| 5,096,815 A | 3/1992 | Ladner et al. |
| 5,143,854 A | 9/1992 | Pirrung et al. |
| 5,175,191 A | 12/1992 | Marks et al. |
| 5,176,996 A | 1/1993 | Hogan et al. |
| 5,198,346 A | 3/1993 | Ladner et al. |
| 5,223,409 A | 6/1993 | Ladner et al. |
| 5,225,173 A | 7/1993 | Wai |
| 5,238,781 A | 8/1993 | Schadeli |
| 5,256,775 A | 10/1993 | Froehler |
| 5,264,564 A | 11/1993 | Matteucci |

(Continued)

FOREIGN PATENT DOCUMENTS

| | | |
|---|---|---|
| DE | 32 42 252 | 5/1984 |
| EP | 0 259 149 A2 | 3/1988 |

(Continued)

OTHER PUBLICATIONS

Frederica Perera, Environment and Cancer: Who are Susceptible?, 278 Science 1068 (Year: 197).*
Paul G. Richardson, et al, Bortezomib (PS-341): A Novel, First-in-Class Proteasome Inhibitor for the Treatment of Multiple Myeloma and Other Cancers, 10 Cancer Control (Year: 2003).*
Julian Adams, Potential for Proteasome Inhibition in the Treatment of Cancer, 8 Drug Disc. Tod. 307 (Year: 2003).*
U.S. Appl. No. 11/386,959 Hideshima Declaration (Year: 2014).*
U.S. Appl. No. 11/386,959 Yang Declaration (Year: 2014).*
International Search Report and Written Opinion for PCT/US2010/002220, dated Apr. 27, 2011.

(Continued)

*Primary Examiner* — Sean M Basquill
(74) *Attorney, Agent, or Firm* — Wolf, Greenfield & Sacks, P.C.

(57) ABSTRACT

The invention relates to methods of treating protein degradation disorders, such cellular proliferative disorders (e.g., cancer) and protein deposition disorders (e.g., neurodegenerative disorders). The invention provides methods and pharmaceutical compositions for treating these diseases using aggresome inhibitors or combinations of aggresome inhibitors and proteasome inhibitors. The invention further relates to methods and pharmaceutical compositions for treating multiple myeloma. New HDAC/TDAC inhibitors and aggresome inhibitors are also provided as well as synthetic methodologies for preparing these compounds.

20 Claims, 65 Drawing Sheets

(56) References Cited

U.S. PATENT DOCUMENTS

| | | |
|---|---|---|
| 5,283,317 A | 2/1994 | Saifer et al. |
| 5,288,514 A | 2/1994 | Ellman |
| 5,304,121 A | 4/1994 | Sahatjian |
| 5,328,470 A | 7/1994 | Nabel et al. |
| 5,359,115 A | 10/1994 | Campbell et al. |
| 5,362,899 A | 11/1994 | Campbell |
| 5,393,741 A | 2/1995 | Pettersen et al. |
| 5,440,016 A | 8/1995 | Blondelle et al. |
| 5,480,971 A | 1/1996 | Houghten et al. |
| 5,534,654 A | 7/1996 | Ohtani et al. |
| 5,659,016 A | 8/1997 | Nakamura et al. |
| 5,700,811 A | 12/1997 | Breslow et al. |
| 5,763,182 A | 6/1998 | Nakamura et al. |
| 5,837,313 A | 11/1998 | Ding et al. |
| 5,886,026 A | 3/1999 | Hunter et al. |
| 5,891,507 A | 4/1999 | Jayaraman |
| 6,030,945 A | 2/2000 | Ashkenazi |
| 6,037,361 A | 3/2000 | Roth et al. |
| 6,068,987 A | 5/2000 | Dulski et al. |
| 6,071,305 A | 6/2000 | Brown et al. |
| 6,099,562 A | 8/2000 | Ding et al. |
| 6,153,252 A | 11/2000 | Hossainy et al. |
| 6,190,619 B1 | 2/2001 | Kilcoin et al. |
| 6,194,612 B1 | 2/2001 | Boger et al. |
| 6,195,612 B1 | 2/2001 | Pack-Harris |
| 6,203,551 B1 | 3/2001 | Wu |
| 6,231,600 B1 | 5/2001 | Zhong |
| 6,248,127 B1 | 6/2001 | Shah et al. |
| 6,251,136 B1 | 6/2001 | Guruwaiya et al. |
| 6,258,121 B1 | 7/2001 | Yang et al. |
| 6,273,913 B1 | 8/2001 | Wright et al. |
| 6,428,960 B1 | 8/2002 | Clark et al. |
| 6,495,719 B2 | 12/2002 | Lan-Hargest et al. |
| 6,503,708 B1 | 1/2003 | Lal et al. |
| 6,512,123 B2 | 1/2003 | Grossmann et al. |
| 6,517,889 B1 | 2/2003 | Jayaraman |
| 6,541,661 B1 | 4/2003 | Delorme et al. |
| 6,777,217 B1 | 8/2004 | Schreiber et al. |
| 6,797,820 B2 | 9/2004 | Patel et al. |
| 6,897,220 B2 | 5/2005 | Delorme et al. |
| 6,960,685 B2 | 11/2005 | Watkins et al. |
| 7,244,853 B2 | 7/2007 | Schreiber et al. |
| 7,250,504 B2 | 7/2007 | Grozinger et al. |
| 7,335,753 B2 | 2/2008 | Wang et al. |
| 7,514,406 B2 | 4/2009 | Bedalov et al. |
| 7,737,172 B2 | 6/2010 | Halperin et al. |
| 7,994,362 B2 | 8/2011 | Schreiber et al. |
| 8,076,116 B2 | 12/2011 | Grozinger et al. |
| 8,178,579 B2 | 5/2012 | Schreiber et al. |
| 8,222,423 B2 | 7/2012 | Bradner et al. |
| 8,304,451 B2 | 11/2012 | Mazitschek et al. |
| 8,329,945 B2 | 12/2012 | Schreiber et al. |
| 8,329,946 B2 | 12/2012 | Schreiber et al. |
| 8,362,084 B2 | 1/2013 | Schreiber et al. |
| 8,383,855 B2 | 2/2013 | Bradner et al. |
| 8,399,233 B2 | 3/2013 | Schreiber et al. |
| 8,426,592 B2 | 4/2013 | Schreiber et al. |
| 8,435,780 B2 | 5/2013 | Grozinger et al. |
| 8,440,716 B2 | 5/2013 | Tang et al. |
| 8,716,344 B2 | 5/2014 | Mazitschek et al. |
| 8,754,237 B2 | 6/2014 | Bradner et al. |
| 8,895,284 B2 | 11/2014 | Grozinger et al. |
| 8,999,289 B2 | 4/2015 | Anderson et al. |
| 9,434,686 B2 | 9/2016 | Tang et al. |
| 9,540,317 B2 | 1/2017 | Mazitschek et al. |
| 9,572,854 B2 | 2/2017 | Anderson et al. |
| 2001/0027340 A1 | 10/2001 | Wright et al. |
| 2003/0004209 A1 | 1/2003 | Hunter et al. |
| 2003/0129724 A1 | 7/2003 | Grozinger et al. |
| 2003/0187027 A1* | 10/2003 | Schreiber ............ C07D 319/06 514/336 |
| 2003/0216345 A1 | 11/2003 | Nakanishi et al. |
| 2004/0072849 A1 | 4/2004 | Schreiber et al. |
| 2004/0087631 A1 | 5/2004 | Bacopoulos et al. |
| 2004/0092598 A1 | 5/2004 | Watkins et al. |
| 2004/0127522 A1 | 7/2004 | Chiao et al. |
| 2004/0138153 A1 | 7/2004 | Ramesh et al. |
| 2005/0014839 A1 | 1/2005 | Kozikowski et al. |
| 2005/0267037 A1 | 12/2005 | Anderson et al. |
| 2005/0287629 A1 | 12/2005 | Grozinger et al. |
| 2006/0020131 A1 | 1/2006 | Raeppel et al. |
| 2006/0079528 A1 | 4/2006 | Finn et al. |
| 2006/0239909 A1 | 10/2006 | Anderson et al. |
| 2007/0093413 A1 | 4/2007 | Schreiber et al. |
| 2007/0148185 A1 | 6/2007 | Rathore et al. |
| 2008/0207590 A1 | 8/2008 | Deziel et al. |
| 2008/0269245 A1 | 10/2008 | Schreiber et al. |
| 2008/0300205 A1 | 12/2008 | Tsai et al. |
| 2009/0036318 A1 | 2/2009 | Grozinger et al. |
| 2009/0209590 A1 | 8/2009 | Mazitschek et al. |
| 2009/0221474 A1 | 9/2009 | Schreiber et al. |
| 2009/0305384 A1 | 12/2009 | Grozinger et al. |
| 2009/0312363 A1 | 12/2009 | Bradner et al. |
| 2010/0041653 A1 | 2/2010 | Pellecchia et al. |
| 2010/0056588 A1 | 3/2010 | Bradner et al. |
| 2010/0137196 A1 | 6/2010 | Schreiber et al. |
| 2011/0172303 A1 | 7/2011 | Tang et al. |
| 2011/0218154 A1 | 9/2011 | Schreiber et al. |
| 2011/0313045 A1 | 12/2011 | Schreiber et al. |
| 2011/0319493 A1 | 12/2011 | Schreiber et al. |
| 2012/0094862 A1 | 4/2012 | Grozinger et al. |
| 2012/0208889 A1 | 8/2012 | Mazitschek et al. |
| 2012/0302510 A1 | 11/2012 | Schreiber et al. |
| 2013/0018103 A1 | 1/2013 | Bradner et al. |
| 2013/0040998 A1 | 2/2013 | Bradner et al. |
| 2013/0331455 A1 | 12/2013 | Tang et al. |
| 2013/0338024 A1 | 12/2013 | Grozinger et al. |
| 2015/0307444 A1 | 10/2015 | Mazitschek et al. |
| 2016/0051619 A1 | 2/2016 | Anderson et al. |
| 2017/0267630 A1 | 9/2017 | Mazitschek et al. |

FOREIGN PATENT DOCUMENTS

| | | |
|---|---|---|
| EP | 0 322 335 A1 | 6/1989 |
| EP | 0 323 590 A2 | 7/1989 |
| EP | 0 331 524 A2 | 9/1989 |
| EP | 0 458 131 A1 | 11/1991 |
| EP | 0 708 112 A1 | 4/1996 |
| GB | 1 394 170 A | 5/1975 |
| GB | 2 169 599 A | 7/1986 |
| JP | 59-139390 A | 8/1984 |
| JP | 04-022948 A | 1/1992 |
| JP | 04-217929 A | 8/1992 |
| JP | 06-001720 A | 1/1994 |
| JP | 8-311321 A | 11/1996 |
| JP | 9-124918 A | 5/1997 |
| JP | 2003-221398 A | 8/2003 |
| JP | 2004-043446 A | 2/2004 |
| WO | WO 91/00257 A1 | 1/1991 |
| WO | WO 91/07087 A1 | 5/1991 |
| WO | WO 92/09690 A2 | 6/1992 |
| WO | WO 92/10092 A1 | 6/1992 |
| WO | WO 92/15694 A1 | 9/1992 |
| WO | WO 93/05807 A2 | 4/1993 |
| WO | WO 93/07148 A1 | 4/1993 |
| WO | WO 93/07867 A1 | 4/1993 |
| WO | WO 93/09668 A1 | 5/1993 |
| WO | WO 93/19778 A1 | 10/1993 |
| WO | WO 93/20242 A1 | 10/1993 |
| WO | WO 94/08051 A1 | 4/1994 |
| WO | WO 94/10300 A1 | 5/1994 |
| WO | WO 97/11366 A1 | 3/1997 |
| WO | WO 97/35990 A2 | 10/1997 |
| WO | WO 98/16830 A2 | 4/1998 |
| WO | WO 98/47869 A1 | 10/1998 |
| WO | WO 98/55449 A1 | 12/1998 |
| WO | WO 00/20415 A1 | 4/2000 |
| WO | WO 00/34313 A1 | 6/2000 |
| WO | WO 00/35911 A1 | 6/2000 |
| WO | WO 00/36132 A1 | 6/2000 |
| WO | WO 00/44709 A2 | 8/2000 |
| WO | WO 02/22577 A2 | 3/2002 |
| WO | WO 02/89782 A2 | 11/2002 |
| WO | WO 2004/001059 A2 | 12/2003 |

(56) References Cited

FOREIGN PATENT DOCUMENTS

| WO | WO 2004/046104 A2 | 6/2004 |
|---|---|---|
| WO | WO 2004/062601 A2 | 7/2004 |
| WO | WO 2004/103369 A1 | 12/2004 |
| WO | WO 2005/007091 A2 | 1/2005 |
| WO | WO 2005/012247 A1 | 2/2005 |
| WO | WO 2005/018578 A2 | 3/2005 |
| WO | WO 2005/058803 A1 | 6/2005 |
| WO | WO 2005/066151 A2 | 7/2005 |
| WO | WO 2005/080335 A1 | 9/2005 |
| WO | WO 2006/060676 A1 | 6/2006 |
| WO | WO 2006/060809 A2 | 6/2006 |
| WO | WO 2007/111948 A2 | 10/2007 |
| WO | WO 2008/040934 A1 | 4/2008 |
| WO | WO 2008/091349 A1 | 7/2008 |
| WO | WO 2009/053808 A2 | 4/2009 |
| WO | WO 2009/063054 A1 | 5/2009 |
| WO | WO 2011/019393 A2 | 2/2011 |

OTHER PUBLICATIONS

International Preliminary Report on Patentability for PCT/US2010/002220, dated Feb. 23, 2012.
Extended European Search Report for EP 07872648.6, dated Apr. 13, 2011.
Invitation to Pay Additional Fees for PCT/US2007/062145, mailed Oct. 29, 2007.
International Search Report and Written Opinion for PCT/US2007/062145, dated Jun. 24, 2008.
International Preliminary Report on Patentability for PCT/US2007/062145, dated Aug. 28, 2008.
Extended European Search Report for EP 07757000.0, dated May 3, 2011.
Invitation to Pay Additional Fees for PCT/US2007/062152, mailed Dec. 7, 2007.
International Search Report and Written Opinion for PCT/US2007/062152, dated Oct. 7, 2008.
International Search Report and Written Opinion for PCT/US2007/062152, dated Oct. 14, 2008.
International Preliminary Report on Patentability for PCT/US2007/062152, dated Mar. 19, 2009.
Extended European Search Report for EP 09800666.1, dated Aug. 24, 2011.
International Search Report and Written Opinion for PCT/US2009/004235, dated Mar. 4, 2010.
International Preliminary Report on Patentability for PCT/US2009/004235, dated Feb. 3, 2011.
Supplementary European Search Report for EP 06748614.2, dated Oct. 16, 2009.
Extended European Search Report for EP 12150229.8, dated Jul. 31, 2012.
International Search Report and Written Opinion for PCT/US2006/010676, dated Jul. 14, 2008.
International Preliminary Report on Patentability for PCT/US2006/010676, dated Mar. 19, 2009.
Extended European Search Report for EP 07776589.9, dated Jun. 1, 2012.
International Search Report and Written Opinion for PCT/US2007/010587, dated Jan. 29, 2008.
International Preliminary Report on Patentability for PCT/US2007/010587, dated Nov. 13, 2008.
International Search Report for PCT/US2002/014835, dated Dec. 20, 2002.
Written Opinion for PCT/US2002/014835, dated Aug. 8, 2003.
International Preliminary Exam Report for PCT/US2002/014835, dated Jun. 4, 2004.
Extended European Search Report for EP 11732077.0, dated May 14, 2014.
International Search Report and Written Opinion for PCT/US2011/020206, dated Jul. 9, 2013.
International Preliminary Report on Patentability for PCT/US2011/020206, dated Aug. 1, 2013.
Invitation to Pay Additional Fees for PCT/US1997/005275, mailed Nov. 21, 1997.
International Search Report for PCT/US1997/005275, dated Feb. 16, 1998.
Written Opinion for PCT/US1997/005275, dated Mar. 5, 1998.
International Preliminary Examination Report for PCT/US1997/005275, dated Jul. 3, 1998.
CAS Registry File RN 456-07-05, STN Entry Date: Nov. 16, 1984.
CAS Registry File RN 505-22-6, STN Entry Date: Nov. 16, 1984.
Genbank Submission: NIH/NCBI, Accession No. AAA68286; GI: 348052, Henkin et al., Jun. 14, 1995.
Genbank Submission: NIH/NCBI, Accession No. AAC18040, GI:3170182, Scanlan et al.; Feb. 9, 1998.
Genbank Submission: NIH/NCBI, Accession No. AAD29046, Grozinger et al.; May 6, 1999.
Genbank Submission: NIH/NCBI, Accession No. AAD29048, Grozinger et al.; May 6, 1999.
Genbank Submission: NIH/NCBI, Accession No. AAF73428, Buggy et al.; Jun. 1, 2000.
Genbank Submission: NIH/NCBI, Accession No. AAP63491; Kieliszewski; Jun. 12, 2003.
Genbank Submission: NIH/NCBI, Accession No. AC_000143, Levy et al.; Jul. 29, 2011.
Genbank Submission: NIH/NCBI, Accession No. AC_000144, Levy et al.; Jul. 29, 2011.
Genbank Submission: NIH/NCBI, Accession No. AC_000149, Levy et al.; Jul. 29, 2011.
Genbank Submission: NIH/NCBI, Accession No. AC_000151, Levy et al.; Jul. 29, 2011.
Genbank Submission: NIH/NCBI, Accession No. AC000054, Burian et al.; Jul. 29, 2009.
Genbank Submission: NIH/NCBI, Accession No. AF039691, GI:3170181, Scanlan et al.; Feb. 9, 1998.
Genbank Submission: NIH/NCBI, Accession No. AK290716, Wakamatsu et al.; Jan. 9, 2008.
Genbank Submission: NIH/NCBI, Accession No. AM270988, Pel et al.; Jun. 30, 2009.
Genbank Submission: NIH/NCBI, Accession No. AM270990, Pel et al.; Jun. 30, 2009.
Genbank Submission: NIH/NCBI, Accession No. BAA22957; GI:2564324; Ohara et al., Mar. 18, 1998.
Genbank Submission: NIH/NCBI, Accession No. BAA22957; GI:6635127; Ohara et al., Dec. 25, 1999.
Genbank Submission: NIH/NCBI, Accession No. BAA25526; GI: 3043724, Ohara et al., Apr. 10, 1998.
Genbank Submission: NIH/NCBI, Accession No. BC009676, Strausberg et al.; Jul. 15, 2006.
Genbank Submission: NIH/NCBI, Accession No. BC012499, Strausberg et al.; Oct. 7, 2003.
Genbank Submission: NIH/NCBI, Accession No. BC111735, Strausberg et al.; Jan. 17, 2006.
Genbank Submission: NIH/NCBI, Accession No. CM000257, Venter et al.; Jun. 29, 2009.
Genbank Submission: NIH/NCBI, Accession No. CM000261, Venter et al.; Jun. 29, 2009.
Genbank Submission: NIH/NCBI, Accession No. CM000262, Venter et al.; Jun. 29, 2009.
Genbank Submission: NIH/NCBI, Accession No. CM000263, Venter et al.; Jun. 29, 2009.
Genbank Submission: NIH/NCBI, Accession No. CM000270, Venter et al.; Jun. 29, 2009.
Genbank Submission: NIH/NCBI, Accession No. CM000663, Lander et al.; Jun. 29, 2009.
Genbank Submission: NIH/NCBI, Accession No. CU678487, Rual et al.; Feb. 19, 2008.
Genbank Submission: NIH/NCBI, Accession No. GL000006, Lander et al.; Jun. 29, 2009.
Genbank Submission: NIH/NCBI, Accession No. GL000052, Lander et al.; Jun. 29, 2009.
Genbank Submission: NIH/NCBI, Accession No. GL000099, Lander et al.; Jun. 29, 2009.

(56) References Cited

OTHER PUBLICATIONS

Genbank Submission: NIH/NCBI, Accession No. NC_000011, Taylor et al.; Jul. 29, 2011.
Genbank Submission: NIH/NCBI, Accession No. NC_000012, Scherer et al.; Jul. 29, 2011.
Genbank Submission: NIH/NCBI, Accession No. NC_000017, Zody et al.; Jul. 29, 2011.
Genbank Submission: NIH/NCBI, Accession No. NC_000019, Grimwood et al.; Jul. 29, 2011.
Genbank Submission: NIH/NCBI, Accession No. NM_001098202, Boulay et al.; Apr. 22, 2012.
Genbank Submission: NIH/NCBI, Accession No. NM_003173, Syreeni et al.; Apr. 28, 2012.
Genbank Submission: NIH/NCBI, Accession No. NM_006497, Boulay et al.; Apr. 22, 2012.
Genbank Submission: NIH/NCBI, Accession No. NM_012237, Krishnan et al.; Apr. 29, 2012.
Genbank Submission: NIH/NCBI, Accession No. NM_030593, Krishnan et al.; Apr. 29, 2012.
Genbank Submission: NIH/NCBI, Accession No. NM_033331, Peddibhotla et al.; Apr. 22, 2012.
Genbank Submission: NIH/NCBI, Accession No. NT_009775, Scherer et al.; Jul. 29, 2011.
Genbank Submission: NIH/NCBI, Accession No. NT_010663, Zody et al.; Jul. 29, 2011.
Genbank Submission: NIH/NCBI, Accession No. NT_166525, Pel; Jun. 1, 2011.
Genbank Submission: NIH/NCBI, Accession No. NW_001838015, Levy et al.; Jul. 29, 2011.
Genbank Submission: NIH/NCBI, Accession No. NW_001838459, Levy et al.; Jul. 29, 2011.
Genbank Submission: NIH/NCBI, Accession No. NW_001838477, Levy et al.; Jul. 29, 2011.
Genbank Submission: NIH/NCBI, Accession No. P56524; GI: 3024889, Ohara et al., Dec. 15, 1998.
Genbank Submission: NIH/NCBI, Accession No. Q48935; GI: 3023317, Sakurada et al., Apr. 20, 2010.
Genbank Submission; NIH/NCBI, Accession No. Q9Z2V5, Verdel et al.; Mar. 2, 2010.
Genbank Submission; NIH/NCBI, Accession No. Q9Z2V6, Verdel et al.; Mar. 2, 2010.
Genbank Submission; NIH/NCBI, Accession No. AB006626; GI:2564323, Ohara et al.; Mar. 18, 1998.
Genbank Submission; NIH/NCBI, Accession No. AB006626; GI:6635126, Ohara et al.; Dec. 25, 1999.
Genbank Submission; NIH/NCBI, Accession No. AF039241, Swensen.; Mar. 11, 2009.
Genbank Submission; NIH/NCBI, Accession No. AF132607, Grozinger et al.; May 6, 1999.
Genbank Submission; NIH/NCBI, Accession No. AF132608, Grozinger et al.; May 6, 1999.
Genbank Submission; NIH/NCBI, Accession No. AF132609, Grozinger et al.; May 6, 1999.
Genbank Submission; NIH/NCBI, Accession No. AF230097, Hu et al., May 31, 2000.
Genbank Submission; NIH/NCBI, Accession No. AF245664, Buggy et al.; Jun. 1, 2000.
Genbank Submission; NIH/NCBI, Accession No. AJ011972, Strom et al.; Oct. 19, 1998.
Genbank Submission; NIH/NCBI, Accession No. CAA09893.1, Strom et al.; Oct. 7, 2008.
Genbank Submission; NIH/NCBI, Accession No. NM_001015053.1, Seo et al.; Mar. 15, 2009.
Genbank Submission; NIH/NCBI, Accession No. NM_006037.3, Chabane et al.; Mar. 29, 2009.
Genbank Submission; NIH/NCBI, Accession No. NM_006044.2, Dhakal et al.; Mar. 15, 2009.
Genbank Submission; NIH/NCBI, Accession No. NM_014707, Muralidhar et al.; Mar. 11, 2011.
Genbank Submission; NIH/NCBI, Accession No. NM_018486, Bailey et al.; Mar. 11, 2011.
Genbank Submission; NIH/NCBI, Accession No. NM_032019, Bailey et al.; Mar. 12, 2011.
Genbank Submission; NIH/NCBI, Accession No. NM_058176, Muralidhar et al.; Feb. 27, 2011.
Genbank Submission; NIH/NCBI, Accession No. NM_058177, Tam et al.; May 7, 2010.
Genbank Submission; NIH/NCBI, Accession No. NM_178423, Muralidhar et al.; Mar. 13, 2011.
Genbank Submission; NIH/NCBI, Accession No. NM_178425, Muralidhar et al.; Feb. 27, 2011.
Genbank Submission; NIH/NCBI, Accession No. NP_001518, Campos et al.; Mar. 13, 2011.
Genbank Submission; NIH/NCBI, Accession No. NP_004955, Dong et al; Mar. 27, 2011.
Genbank Submission; NIH/NCBI, Accession No. NP_005465, Huynh; Mar. 11, 2011.
Genbank Submission; NIH/NCBI, Accession No. NP_006035; Aldana-Masangkay et al.; Mar. 13, 2011.
Genbank Submission; NIH/NCBI, Accession No. O15739, Loomis et al.; Oct. 31, 2006.
Genbank Submission; NIH/NCBI, Accession No. R64669, Wilson; May 26, 1995.
Genbank Submission; NIH/NCBI, Accession No. U31814, Yang et al.; Nov. 13, 1996.
Genbank Submission; NIH/NCBI, Accession No. U31814, Yang et al.; Nov. 14, 1996.
NCBI annotation project, GenBank Accession No. XM_002252, Oct. 16, 2001.
NCBI annotation project, GenBank Accession No. XM_004963, Feb. 9, 2001.
NCBI annotation project, GenBank Accession No. XM_004963.2, Oct. 16, 2001.
NCBI annotation project, GenBank Accession No. XM_007047, Nov. 16, 2000.
NCBI annotation project, GenBank Accession No. XM_008359, Oct. 16, 2001.
NCBI annotation project, GenBank Accession No. XP_002252, Oct. 16, 2001.
NCBI annotation project, GenBank Accession No. XP_008359.2, Feb. 10, 2001.
PubChemCompound, datasheet [online compound summary] Retrieved from the Internet: <URL:http://pubchem.ncbi.nlm.nih.gov/search/search.cgi> See CID 11593538, CID 4215571, CID 24701534, CID 24694283, CID 19936521, CID 137190, CID 144926, CID 24692493, CID 15952018, CID 11643995, etc.
UniProtKB/Swiss-Prot; Accession No. A8K8P3; Jun. 13, 2012.
UniProtKB/Swiss-Prot; Accession No. O15379; Dangond et al.; Apr. 18, 2012.
UniProtKB/Swiss-Prot; Accession No. Q13547; Taunton et al.; Apr. 18, 2012.
UniProtKB/Swiss-Prot; Accession No. Q8WU14; Strausberg et al.; Oct. 31, 2006.
UniProtKB/Swiss-Prot; Accession No. Q92769; Yang et al.; Apr. 18, 2012.
UniProtKB/Swiss-Prot; Accession No. Q9BY41; Hu et al.; Apr. 18, 2012.
UniProtKB/Swiss-Prot; Accession No. Q9UBN7; Grozinger et al.; Apr. 18, 2012.
UniProtKB/Swiss-Prot; Accession No. Q9UQL6; Grozinger et al.; Apr. 18, 2012.
[No Author Listed] Inhibitor. Available at http://www.biology-online.org/dictionary/inhibitor. Last accessed Apr. 6, 2011. 1 page.
[No Author Listed] Targeting the aggresome with an HDAC6 inhibitor in combination with velcade for myeloma therapy. Cancer Biology and Therapy. 2005;4(7):i-iv.
[No Author Listed] TopoTarget. Executive Informational Overview. Jan. 26, 2005. 52 pages.
Abremski et al., Bacteriophage P1 site-specific recombination. Purification and properties of the Cre recombinase protein. J Biol Chem. Feb. 10, 1984;259(3):1509-14.

(56) References Cited

OTHER PUBLICATIONS

Adams et al., Initial assessment of human gene diversity and expression patterns based upon 83 million nucleotides of cDNA sequence. Nature. Sep. 28, 1995;377(6547 Suppl):3-174.
Adams, The proteasome: a suitable antineoplastic target. Nat Rev Cancer. May 2004;4(5):349-60.
Afshar et al., Characterization of a human gene with sequence homology to *Saccharomyces cerevisiae* SIR2. Gene. Jun. 24, 1999;234(1):161-8.
Aggarwal et al., Trifluoromethanesulfonic Acid, an Efficient Catalyst for the Hetero Diels-Alder Reaction and an Improved Synthesis of Mefrosol. Tetrahedron Letters. 1997;38:2569-72.
Ahringer, NuRD and SIN3 histone deacetylase complexes in development. Trends Genet. Aug. 2000;16(8):351-6.
Alonso et al., A novel yeast histone deacetylase: partial characterization and development of an activity assay. Biochim Biophys Acta. Mar. 26, 1986;866(2-3):161-9.
Anderson et al., [PL5.05] Overview Of New Therapies And Future Directions. Jan. 11, 2004. Available at: http://www.cancereducation.com/CancerSysPagesNB/abstracts/mmrf/62/aays1.pdf. 2 pages.
Anderson et al., Analytical Techniques in Combinatorial Chemistry: MAS CH Correlation in Solvent-Swollen Resin. J Org Chem. 1995;60:2650-51.
Andrews et al., Anti-malarial effect of histone deacetylation inhibitors and mammalian tumour cytodifferentiating agents. Int J Parasitol. May 2000;30(6):761-8.
Anklesaria et al., Engraftment of a clonal bone marrow stromal cell line in vivo stimulates hematopoietic recovery from total body irradiation. Proc Natl Acad Sci U S A. Nov. 1987;84(21):7681-5.
Antón et al., Intracellular localization of proteasomal degradation of a viral antigen. J Cell Biol. Jul. 12, 1999;146(1):113-24.
Antonjuk et al., Asymmetric Induction in the Additions of Anions of Allylic Sulfoxides to Benzaldehyde. Aust J Chem. 1980;33:2635-51.
Aparicio et al., Modifiers of position effect are shared between telomeric and silent mating-type loci in *S. cerevisiae*. Cell. Sep. 20, 1991;66(6):1279-87.
Arkin et al., An algorithm for protein engineering: simulations of recursive ensemble mutagenesis. Proc Natl Acad Sci U S A. Aug. 15, 1992;89(16):7811-5.
Attal et al., Single versus double autologous stem-cell transplantation for multiple myeloma. N Engl J Med. Dec. 25, 2003;349(26):2495-502.
Auffray et al., [Image: molecular integration of the analysis of the human genome and its expression.] C R Acad Sci III. Feb. 1995;318(2):263-72. French.
Baer et al., Eukaryotic RNA polymerase II binds to nucleosome cores from transcribed genes. Nature. Feb. 10, 1983;301(5900):482-8.
Baker et al., Carfilzomib demonstrates broad antitumor activity in preclinical lung cancer models. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr 1022. doi:10.1158/1538-7445. AM2013-1022. Abtract Only.
Baldwin et al., Total Synthesis of Antitumor Agent At-125-(Aphas, 5S)-Alpha-Amino-3-Chloro-4,5-Isoxazoleacetic Acid. Tetrahedron. 1985;41(22):5241-60.
Ballestar et al., Methyl-CpG-binding proteins. Targeting specific gene repression. Eur J Biochem. Jan. 2001;268(1):1-6.
Barbas et al., Semisynthetic combinatorial antibody libraries: a chemical solution to the diversity problem. Proc Natl Acad Sci U S A. May 15, 1992;89(10):4457-61.
Bartel et al., Elimination of false positives that arise in using the two-hybrid system. Biotechniques. Jun. 1993;14(6):920-4.
Beck-Sickinger et al., Neuropeptide Y: identification of the binding site. Int J Pept Protein Res. Dec. 1990;36(6):522-30.

Beck-Sickinger et al., Semiautomated T-bag peptide synthesis using 9-fluorenyl-methoxycarbonyl strategy and benzotriazol-1-yl-tetramethyl-uronium tetrafluoroborate activation. Pept Res. Mar.-Apr. 1991;4(2):88-94.
Beck-Sickinger et al., Structure/activity relationships of C-terminal neuropeptide Y peptide segments and analogues composed of sequence 1-4 linked to 25-36. Eur J Biochem. Dec. 12, 1990;194(2):449-56.
Ben-Bassat et al., Processing of the initiation methionine from proteins: properties of the *Escherichia coli* methionine aminopeptidase and its gene structure. J Bacteriol. Feb. 1987;169(2):751-7.
Bennett et al., Global impairment of the ubiquitin-proteasome system by nuclear or cytoplasmic protein aggregates precedes inclusion body formation. Mol Cell. Feb. 4, 2005;17(3):351-65.
Berenbaum et al., What is synergy? Pharmacol Rev. Jun. 1989;41(2):93-141.
Berg et al., Long-Chain Polystyrene-Grafted Polyethylene Film Matrix: A New Support for Solid-Phase Peptide Synthesis. J Am Chem Soc. 1989;111:8024-26.
Berge et al., Pharmaceutical salts. J Pharm Sci. Jan. 1977;66(1):1-19.
Bernstein et al., Genomewide studies of histone deacetylase function in yeast. Proc Natl Acad Sci U S A. Dec. 5, 2000;97(25):13708-13.
Berridge et al., Tetrazolium dyes as tools in cell biology: new insights into their cellular reduction. Biotechnol Annu Rev. 2005;11:127-52.
Blackwell et al., A one-bead, one-stock solution approach to chemical genetics: part 1. Chem Biol. Dec. 2001;8(12):1167-82.
Blankemeyer-Menge et al., Simultaneous Multiple Synthesis of Protected Peptide Fragments on "Allyl"—Functionalized Cellulose Disc Supports. Tetrahedron Lett. 1988;29:5871-74.
Blondelle et al., Soluble combinatorial libraries of organic, peptidomimetic and peptide diversities. Trends Anal Chem. 1995;14:83-92.
Bold et al., Chemosensitization of pancreatic cancer by inhibition of the 26S proteasome. J Surg Res. Sep. 2001;100(1):11-7.
Bolden et al., Anticancer activities of histone deacetylase inhibitorsNat Rev Drug Discov. Sep. 2006;5(9):769-84.
Bolger et al., Intracellular trafficking of histone deacetylase 4 regulates neuronal cell death. J Neurosci. Oct. 12, 2005;25(41):9544-53.
Borchardt et al., Synthetic Receptor Binding Elucidated with an Encoded Combinatorial Library. J Am Chem Soc. 1994;116:373-74.
Bottomley et al., Structural and functional analysis of the human HDAC4 catalytic domain reveals a regulatory structural zinc-binding domain. J Biol Chem. Sep. 26, 2008;283(39):26694-704. Epub Jul. 8, 2008.
Bowdish et al., Analysis of RIM11, a yeast protein kinase that phosphorylates the meiotic activator IME1. Mol Cell Biol. Dec. 1994;14(12):7909-19.
Bowdish et al., Bipartite structure of an early meiotic upstream activation sequence from *Saccharomyces cerevisiae*. Mol Cell Biol. Apr. 1993;13(4):2172-81.
Bowers et al., Synthesis and Conformation-Activity Relationships of the Peptide Isosteres of FK228 and Largazole. J Am Chem Soc. 2009;131:2900-05.
Bowers et al., Total synthesis and biological mode of action of largazole: a potent class I histone deacetylase inhibitor. J Am Chem Soc. Aug. 20, 2008;130(33):11219-22. Epub Jul. 19, 2008.
Brachman et al., The SIR2 gene family, conserved from bacteria to humans, functions in silencing, cell cycle progression, and chromosome stability. Genes Dev. Dec. 1, 1995;9(23):2888-902.
Bradley et al., Formation of germ-line chimaeras from embryo-derived teratocarcinoma cell lines. Nature. May 17-23, 1984;309(5965):255-6.
Bradner et al., Chemical phylogenetics of histone deacetylases. Nat Chem Biol. Mar. 2010;6(3):238-243. Epub Feb. 7, 2010.
Branden et al., Chapter 16. Prediction, Engineering, and Design of Protein Structures. In: Introduction to Protein Structure. Garland Publishing Inc., New York. 1991:247.

(56) References Cited

OTHER PUBLICATIONS

Braunstein et al., Efficient transcriptional silencing in *Saccharomyces cerevisiae* requires a heterochromatin histone acetylation pattern. Mol Cell Biol. Aug. 1996;16(8):4349-56.
Braunstein et al., Transcriptional silencing in yeast is associated with reduced nucleosome acetylation. Genes Dev. Apr. 1993;7(4):592-604.
Bray et al., Gas Phase Cleavage of Peptides from a Solid Support with Ammonia Vapour. Application in Simultaneous Multiple Peptide Synthesis. Tetrahedron Lett. 1991;32:6163-66.
Bray et al., The Simultaneous Multiple Production of Solution Phase Peptides; Assessment of the Geysen Method of Simultaneous Peptide Synthesis. Tetrahedron Lett. 1990;31:5811-14.
Brenner et al., Encoded combinatorial chemistry. Proc Natl Acad Sci U S A. Jun. 15, 1992;89(12):5381-3.
Breslow et al., Potent cytodifferentiating agents related to hexamethylenebisacetamide. Proc Natl Acad Sci U S A. Jul. 1, 1991;88(13):5542-6.
Brinster et al., Factors affecting the efficiency of introducing foreign DNA into mice by microinjecting eggs. Proc Natl Acad Sci U S A. Jul. 1985;82(13):4438-42.
Brownell et al., Tetrahymena histone acetyltransferase A: a homolog to yeast Gcn5p linking histone acetylation to gene activation. Cell. Mar. 22, 1996;84(6):843-51.
Brummel et al., A mass spectrometric solution to the address problem of combinatorial libraries. Science. Apr. 15, 1994;264(5157):399-402.
Brunet et al., Nuclear translocation of p42/p44 mitogen-activated protein kinase is required for growth factor-induced gene expression and cell cycle entry. EMBO J. Feb. 1, 1999;18(3):664-74.
Buiting et al., Detection of aberrant DNA methylation in unique Prader-Willi syndrome patients and its diagnostic implications. Hum Mol Genet. Jun. 1994;3(6):893-5.
Bundgaard, Chapter 1. Design of prodrugs: Bioreversible derivatives for various functional groups and chemical entities. In: Design of Prodrugs. Elsevier. 1985:1-3.
Burbaum et al., A paradigm for drug discovery employing encoded combinatorial libraries. Proc Natl Acad Sci U S A. Jun. 20, 1995;92(13):6027-31.
Burbelo et al., 14-3-3 proteins. Hot numbers in signal transduction. Curr Biol. Feb. 1, 1995;5(2):95-6.
Byrd et al., Depsipeptide (FR901228): a novel therapeutic agent with selective, in vitro activity against human B-cell chronic lymphocytic leukemia cells. Blood. Aug. 15, 1999;94(4):1401-8.
Calí et al., Nucleotide sequence of a cDNA encoding the human muscle-specific enolase (MSE). Nucleic Acids Res. Apr. 11, 1990;18(7):1893.
Cameron, Recent advances in transgenic technology. Mol Biotechnol. Jun. 1997;7(3):253-65.
Caravita et al., Bortezomib: efficacy comparisons in solid tumors and hematologic malignancies. Nat Clin Pract Oncol. Jul. 2006;3(7):374-87.
Carmen et al., HDA1 and HDA3 are components of a yeast histone deacetylase (HDA) complex. J Biol Chem. Jun. 28, 1996;271(26):15837-44.
Carter et al., Chemotherapy of Cancer. 2nd ed. John Wiley & Sons, N.Y., N.Y., 1981:362-65.
Catley et al., NVP-LAQ824 is a potent novel histone deacetylase inhibitor with significant activity against multiple myeloma. Blood. Oct. 1, 2003;102(7):2615-22. Epub Jun. 19, 2003.
Cavenee et al., Expression of recessive alleles by chromosomal mechanisms in retinoblastoma. Nature. Oct. 27-Nov. 2, 1983;305(5937):779-84.
Chauhan et al., Blockade of Hsp27 overcomes Bortezomib/proteasome inhibitor PS-341 resistance in lymphoma cells. Cancer Res. Oct. 1, 2003;63(19):6174-7.
Chauhan et al., Hsp27 inhibits release of mitochondrial protein Smac in multiple myeloma cells and confers dexamethasone resistance. Blood. Nov. 1, 2003;102(9):3379-86. Epub Jul. 10, 2003.

Chen et al., "Analogous" Organic Synthesis of Small-Compound Libraries: Validation of Combinatorial Chemistry in Small-Molecule Synthesis. JACS. 1994;116:2661-62.
Chen et al., Gene therapy for brain tumors: regression of experimental gliomas by adenovirus-mediated gene transfer in vivo. Proc Natl Acad Sci U S A. Apr. 12, 1994;91(8):3054-7.
Chu et al., Free Solution Identification of Candidate Peptides from Combinatorial Libraries by Affinity Capillary Electrophoresis/Mass Spectrometry. J Am Chem Soc. 1995;117:5419-20.
Clackson et al., Making antibody fragments using phage display libraries. Nature. Aug. 15, 1991;352(6336):624-8.
Clemons et al., A one-bead, one-stock solution approach to chemical genetics: part 2. Chem Biol. Dec. 2001;8(12):1183-95.
Clipstone et al., Identification of calcineurin as a key signalling enzyme in T-lymphocyte activation. Nature. Jun. 25, 1992;357(6380):695-7.
Cockell et al., Nuclear compartments and gene regulation. Curr Opin Genet Dev. Apr. 1999;9(2):199-205.
Cohen et al., The histone deacetylase HDAC4 connects neural activity to muscle transcriptional reprogramming. J Biol Chem. Nov. 16, 2007;282(46):33752-9. Epub Sep. 16, 2007.
Corcoran et al., A novel action of histone deacetylase inhibitors in a protein aggresome disease model. Curr Biol. Mar. 23, 2004;14(6):488-92.
Cress et al., Histone deacetylases, transcriptional control, and cancer. J Cell Physiol. Jul. 2000;184(1):1-16.
Csordas, On the biological role of histone acetylation. Biochem J. Jan. 1, 1990;265(1):23-38.
Cuperus et al., Locus specificity determinants in the multifunctional yeast silencing protein Sir2. EMBO J. Jun. 1, 2000;19(11):2641-51.
Curtin et al., Succinimide hydroxamic acids as potent inhibitors of histone deacetylase (HDAC). Bioorg Med Chem Lett. Oct. 21, 2002;12(20):2919-23.
Cwirla et al., Peptides on phage: a vast library of peptides for identifying ligands. Proc Natl Acad Sci U S A. Aug. 1990;87(16):6378-82.
Dancey et al., Strategies for optimizing combinations of molecularly targeted anticancer agents. Nat Rev Drug Discov. Aug. 2006;5(8):649-59.
Dangond et al., Differential display cloning of a novel human histone deacetylase (HDAC3) cDNA from PHA-activated immune cells. Biochem Biophys Res Commun. Jan. 26, 1998;242(3):648-52.
Dankwardt et al., Solid-phase synthesis of di- and tripeptidic hydroxamic acids as inhibitors of procollagen C-proteinase. Bioorg Med Chem Lett. Nov. 20, 2000;10(22):2513-6.
Dann et al., Human renin: a new class of inhibitors. Biochem Biophys Res Commun. Jan. 14, 1986;134(1):71-7.
David et al., Histone deacetylase associated with mSin3A mediates repression by the acute promyelocytic leukemia-associated PLZF protein. Oncogene. May 14, 1998;16(19):2549-56.
Davie et al., Multiple functions of dynamic histone acetylation. J Cell Biochem. May 1994;55(1):98-105.
De Ruijter et al., Histone deacetylases (HDACs): characterization of the classical HDAC family. Biochem J. Mar. 15, 2003;370(Pt 3):737-49.
Delgrave et al., Recursive ensemble mutagenesis. Protein Engineer. 1993;6(3):327-31.
Denlinger et al., Proteasome inhibition sensitizes non-small cell lung cancer to histone deacetylase inhibitor-induced apoptosis through the generation of reactive oxygen species. J Thorac Cardiovasc Surg. Nov. 2004;128(5):740-8.
Dessolin et al., No. 454. Réactivité des acides hydroxamiques vis-à-vis d'esters activés. Étude cinétique. Bull Soc Chim Fr. 1970;7:2573-80.
Dev et al., Electrochemotherapy—a novel method of cancer treatment. Cancer Treat Rev. Jan. 1994;20(1):105-15.
Devlin et al., Random peptide libraries: a source of specific protein binding molecules. Science. Jul. 27, 1990;249(4967):404-6.
Dower et al., Chapter 28. The Search for Molecular Diversity (II): Recombinant and Synthetic Randomized Peptide Libraries. Annu Rep Med Chem. 1991;26:271-80.

(56) References Cited

OTHER PUBLICATIONS

Dul et al., Hsp70 and antifibrillogenic peptides promote degradation and inhibit intracellular aggregation of amyloidogenic light chains. J Cell Biol. Feb. 19, 2001;152(4):705-15.
Egner et al., Solid Phase Chemistry: Direct Monitoring by Matrix-Assisted Laser Desorption/Ionization Time of Flight Mass Spectrometry. A Tool for Combinatorial Chemistry. J Org Chem. 1995;60:2652-53.
Eichler et al., Application of Cellulose Paper as Support Material in Simultaneous Solid Phase Peptide Synthesis. Collect Czech Chem Commun. 1989;54:1746-52.
Eichler et al., Evaluation of cotton as a carrier for solid-phase peptide synthesis. Pept Res. Sep.-Oct. 1991;4(5):296-307.
Eliel et al., Conformational analysis. XX. Stereochemistry of reaction of Grignard reagents with ortho esters. Synthesis of 1,3-dioxanes with axial substituents at C-2. J Am Chem Soc. 1970;92(3):584-590.
Ellison et al., Epitope-tagged ubiquitin. A new probe for analyzing ubiquitin function. J Biol Chem. Nov. 5, 1991;266(31):21150-7.
Emiliani et al., Characterization of a human RPD3 ortholog, HDAC3. Proc Natl Acad Sci U S A. Mar. 17, 1998;95(6):2795-800.
Evans et al., An engineered poliovirus chimaera elicits broadly reactive HIV-1 neutralizing antibodies. Nature. Jun. 1, 1989;339(6223):385-8.
Evans et al., Establishment in culture of pluripotential cells from mouse embryos. Nature. Jul. 9, 1981;292(5819):154-6.
Ewenson et al., Ketomethylene pseudopeptide analogues of substance P: synthesis and biological activity. J Med Chem. Feb. 1986;29(2):295-9.
Fabian et al., A small molecule-kinase interaction map for clinical kinase inhibitors. Nat Biotechnol. Mar. 2005;23(3):329-36. Epub Feb. 13, 2005.
Fabunmi et al., Activity and regulation of the centrosome-associated proteasome. J Biol Chem. Jan. 7, 2000;275(1):409-13.
Farkas et al., A comparison between the chelating properties of some dihydroxamic acids, desferrrioxamine B and acetohydroxamic acid. Polyhedron. 1999;18(1999):2391-98.
Feling et al., *Salinosporamide A*: a highly cytotoxic proteasome inhibitor from a novel microbial source, a marine bacterium of the new genus *salinospora*. Angew Chem Int Ed Engl. Jan. 20, 2003;42(3):355-7.
Felsenfeld, Chromatin as an essential part of the transcriptional mechanism. Nature. Jan. 16, 1992;355(6357):219-24.
Peng et al., Progressive sequence alignment as a prerequisite to correct phylogenetic trees. J Mol Evol. 1987;25(4):351-60.
Finnin et al., Structures of a histone deacetylase homologue bound to the TSA and SAHA inhibitors. Nature. Sep. 9, 1999;401(6749):188-93.
Fischle et al., A new family of human histone deacetylases related to *Saccharomyces cerevisiae* HDA1p. J Biol Chem. Apr. 23, 1999;274(17):11713-20.
Fitch et al., High-Resolution 1H NMR in Solid-Phase Organic Synthesis. J Org Chem. 1994;59:7955-56.
Fitch, Distinguishing Homologous from Analogous Proteins. Syst Zool. 1970;19:99-113.
Fleming et al., The total synthesis of ( )-trichostatin A: Some observations on the acylation and alkylation of silyl enol ethers, silyl dienol ethers and a silyl trienol ether. Tetrahedron. 1983;39:841-46.
Fodor et al., Light-directed, spatially addressable parallel chemical synthesis. Science. Feb. 15, 1991;251(4995):767-73.
Frank et al., Simultaneous Multiple Peptide Synthesis Under Continuous Flow Conditions on Cellulose Paper Discs as Segmental Solid Supports. Tetrahedron. 1988;44:6031-40.
Frank, Spot-Synthesis: An Easy Technique for the Positionally Addressable, Parallel Chemical Synthesis on a Membrane Support. Tetrahedron. 1992;48:9217-32.
Frank, Strategies and Techniques in Simultaneous Solid Phase Synthesis Based on the Segmentation of Membrane Type Supports. Bioorg Med Chem Lett. 1993;3:425-30.

Friend et al., Deletions of a DNA sequence in retinoblastomas and mesenchymal tumors: organization of the sequence and its encoded protein. Proc Natl Acad Sci U S A. Dec. 1987;84(24):9059-63.
Frye et al., Characterization of Five Human cDNAs with Homology to the Yeast SIR2 Gene: Sir2-like Proteins (Sirtuins) Metabolize NAD and May Have Protein ADP-Ribosyltransferase Activity. Biochem Biophys Res Commun. 1999;260:273-79.
Frye, Phylogenetic classification of prokaryotic and eukaryotic Sir2-like proteins. Biochem Biophys Res Commun. Jul. 5, 2000;273(2):793-8.
Furukawa et al., Isolation and mapping of a human gene (RPD3L1) that is homologous to RPD3, a transcription factor in *Saccharomyces cerevisiae*. Cytogenet Cell Genet. 1996;73(1-2):130-3.
Furumai et al., Potent histone deacetylase inhibitors built from trichostatin A and cyclic tetrapeptide antibiotics including trapoxin. Proc Natl Acad Sci U S A. Jan. 2, 2001;98(1):87-92.
Gallop et al., Applications of combinatorial technologies to drug discovery. 1. Background and peptide combinatorial libraries. J Med Chem. Apr. 29, 1994;37(9):1233-51.
Gammon et al., T cell determinant structure: cores and determinant envelopes in three mouse major histocompatibility complex haplotypes. J Exp Med. Mar. 1, 1991;173(3):609-17.
García-Mata et al., Characterization and dynamics of aggresome formation by a cytosolic GFP-chimera. J Cell Biol. Sep. 20, 1999;146(6):1239-54.
Garcia-Mata et al., Hassles with taking out the garbage: aggravating aggresomes. Traffic. Jun. 2002;3(6):388-96.
Garcia-Ramirez et al., Role of the histone "tails" in the folding of oligonucleosomes depleted of histone H1. J Biol Chem. Sep. 25, 1992;267(27):19587-95.
Gardlik et al., Vectors and delivery systems in gene therapy. Med Sci Monit. Apr. 2005;11(4):RA110-21. Epub Mar. 24, 2005.
Gartenberg, The Sir proteins of *Saccharomyces cerevisiae*: mediators of transcriptional silencing and much more. Curr Opin Microbiol. Apr. 2000;3(2):132-7.
Gelmetti et al., Aberrant recruitment of the nuclear receptor corepressor-histone deacetylase complex by the acute myeloid leukemia fusion partner ETO. Mol Cell Biol. Dec. 1998;18(12):7185-91.
Geysen et al., Use of peptide synthesis to probe viral antigens for epitopes to a resolution of a single amino acid. Proc Natl Acad Sci U S A. Jul. 1984;81(13):3998-4002.
Giacomelli et al., Simple one-flask method for the preparation of hydroxamic acids. Org Lett. Jul. 24, 2003;5(15):2715-7.
Gordon et al., Applications of combinatorial technologies to drug discovery. 2. Combinatorial organic synthesis, library screening strategies, and future directions. J Med Chem. May 13, 1994;37(10):1385-401.
Gordon et al., Design of peptide derived amino alcohols as transition-state analog inhibitors of angiotensin converting enzyme. Biochem Biophys Res Commun. Jan. 16, 1985;126(1):419-26.
Görlich, Nuclear protein import. Curr Opin Cell Biol. Jun. 1997;9(3):412-9.
Gossler et al., Transgenesis by means of blastocyst-derived embryonic stem cell lines. Proc Natl Acad Sci U S A. Dec. 1986;83(23):9065-9.
Goy et al., Phase II study of proteasome inhibitor bortezomib in relapsed or refractory B-cell non-Hodgkin's lymphoma. J Clin Oncol. Feb. 1, 2005;23(4):667-75. Epub Dec. 21, 2004.
Gravemann et al., Hydroxamic acid and fluorinated derivatives of valproic acid: anticonvulsant activity, neurotoxicity and teratogenicity. Neurotoxicol Teratol. Sep.-Oct. 2008;30(5):390-4. doi: 10.1016/j.ntt.2008.03.060. Epub Mar. 19, 2008.
Gray et al., The human histone deacetylase family. Exp Cell Res. Jan. 15, 2001;262(2):75-83.
Green, When the products of oncogenes and anti-oncogenes meet. Cell. Jan. 13, 1989;56(1):1-3.
Gregoretti et al., Molecular evolution of the histone deacetylase family: functional implications of phylogenetic analysis J Mol Biol. Apr. 16, 2004;338(1):17-31.
Gregory et al., Combination chemotherapy versus melphalan and prednisolone in the treatment of multiple myeloma: an overview of published trials. J Clin Oncol. Feb. 1992;10(2):334-42.

(56) References Cited

OTHER PUBLICATIONS

Griffiths et al., Human anti-self antibodies with high specificity from phage display libraries. EMBO J. Feb. 1993;12(2):725-34.
Grignani et al., Fusion proteins of the retinoic acid receptor-alpha recruit histone deacetylase in promyelocytic leukaemia. Nature. Feb. 19, 1998;391(6669):815-8.
Grozinger et al., Deacetylase enzymes: biological functions and the use of small-molecule inhibitors. Chem Biol. Jan. 2002;9(1):3-16.
Grozinger et al., Regulation of histone deacetylase 4 and 5 and transcriptional activity by 14-3-3-dependent cellular localization. Proc Natl Acad Sci U S A. Jul. 5, 2000;97(14):7835-40.
Grozinger et al., Three proteins define a class of human histone deacetylases related to yeast Had1p. Proc Natl Acad Sci U S A. Apr. 27, 1999;96(9):4868-73.
Grunstein, Histone acetylation in chromatin structure and transcription. Nature. Sep. 25, 1997;389(6649):349-52.
Grunstein, Molecular model for telomeric heterochromatin in yeast. Curr Opin Cell Biol. Jun. 1997;9(3):383-7.
Gu et al., Activation of p53 sequence-specific DNA binding by acetylation of the p53 C-terminal domain. Cell. Aug. 22, 1997;90(4):595-606.
Guarente, Sir2 links chromatin silencing, metabolism, and aging. Genes Dev. May 1, 2000;14(9):1021-6.
Guo et al., Protein tolerance to random amino acid change. Proc Natl Acad Sci U S A. Jun. 22, 2004;101(25):9205-10. Epub Jun. 14, 2004.
Habig et al., Glutathione S-transferases. The first enzymatic step in mercapturic acid formation. J Biol Chem. Nov. 25, 1974;249(22):7130-9.
Haggarty et al., Dissecting cellular processes using small molecules: identification of colchicine-like, taxol-like and other small molecules that perturb mitosis. Chem Biol. Apr. 2000;7(4):275-86.
Haggarty et al., Domain-selective small-molecule inhibitor of histone deacetylase 6 (HDAC6)-mediated tubulin deacetylation. Proc Natl Acad Sci U S A. Apr. 15, 2003;100(8):4389-94. Epub Apr. 3, 2003.
Haggarty et al., Mapping chemical space using molecular descriptors and chemical genetics: deacetylase inhibitors. Comb Chem High Throughput Screen. Nov. 2004;7(7):669-76.
Haggarty et al., Multidimensional chemical genetic analysis of diversity-oriented synthesis-derived deacetylase inhibitors using cell-based assays. Chem Biol. May 2003;10(5):383-96.
Hansen et al., Retinoblastoma and the progression of tumor genetics. Trends Genet. May 1988;4(5):125-8.
Hardwick et al., Rapamycin-modulated transcription defines the subset of nutrient-sensitive signaling pathways directly controlled by the Tor proteins. Proc Natl Acad Sci U S A. Dec. 21, 1999;96(26):14866-70.
Hassig et al., A role for histone deacetylase activity in HDAC1-mediated transcriptional repression. Proc Natl Acad Sci U S A. Mar. 31, 1998;95(7):3519-24.
Hassig et al., Histone deacetylase activity is required for full transcriptional repression by mSin3A. Cell. May 2, 1997;89(3):341-7.
Hassig et al., Nuclear histone acetylases and deacetylases and transcriptional regulation: HATs off to HDACs. Curr Opin Chem Biol. Oct. 1997;1(3):300-8.
Hathaway et al., Dissecting cell biology with chemical scalpels. Curr Opin Cell Biol. Feb. 2005;17(1):12-9.
Hay et al., Histone deacetylase. Association with a nuclease resistant, high molecular weight fraction of HeLa cell chromatin. J Biol Chem. Mar. 25, 1983;258(6):3726-34.
Hayes et al., Histones H2A/H2B inhibit the interaction of transcription factor IIIA with the Xenopus borealis somatic 5S RNA gene in a nucleosome. Proc Natl Acad Sci U S A. Feb. 15, 1992;89(4):1229-33.
He et al., Distinct interactions of PML-RARalpha and PLZF-RARalpha with co-repressors determine differential responses to RA in APL. Nat Genet. Feb. 1998;18(2):126-35.
Hearn et al., Palindromic dihydrazones from N-aminophthalimide. J Chem Eng Data. 1986;31(2):255-6.

Hecht et al., Histone H3 and H4 N-termini interact with SIR3 and SIR4 proteins: a molecular model for the formation of heterochromatin in yeast. Cell. Feb. 24, 1995;80(4):583-92.
Hicks et al., Protein import into the nucleus: an integrated view. Annu Rev Cell Dev Biol. 1995;11:155-88.
Hideshima et al., Antitumor activity of lysophosphatidic acid acyltransferase-beta inhibitors, a novel class of agents, in multiple myeloma. Cancer Res. Dec. 1, 2003;63(23):8428-36.
Hideshima et al., Molecular mechanisms mediating antimyeloma activity of proteasome inhibitor PS-341. Blood. Feb. 15, 2003;101(4):1530-4. Epub Sep. 26, 2002.
Hideshima et al., Molecular mechanisms of novel therapeutic approaches for multiple myeloma. Nat Rev Cancer. Dec. 2002;2(12):927-37.
Hideshima et al., NF-κB as a therapeutic target in multiple myeloma. J Biol Chem. May 10, 2002;277(19):16639-47. Epub Feb. 28, 2002.
Hideshima et al., Novel therapeutic approaches for multiple myeloma. Immunol Rev. Aug. 2003;194:164-76.
Hideshima et al., p38 MAPK inhibition enhances PS-341 (bortezomib)-induced cytotoxicity against multiple myeloma cells. Oncogene. Nov. 18, 2004;23(54):8766-76.
Hideshima et al., Proteasome inhibitor PS-341 abrogates IL-6 triggered signaling cascades via caspase-dependent downregulation of gp130 in multiple myeloma. Oncogene. Nov. 20, 2003;22(52):8386-93.
Hideshima et al., Small-molecule inhibition of proteasome and aggresome function induces synergistic antitumor activity in multiple myeloma. Proc Natl Acad Sci U S A. Jun. 14, 2005;102(24):8567-72. Epub Jun. 3, 2005.
Hideshima et al., The proteasome inhibitor PS-341 inhibits growth, induces apoptosis, and overcomes drug resistance in human multiple myeloma cells. Cancer Res. Apr. 1, 2001;61(7):3071-6.
Hideshima et al., The role of tumor necrosis factor alpha in the pathophysiology of human multiple myeloma: therapeutic applications. Oncogene. Jul. 27, 2001;20(33):4519-27.
Hochuli et al., New metal chelate adsorbent selective for proteins and peptides containing neighbouring histidine residues. J Chromatogr. Dec. 18, 1987;411:177-84.
Holbeck et al., Analysis of Food and Drug Administration-approved anticancer agents in the NCI60 panel of human tumor cell lines. Mol Cancer Ther. May 2010;9(5):1451-60. doi: 10.1158/1535-7163.MCT-10-0106. Epub May 4, 2010.
Hostein et al., Inhibition of signal transduction by the Hsp90 inhibitor 17-allylamino-17-demethoxygeldanamycin results in cytostasis and apoptosis. Cancer Res. May 15, 2001;61(10):4003-9.
Houdebine, The methods to generate transgenic animals and to control transgene expression. J Biotechnol. Sep. 25, 2002;98(2-3):145-60.
Houghten et al., Simplified procedure for carrying out simultaneous multiple hydrogen fluoride cleavages of protected peptide resins. Int J Pept Protein Res. Jun. 1986;27(6):673-8.
Houghten, General method for the rapid solid-phase synthesis of large numbers of peptides: specificity of antigen-antibody interaction at the level of individual amino acids. Proc Natl Acad Sci U S A. Aug. 1985;82(15):5131-5.
Hu et al., Cloning and characterization of a novel human class I histone deacetylase that functions as a transcription repressor. J Biol Chem. May 19, 2000;275(20):15254-64.
Huang et al., Nuclear receptor corepressors partner with class II histone deacetylases in a Sin3-independent repression pathway. Genes Dev. Jan. 1, 2000;14(1):45-54.
Huang et al., Vaccinia virus recombinants expressing an 11-kilodalton beta-galactosidase fusion protein incorporate active beta-galactosidase in virus particles. J Virol. Oct. 1988;62(10):3855-61.
Hubbert et al., HDAC6 is a microtubule-associated deacetylase. Nature. May 23, 2002;417(6887):455-8.
Hunter et al., An Enantioselective Synthesis of Benzylidene-Protected syn-3,5-Dihydroxy Carboxylate Esters via Osmium, Palladium, and Base Catalysis. Org Letter. 2001;3(7):1049-52.
Hynes, Hydroxylamine derivatives as potential antimalarial agents. 1. Hydroxamic acids. J Med Chem. Nov. 1970;13(6):1235-7.

(56) References Cited

OTHER PUBLICATIONS

Ike et al., Solid phase synthesis of polynucleotides. VIII. Synthesis of mixed oligodeoxyribonucleotides by the phosphotriester solid phase method. Nucleic Acids Res. Jan. 25, 1983;11(2):477-88.

Imai et al., Transcriptional silencing and longevity protein Sir2 is an NAD-dependent histone deacetylase. Nature. Feb. 17, 2000;403(6771):795-800.

Imamoto et al., Preparation and Synthetic Use of Trimethylsilyl Polyphosphate. A New Stereoselective Aldol-Type Reaction in the Presence of Trimethylsilyl Polyphosphate. J Org Chem. 1984;49:1105-10.

Imamoto et al., The Reaction of Aryl Methyl Ketones with Aromatic Aldehydes in Trimethylsilyl Polyphosphate (PPSE). Formation of MESO-2,4,6-Trisubstituted-5-ACYL-1,3-Dioxl. Tetrahedron Letters. 1982;23(14):1467-70.

Imhof et al., Acetylation of general transcription factors by histone acetyltransferases. Curr Biol. Sep. 1, 1997;7(9):689-92.

Itakura et al., Expression in *Escherichia coli* of a Chemically Synthesized Gene for the Hormone Somatostatin. Science. 1984;198:1056-63.

Itakura et al., Synthesis and use of synthetic oligonucleotides. Annu Rev Biochem. 1984;53:323-56.

Iwabuchi et al., Use of the two-hybrid system to identify the domain of p53 involved in oligomerization. Oncogene. Jun. 1993;8(6):1693-6.

Jacobs et al., Combinatorial chemistry—applications of light-directed chemical synthesis. Trends Biotechnol. Jan. 1994;12(1):19-26.

Jaenisch, Germ line integration and Mendelian transmission of the exogenous Moloney leukemia virus. Proc Natl Acad Sci U S A. Apr. 1976;73(4):1260-4.

Jaenisch, Transgenic animals. Science. Jun. 10, 1988;240(4858):1468-74.

Jähner et al., De novo methylation and expression of retroviral genomes during mouse embryogenesis. Nature. Aug. 12, 1982;298(5875):623-8.

Jähner et al., Insertion of the bacterial gpt gene into the germ line of mice by retroviral infection. Proc Natl Acad Sci U S A. Oct. 1985;82(20):6927-31.

Janknecht et al., Rapid and efficient purification of native histidine-tagged protein expressed by recombinant vaccinia virus. Proc Natl Acad Sci U S A. Oct. 15, 1991;88(20):8972-6.

Jin et al., Transcriptional regulation of the MDR1 gene by histone acetyltransferase and deacetylase is mediated by NF-Y. Mol Cell Biol. Jul. 1998;18(7):4377-84.

Johnson et al., Deacetylase activity associates with topoisomerase II and is necessary for etoposide-induced apoptosis. J Biol Chem. Feb. 16, 2001;276(7):4539-42. Epub Jan. 2, 2001.

Johnson et al., Genetic evidence for an interaction between SIR3 and histone H4 in the repression of the silent mating loci in *Saccharomyces cerevisiae*. Proc Natl Acad Sci U S A. Aug. 1990;87(16):6286-90.

Johnson et al., Molecular cloning of *Drosophila melanogaster* cDNAs that encode a novel histone deacetylase dHDAC3. Gene. Oct. 9, 1998;221(1):127-34.

Johnson, The ubiquitin-proteasome system: opportunities for therapeutic intervention in solid tumors. Endocr Relat Cancer. Mar. 21, 2014.

Johnston et al., Aggresomes: a cellular response to misfolded proteins. J Cell Biol. Dec. 28, 1998;143(7):1883-98.

Johnstone, Histone-deacetylase inhibitors: novel drugs for the treatment of cancer. Nat Rev Drug Discov. Apr. 2002;1(4):287-99.

Jones et al., Probing the elusive catalytic activity of vertebrate class IIa histone deacetylases. Bioorg Med Chem Lett. Mar. 15, 2008;18(6):1814-9. Epub Feb. 14, 2008.

Jung et al., Amide analogues of trichostatin A as inhibitors of histone deacetylase and inducers of terminal cell differentiation. J Med Chem. Nov. 4, 1999;42(22):4669-79.

Junn et al., Parkin accumulation in aggresomes due to proteasome impairment. J Biol Chem. Dec. 6, 2002;277(49):47870-7. Epub Oct. 2, 2002.

Kao et al., Isolation of a novel histone deacetylase reveals that class I and class II deacetylases promote SMRT-mediated repression. Genes Dev. Jan. 1, 2000;14(1):55-66.

Kappel et al., Regulating gene expression in transgenic animals. Curr Opin Biotechnol. Oct. 1992;3(5):548-53.

Katoh et al., MAFFT: a novel method for rapid multiple sequence alignment based on fast Fourier transform. Nucleic Acids Res. Jul. 15, 2002;30(14):3059-66.

Kawaguchi et al., The deacetylase HDAC6 regulates aggresome formation and cell viability in response to misfolded protein stress. Cell. Dec. 12, 2003;115(6):727-38.

Kelly et al., Phase I clinical trial of histone deacetylase inhibitor: suberoylanilide hydroxamic acid administered intravenously. Clin Cancer Res. Sep. 1, 2003;9(10 Pt 1):3578-88.

Kennedy et al., Redistribution of silencing proteins from telomeres to the nucleolus is associated with extension of life span in *S. cerevisiae*. Cell. May 2, 1997;89(3):381-91.

Kerr et al., Encoded Combinatorial Peptide Libraries Containing Non-Natural Amino Acids. J Am Chem, Soc. 1993;115:2529-31.

Khockbin et al., Functional significance of histone deacetylase diversity. Curr Opin Genet Dev. Apr. 2001;11(2):162-6.

Khomutov et al., Directed synthesis of inhibitors of enzymic changes of glutamic acid. Doklady Akademii Nauk SSSR. 1965;161(5):1227-30. Russian.

Kijima et al., Trapoxin, an antitumor cyclic tetrapeptide, is an irreversible inhibitor of mammalian histone deacetylase. J Biol Chem. Oct. 25, 1993;268(30):22429-35.

Kikuchi et al., Multiplicity of histone deacetylase from calf thymus. FEBS Lett. Feb. 1, 1973;29(3):280-282.

Kleff et al., Identification of a gene encoding a yeast histone H4 acetyltransferase. J Biol Chem. Oct. 20, 1995;270(42):24674-7.

Koeller et al., Chemical genetic modifier screens: small molecule trichostatin suppressors as probes of intracellular histone and tubulin acetylation. Chem Biol. May 2003;10(5):397-410.

Kohler et al., Continuous cultures of fused cells secreting antibody of predefined specificity. Nature. Aug. 7, 1975;256(5517):495-7.

Kopito et al., Aggresomes and Russell bodies. Symptoms of cellular indigestion? EMBO Rep. Sep. 2000;1(3):225-31.

Kopito, Aggresomes, inclusion bodies and protein aggregation. Trends Cell Biol. Dec. 2000;10(12):524-30.

Kouzarides, Acetylation: a regulatory modification to rival phosphorylation? EMBO J. Mar. 15, 2000;19(6):1176-9.

Kozbar et al., The production of monoclonal antibodies from human lymphocytes. Immunology Today. 1983;4:72-79.

Krieger et al., Chemical studies of histone acetylation. Substrate specificity of a histone deacetylase from calf thymus nuclei. J Biol Chem. Jan. 10, 1974;249(1):332-4.

Kumar et al., MEGA: a biologist-centric software for evolutionary analysis of DNA and protein sequences. Brief Bioinform. Jul. 2008;9(4):299-306. Epub Apr. 16, 2008.

Kuruvilla et al., Dissecting glucose signaling with diversity-oriented synthesis and small-molecule microarrays. Nature. Apr. 11, 2002;416(6881):653-7.

Kwon et al., Depudecin induces morphological reversion of transformed fibroblasts via the inhibition of histone deacetylase. Proc Natl Acad Sci U S A. Mar. 31, 1998;95(7):3356-61.

Lahm et al., Unraveling the hidden catalytic activity of vertebrate class IIa histone deacetylases. Proc Natl Acad Sci U S A. Oct. 30, 2007;104(44):17335-40. Epub Oct. 23, 2007.

Lam et al., The "One-Bead-One-Compound" Combinatorial Library Method. Chem Rev. Apr. 1, 1997;97(2):411-48.

Landegren et al., A ligase-mediated gene detection technique. Science. Aug. 26, 1988;241(4869):1077-80.

Landry et al., The silencing protein SIR2 and its homologs are NAD-dependent protein deacetylases. Proc Natl Acad Sci U S A. May 23, 2000;97(11):5807-11.

Lasko et al., Targeted oncogene activation by site-specific recombination in transgenic mice. Proc Natl Acad Sci U S A. Jul. 15, 1992;89(14):6232-6.

(56) References Cited

OTHER PUBLICATIONS

Lee et al., A positive role for histone acetylation in transcription factor access to nucleosomal DNA. Cell. Jan. 15, 1993;72(1):73-84.
Lee et al., A Strategy for Macrocyclic Ring Closure and Functionalization Aimed toward Split-Pool Syntheses. J Am Chem Soc. 1999;121(45):10648-49.
Lee et al., Histone acetyltransferase complexes: one size doesn't fit all. Nat Rev Mol Cell Biol. Apr. 2007;8(4):284-95.
Lee et al., Proteasome inhibitors disrupt the unfolded protein response in myeloma cells. Proc Natl Acad Sci U S A. Aug. 19, 2003;100(17):9946-51. Epub Aug. 5, 2003.
Lin et al., Combination of proteasome and HDAC inhibitors for uterine cervical cancer treatment.Clin Cancer Res. Jan. 15, 2009;15(2):570-7.
Lin et al., Generation and Aldol Reaction of Endlate Anion Adjacnet to a η3-Allyl-Mo(Co)2Cp Moiety. A New Approach to the Stereoselctive Synthesis of 1,3,5-Triol and 2-Vinyl-3-Hydroxyl-Tetrahydrofuran. Tetrahedron Letters.1990;31(52):7645-48.
Lin et al., Role of the histone deacetylase complex in acute promyelocytic leukaemia. Nature. Feb. 19, 1998;391(6669):811-4.
Lizcano et al., Cell type-specific roles of histone deacetylase in TR ligand-independent transcriptional repression. Mol Cell Endocrinol. Feb. 14, 2001;172(1-2):13-20.
Look et al., Methods for Combinatorial Organic Synthesis: The Use of Fast 13C NMR Analysis for Gel Phase Reaction Monitoring. J Org Chem. 1994;59:7588-90.
Lopez-Girona et al., Nuclear localization of Cdc25 is regulated by DNA damage and a 14-3-3 protein. Nature. Jan. 14, 1999;397(6715):172-5.
Luger et al., Crystal structure of the nucleosome core particle at 2.8 A resolution. Nature. Sep. 18, 1997;389(6648):251-60.
Lutterbach et al., ETO, a target of t(8;21) in acute leukemia, interacts with the N-CoR and mSin3 corepressors. Mol Cell Biol. Dec. 1998;18(12):7176-84.
Macbeath et al., Printing proteins as microarrays for high-throughput function determination. Science. Sep. 8, 2000;289(5485):1760-3.
Macherla et al., Structure-activity relationship studies of salinosporamide A (NPI-0052), a novel marine derived proteasome inhibitor. J Med Chem. Jun. 2, 2005;48(11):3684-7.
Maddry et al., Inhibition of the Her2 Tyrosine Kinase and Characterization of a Hydrophobic Site Near the Nucleotide Binding Domain. Bioorganic Med Chem Letter. 1997;7(16):2109-14.
Madura et al., N-recognin/Ubc2 interactions in the N-end rule pathway. J Biol Chem. Jun. 5, 1993;268(16):12046-54.
Maeji et al., Multi-pin peptide synthesis strategy for T cell determinant analysis J Immunol. Methods. Nov. 6, 1990;134(1):23-33.
Magnaghi-Jaulin et al., Retinoblastoma protein represses transcription by recruiting a histone deacetylase. Nature. Feb. 5, 1998;391(6667):601-4.
Mahboobi et al., Design of chimeric histone deacetylase- and tyrosine kinase-inhibitors: a series of imatinib hybrides as potent inhibitors of wild-type and mutant BCR-ABL, PDGF-Rbeta, and histone deacetylases. J Med Chem. Apr. 23, 2009;52(8):2265-79.
Mai et al., Class II (IIa)-selective histone deacetylase inhibitors. 1. Synthesis and biological evaluation of novel (aryloxopropenyl)pyrrolyl hydroxyamides. J Med Chem. May 5, 2005;48(9):3344-53.
Manetto et al., Selective presence of ubiquitin in intracellular inclusions. Am J Pathol. Mar. 1989;134(3):505-13.
Marcand et al., Silencing of genes at nontelomeric sites in yeast is controlled by sequestration of silencing factors at telomeres by Rap 1 protein. Genes Dev. Jun. 1, 1996;10(11):1297-309.
Marchion et al., Development of histone deacetylase inhibitors for cancer treatment. Expert Rev Anticancer Ther. Apr. 2007;7(4):583-98.
Marks et al., Histone deacetylases and cancer: causes and therapies. Nat Rev Cancer. Dec. 2001;1(3):194-202.
Marks et al., Histone deacetylases. Curr Opin Pharmacol. Aug. 2003;3(4):344-51.
Marks et al., Molecular evolution of proteins on filamentous phage. Mimicking the strategy of the immune system. J Biol Chem. Aug. 15, 1992;267(23):16007-10.
Marks et al., Polar/apolar chemical inducers of differentiation of transformed cells: strategies to improve therapeutic potential. Proc Natl Acad Sci U S A. Aug. 1989;86(16):6358-62.
Marmuse et al., "Click chemistry" en route to pseudo-starch. Org Biomol Chem. Jun. 21, 2005;3(12):2225-7. Epub May 11, 2005.
Martinelli et al., Molecular therapy for multiple myeloma. Haematologica. Sep. 2001;86(9):908-17.
Marushige et al., Template properties of liver chromatin. J Mol Biol. Jan. 1966;15(1):160-74.
Marx et al., Bench to bedside: the development of rapamycin and its application to stent restenosis. Circulation. Aug. 21, 2001;104(8):852-5.
Massa et al., Synthesis and antimicrobial and cytotoxic activities of pyrrole-containing analogues of trichostatin A. J Med Chem. Oct. 1990;33(10):2845-9.
Mckenzie et al., The centromere and promoter factor, 1, CPF1, of *Saccharomyces cerevisiae* modulates gene activity through a family of factors including SPT21, RPD1 (SIN3), RPD3 and CCR4. Mol Gen Genet. Sep. 1993;240(3):374-86.
Megee et al., Genetic analysis of histone H4: essential role of lysines subject to reversible acetylation. Science. Feb. 16, 1990;247(4944):841-5.
Meinke et al., Histone deacetylase: a target for antiproliferative and antiprotozoal agents. Curr Med Chem. Feb. 2001;8(2):211-35.
Meinke et al., Synthesis of apicidin-derived quinolone derivatives: parasite-selective histone deacetylase inhibitors and antiproliferative agents. J Med Chem. Dec. 14, 2000;43(25):4919-22.
Menger et al., Chemical Reaction between Colliding Vesicles. Angew Chem Int Ed Engl. Oct. 15, 2001;40(20):3905-3907.
Merrifield, Solid Phase Peptide Syntheses. I. The Synthesis of a Tetrapeptide. J Am Chem Soc. 1963;85:2149-54.
Metzger et al., Ion-Spray Mass Spectrometry and High-Performance Liquid Chromatography-Mass Spectrometry of Synthetic Peptide Libraries. Angew Chem Int Ed Engl. 1993;32:894-96.
Miano et al., HDAC7 supports vascular integrity. Nat Med. Sep. 2006;12(9):997-8.
Miller et al., Histone deacetylase inhibitors. J Med Chem. Nov. 20, 2003;46(24):5097-116.
Miller et al., N-terminal methionine-specific peptidase in Salmonella typhimurium. Proc Natl Acad Sci U S A. May 1987;84(9):2718-22.
Minucci et al., Histone deacetylase inhibitors and the promise of epigenetic (and more) treatments for cancer. Nat Rev Cancer. Jan. 2006;6(1):38-51.
Miska et al., HDAC4 deacetylase associates with and represses the MEF2 transcription factor. EMBO J. Sep. 15, 1999;18(18):5099-107.
Mitchison, Towards a pharmacological genetics. Chem Biol. Sep. 1994;1(1):3-6.
Mitsiades et al., Focus on multiple myeloma. Cancer Cell. Nov. 2004;6(5):439-44.
Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-30.
Mitsiades et al., Molecular sequelae of histone deacetylase inhibition in human malignant B cells. Blood. May 15, 2003;101(10):4055-62. Epub Jan. 16, 2003.
Mitsiades et al., Molecular sequelae of proteasome inhibition in human multiple myeloma cells. Proc Natl Acad Sci U S A. Oct. 29, 2002;99(22):14374-9. Epub Oct. 21, 2002.
Mitsiades et al., Novel biologically based therapies for Waldenstrom's macroglobulinemia. Semin Oncol. Apr. 2003;30(2):309-12.
Mitsiades et al., The proteasome inhibitor PS-341 potentiates sensitivity of multiple myeloma cells to conventional chemotherapeutic agents: therapeutic applications. Blood. Mar. 15, 2003;101(6):2377-80. Epub Nov. 7, 2002.

(56) References Cited

OTHER PUBLICATIONS

Mitsiades et al., Transcriptional signature of histone deacetylase inhibition in multiple myeloma: biological and clinical implications. Proc Natl Acad Sci U S A. Jan. 13, 2004;101(2):540-5. Epub Dec. 26, 2003.

Moazed, Enzymatic activities of Sir2 and chromatin silencing. Curr Opin Cell Biol. Apr. 2001;13(2):232-8.

Mori et al., Synthesis of trichostatin A, a potent differentiation inducer of friend leukemic cells, and its antipode. Tetrahedron. 1988;44:6013-20.

Mottet et al., Histone deacetylase 7 silencing alters endothelial cell migration, a key step in angiogenesis. Circ Res. Dec. 7, 2007;101(12):1237-46. Epub Oct. 18, 2007.

Mowat et al., Rearrangements of the cellular p53 gene in erythroleukaemic cells transformed by Friend virus. Nature. Apr. 18-24, 1985;314(6012):633-6.

Mullins et al., Transgenesis in nonmurine species. Hypertension. Oct. 1993;22(4):630-3.

Munegumi et al., Amidation of carboxyl group involved in N-protected amino acids using O-benzylhydroxylamine. Peptide Chemistry. 1993;31:49-52.

Munshi et al., Acetylation of HMG I(Y) by CBP turns off IFN beta expression by disrupting the enhanceosome. Mol Cell. Oct. 1998;2(4):457-67.

Mutch et al., Effects of end groups on the stimulatory capacity of minimal length T cell determinant peptides. Pept Res. May-Jun. 1991;4(3):132-7.

Myers et al., Preparation of the Chiral, C-Protected α-Amino Aldehydes of High Optical Purity and Their Use as Condensation Components in a Linear Synthesis Strategy. J Am Chem Soc. 1999;121:8401-02.

Nagai et al., Synthesis of a Bicyclic Dipeptide with the Shape of β-Turn Central Part. Tetrahedron Lett. 1985;26:647-50.

Nagy et al., Nuclear receptor repression mediated by a complex containing SMRT, mSin3A, and histone deacetylase. Cell. May 2, 1997;89(3):373-80.

Nakatsuka et al., Total Synthesis of FK506 and an FKBP Probe Reagent, (C8, C9-13C2)-FK506. J. Am. Chem. Soc. 1990; 112:5583-5601.

Nakazawa et al., UV and skin cancer: specific p53 gene mutation in normal skin as a biologically relevant exposure measurement. Proc Natl Acad Sci U S A. Jan. 4, 1994;91(1):360-4.

Narang, DNA Synthesis. Tetrahedron. 1983;39:3-22.

Nardelii et al., A chemically defined synthetic vaccine model for HIV-1. J Immunol. Feb. 1, 1992;148(3):914-20.

Nasmyth et al., Both positive and negative regulators of HO transcription are required for mother-cell-specific mating-type switching in yeast. Cell. Feb. 27, 1987;48(4):579-87.

Needleman et al., A general method applicable to the search for similarities in the amino acid sequence of two proteins. J Mol Biol. Mar. 1970;48(3):443-53.

Needles et al., Generation and screening of an oligonucleotide-encoded synthetic peptide library. Proc Natl Acad Sci. 1993;90:10700-04.

Neer et al., The ancient regulatory-protein family of WD-repeat proteins. Nature. Sep. 22, 1994;371(6495):297-300.

Nefzi et al., The Current Status of Heterocyclic Combinatorial Libraries. Chem Rev. Apr. 1, 1997;97(2):449-472.

Nestler et al., A General Method for Molecular Tagging of Encoded Combinatorial Chemistry Libraries. J Org Chem. 1994;59:4723-24.

Newman et al., The influence of natural products upon drug discovery. Nat Prod Rep. Jun. 2000;17(3):215-34.

Ng et al., Histone deacetylases: silencers for hire. Trends Biochem Sci. Mar. 2000;25(3):121-6.

Ngo et al., Computational complexity, protein structure prediction, and the ILeventhal paradox. In: The Protein Folding Problem and Tertiary Structure Prediction. Merz et al., eds, Birhauser, Boston, MA. 1994:433-506.

Nielsen et al., Crystal structure of a bacterial class 2 histone deacetylase homologue. J Mol Biol. Nov. 18, 2005;354(1):107-20. Epub Oct. 7, 2005.

Nielsen et al., Synthetic Methods for the Implementation of Encoded Combinatorial Chemistry. J Am Chem Soc. 1993;115:9812-13.

Nielsen et al., Toward Chemical Implementation of Encoded Combinatorial Libraries. Methods Compan Methods Enzymol. 1994;6:361-71.

Nikolaiev et al., Peptide-encoding for structure determination of nonsequenceable polymers within libraries synthesized and tested on solid-phase supports. Pept Res. May-Jun. 1993;6(3):161-70.

Noll, Characterization of macromolecules by constant velocity sedimentation. Nature. Jul. 22, 1967;215(5099):360-3.

Notterpek et al., PMP22 accumulation in aggresomes: implications for CMT1A pathology. Neurobiol Dis. Oct. 1999;6(5):450-60.

O'Connor, Developing new drugs for the treatment of lymphoma. European Journal of Haematology. 2005;75:150-58.

O'Gorman et al., Recombinase-mediated gene activation and site-specific integration in mammalian cells. Science. Mar. 15, 1991;251(4999):1351-5.

Ohlmeyer et al., Complex synthetic chemical libraries indexed with molecular tags. Proc Natl Acad Sci U S A. Dec. 1, 1993;90(23):10922-6.

Oliva et al., Histone hyperacetylation can induce unfolding of the nucleosome core particle. Nucleic Acids Res. May 11, 1990;18(9):2739-47.

Orban et al., Tissue- and site-specific DNA recombination in transgenic mice. Proc Natl Acad Sci U S A. Aug. 1, 1992;89(15):6861-5.

Park et al., Point mutations in the yeast histone H4 gene prevent silencing of the silent mating type locus HML. Mol Cell Biol. Sep. 1990;10(9):4932-4.

Parra et al., Protein kinase D1 phosphorylates HDAC7 and induces its nuclear export after T-cell receptor activation J Biol Chem. Apr. 8, 2005;280(14):13762-70. Epub Dec. 28, 2004.

Patani et al., Bioisosterism: A Rational Approach in Drug Design. Chem Rev. Dec. 19, 1996;96(8):3147-3176.

Pátek et al., Safety-catch anchoring linkage for synthesis of peptide amides by Boc/Fmoc strategu. Tetrahedron Lett. 1991;32:3891-94.

Patel et al., Identification and characterization of small molecule inhibitors of a class I histone deacetylase from Plasmodium falciparum. J Med Chem. Apr. 23, 2009;52(8):2185-7.

Pei et al., Synergistic induction of oxidative injury and apoptosis in human multiple myeloma cells by the proteasome inhibitor bortezomib and histone deacetylase inhibitors. Clin Cancer Res. Jun. 1, 2004;10(11):3839-52.

Perera et al., Environment and cancer: who are susceptible? Science. Nov. 7, 1997;278(5340):1068-73.

Perrod et al., A cytosolic NAD-dependent deacetylase, Hst2p, can modulate nucleolar and telomeric silencing in yeast. EMBO J. Jan. 15, 2001;20(1-2):197-209.

Peterson et al., Small molecule developmental screens reveal the logic and timing of vertebrate development. Proc Natl Acad Sci U S A. Nov. 21, 2000;97(24):12965-9.

Phillips, The challenge of gene therapy and DNA delivery. J Pharm Pharmacol. Sep. 2001;53(9):1169-74.

Posnett et al., A novel method for producing anti-peptide antibodies. Production of site-specific antibodies to the T cell antigen receptor beta-chain. J Biol Chem. Feb. 5, 1988;263(4):1719-25.

Powell et al., Anti-1,3-diols by Addition of Dialkylzinc Reagents to 4-Acetoxy-1,3-dioxanes. J Org Chem. Mar. 19, 1999;64(6):2026-2037.

Presbitero et al., Drug-eluting stents do they make the difference? Minerva Cardioangiol. Oct. 2002;50(5):431-42. Italian.

Probst et al., Human liver arylacetamide deacetylase. Molecular cloning of a novel esterase involved in the metabolic activation of arylamine carcinogens with high sequence similarity to hormone-sensitive lipase. J Biol Chem. Aug. 26, 1994;269(34):21650-6.

Pyne et al., Reactions of Lithiated N-Tosyl S-Phenyl S-2-Propenyl Sulfoximine with Aldehydes. Sulfur Letters. 1997;20(6):255-60.

Qian et al., A retinoblastoma-binding protein related to a negative regulator of Ras in yeast. Nature. Aug. 12, 1993;364(6438):648-52.

(56) References Cited

OTHER PUBLICATIONS

Raje et al., Combination of the mTOR inhibitor rapamycin and CC-5013 has synergistic activity in multiple myeloma. Blood. Dec. 15, 2004;104(13):4188-93. Epub Aug. 19, 2004.
Remiszewski, The discovery of NVP-LAQ824: from concept to clinic. Curr Med Chem. Nov. 2003;10(22):2393-402.
Renthal et al., Histone deacetylase 5 epigenetically controls behavioral adaptations to chronic emotional stimuli. Neuron. Nov. 8, 2007;56(3):517-29.
Reuben et al., A new group of potent inducers of differentiation in murine erythroleukemia cells. Proc Natl Acad Sci U S A. Mar. 1976;73(3):862-6.
Richardson et al., A phase 2 study of bortezomib in relapsed, refractory myeloma. N Engl J Med. Jun. 26, 2003;348(26):2609-17.
Richardson et al.,Bortezomib (PS-341): a novel, first-in-class proteasome inhibitor for the treatment of multiple myeloma and other cancers. Cancer Control. Sep.-Oct. 2003;10(5):361-9.
Richon et al., A class of hybrid polar inducers of transformed cell differentiation inhibits histone deacetylases. Proc Natl Acad Sci U S A. Mar. 17, 1998;95(6):3003-7.
Richon et al., Histone deacetylase inhibitor selectively induces p21WAF1 expression and gene-associated histone acetylation. Proc Natl Acad Sci U S A. Aug. 29, 2000;97(18):10014-9.
Richon et al., Second generation hybrid polar compounds are potent inducers of transformed cell differentiation. Proc Natl Acad Sci U S A. Jun. 11, 1996;93(12):5705-8.
Riester et al., Members of the histone deacetylase superfamily differ in substrate specificity towards small synthetic substrates. Biochem Biophys Res Commun. Nov. 19, 2004;324(3):1116-23.
Rine et al., Four genes responsible for a position effect on expression from HML and HMR in *Saccharomyces cerevisiae*. Genetics. May 1987;116(1):9-22.
Rittinger et al., Structural analysis of 14-3-3 phosphopeptide complexes identifies a dual role for the nuclear export signal of 14-3-3 in ligand binding. Mol Cell. Aug. 1999;4(2):153-66.
Roberts et al., Directed evolution of a protein: selection of potent neutrophil elastase inhibitors displayed on M13 fusion phage. Proc Natl Acad Sci U S A. Mar. 15, 1992;89(6):2429-33.
Robertson et al., Germ-line transmission of genes introduced into cultured pluripotential cells by retroviral vector. Nature. Oct. 2-8, 1986;323(6087):445-8.
Rosato et al., Histone deacetylase inhibitors in clinical development. Expert Opin Investig Drugs. Jan. 2004;13(1):21-38.
Rudinger, Characteristics of the amino acids as components of a peptide hormone sequence. In: Peptide Hormones. J.A. Parsons, ed. University Park Press, Baltimore, MD. 1976;1-7.
Rundlett et al., HDA1 and RPD3 are members of distinct yeast histone deacetylase complexes that regulate silencing and transcription. Proc Natl Acad Sci U S A. Dec. 10, 1996;93(25):14503-8.
Ruygrok et al., Rapamycin in cardiovascular medicine. Intern Med J. Mar. 2003;33(3):103-9.
Saikachi et al., Synthesis of Furan Derivatives. XV. 5-Nitrofuryl Polyene Aldehydes. J Am Chem Soc. 1958;80:3642-45.
Saitou et al., The neighbor-joining method: a new method for reconstructing phylogenetic trees. Mol Biol Evol. Jul. 1987;4(4):406-25.
Sanchez Del Pino et al., Properties of the yeast nuclear histone deacetylase. Biochem J. Nov. 1, 1994;303 ( Pt 3):723-9.
Sarraf et al., Rhodium-catalyzed formylation of organomercurials: application to efficient polyol synthesis. Org Lett. Oct. 5, 2000;2(20):3205-8.
Sasaki et al., Ligand-induced recruitment of a histone deacetylase in the negative-feedback regulation of the thyrotropin beta gene. EMBO J. Oct. 1, 1999;18(19):5389-98.
Sato et al., Synthesis and Antibiotic Activity of a Gramicidin S Analogue containing Bicyclic β-Turn Dipeptides. J Chem Soc Perkin Trans. 1986;1:1231-34.
Sawa et al., Histone deacetylase inhibitors such as sodium butyrate and trichostatin A induce apoptosis through an increase of the bcl-2-related protein Bad. Brain Tumor Pathol. 2001;18(2):109-14.
Schena, Quantitative Monitoring of Gene Expression Patterns with a Complementary DNA Microarray. Science. 1995;270:467-70.
Schlienger et al., Human immunodeficiency virus type 1 major neutralizing determinant exposed on hepatitis B surface antigen particles is highly immunogenic in primates. J Virol. Apr. 1992;66(4):2570-6.
Schmidt et al., Rapid determination of methadone in plasma, cerebrospinal fluid, and urine by gas chromatography and its application to routine drug monitoring. Pharm Res. Mar. 1993;10(3):441-4.
Schreiber, Chemical genetics resulting from a passion for synthetic organic chemistry. Bioorg Med Chem. Aug. 1998;6(8):1127-52.
Schreiber, Target-oriented and diversity-oriented organic synthesis in drug discovery. Science. Mar. 17, 2000;287(5460):1964-9.
Schreiber, Using the Principles of Organic Chemistry to Explore Cell Biology. Chem and Eng News. 1992; 70(43): 22-32.
Schuetz et al., Human HDAC7 harbors a class IIa histone deacetylase-specific zinc binding motif and cryptic deacetylase activity. J Biol Chem. Apr. 25, 2008;283(17):11355-63. Epub Feb. 19, 2008.
Scott et al., Searching for peptide ligands with an epitope library. Science. Jul. 27, 1990;249(4967):386-90.
Secrist et al., HDAC inhibitors for the treatment of cancer. Curr Opin Investig Drugs. Dec. 2003;4(12):1422-7.
Seffernick et al., Melamine deaminase and atrazine chlorohydrolase: 98 percent identical but functionally different. J Bacteriol. Apr. 2001;183(8):2405-10.
Serrador et al., HDAC6 deacetylase activity links the tubulin cytoskeleton with immune synapse organization. Immunity. Apr. 2004;20(4):417-28.
Shoemaker, The NCI60 human tumour cell line anticancer drug screen. Nat Rev Cancer. Oct. 2006;6(10):813-23.
Shpaer, GeneAssist. Smith-Waterman and other database similarity searches and identification of motifs. Methods Mol Biol. 1997;70:173-87.
Sikorski et al., A system of shuttle vectors and yeast host strains designed for efficient manipulation of DNA in *Saccharomyces cerevisiae*. Genetics. May 1989;122(1):19-27.
Singh et al., Chemistry and structure-activity relationship of HIV-1 integrase inhibitor integracide B and related natural products. J Nat Prod. Oct. 2003;66(10):1338-44.
Smith et al., A phylogenetically conserved NAD+-dependent protein deacetylase activity in the Sir2 protein family. Proc Natl Acad Sci U S A. Jun. 6, 2000;97(12):6658-63.
Smith et al., Comparison of biosequences. Adv Appl Math. 1981;2:482-89.
Smith et al., Mechanisms and molecular probes of sirtuins. Chem Biol. Oct. 20, 2008;15(10):1002-13.
Somoza et al., Structural snapshots of human HDAC8 provide insights into the class I histone deacetylases. Structure. Jul. 2004;12(7):1325-34.
Stamatakis et al., A rapid bootstrap algorithm for the RAxML Web servers. Syst Biol. Oct. 2008;57(5):758-71.
Sternson et al., Split—pool synthesis of 1,3-dioxanes leading to arrayed stock solutions of single compounds sufficient for multiple phenotypic and protein-binding assays. J Am Chem Soc. Feb. 28, 2001;123(8):1740-7.
Sternson et al., Synthesis of 7200 small molecules based on a substructural analysis of the histone deacetylase inhibitors trichostatin and trapoxin. Org Lett. Dec. 27, 2001;3(26):4239-42.
Stevanovic et al., Natural and Synthetic Peptide Pools: Characterization by Sequencing and Electrospray Mass Spectrometry. Bioorg Med Chem Lett. 1993;3(3):431-36.
Stewart et al., Expression of retroviral vectors in transgenic mice obtained by embryo infection. EMBO J. Feb. 1987;6(2):383-8.
Stillman et al., Epistasis analysis of suppressor mutations that allow HO expression in the absence of the yeast SW15 transcriptional activator. Genetics. Mar. 1994;136(3):781-8.
Stowell et al., The synthesis of N-hydroxy-N'-phenyloctanediamide and its inhibitory effect on proliferation of AXC rat prostate cancer cells. J Med Chem. Apr. 14, 1995;38(8):1411-3.
Strebhardt et al., Additional member of the protein-tyrosine kinase family: the src- and lck-related protooncogene c-tkl. Proc Natl Acad Sci U S A. Dec. 1987;84(24):8778-82.

(56) References Cited

OTHER PUBLICATIONS

Sullivan et al., Localization of the BiP molecular chaperone with respect to endoplasmic reticulum foci containing the cystic fibrosis transmembrane conductance regulator in yeast. J Histochem Cytochem. Apr. 2003;51(4):545-8.

Suzuki et al., Synthesis and histone deacetylase inhibitory activity of new benzamide derivatives. J Med Chem. Jul. 29, 1999;42(15):3001-3.

Tallarico et al., An alkylsilyl-tethered, high-capacity solid support amenable to diversity-oriented synthesis for one-bead, one-stock solution chemical genetics. J Comb Chem. May-Jun. 2001;3(3):312-8.

Tan et al., Novel histone deacetylase inhibitors in clinical trials as anti-cancer agents. J Hematol Oncol. Feb. 4, 2010;3:5. doi: 10.1186/1756-8722-3-5. 13 pages Tan et al., Stereoselective Synthesis of over Two Million Compounds Having Structural Features Both Reminiscent of Natural Products and Compatible with Miniaturized Cell-Based Assays. J. Am. Chem. Soc. 1998; 120: 8565-66.

Tanaka et al., Syntheses and anti-inflammatory and analgesic activities of hydroxamic acids and acid hydrazides. Chem Pharm Bull (Tokyo). Aug. 1983;31(8):2810-9.

Tanner et al., Silent information regulator 2 family of NAD-dependent histone/protein deacetylases generates a unique product, 1-O-acetyl-ADP-ribose. Proc Natl Acad Sci U S A. Dec. 19, 2000;97(26):14178-82.

Tanny et al., Coupling of histone deacetylation to NAD breakdown by the yeast silencing protein Sir2: Evidence for acetyl transfer from substrate to an NAD breakdown product. Proc Natl Acad Sci U S A. Jan. 16, 2001;98(2):415-20. Epub Dec. 26, 2000.

Tao et al., Deacetylase inhibition promotes the generation and function of regulatory T cells. Nat Med. Nov. 2007;13(11):1299-307. Epub Oct. 7, 2007.

Taunton et al., A mammalian histone deacetylase related to the yeast transcriptional regulator Rpd3p. Science. Apr. 19, 1996;272(5260):408-11.

Taunton et al., Deacetylation. The Scientist. 1999;13:13.

Taunton et al., Synthesis of Natural and Modified Trapoxins, Useful Reagents for Exploring Histone Deacetylase Function. J Am Chem Soc. 1996;118:10412-22.

Thornton et al., Protein Engineering: Editorial Overview. Curr Opin Biotechnol. 1995;6(4):367-69.

Tissenbaum et al., Increased dosage of a sir-2 gene extends lifespan in Caenorhabditis elegans. Nature. Mar. 8, 2001;410(6825):227-30.

Tong et al., Chromatin deacetylation by an ATP-dependent nucleosome remodeling complex. Nature. 1997;395:917-21.

Tsang et al., CobB, a new member of the SIR2 family of eucaryotic regulatory proteins, is required to compensate for the lack of nicotinate mononucleotide:5,6-dimethylbenzimidazole phosphoribosyltransferase activity in cobT mutants during cobalamin biosynthesis in *Salmonella typhimurium* LT2. J Biol Chem. Nov. 27, 1998;273(48):31788-94.

Tsankova et al., Sustained hippocampal chromatin regulation in a mouse model of depression and antidepressant action. Nat Neurosci. Apr. 2006;9(4):519-25. Epub Feb. 26, 2006.

Turner, Decoding the nucleosome. Cell. Oct. 8, 1993;75(1):5-8.

Uchiyama et al., Adhesion of human myeloma-derived cell lines to bone marrow stromal cells stimulates interleukin-6 secretion. Blood. Dec. 15, 1993;82(12):3712-20.

Uong et al., Stereocontrolled Functionalization of Acyclic Molybdenum-η3-Allyl Complexes: A New Approach to the Stereoselective Synthesis of 1,3-Diols. J Chem Soc Chem Commun. 1990:1285-87.

Urnov et al., Targeting of N-CoR and histone deacetylase 3 by the oncoprotein v-erbA yields a chromatin infrastructure-dependent transcriptional repression pathway. EMBO J. Aug. 1, 2000;19(15):4074-90.

Valerio et al., Multipin peptide synthesis at the micromole scale using 2-hydroxyethyl methacrylate grafted polyethylene supports. Int J Pept Protein Res. Jul. 1993;42(1):1-9.

Valerio et al., Synthesis of peptide analogues using the multipin peptide synthesis method. Anal Biochem. Aug. 15, 1991;197(1):168-77.

Van Der Krol et al., Modulation of eukaryotic gene expression by complementary RNA or DNA sequences. Biotechniques. Nov.-Dec. 1988;6(10):958-76.

Van Der Putten et al., Efficient insertion of genes into the mouse germ line via retroviral vectors. Proc Natl Acad Sci U S A. Sep. 1985;82(18):6148-52.

Vannini et al., Crystal structure of a eukaryotic zinc-dependent histone deacetylase, human HDAC8, complexed with a hydroxamic acid inhibitor. Proc Natl Acad Sci U S A. Oct. 19, 2004;101(42):15064-9. Epub Oct. 11, 2004.

Varga-Weisz et al., Chromatin-remodeling factors: machines that regulate? Curr Opin Cell Biol. Jun. 1998;10(3):346-53.

Vegas et al., Fluorous-based small-molecule microarrays for the discovery of histone deacetylase inhibitors. Angew Chem Int Ed Engl. 2007;46(42):7960-4.

Venter et al., The sequence of the human genome. Science. Feb. 16, 2001;291(5507):1304-51.

Verdel et al., Identification of a new family of higher eukaryotic histone deacetylases. Coordinate expression of differentiation-dependent chromatin modifiers. J Biol Chem. Jan. 22, 1999;274(4):2440-5.

Vidal et al., RPD3 encodes a second factor required to achieve maximum positive and negative transcriptional states in *Saccharomyces cerevisiae*. Mol Cell Biol. Dec. 1991;11(12):6317-27.

Vong et al., Regio-and Stereocontrolled Functionalization of Acyclic Molybdenum-η3-Allyl Complexes. J Am Chem Soc. 1991;113:573-82.

Walker et al., Affinity chromatography of mammalian and yeast nucleosomes. Two modes of binding of transcriptionally active mammalian nucleosomes to organomercurial-agarose columns, and contrasting behavior of the active nucleosomes of yeast. J Biol Chem. Apr. 5, 1990;265(10):5736-46.

Wallace et al., Understanding cytochrome c function: engineering protein structure by semisynthesis. FASEB J. Apr. 1, 1993;7(6):505-15.

Wang et al., ETO, fusion partner in t(8;21) acute myeloid leukemia, represses transcription by interaction with the human N-CoR/mSin3/HDAC1 complex. Proc Natl Acad Sci U S A. Sep. 1, 1998;95(18):10860-5.

Wang et al., HDAC4, a human histone deacetylase related to yeast HDA1, is a transcriptional corepressor. Mol Cell Biol. Nov. 1999;19(11):7816-27.

Wang et al., Isolation of high-affinity peptide antagonists of 14-3-3 proteins by phage display. Biochemistry. Sep. 21, 1999;38(38):12499-504.

Wang et al., Zinc binding in HDAC inhibitors: a DFT study. J Org Chem. Jul. 6, 2007;72(14):5446-9. Epub Jun. 19, 2007.

Warrell et al., Therapeutic targeting of transcription in acute promyelocytic leukemia by use of an inhibitor of histone deacetylase. J Natl Cancer Inst. Nov. 4, 1998;90(21):1621-5.

Wegener et al., A fluorogenic histone deacetylase assay well suited for high-throughput activity screening. Chem Biol. Jan. 2003;10(1):61-8.

Weinberg, Finding the anti-oncogene. Sci Am. Sep. 1988;259(3):44-51.

Wennemers et al., Cyclooligomeric Receptors Based on Trimesic Acid and 1,2-Diamines. Minimal Structure for Sequence-Selective Peptide Binding. J Org Chem. 1995;60:1108-09.

Whelan et al., A general empirical model of protein evolution derived from multiple protein families using a maximum-likelihood approach. Mol Biol Evol. May 2001;18(5):691-9.

Wilen et al., Strategies in Optical Resolution. Tetrahedron. 1977;33:2725-36.

Witkowski et al., Conversion of a beta-ketoacyl synthase to a malonyl decarboxylase by replacement of the active-site cysteine with glutamine. Biochemistry. Sep. 7, 1999;38(36):11643-50.

Wong et al., Modular synthesis and preliminary biological evaluation of stereochemically diverse 1,3-dioxanes. Chem Biol. Sep. 2004;11(9):1279-91.

(56) References Cited

OTHER PUBLICATIONS

Wong et al., Structural biasing elements for in-cell histone deacetylase paralog selectivity. J Am Chem Soc. May 14, 2003;125(19):5586-7.
Workman et al., Alteration of nucleosome structure as a mechanism of transcriptional regulation. Annu Rev Biochem. 1998;67:545-79.
Xie et al., Sum1 and Hst1 repress middle sporulation-specific gene expression during mitosis in *Saccharomyces cerevisiae*. EMBO J. Nov. 15, 1999;18(22):6448-54.
Xu et al., Coactivator and corepressor complexes in nuclear receptor function. Curr Opin Genet Dev. Apr. 1999;9(2):140-7.
Xue et al., NURD, a novel complex with both ATP-dependent chromatin-remodeling and histone deacetylase activities. Mol Cell. Dec. 1998;2(6):851-61.
Yaffe et al., The structural basis for 14-3-3:phosphopeptide binding specificity. Cell. Dec. 26, 1997;91(7):961-71.
Yang et al., Cloning and characterization of two mouse genes with homology to the yeast Sir2 gene. Genomics. Nov. 1, 2000;69(3):355-69.
Yang et al., Isolation and characterization of cDNAs corresponding to an additional member of the human histone deacetylase gene family. J Biol Chem. Oct. 31, 1997;272(44):28001-7.
Yang et al., Maintenance of G2 arrest in the Xenopus oocyte: a role for 14-3-3-mediated inhibition of Cdc25 nuclear import. EMBO J. Apr. 15, 1999;18(8):2174-83.
Yang et al., Transcriptional repression by YY1 is mediated by interaction with a mammalian homolog of the yeast global regulator RPD3. Proc Natl Acad Sci U S A. Nov. 12, 1996;93(23):12845-50.
Yoon et al., Cyclooligomeric Receptors for the Sequence Selective Binding of Peptides. A Tetrahedral Receptor from the Trimesic Acid and 1,2-Diamines. Tetrahedron Lett. 1994;35:8557-60.
Yoshida et al., A novel tetracyclic peptide, trapoxin, induces phenotypic change from transformed to normal in sis-oncogene-transformed NIH3T3 cells. Jpn J Cancer Res. Apr. 1992;83(4):324-8.
Yoshida et al., Potent and specific inhibition of mammalian histone deacetylase both in vivo and in vitro by trichostatin A. J Biol Chem. Oct. 5, 1990;265(28):17174-9.
Yoshida et al., Trichostatin A and trapoxin: novel chemical probes for the role of histone acetylation in chromatin structure and function. Bioessays. May 1995;17(5):423-28.
Youngquist et al., Matrix-assisted laser desorption ionization for rapid determination of the sequences of biologically active peptides isolated from support-bound combinatorial peptide libraries. Rapid Commun Mass Spectrom. Jan. 1994;8(1):77-81.
Yu et al., The proteasome inhibitor bortezomib interacts synergistically with histone deacetylase inhibitors to induce apoptosis in Bcr/Abl+ cells sensitive and resistant to STI571. Blood. Nov. 15, 2003;102(10):3765-74. Epub Jul. 31, 2003.
Zervos et al., Mxi1, a protein that specifically interacts with Max to bind Myc-Max recognition sites. Cell. Jan. 29, 1993;72(2):223-32.
Zhang et al., The dermatomyositis-specific autoantigen Mi2 is a component of a complex containing histone deacetylase and nucleosome remodeling activities. Cell. Oct. 16, 1998;95(2):279-89.
Zhou et al., Cloning and characterization of a histone deacetylase, HDAC9. Proc Natl Acad Sci U S A. Sep. 11, 2001;98(19):10572-7. Epub Sep. 4, 2001.
Zhou et al., Identification of a transcriptional repressor related to the noncatalytic domain of histone deacetylases 4 and 5. Proc Natl Acad Sci U S A. Feb. 1, 2000;97(3):1056-61.
Zhu et al., Phosphine-catalyzed synthesis of 1,3-dioxan-4-ylidenes. Org Lett. Mar. 31, 2005;7(7):1387-90.
Zimmermann et al., Conformational and epitope mapping of herpes-simplex-virus type-1 thymidine kinase using synthetic peptide segments. Eur J Biochem. Sep. 1, 1991;200(2):519-28.
Sausville et al., Contributions of human tumor xenografts to anti-cancer drug development. Cancer Res. Apr. 1, 2006;66(7):3351-4, discussion 3354.
Johnson et al., Relationships between drug activity in NCI preclinical in vitro and in vivo models and early clinical trials. Br J Cancer. May 18, 2001;84(10):1424-31.
Kim et al., Histone deacetylase inhibitors: molecular mechanisms of action and clinical trials as anti-cancer drugs. Am J Transl Res. Feb. 2011;3(2):166-79. Epub Dec. 26, 2010.
U.S. Appl. No. 13/389,814, filed Apr. 24, 2012, Mazitschek et al.
U.S. Appl. No. 14/271,170, filed May 6, 2014, Mazitschek et al.
U.S. Appl. No. 15/399,550, filed Jan. 5, 2017, Mazitschek et al.
U.S. Appl. No. 12/279,440, filed Aug. 11, 2009, Bradner et al.
U.S. Appl. No. 13/550,110, filed Jul. 16, 2012, Bradner et al.
U.S. Appl. No. 12/279,398, filed Oct. 19, 2009, Bradner et al.
U.S. Appl. No. 13/055,241, filed Apr. 1, 2011, Tang et al.
U.S. Appl. No. 13/861,519, filed Apr. 12, 2013, Tang et al.
U.S. Appl. No. 11/386,959, filed Mar. 22, 2006, Anderson et al.
U.S. Appl. No. 14/679,800, filed Apr. 6, 2015, Anderson et al.
U.S. Appl. No. 12/299,430, filed Mar. 26, 2009, Mazitschek et al.
U.S. Appl. No. 10/144,316, filed May 9, 2002, Schreiber et al.
U.S. Appl. No. 10/621,276, filed Jul. 17, 2003, Schreiber et al.
U.S. Appl. No. 11/879,466, filed Jul. 17, 2007, Schreiber et al.
U.S. Appl. No. 13/520,650, filed Oct. 17, 2012, Bradner et al.
U.S. Appl. No. 08/624,735, filed Mar. 26, 1996, Schreiber et al.
U.S. Appl. No. 10/919,217, filed Aug. 16, 2004, Schreiber et al.
U.S. Appl. No. 12/196,878, filed Aug. 22, 2008, Schreiber et al.
U.S. Appl. No. 12/196,946, filed Aug. 22, 2008, Schreiber et al.
U.S. Appl. No. 13/030,086, filed Feb. 17, 2011, Schreiber et al.
U.S. Appl. No. 13/221,602, filed Aug. 30, 2011, Schreiber et al.
U.S. Appl. No. 13/221,561, filed Aug. 30, 2011, Schreiber et al.
U.S. Appl. No. 13/566,803, filed Aug. 3, 2012, Schreiber et al.
U.S. Appl. No. 09/800,187, filed Mar. 5, 2001, Grozinger et al.
U.S. Appl. No. 10/964,313, filed Oct. 13, 2004, Grozinger et al.
U.S. Appl. No. 11/831,303, filed Jul. 31, 2007, Grozinger et al.
U.S. Appl. No. 12/370,390, filed Feb. 12, 2009, Grozinger et al.
U.S. Appl. No. 13/324,036, filed Dec. 13, 2011, Grozinger et al.
U.S. Appl. No. 13/888,937, filed May 7, 2013, Grozinger et al.
PCT/US2002/014835, Jun. 4, 2004, **International Preliminary Report on Patentability.
Extended European Search Report for EP 18157889.9, dated Jun. 6, 2018.
Rosik et al., Limited efficacy of specific HDAC6 inhibition in urothelial cancer cells. Cancer Biol Ther. Jun. 1, 2014;15(6):742-57. doi: 10.4161/cbt.28469. Epub Mar. 11, 2014.

\* cited by examiner

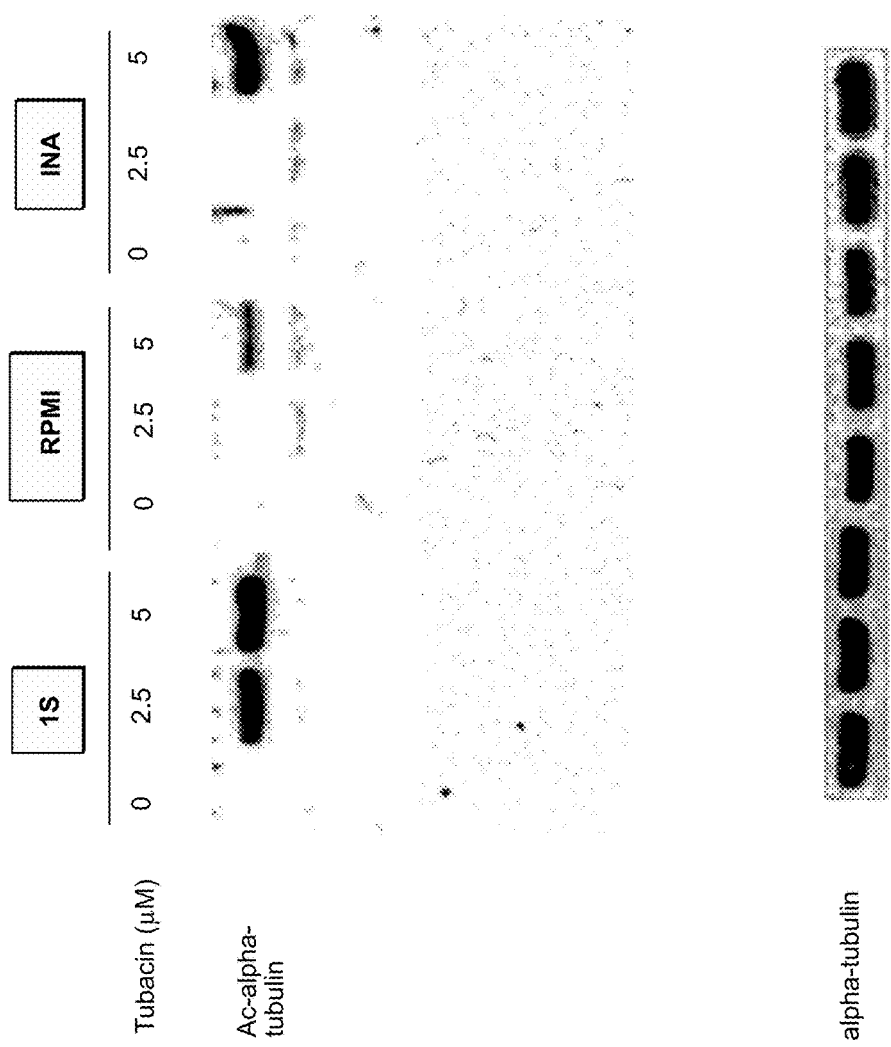

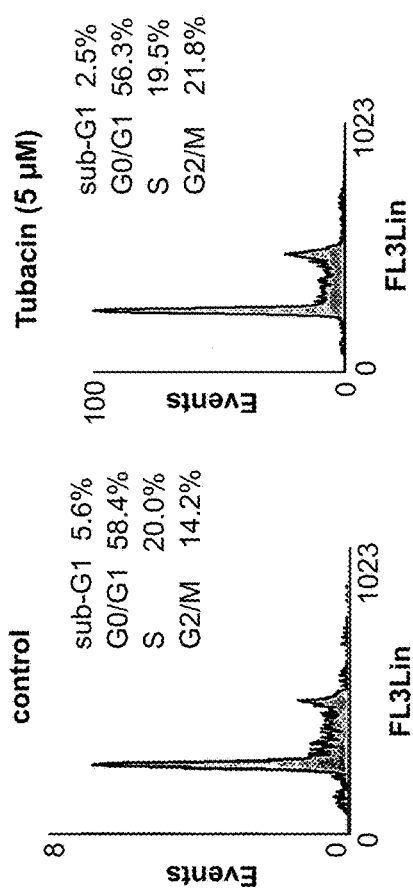
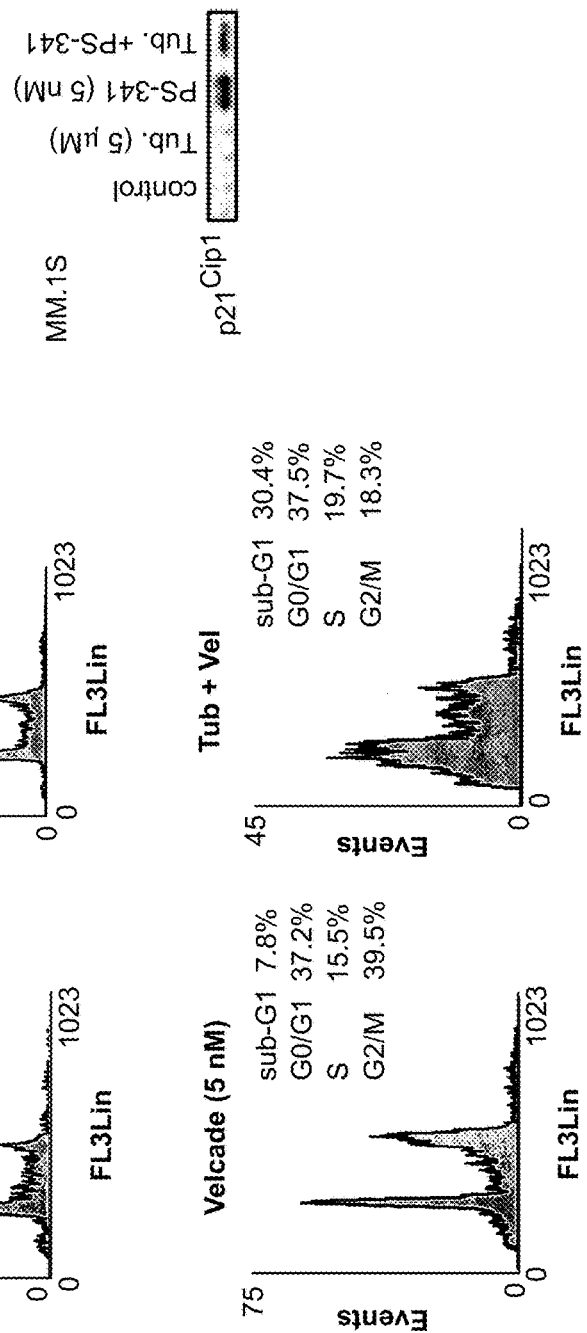
Figure 7A
Figure 7B

Tubacin

Niltubacin

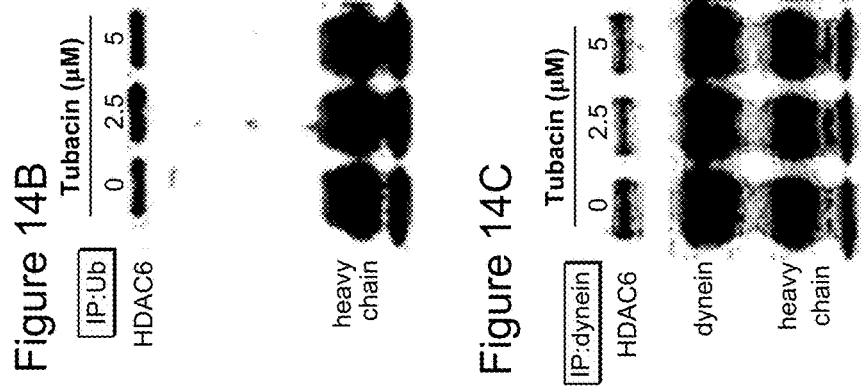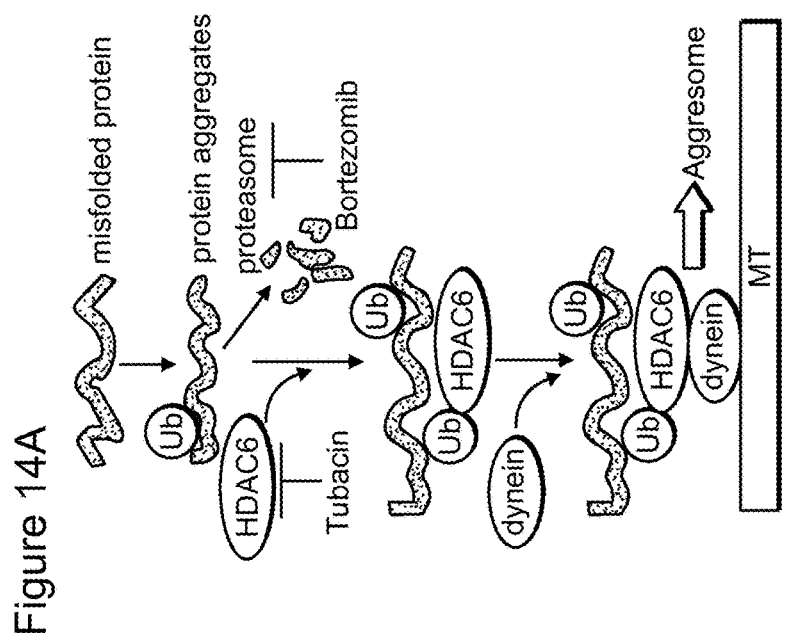

Medicinal Chemistry: Development of HT/IF Quantitative Assay

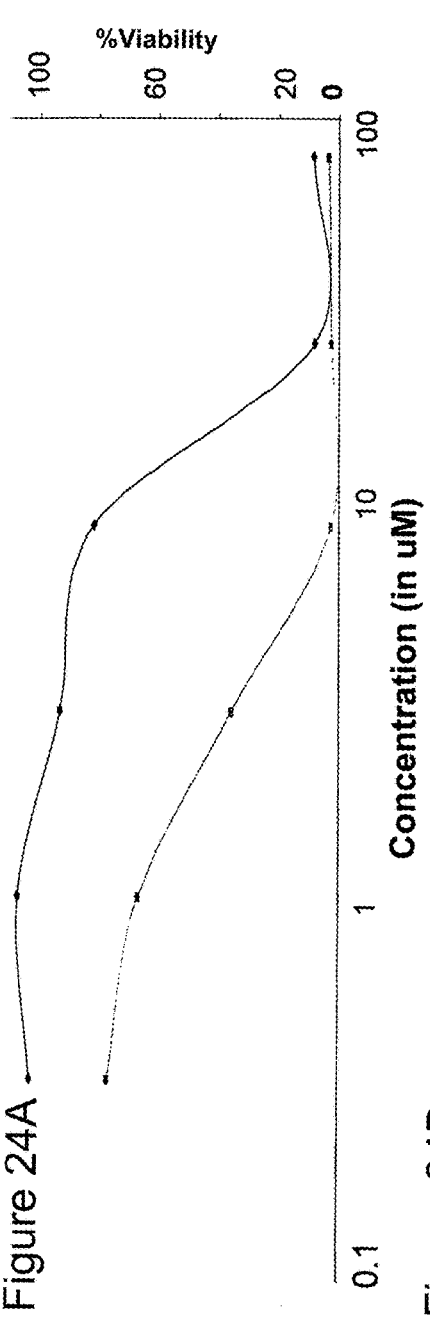
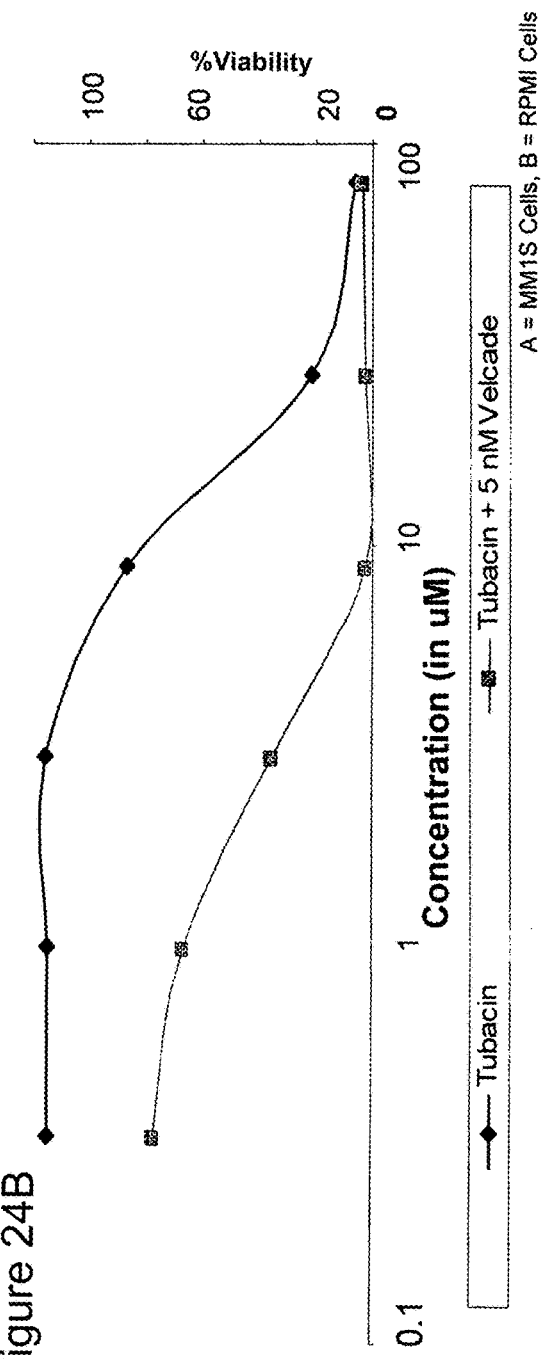
Figure 24A
Figure 24B
Synergy between Tubacin and Velcade in Myeloma Cells
A = MM1S Cells, B = RPMI Cells DHM-Tubacin
Molecular Weight: 691.84

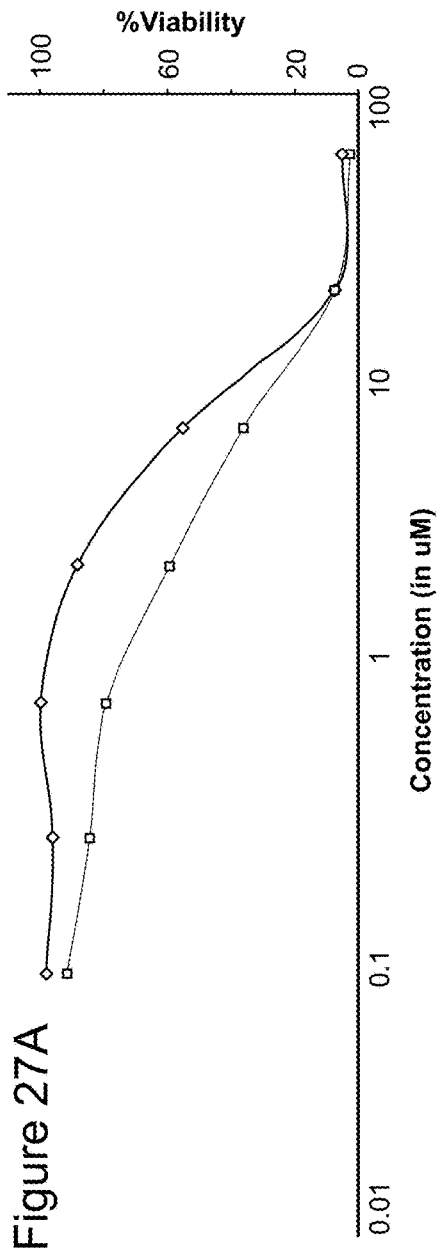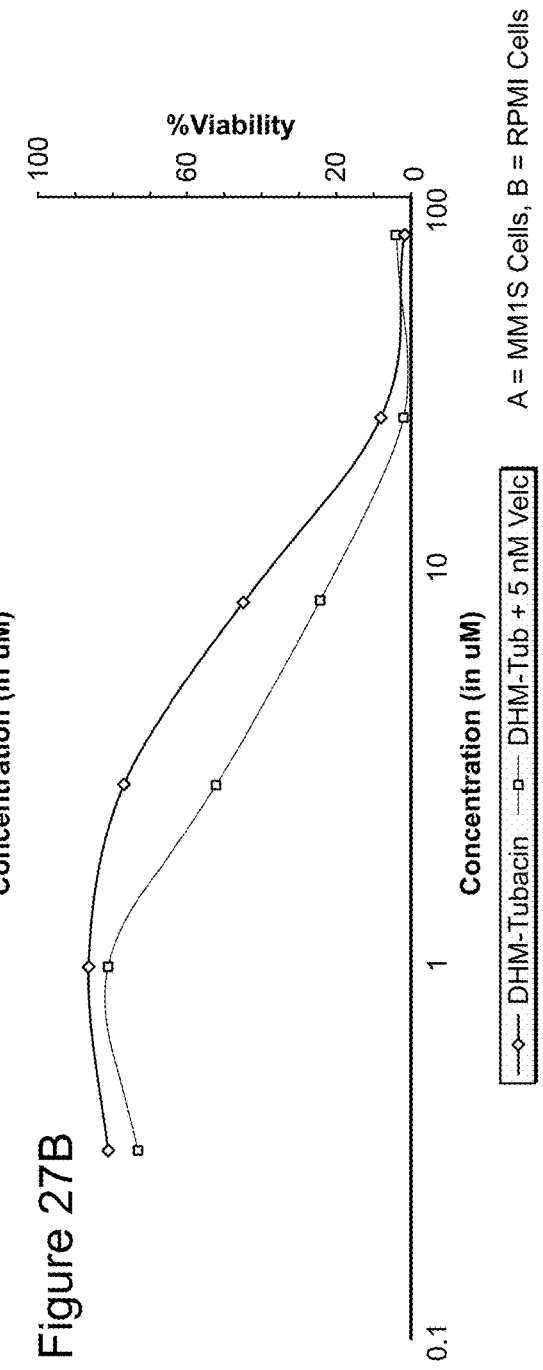

NKI-81-1
Molecular Weight: 736.83

NKI-94-1
Molecular Weight: 516.65

NKI-59-1
Molecular Weight: 605.77

NKI-60-1
Molecular Weight: 549.68

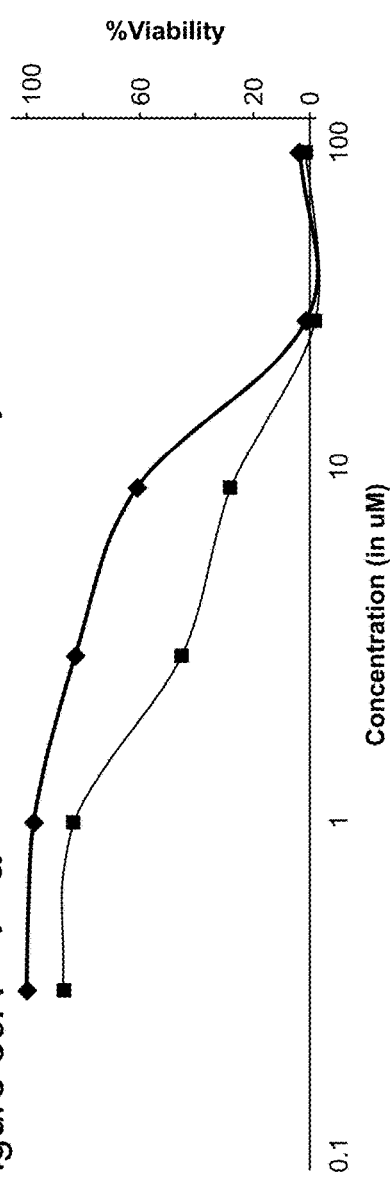
Figure 39A Synergy between NKI-60-1 and Velcade in Myeloma Cells
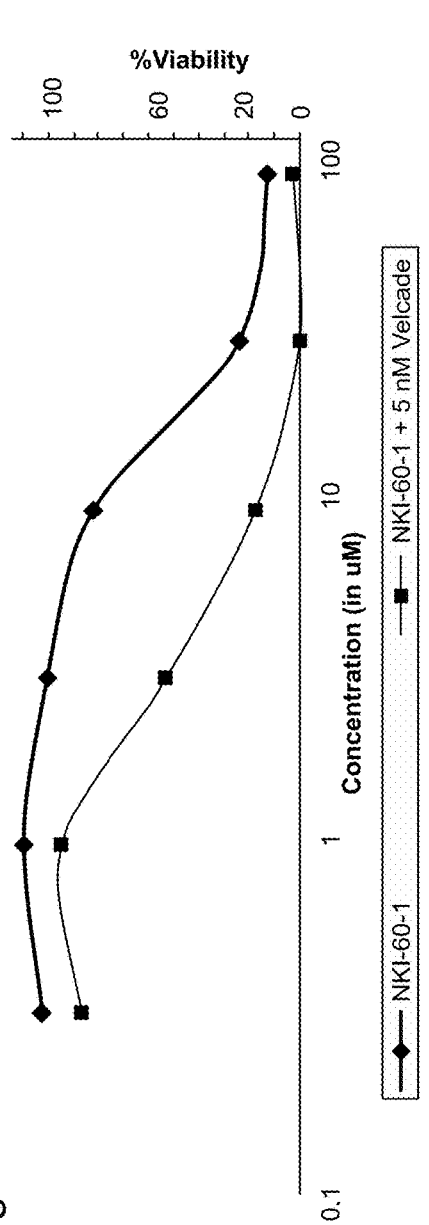
Figure 39B
A = MM1S Cells, B = RPMI Cells Synergy between NKI-82-1 and Velcade in Myeloma Cells A = MM1S Cells, B = RPMI Cells NKI-84-1
Molecular Weight: 549.68

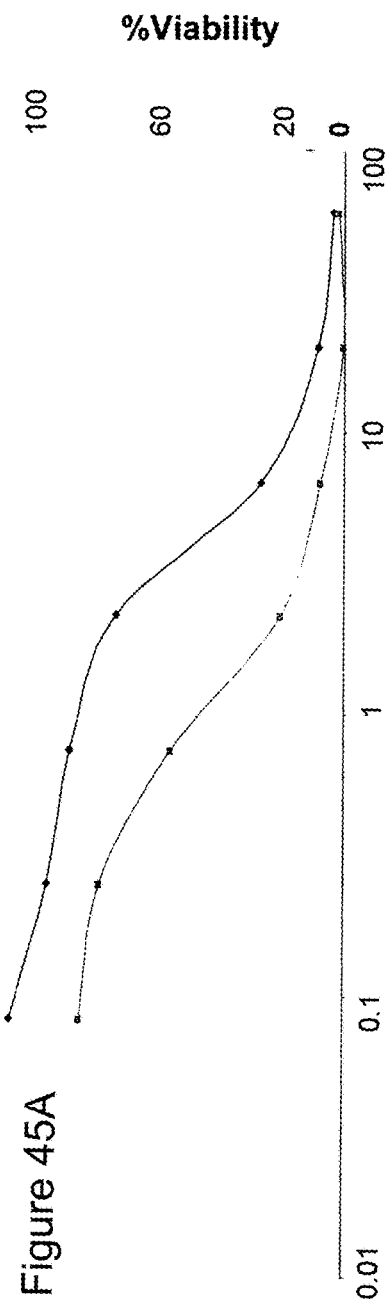
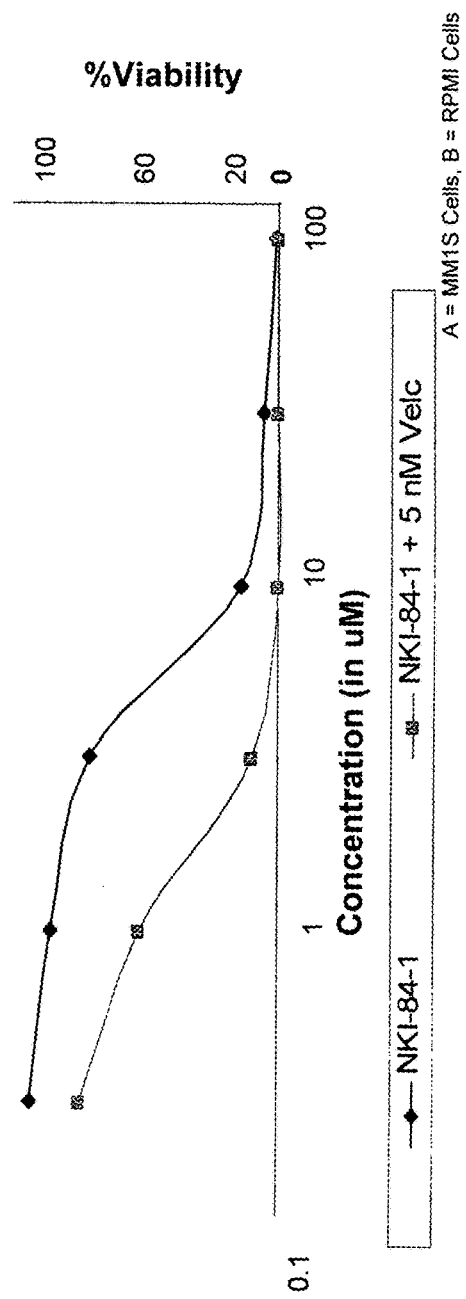
Figure 45A
Figure 45B

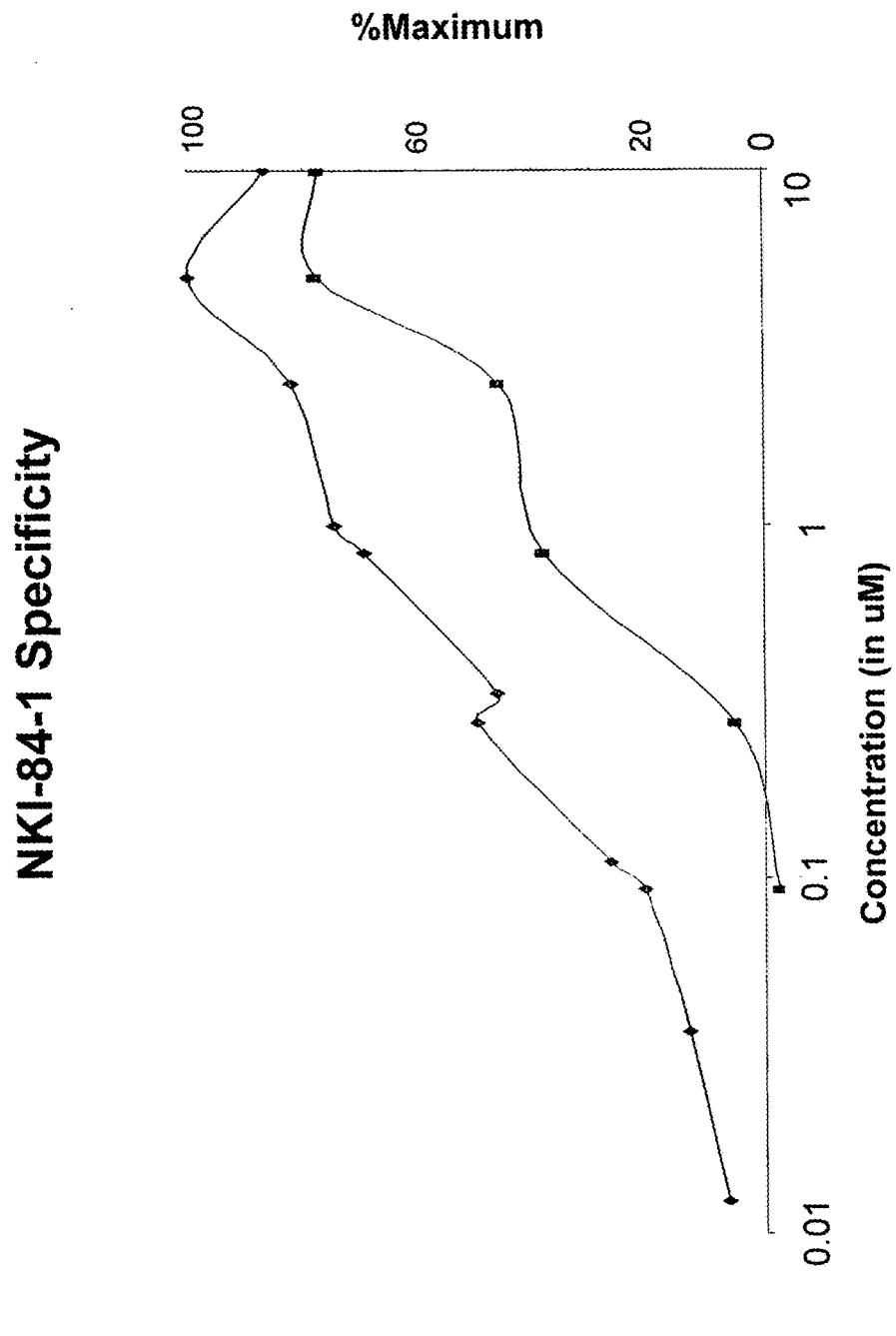

ADME-Tox: HSA Binding by SPR

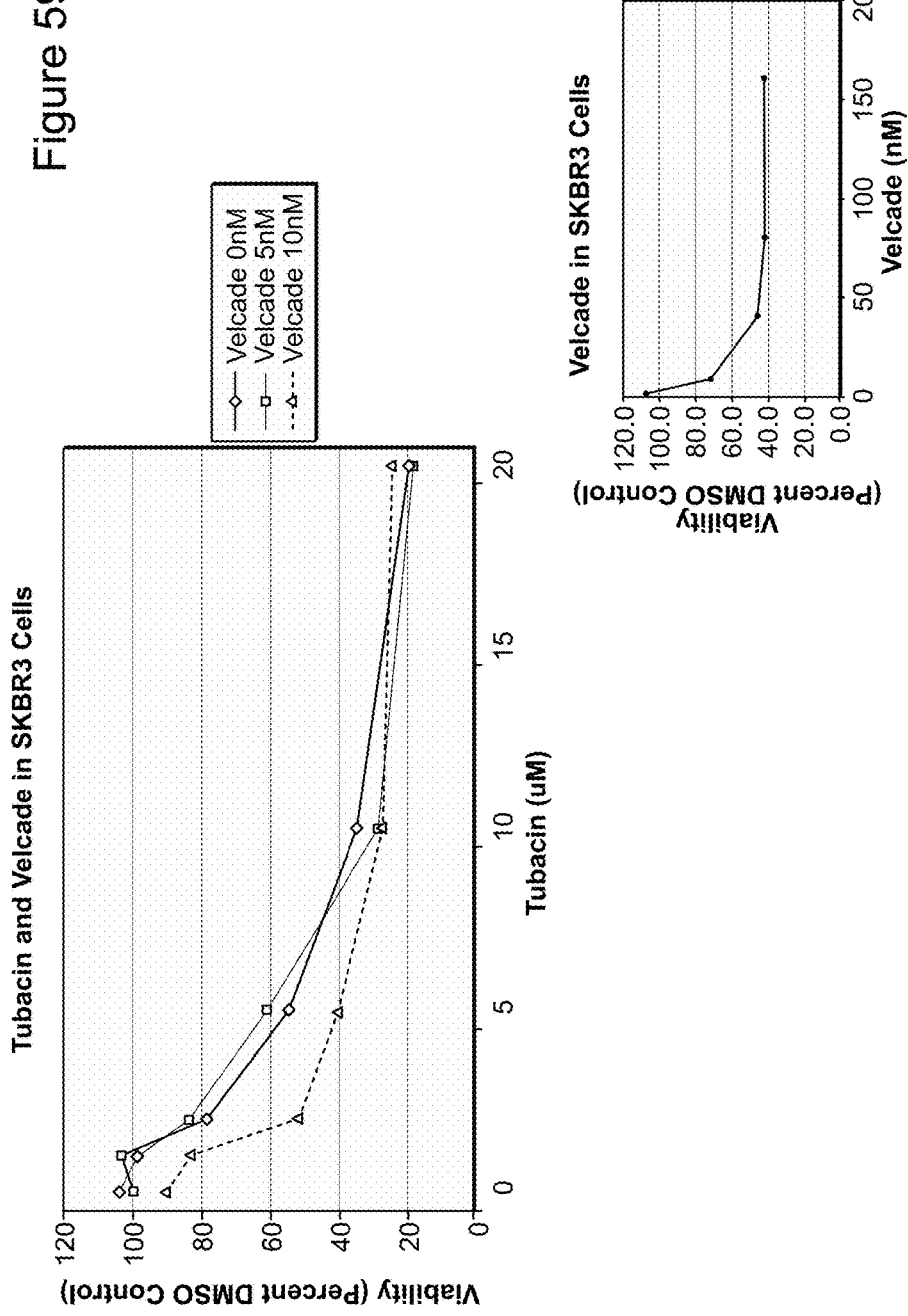

TREATMENT OF PROTEIN DEGRADATION DISORDERS

RELATED APPLICATIONS

The present application is a continuation of and claims priority under 35 U.S.C. § 120 to U.S. application, U.S. Ser. No. 14/679,800, filed Apr. 6, 2015, which is a continuation of and claims priority under 35 U.S.C. § 120 to U.S. application, U.S. Ser. No. 11/386,959, filed Mar. 22, 2006, now U.S. Pat. No. 8,999,289, which claims priority under 35 U.S.C. § 119(e) to U.S. provisional patent application, U.S. Ser. No. 60/664,470, filed Mar. 22, 2005, each of which is incorporated herein by reference.

GOVERNMENT SUPPORT

This invention was made with government support under grant numbers CA078048 and GM076262 awarded by the National Institutes of Health. The government has certain rights in the invention.

BACKGROUND OF THE INVENTION

Dynamic cellular states require a rapid, efficient mechanism of protein catabolism. Cancer cells are highly dependent on protein degradation due to continuous cell cycling, hypermutation, and chromosomal rearrangements (Adams J. The proteasome: a suitable antineoplastic target. Nat Rev Cancer. 2004; 4:349-360; incorporated herein by reference). The proteasome and the aggresome are the two principal cellular structures involved in intracellular protein catabolism. The biology of the proteasome is well-characterized in normal and neoplastic cells. Proteasome complexes reside in numerous locations throughout the cell such as the endoplasmic reticulum (ER), nucleus, and cytoplasm. The primary role of the proteasome is the targeted degradation of ubiquitinated proteins. The aggresome is a juxtanuclear complex of misfolded proteins, chaperones, and proteasome components, which expands in response to proteasome inhibition or protein stress associated with certain pathologic states (Kopito R R. Aggresomes, inclusion bodies and protein aggregation. Trends Cell Biol. 2000; 10:524-530; incorporated herein by reference). There are no known treatments targeting these pathologic states.

Aberrant protein catabolism is a hallmark of cancer, and is implicated in the stabilization of oncogenic proteins and the degradation of tumor suppressors (Adams J. The proteasome: a suitable antineoplastic target. Nat Rev Cancer. 2004; 4:349-360; incorporated herein by reference). Thus, there is a need in the art for treatments for diseases that involve aberrant protein catabolism as well as screening methods to develop new therapeutics to treat the diseases (e.g., cancer) by targeting protein degradation pathways and components.

SUMMARY OF THE INVENTION

In one aspect, the invention provides a method of treating a subject suffering from or susceptible to a protein degradation disorder. The method includes the step of administering to a subject in need thereof a therapeutically effective amount of at least one protein degradation inhibitor. In certain embodiments, an inhibitor of the proteasome is administered in combination with an inhibitor of the aggresome. In certain embodiments, the protein degradation disorder is a cellular proliferation disorder or a protein deposition disorder. In particular, the cellular proliferation disorder is cancer. In preferred embodiments, wherein the cancer is one or more of multiple myeloma, leukemia, lymphoma, breast cancer, lung cancer, ovarian cancer, prostate cancer, and liver cancer. In other embodiments, the protein deposition disorder is Wilson's disease, spinocerebellar ataxia, prion disease, Parkinson's disease, Huntington's disease, familial amytrophic lateral sclerosis, amyloidosis, Alzheimer's disease, Alexander's disease, alcoholic liver disease, cystic fibrosis, Pick's disease, or Lewy body dementia.

In another aspect, the invention provides a method of treating a cell exhibiting symptoms of a protein degradation disorder. The method includes the step of administering a therapeutically effective amount of a protein degradation inhibitor to the cell. In certain embodiments, the cell is one or more of a cell from a subject or a cultured cell. In certain embodiments, the cell from a subject is one or more of bone marrow stromal cell (BMSC), a peripheral blood mononuclear cell (PBMC), lymphocytes, hair follicles, hematopoietic cells, blood cells, epithelial cells, bone marrow plasma cells, primary cancer cells, patient derived tumor cells, normal or cancerous hematopoietic stem cells, neural stem cells, solid tumor cells, or astrocytes. In certain embodiments, the cultured cell is one or more of MM.1S, U266, RPMI8226, DOX40, MM.1R, INA-6, LR5, primary and established cancer cell lines, primary and established normal cell lines. Inhibition of protein degradation pathways in cells under protein stress leads to cell death; therefore, treatment of diseases such as cancer in which the cancer cells are under protein stress using a protein degradation inhibitor provides a new way of killing cancer cells.

In another aspect, the invention provides a method of treating a subject suffering from or susceptible to multiple myeloma. The method includes the step of administering to a subject in need thereof a therapeutically effective amount of a protein degradation inhibitor, to thereby treat the subject suffering from or susceptible to multiple myeloma. Due to the production of immunoglobulin, the cells are under protein stress and are susceptible to cell death upon inhibition of protein degradation.

In another aspect, the invention provides a method of treating a subject suffering from or susceptible to breast or ovarian cancer. The method includes the step of administering to a subject in need thereof a therapeutically effective amount of a protein degradation inhibitor, to thereby treat the subject suffering from or susceptible to breast or ovarian cancer.

In yet another aspect, the invention provides a method of assessing the efficacy of a protein degradation disorder treatment in a subject. The method includes the steps of determining one or more pre-treatment phenotypes; administering a therapeutically effective amount of a protein degradation inhibitor to the subject; and determining the one or more phenotypes after an initial period of treatment with the protein degradation inhibitor; wherein the modulation of the one or more phenotypes indicates efficacy of a protein degradation inhibitor treatment.

In yet another aspect, the invention provides a method of monitoring the progress of a subject being treated with an aggresome inhibitor. The method includes the steps of determining one or more pre-treatment phenotypes; administering a therapeutically effective amount of an aggresome inhibitor to the subject; and determining one or more phenotypes after an initial period of treatment with the aggresome inhibitor; wherein the modulation of one or more of the phenotypes indicates efficacy of aggresome inhibition treatment.

In a yet further aspect, the invention provides a method of selecting a subject with a protein degradation disorder for treatment with a protein degradation inhibitor. The method includes the steps of determining one or more pre-treatment phenotypes; administering a therapeutically effective amount of a protein degradation inhibitor to the subject; determining the one or more phenotypes after an initial period of treatment with the protein degradation inhibitor, wherein the modulation of the one or more phenotype is an indication that the disorder is likely to have a favorable clinical response to treatment with a protein degradation inhibitor.

In any of the above-described aspects, the protein degradation inhibitor is preferably selected from one or more of tubacin, tubacin-like compounds, tubacin derivatives, bortezomib (VELCADE®), SAHA, R115777 FTI, [166]Holmium-DOTMP, arsenic trioxide, 17-AAG, MG132, sapojargon, NPI-0052, or other compounds described herein. Tubacin, tubacin-like compounds, and tubacin derivatives are described in U.S. patent applications U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference.

In certain preferred embodiments of the above-described aspects, the protein degradation inhibitor is a compound of formula:

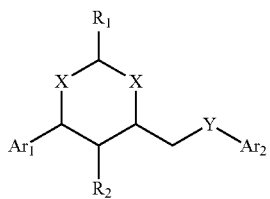

wherein
  each X is independently O, S, $CH_2$, or $NR_3$;
  Y is O, S, $CH_2$, or $NR_4$;
  $Ar_1$ and $Ar_2$ are each independently an aryl group;
  $R_1$ is a lower alkyl group or an aryl group;
  $R_2$ is hydrogen, a lower alkyl group or an aryl group; and
  $R_3$ is hydrogen, a lower alkyl group, an aryl group, an alkylcarbonyl, an alkoxycarbonyl group, or an aminocarbonyl group. In certain preferred embodiments, X is for both occurrences O. In certain preferred embodiments, Y is S. In certain preferred embodiments, $Ar_1$ is phenyl or substituted phenyl. In certain preferred embodiments, $Ar_2$ is heteroaryl, more preferably optionally substituted oxazolyl. In certain preferred embodiments, $R_1$ is phenyl or substituted phenyl, more preferably 4-aminosubstituted phenyl. In certain preferred embodiments, $R_2$ is hydrogen.

In certain embodiments, the protein degradation inhibitor is of one of the formulae:

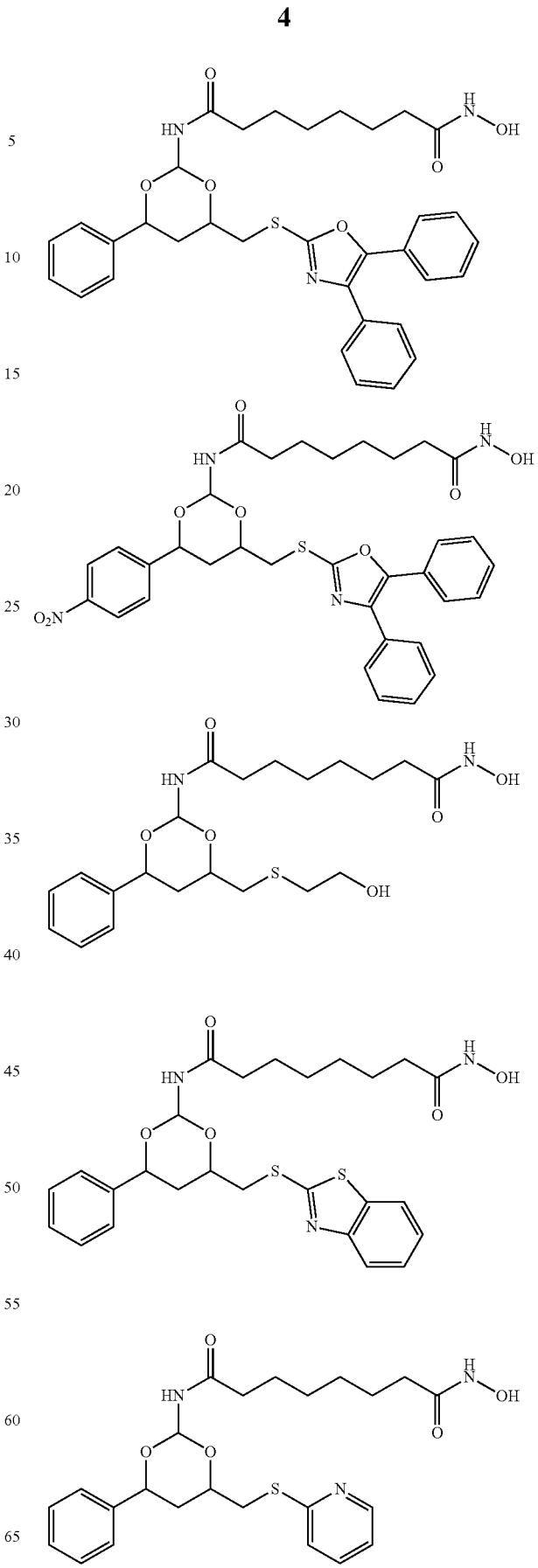

-continued

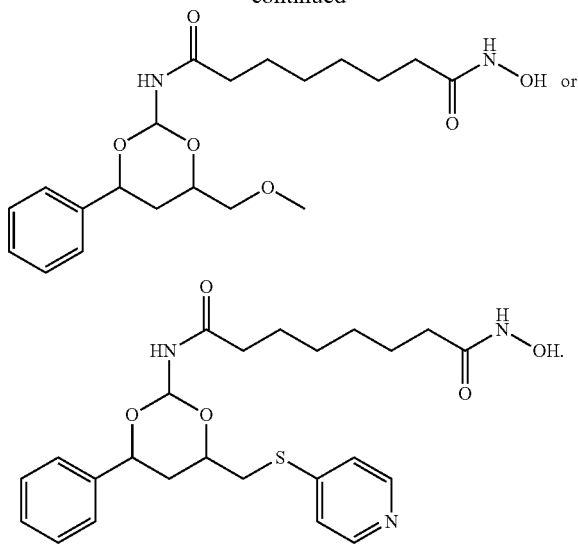

In certain preferred embodiments, the protein degradation inhibitor is a compound of the formula below with the stereochemistry as shown:

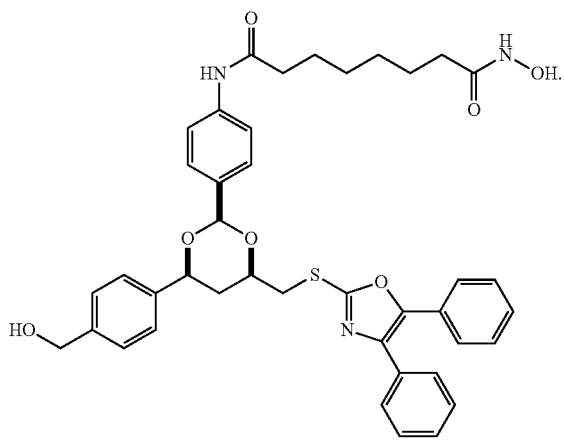

These compounds of the invention are particularly useful in the methods, pharmaceutical compositions, and kits of the invention.

In any of the above-described aspects, the protein degradation inhibitor is an HDAC inhibitor. Compounds known to inhibit HDACs are described in U.S. patent applications, U.S. Ser. No. 60/773,510, filed Feb. 14, 2006; U.S. Ser. No. 60/773,172, filed Feb. 14, 2006; U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference. In certain embodiments, the protein degradation inhibitor preferably inhibits HDAC6. In certain embodiments, the protein degradation inhibitor is specific for HDAC6.

In any of the above-described aspects, the protein degradation inhibitor preferably inhibits HDAC6 enzymatic activity, thereby inhibiting aggresome mediated protein degradation. In preferred embodiments, the protein degradation inhibitor inhibits the C-terminal aceylation activity of HDAC6, thereby inhibiting aggresome mediated protein degradation.

In certain embodiments, the inhibitor of HDAC6 leads to the acetylation of Hsp90. The acetylation of Hsp90 renders this protein less active towards a number of Hsp90's client proteins, thereby augmenting protein stress in the cell. In particular, for prostate and breast cancer, the inhibition of HDAC6 and the subsequent acetylation of Hsp90 leads to diminished activity of steroid-binding receptors due to the finding that glucocorticoid receptors require Hsp90 function to engage glucorticoids. Therefore, HDAC6 inhibition leads to decreased sensitivity to estrogen in breast cancer and androgens in prostate cancer.

In any of the above-described aspects, in certain preferred embodiments, the protein degradation inhibitor is an aggresome inhibitor. In certain preferred embodiments, the aggresome inhibitor is one or more of tubacin, scriptade, or a compounds described herein. In certain other embodiments, the aggresome inhibitor is one or more of the compounds described in U.S. patent applications, U.S. Ser. No. 60/773,510, filed Feb. 14, 2006; U.S. Ser. No. 60/773,172, filed Feb. 14, 2006; U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference.

In any of the above-described aspects, in certain preferred embodiments, the protein degradation inhibitor is a proteasome inhibitor. In certain preferred embodiments, the proteasome inhibitor is one or more of bortezomib, MG132, sapojargon, and NPI-0052. In certain embodiments, the proteasome inhibitor is a compound described herein.

In any of the above-described aspects, in certain preferred embodiments, the protein degradation inhibitor is a peptide derived from HDAC6, dynein, an N-terminal peptide of HDAC6, or C-terminal peptide of HDAC6. In certain preferred embodiments, the C-terminal HDAC6 peptide is sufficient to modulate a phenotype of a cell.

In any of the above-described aspects, in certain preferred embodiments, the phenotype can be biological or clinical sequelae in response to a particular treatment or compound, anemia, thrombocytopenia, neutropenia, osteolytic lesions, bone pain, immunodeficiency, renal insufficiency, hypercalcemia, aneuploidy of mature plasma cells, percentage of malignant cells, acetylation state of tubulin, apoptosis of mature plasma cells, level of aggresomes in mature plasma cells, HDAC6 ubiquitination in mature plasma cells, HDAC6 association with dynein in mature plasma cells, cellular levels of ubiquintinated proteins in mature plasma cells, level of caspase-8 in mature plasma cells, level of PARP in mature plasma cells, thymidine uptake in mature plasma cells, dilated ER cisternae, aggregation of mature plasma cells, deposits of immunoglobulins in mature plasma cells, acetylation state of non-histone proteins, acetylation of histone proteins, global ubiquitination state of the cellular proteins, state of cell cycle regulation, necrosis, markers of apoptosis, apoptosis state, Russell body formation, cystic fibrosis transmembrane protein receptor state, and modulation of cellular protein deposits, or global acetylation state of cellular or extracellular proteins.

In preferred embodiments, a decrease in one or more of level of aggresomes, thrombocytopenia, neutropenia, osteolytic lesions, bone pain, immunodeficiency, renal insufficiency, hypercalcemia, aneuploidy of mature plasma cells, percentage of malignant cells, thymidine uptake in mature plasma cells, level of full length caspase-8 in mature plasma cells, level of full length PARP in mature plasma cells, or aggregation of mature plasma cells, indicates that the treatment is efficacious.

In preferred embodiments, an increase in acetylation state of tubulin, HDAC6 ubiquitination in mature plasma cells, level of cleaved form of caspase-8, level of cleaved form of PARP, necrosis, acetylation state of non-histone proteins, cellular ubiquitination levels, apoptosis, markers of apoptosis, cell cycle deregulation, or deposits of immunoglobulins in mature plasma cells indicates that the treatment is efficacious.

In any of the above-described aspects, in certain preferred embodiments, the method includes the further step of obtaining a biological sample from a subject, and, in certain embodiments, can include the further step of obtaining a second biological sample from the subject.

In any of the above-described aspects, in certain preferred embodiments, the method includes the further step of determining the subject's phenotype after a second period of treatment with the protein degradation inhibitor.

In any of the above-described aspects, in certain preferred embodiments, the method further includes the step of administering a therapeutically effective amount of one or more additional protein degradation inhibitors to the subject or cell. In certain preferred embodiments, at least one of the additional protein degradation inhibitors is an aggresome inhibitor. In certain preferred embodiments, at least one of the additional protein degradation inhibitors is a proteasome inhibitor. In preferred embodiments, the additional protein degradation inhibitor is one or more of bortezomib, tubacin, MG132, sapojargon, NPI-0052, or a compound described herein. In certain other embodiments, the protein degradation inhibitor is one or more of the compounds described in U.S. patent applications, U.S. Ser. No. 60/773,510, filed Feb. 14, 2006; U.S. Ser. No. 60/773,172, filed Feb. 14, 2006; U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference.

In any of the above-described aspects, in certain preferred embodiments, the method further includes monitoring the treatment or progress of the cell or subject.

In any of the above-described aspects, in certain preferred embodiments, the method further includes obtaining the protein degradation inhibitor.

In any of the above-described aspects, in certain preferred embodiments, the method further includes co-administering one or more of a chemotherapeutic agent, radiation agent, hormonal agent, biological agent, or an anti-inflammatory agent to the subject. In certain embodiments, the chemotherapeutic agent is tamoxifen, trastuzamab, raloxifene, doxorubicin, fluorouracil/5-FU, pamidronate disodium, anastrozole, exemestane, cyclophos-phamide, epirubicin, letrozole, toremifene, fulvestrant, fluoxymesterone, trastuzumab, methotrexate, megastrol acetate, docetaxel, paclitaxel, testolactone, aziridine, vinblastine, capecitabine, goselerin acetate, zoledronic acid, taxol, vinblastine, or vincristine.

In any of the above-described aspects, in certain preferred embodiments, the method further includes comparing one or more of the pre-treatment or post-treatment phenotypes to a standard phenotype. In preferred embodiments, the standard phenotype is the corresponding phenotype in a reference cell or population of cells. In preferred embodiments, the reference cell is one or more of the following, cells from the subject, cultured cells, cultured cells from the subject, or cells from the subject pre-treatment. In certain embodiments, the cells from the subject are bone marrow stromal cell, (BMSC), a peripheral blood mononuclear cell (PBMC), lymphocytes, hair follicles, blood cells, other epithelial cells, bone marrow plasma cells, primary cancer cells, patient derived tumor cells, normal or cancerous hematopoietic stem cells, neural stem cells, solid tumor cells, or astrocytes.

In another aspect, the invention provides a method of inhibiting aggresome mediated protein degradation in a cell. The method includes the step of contacting the cell with an aggresome inhibitor. In preferred embodiments, the aggresome protein degradation is mediated by HDAC6. In certain preferred embodiments, the method further includes the step of inhibiting proteasome protein degradation in the cell. In certain preferred embodiments, the aggresome inhibitor is tubacin, a compound described herein, or a compound identified by a method of identifying candidate compounds as described herein below. In certain other embodiments, the aggresome inhibitor is one or more of the compounds described in U.S. patent applications, U.S. Ser. No. 60/773,510, filed Feb. 14, 2006; U.S. Ser. No. 60/773,172, filed Feb. 14, 2006; U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference.

In another aspect, the invention provides a method of identifying a candidate compound or molecule to inhibit protein degradation in a cell. The method includes the steps of contacting a cell exhibiting aggresome formation with a candidate compound, and determining a phenotype of the cell, wherein modulation of the phenotype is indicative of the efficacy of the compound. In certain embodiments, the candidate molecule is one or more of a small molecule, a peptide (or peptidomimetic), or a nucleic acid (or a mimetic thereof (including, e.g., peptide nucleic acids (PNAs)). In certain preferred embodiments, the nucleic acid is an RNA, mRNA, RNAi, siRNA or DNA. In certain preferred embodiments, the peptide is a peptide derived from the HDAC6, the dynein-binding domain of HDAC6, the TDAC domain of HDAC6, the N-terminus of HDAC6 or the C-terminus of HDAC6. In certain preferred embodiments, the small molecule is contained in or derived from a library of compounds. In certain preferred embodiments, the step of determining the phenotype comprises using image-based multidimensional screening.

In a yet further aspect, the invention provides a method for evaluating a test compound. The method includes the steps of contacting a cell exhibiting aggresome formation with a test compound, and evaluating the cell following contact, wherein a correlation of a modulation of one or more phenotypes to a reference value is an indication that the test compound may be useful as a protein degradation disorder treatment. In certain preferred embodiments, the test compound is one or more of a small molecule, a peptide, or a nucleic acid.

In certain preferred embodiments of the above methods, the method further includes the step of determining a phenotype of the cell after an initial period of treatment with the protein degradation inhibitor. In certain preferred embodiments of the above methods, the phenotype is a biological or clinical sequelae in response to a particular treatment or compound. Phenotypes include, anemia, thrombocytopenia, neutropenia, osteolytic lesions, bone pain, immunodeficiency, renal insufficiency, hypercalcemia, aneuploidy of mature plasma cells, percentage of malignant cells, acetylation state of tubulin, apoptosis of mature plasma cells, level of aggresomes, level of aggresomes in mature plasma cells, HDAC6 ubiquitination, HDAC6 ubiquitination in mature plasma cells, HDAC6 association with dynein in mature plasma cells, cellular levels of ubiquintinated proteins in mature plasma cells, level of caspase-8 in mature plasma cells, level of PARP in mature plasma cells, thymidine uptake in mature plasma cells, dilated ER cisternae, aggregation of mature plasma cells, deposits of immunoglobulins in mature plasma cells, acetylation state of non-histone proteins, global ubiquitination state of the cellular proteins, state of cell cycle regulation, necrosis, markers of apoptosis, apoptosis state, Russell body formation, Cystic Fibrosis transmembrane protein receptor state, and modulation of cellular protein deposits, or global acetylation state of cellular and extracellular proteins. In certain preferred embodiments, a decrease in one or more of anemia, level of aggresomes, thrombocytopenia, neutropenia, osteolytic lesions, bone pain, immunodeficiency, renal insufficiency, hypercalcemia, aneuploidy of mature plasma cells, percentage of malignant cells, thymidine uptake in mature plasma cells, level of full length caspase-8 in mature plasma cells, level of full length PARP in mature plasma cells, or aggregation of mature plasma cells, indicates that the treatment is efficacious. In certain preferred embodiments, an increase in acetylation state of tubulin, global acetylation state, acetylation state on non-histone proteins, HDAC6 ubiquitination in mature plasma cells, level of cleaved form of caspase-8, level of cleaved form of PARP, necrosis, acetylation state of non-histone proteins, cellular ubiquitination levels, apoptosis, markers of apoptosis, cell cycle deregulation, or deposits of immunoglobulins in mature plasma cells indicates that the treatment is efficacious.

In certain embodiments of any of the above-described methods, the subject or the cell is a human. In certain embodiments of any of the above-described methods, the subject or the cell is a mammalian. In certain embodiments of any of the above-described methods, the subject is or the cell is derived from a domesticated animal (e.g., dog, cat, rodent, cow, pig, goat, sheep, etc.). In other embodiments of any of the above-described methods, the subject is or the cell is derived from an experimental animal (e.g., mouse, rat, pig, dog, primate, monkey, chimpanzee, etc.).

In another aspect, the invention provides a kit for treating a protein degradation disorder in a subject. The kit includes a compound as described herein or pharmaceutically acceptable esters, salts, and prodrugs thereof; and instructions for use. In certain preferred embodiments, the compound is present as a pharmaceutical composition comprising a therapeutically effective amount of the compound and a pharmaceutically acceptable carrier.

In still a further aspect, the invention provides a packaged composition. The packaged compositions includes a therapeutically effective amount of an a protein degradation inhibitor and a pharmaceutically acceptable carrier or diluent, wherein the composition is formulated for treating a subject suffering from or susceptible to a protein degradation disorder, and packaged with instructions to treat a subject suffering from or susceptible to a protein degradation disorder.

In still another aspect, the invention provides an isolated nucleic acid molecule which encodes a polypeptide derived from HDAC6, wherein the polypeptide when expressed in cell exhibiting aggresomes causes an inhibition of protein degradation. In certain preferred embodiments, the nucleic acid is derived from the nucleic acid encoding the C-terminus of HDAC6, amino acids 439-503 of HDAC6, amino acids 500-790 of HDAC 6, amino acids 781-931 of HDAC6, or the amino acids 1-460. In certain preferred embodiments, the nucleic acid is at least about 60% identical to the C-terminus of HDAC6, amino acids 439-503 of HDAC6, amino acids 500-790 of HDAC 6, amino acids 781-931 of HDAC6, or the amino acids 1-460. In certain preferred embodiments, the nucleic acid is is at least about 80% identical to the C-terminus of HDAC6, amino acids 439-503 of HDAC6, amino acids 500-790 of HDAC 6, amino acids 781-931 of HDAC6, or the amino acids 1-460. In certain preferred embodiments, the nucleic acid is is at least about 90% identical to the C-terminus of HDAC6, amino acids 439-503 of HDAC6, amino acids 500-790 of HDAC 6, amino acids 781-931 of HDAC6, or the amino acids 1-460. In certain preferred embodiments, the nucleic acid is is at least about 99.9% identical to the C-terminus of HDAC6, amino acids 439-503 of HDAC6, amino acids 500-790 of HDAC 6, amino acids 781-931 of HDAC6, or the amino acids 1-460.

In still another aspect, the invention provides an isolated polypeptide derived from HDAC6, wherein the polypeptide inhibits aggresome mediated protein degradation. In certain preferred embodiments, the isolated polypeptide comprises an amino acid sequence as identified by C-terminus of HDAC6, amino acids 439-503 of HDAC6, amino acids 500-790 of HDAC 6, amino acids 781-931 of HDAC6, or the amino acids 1-460. In certain preferred embodiments, the peptide is at least about 60% identical to any one or more of the C-terminus of HDAC6, amino acids 439-503 of HDAC6, amino acids 500-790 of HDAC 6, amino acids 781-931 of HDAC6, or the amino acids 1-460. In certain preferred embodiments, the peptide is at least about 80% identical to any one or more of the C-terminus of HDAC6, amino acids 439-503 of HDAC6, amino acids 500-790 of HDAC 6, amino acids 781-931 of HDAC6, or the amino acids 1-460. In certain preferred embodiments, the peptide is at least about 90% identical to any one or more of the C-terminus of HDAC6, amino acids 439-503 of HDAC6, amino acids 500-790 of HDAC 6, amino acids 781-931 of HDAC6, or the amino acids 1-460. In certain preferred embodiments, the peptide is at least about 99.9% identical to any one or more of the C-terminus of HDAC6, amino acids 439-503 of HDAC6, amino acids 500-790 of HDAC 6, amino acids 781-931 of HDAC6, or the amino acids 1-460.

In yet another aspect, the invention provides a vector which contains a polynucleotide capable of encoding a polypeptide having at least about 80% sequence identity to the C-terminus of HDAC6, amino acids 439-503 of HDAC6, amino acids 500-790 of HDAC 6, amino acids 781-931 of HDAC6, or the amino acids 1-460, and characterized by the ability to inhibit protein degradation.

In still another aspect, the invention provides a method of treating a protein degradation disorder or cellular proliferation disorder. The method includes the step of administering to a subject in need thereof an effective amount of an RNA to specifically bind and inactivate the HDAC6. In certain preferred embodiments, the RNA is an RNAi, siRNA, antisense RNA, or ribozyme. Examples of active siRNA reagents include, but are not limited to, double-stranded or hairpin sequences corresponding to amino acids of HDAC6 at nucleotides 211-231 or 217-237 (see, e.g., Hubbert et al., Nature (2002) 417(6887):455-8).

BRIEF DESCRIPTION OF THE DRAWING

FIG. 1 demonstrates MM cell lines (lane 1-7) constitutively express HDAC6 protein.

FIG. 2 shows the induction of acetylated α-tubulin by tubacin in MM cell lines. MM.1S, RPMI8226 and INA-6 cells were incubated with tubacin (0-5 μM) for 24 h.

Acetylation of α-tubulin was assessed by Western blotting using anti-acetylated lysine antibody. FIG. 2 demonstrates that tubacin specifically induces acetylation of t-tubulin in a dose-dependent fashion.

FIG. 3 demonstrates dose-dependent growth inhibitory effect of tubacin as single agent in MM cell lines.

FIG. 4 demonstrates that IL-6 which is one of the major growth factor in MM, did not overcome growth inhibitory effect of tubacin.

FIGS. 6A to 6B demonstrate that tubacin significantly (p<0.01) augmented cytotoxicity triggered by Velcade in both cell lines.

FIGS. 7A to 7B show that tubacin inhibits G2/M arrest triggered by Velcade in MM cells. MM.1S cells were incubated with Velcade (5 nM) in the presence (5 µM) or absence of tubacin for 24 h. Cell cycle was examined by flow cytometric analysis using propidium iodine staining (FIG. 7A). Tubacin significantly inhibits G2/M arrest associated down regulation of $p21^{Cip1}$, triggered by Velcade and induced sub-G0/G1 phase (apoptosis) in MM.1S cells (FIG. 7B).

FIG. 8 demonstrates that combination of Velcade with tubacin markedly augmented (induces) caspase/PARP cleavage in both cell lines.

FIG. 9 demonstrates that tubacin significantly (p<0.01) augments cytotoxicity triggered by Velcade in patient tumor cells.

FIG. 10 demonstrates that combination treatment of Velcade with tubacin did not trigger cytotoxicity in PBMCs.

FIG. 11 demonstrates that tubacin significantly inhibits MM.1S cell growth even in the presence of BMSCs. Moreover, tubacin further augmented cytotoxicity of Velcade.

(FIG. 12A) Chemical structures of tubacin and an inactive analog nil-tubacin. (FIG. 12B) Western blot of baseline expression of HDAC6 in MM cell lines. (FIG. 12C) MM.1S and RPMI8226 cells were cultured for 24 h in the presence (2.5 and 5 µM) or absence of tubacin. (FIG. 12D) RPMI8226 cells were cultured for the time indicated times in the presence of tubacin (5 µM). Whole cell lysates were subjected to Western blot using anti-Ac lysine Ab. Immunoblotting with anti-α-tubulin serves confirms equal protein loading. (FIG. 12E) MM.1S and RPMI8226 cells were cultured for 24 h in the presence (2.5 and 5 µM) or absence of SAHA. Whole cell lysates were subjected to Western blotting using anti-Ac lysine Ab. In contrast to tubacin, SAHA markedly triggers acetylation of histones H3 and H4.

(FIG. 13C) PBMC form normal volunteers (n=3) were cultured in the presence of tubacin (2.5-20 µM) for 48 h. Cell growth was assessed by MTT assay, and data represent mean (±SD) of quadruplicate cultures. (FIG. 13D) MM.1S and RPMI8226 cells were cultured with tubacin (10 µM) for the times indicated. Whole cell lysates were subjected to Western blotting using anti-caspase-8 and PARP Abs.

FIGS. 14A to 14E demonstrate that tubacin inhibits binding of HDAC6 with dynein and when combined with bortezomib, it induces significant accumulation of polyubiquitinated proteins. (FIG. 14A) Hypothetical rationale whereby tubacin enhances cytotoxicity induced by bortezomib (adapted from Kawaguchi et al (17)). (FIG. 14B) MM.1S cells were cultured with tubacin (2.5 and 5 µM) for 8 h. Whole cell lysates were immunoprecipitated with anti-Ub Ab. Immunoprecipitates were subjected to Western blotting using ant-HDAC6 Ab. (FIG. 14C) MM.1S cells were cultured with tubacin (2.5 and 5 µM) for 8 h. Whole cell lysates were immunoprecipitated with anti-dynein Ab. Immunoprecipitates were then subjected to Western blotting using anti-HDAC6 and dynein Abs. (FIG. 14D) MM.1S and RPMI8226 cells were cultured with tubacin (2.5 and 5 µM) for 24 h. Whole cell lysates were subjected to Western blot using anti-Ub Ab. (FIG. 14E) MM.1S and RPMI8226 cells were cultured with tubacin (T: 5 µM) and/or bortezomib (B: 5 nM) for 12 h. Whole cell lysates were subjected to Western blotting using anti-Ub Ab.

(FIG. 15A) MM.1S and RPMI8226 MM cells were cultured for 24 h in the presence or absence of tubacin (5 µM) in control media (□), as well as with 5 nM (■) or 10 nM (■) bortezomib; cytotoxicity was assessed by MTT assay. (FIG. 15B) MM.1S cells were cultured for 24 h in the presence or absence of tubacin (5 µM) and/or bortezomib (5 nM); cell cycle profile was assessed by flow cytometry using PI staining. (FIG. 15C) MM.1S cells were cultured for 24 h in the presence or absence of tubacin (T: 5 µM) and/or bortezomib (B: 5 nM); whole cell lysates were subjected to Western blotting using anti-p21$^{Cip1}$, p-JNK (SAPK), caspase-9, caspase-8, caspase-3 and PARP Abs. MM.1S cell were transiently transfected with HDAC6 siRNA. Cells were then subjected to (FIG. 15D) Western blotting using anti-HDAC6 Ab or (FIG. 15E) MTT assay, in the presence or absence of 5 nM bortezomib (■). MM.1S cells were cultured for 24 h with niltubacin (2.5 and 5 µM) or tubacin (2.5 and 5 µM). Cells were then subjected to (FIG. 15F) Western blotting using Ac-Lys Ab, or (FIG. 15G) MTT assay, in the presence or absence of 5 nM bortezomib (■). Data represent mean (±SD) of quadruplicate cultures.

(FIG. 16E) MM patient PBMCs were cultured in the presence or absence of tubacin (5 µM). Whole cell lysates were subjected to Western blotting using anti-HDAC6, Ac-Lys, or α-tubulin Abs.

FIGS. 24A to 24B show the synergy between Tubacin and Velcade in myeloma cell lines (FIG. 24A) MM.1S, and (FIG. 24B) RPMI cells.

FIGS. 27A to 27B show the synergy between DHM-Tubacin and Velcade in myeloma cell lines (FIG. 27A) MM.1S, and (FIG. 27B) RPMI cells.

FIGS. 39A to 39B show the synergy between NKI-60-1 and Velcade in myeloma cell lines (FIG. 39A) MM.1S, and (FIG. 39B) RPMI cells.

FIGS. 45A to 45B show the synergy between NKI-84-1 and Velcade in myeloma cell lines (FIG. 45A) MM.1S, and (FIG. 45B) RPMI cells.

FIG. 46 demonstrates the specificity of NKI-84-1 for tubulin acetylation versus lysine acetylation in 293T cells.

FIG. 59 demonstrates the synergy between bortezomib (VELCADE®) and tubacin in breast cancer. The use of an HDAC6 inhibitor such as tubcin renders the breast cancer cells sensitive to proteasome inhibition (e.g., bortezomib).

DETAILED DESCRIPTION OF CERTAIN EMBODIMENTS OF THE INVENTION

Figure 1:
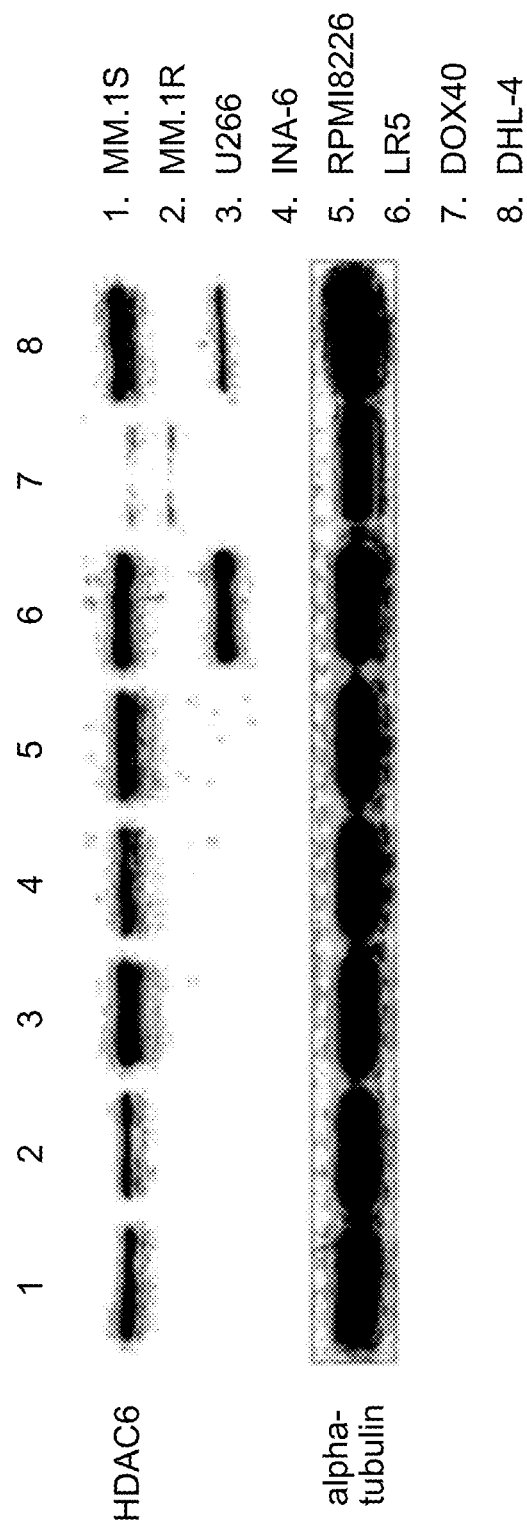
FIG. 1 shows the expression of HDAC6 in multiple myeloma (MM) cell lines. MM cell lines were lysed and whole cell lysates were subjected Western blotting to assess protein expression of HDAC6.

The present invention provides novel HDAC and TDAC inhibitors. Certain of these compounds are inhibitors of the aggresome. The present invention also provides method of treating intracellular protein degradation disorders mediated by the aggresome and/or proteasome. The aggresome is a novel therapeutic target as are therapeutic strategies targeting both the aggresome and proteasome. The novel therapeutic strategies of the invention overcome the problems of former therapeutics, for example, drug resistance and toxicity.

The proteasome is well-characterized in cancer cell biology. The aggresome is a juxtanuclear proteolytic complex, which forms in response to proteasome inhibition or misfolded protein stress. It is directly implicated in the pathophysiology of cystic fibrosis and certain neurodegenerative diseases characterized by protein deposition. A specific role for the aggresome in cancer has not been described.

Recently, a cytoplasmic histone deacetylase protein, HDAC6, was identified as necessary for aggresome formation and for survival of cells following ubiquitinated misfolded protein stress. The aggresome is an integral component of survival in cancer cells. The mechanism of HDAC6-mediated aggresome formation is a consequence of the catalytic activity of the carboxy-terminal deacetylase domain, targeting an uncharacterized non-histone target. The present invention also provides small molecule inhibitors of HDAC6. In certain embodiments, these new compounds are potent and selective inhibitors of HDAC6.

The aggresome was first described in 1998, when it was reported that there was an appearance of microtubule-associated perinuclear inclusion bodies in cells over-expressing the pathologic ΔF508 allele of the cystic fibrosis transmembrane conductance receptor (CFTR). Subsequent reports identified a pathologic appearance of the aggresome with over-expressed presenilin-1(Johnston J A, Ward C L, Kopito R R. Aggresomes: a cellular response to misfolded proteins. J Cell Biol. 1998; 143:1883-1898; incorporated herein by reference), parkin (Junn E, Lee S S, Suhr U T, Mouradian M M. Parkin accumulation in aggresomes due to proteasome impairment. J Biol Chem. 2002; 277:47870-47877; incorporated herein by reference), peripheral myelin protein PMP22 (Notterpek L, Ryan M C, Tobler A R, Shooter E M. PMP22 accumulation in aggresomes: implications for CMT1A pathology. Neurobiol Dis. 1999; 6:450-460; incorporated herein by reference), influenza virus nucleoprotein (Anton L C, Schubert U, Bacik I, Princiotta M F, Wearsch P A, Gibbs J, Day P M, Realini C, Rechsteiner M C, Bennink J R, Yewdell J W. Intracellular localization of proteasomal degradation of a viral antigen. J Cell Biol. 1999; 146:113-124; incorporated herein by reference), a chimera of GFP and the membrane transport protein p115 (Garcia-Mata R, Bebok Z, Sorscher E J, Sztul E S. Characterization and dynamics of aggresome formation by a cytosolic GFP-chimera. J Cell Biol. 1999; 146:1239-1254; incorporated herein by reference) and notably amyloidogenic light chains (Dul J L, Davis D P, Williamson E K, Stevens F J, Argon Y. Hsp70 and antifibrillogenic peptides promote degradation and inhibit intracellular aggregation of amyloidogenic light chains. J Cell Biol. 2001; 152:705-716; incorporated herein by reference). Model systems have been established to study ubiquitinated (ΔF508 CFTR) (Johnston J A, Ward C L, Kopito R R. Aggresomes: a cellular response to misfolded proteins. J Cell Biol. 1998; 143:1883-1898; incorporated herein by reference) and non-ubiquitinated (GFP-250) (Garcia-Mata R, Bebok Z, Sorscher E J, Sztul E S. Characterization and dynamics of aggresome formation by a cytosolic GFP-chimera. J Cell Biol. 1999; 146:1239-1254; incorporated herein by reference) protein aggregate transport to the aggresome. Secretory, mutated, and wild-type proteins may assume unstable kinetic intermediates resulting in stable aggregates incapable of degradation through the narrow channel of the 26S proteasome. These complexes undergo active, retrograde transport by dynein to the pericentriolar aggresome, mediated in part by a cytoplasmic histone deacetylase, HDAC6 (Kawaguchi Y, Kovacs J J, McLaurin A, Vance J M, Ito A, Yao T P. The deacetylase HDAC6 regulates aggresome formation and cell viability in response to misfolded protein stress. Cell. 2003; 115:727-738; incorporated herein by reference).

Histone deacetylases (HDACs) are a family of at least 11 zinc-binding hydrolases, which catalyze the deacetylation of lysine residues on histone proteins. HDAC inhibition results in hyperacetylation of chromatin, alterations in transcription, growth arrest, and apoptosis in cancer cell lines. Early phase clinical trials with available nonselective HDAC inhibitors demonstrate responses in hematologic malignancies including multiple myeloma, although with significant toxicity. Of note, in vitro synergy of conventional chemotherapy agents (such as melphalan) with bortezomib has been reported in myeloma cell lines, though dual proteasome-aggresome inhibition was not proposed. Until recently selective HDAC inhibitors have not been realized.

HDAC6 is required for aggresome formation with ubiquitinated protein stress and is essential for cellular viability in this context. HDAC6 is believed to bind ubiquitinated proteins through a zinc finger domain and interacts with the dynein motor complex through another discrete binding motif. HDAC6 possesses two catalytic deacetylase domains. It is not presently known whether the amino-terminal histone deacetylase or the carboxy-terminal tubulin deacetylase (TDAC) domain mediates aggresome formation.

Aberrant protein catabolism is a hallmark of cancer, and is implicated in the stabilization of oncogenic proteins and the degradation of tumor suppressors (Adams J. The proteasome: a suitable antineoplastic target. Nat Rev Cancer. 2004; 4:349-360; incorporated herein by reference). Tumor necrosis factor alpha induced activation of nuclear factor kappa B (NFκB) is a relevant example, mediated by NFκB inhibitor beta (IκB) proteolytic degradation in malignant plasma cells. The inhibition of IκB catabolism by proteasome inhibitors explains, in part, the apoptotic growth arrest of treated myeloma cells (Hideshima T, Richardson P, Chauhan D, Palombella V J, Elliott P J, Adams J, Anderson K C. The proteasome inhibitor PS-341 inhibits growth, induces apoptosis, and overcomes drug resistance in human multiple myeloma cells. Cancer Res. 2001; 61:3071-3076; incorporated herein by reference). Multiple myeloma is an ideal system for studying the mechanisms of protein degradation in cancer. Since William Russell in 1890, cytoplasmic inclusions have been regarded as a defining histological feature of malignant plasma cells. Though the precise composition of Russell bodies is not known, they are regarded as ER-derived vesicles containing aggregates of monotypic immunoglobulins (Kopito R R, Sitia R. Aggresomes and Russell bodies. Symptoms of cellular indigestion? EMBO Rep. 2000; 1:225-231; incorporated herein by reference) and stain positive for ubiquitin (Manetto V, Abdul-Karim F W, Perry G, Tabaton M, Autilio-Gambetti L, Gambetti P. Selective presence of ubiquitin in intracellular inclusions. Am J Pathol. 1989; 134:505-513; incorporated herein by reference). Russell bodies have been described with CFTR over-expression in yeast (Sullivan M L, Youker R T, Watkins S C, Brodsky J L. Localization of the BiP molecular chaperone with respect to endoplasmic reticulum foci containing the cystic fibrosis transmembrane conductance regulator in yeast. J. Histochem. Cytochem. 2003; 51:545-548; incorporated herein by reference), thus raising the suspicion that these structures may be linked to overwhelmed protein catabolism, and potentially the aggresome. The role of the aggresome in cancer remains undefined.

Multiple myeloma (MM) is a plasma cell malignancy which remains incurable despite conventional treatment (Gregory, W. M., Richards, M. A. & Malpas, J. S. (1992) *J Clin Oncol* 10, 334-342; incorporated herein by reference) as well as high dose therapy and stem cell transplantation (Attal, M., Harousseau, J. L., Facon, T., Guilhot, F., Doyen, C., Fuzibet, J. G., Monconduit, M., Hulin, C., Caillot, D., Bouabdallah, R., Voillat, L., Sotto, J. J., Grosbois, B. & Bataille, R. (2003) *N Engl J Med* 349, 2495-2502; incorporated herein by reference). Novel agents have recently been developed which target not only MM cells, but also the bone marrow (BM) microenvironment, and can overcome conventional drug resistance (Hideshima, T. & Anderson, K. C. (2002) *Nat Rev Cancer* 2, 927-937; incorporated herein by reference). For example, the proteasome inhibitor bortezomib (formally PS-341) induces significant anti-tumor activity in human MM cell lines and freshly isolated patient MM cells (Hideshima, T. & Anderson, K. C. (2002) *Nat Rev Cancer* 2, 927-937; Hideshima, T., Richardson, P., Chauhan, D., Palombella, V., Elliott, P., Adams, J. & Anderson, K. C. (2001) *Cancer Res.* 61, 3071-3076; Mitsiades, N., Mitsiades, C. S., Poulaki, V., Chauhan, D., Gu, X., Bailey, C., Joseph, M., Libermann, T. A., Treon, S. P., Munshi, N. C., Richardson, P. G., Hideshima, T. & Anderson, K. C. (2002) *Proc Natl Acad Sci USA* 99, 14374-14379; Hideshima, T., Chauhan, D., Richardson, P., Mitsiades, C., Mitsiades, N., Hayashi, T., Munshi, N., Dang, L., Castro, A., Palombella, V., Adams, J. & Anderson, K. C. (2002) *J Biol Chem* 277, 16639-47; Mitsiades, N., Mitsiades, C. S., Richardson, P. G., Poulaki, V., Tai, Y. T., Chauhan, D., Fanourakis, G., Gu, X., Bailey, C., Joseph, M., Libermann, T. A., Schlossman, R., Munshi, N. C., Hideshima, T. & Anderson, K. C. (2003) *Blood* 101, 2377-80; Chauhan, D., Li, G., Shringarpure, R., Podar, K., Ohtake, Y., Hideshima, T. & Anderson, K. C. (2003) *Cancer Res* 63, 6174-6177; Hideshima, T., Mitsiades, C., Akiyama, M., Hayashi, T., Chauhan, D., Richardson, P., Schlossman, R., Podar, K., Munshi, N. C., Mitsiades, N. & Anderson, K. C. (2003) *Blood* 101, 1530-1534; Hideshima, T., Chauhan, D., Hayashi, T., Akiyama, M., Mitsiades, N., Mitsiades, C., Podar, K., Munshi, N. C., Richardson, P. G. & Anderson, K. C. (2003) *Oncogene* 22, 8386-8393; Hideshima, T., Podar, K., Chauhan, D., Ishitsuka, K., Mitsiades, C., Tai, Y.-Z., Hamasaki, M., Raje, N., Hideshima, H., Schreiner, G., Nguyen, A. N., Navas, T., Munshi, N. C., Richardson, P. G., Higgins, L. S. & Anderson, K. C. (2004) *Oncogene* 23, 8766-8776; each of which is incorporated herein by reference) associated with c-Jun NH$_2$-terminal kinase (JNK) (also known as stress-activated protein kinase) and caspase activation, followed by apoptosis (Hideshima, T., Richardson, P., Chauhan, D., Palombella, V., Elliott, P., Adams, J. & Anderson, K. C. (2001) *Cancer Res.* 61, 3071-3076; Mitsiades, N., Mitsiades, C. S., Poulaki, V., Chauhan, D., Gu, X., Bailey, C., Joseph, M., Libermann, T. A., Treon, S. P., Munshi, N. C., Richardson, P. G., Hideshima, T. & Anderson, K. C. (2002) *Proc Natl Acad Sci USA* 99, 14374-14379; Hideshima, T., Mitsiades, C., Akiyama, M., Hayashi, T., Chauhan, D., Richardson, P., Schlossman, R., Podar, K., Munshi, N. C., Mitsiades, N. & Anderson, K. C. (2003) *Blood* 101, 1530-1534; each of which is incorporated herein by reference). Bortezomib also inhibits adherence of MM cells to bone marrow stromal cells (BMSCs) by downregulating adhesion molecules (ICAM-1 and VCAM-1) (Hideshima, T., Chauhan, D., Schlossman, R. L., Richardson, P. R. & Anderson, K. C. (2001) *Oncogene* 20, 4519-4527; incorporated herein by reference); as well as induces cleavage of DNA-protein kinase catalytic subunit and ataxia telangiectasia mutated, suggesting that bortezomib also inhibits DNA repair. Neither IL-6 nor adherence of MM cells to BMSCs protects against bortezomib-induced apoptosis. Without wishing to be bound by any scientific theory, bortezomib enhances sensitivity and can overcome resistance in MM cells to conventional chemotherapeutic agents, especially to DNA damaging agents (Mitsiades, N., Mitsiades, C. S., Richardson, P. G., Poulaki, V., Tai, Y. T., Chauhan, D., Fanourakis, G., Gu, X., Bailey, C., Joseph, M., Libermann, T. A., Schlossman, R., Munshi, N. C., Hideshima, T. & Anderson, K. C. (2003) *Blood* 101, 2377-80; incorporated herein by reference). In support of this, a phase II trial of bortezomib treatment of 202 patients with refractory relapsed MM demonstrated 35% responses, including 10% complete and near complete responses (Richardson, P. G., Barlogie, B., Berenson, J., Singhal, S., Jagannath, S., Irwin, D., Rajkumar, S. V., Srkalovic, G., Alsina, M., Alexanian, R., Siegel, D., Orlowski, R. Z., Kuter, D., Limentani, S. A., Lee, S., Hideshima, T., Esseltine, D. L., Kauffman, M., Adams, J., Schenkein, D. P. & Anderson, K. C. (2003) *N Engl J Med* 348, 2609-2617; incorporated herein by reference); however, 65% of patients did not respond. Heat-shock protein (hsp)-27 mediates bortezomib-resistance; conversely, inhibiting hsp-27 expression using hsp-27 antisense, p38 mitogen-activated protein kinase (MAPK) siRNA, or p38 MAPK inhibitor to downregulate hsp-27 can restore MM cell susceptibility to bortezomib (Chauhan, D., Li, G., Shringarpure, R., Podar, K., Ohtake, Y., Hideshima, T. & Anderson, K. C. (2003) *Cancer Res* 63, 6174-6177; Hideshima, T., Podar, K., Chauhan, D., Ishitsuka, K., Mitsiades, C., Tai, Y.-Z., Hamasaki, M., Raje, N., Hideshima, H., Schreiner, G., Nguyen, A. N., Navas, T., Munshi, N. C., Richardson, P. G., Higgins, L. S. & Anderson, K. C. (2004) *Oncogene* 23, 8766-8776; each of which is incorporated herein by reference).

The aggresome is an alternative system to the proteasome for degradation of polyubiquitinated misfolded/unfolded proteins (Kopito, R. R. (2000) *Trends Cell Biol* 10, 524-530; Bennett, E. J., Bence, N. F., Jayakumar, R. & Kopito, R. R. (2005) *Mol Cell* 17, 351-365; each of which is incorporated herein by reference). Aggresome formation induces autophagic clearance, which terminates in lysosomal degradation. The aggresome pathway therefore likely provides a novel system for delivery of aggregated proteins from cytoplasm to lysosomes for degradation (Garcia-Mata, R., Gao, Y. S. & Sztul, E. (2002) *Traffic* 3, 388-396; incorporated herein by reference). In aggresomal protein degradation, histone deacetylase6 (HDAC6) binds both polyubiquitinated proteins and dynein motors, thereby acting to recruit protein cargo to dynein motors for transport to aggresomes (Kawaguchi, Y., Kovacs, J. J., McLaurin, A., Vance, J. M., Ito, A. & Yao, T. P. (2003) *Cell* 115, 727-738; incorporated herein by reference). In the methods of the invention include the inhibition of both proteasomal and aggresomal protein degradation systems. Without wishing to be bound by any theories, the inhibition induces accumulation of polyubiquitinated proteins and significant cell stress, followed by activation of apoptotic cascades. For example, bortezomib was utilized to inhibit the proteasome and tubacin, which specifically inhibits HDAC6 (Haggarty, S. J., Koeller, K. M., Wong, J. C., Grozinger, C. M. & Schreiber, S. L. (2003) *Proc Natl Acad Sci USA* 100, 4389-4394; Haggarty, S. J., Koeller, K. M., Wong, J. C., Butcher, R. A. & Schreiber, S. L. (2003) *Chem Biol* 10, 383-396; Wong, J. C., Hong, R. & Schreiber, S. L. (2003) *J Am Chem Soc* 125, 5586-5587; incorporated herein by reference) to block the aggresome. In the methods of the invention, tubacin or other HDAC6 inhibitors combined with bortezomib induces synergistic cytotoxicity in multiple myeloma cell lines as well as freshly isolated bone marrow plasma cells from multiple myeloma patients.

Definitions

Before further description of the present invention, and in order that the invention may be more readily understood, certain terms are first defined and collected here for convenience.

Certain compounds of the present invention, and definitions of specific functional groups are also described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., C, O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference. Furthermore, a variety of carbon protecting groups are described in Myers, A.; Kung, D. W.; Zhong, B.; Movassaghi, M.; Kwon, S. *J. Am. Chem. Soc.* 1999, 121, 8401-8402, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "acyl", as used herein, refers to a carbonyl-containing functionality, e.g., —C(=O)R' wherein R is an aliphatic, alycyclic, heteroaliphatic, heterocyclic, aryl, heteroaryl, (aliphatic)aryl, (heteroaliphatic)aryl, heteroaliphatic (aryl) or heteroaliphatic(heteroaryl) moiety, whereby each of the aliphatic, heteroaliphatic, aryl, or heteroaryl moieties is substituted or unsubstituted, or is a substituted (e.g., hydrogen or aliphatic, heteroaliphatic, aryl, or heteroaryl moieties) oxygen or nitrogen containing functionality (e.g., forming a carboxylic acid, ester, or amide functionality).

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$— cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2Rx$; —$NR_x(CO)R_x$ wherein each occurrence of $R_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least on heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl) aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6-, or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio;

heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OOH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein. The terms "halo" and "halogen" as used herein refer to an atom selected from fluorine, chlorine, bromine and iodine.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N+R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkylidene", as used herein, refers to a substituted or unsubstituted, linear or branched saturated divalent radical consisting solely of carbon and hydrogen atoms, having from one to n carbon atoms, having a free valence "—" at both ends of the radical.

The term "alkenylidene", as used herein, refers to a substituted or unsubstituted, linear or branched unsaturated divalent radical consisting solely of carbon and hydrogen atoms, having from two to n carbon atoms, having a free valence "—" at both ends of the radical, and wherein the unsaturation is present only as double bonds and wherein a double bond can exist between the first carbon of the chain and the rest of the molecule.

The term "alkynylidene", as used herein, refers to a substituted or unsubstituted, linear or branched unsaturated divalent radical consisting solely of carbon and hydrogen atoms, having from two to n carbon atoms, having a free valence "—" at both ends of the radical, and wherein the unsaturation is present only as triple bonds and wherein a triple bond can exist between the first carbon of the chain and the rest of the molecule.

Unless otherwise indicated, as used herein, the terms "alkyl", "alkenyl", "alkynyl", "heteroalkyl", "heteroalkenyl", "heteroalkynyl", "alkylidene", alkenylidene", -(alkyl) aryl, -(heteroalkyl)aryl, -(heteroalkyl)aryl, -(heteroalkyl) heteroaryl, and the like encompass substituted and unsubstituted, and linear and branched groups. Similarly, the terms "aliphatic", "heteroaliphatic", and the like encompass substituted and unsubstituted, saturated and unsaturated, and linear and branched groups. Similarly, the terms "cycloalkyl", "heterocycle", "heterocyclic", and the like encompass substituted and unsubstituted, and saturated and unsaturated groups. Additionally, the terms "cycloalkenyl", "cycloalkynyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Pharmaceutically acceptable derivatives also include "reverse pro-drugs." Reverse pro-drugs, rather than being activated, are inactivated upon absorption. For example, as discussed herein, many of the ester-containing compounds of the invention are biologically active but are inactivated upon exposure to certain physiological environments such as a blood, lymph, serum, extracellular fluid, etc. which contain esterase activity. The biological activity of reverse pro-drugs and pro-drugs may also be altered by appending a functionality onto the compound, which may be catalyzed by an enzyme. Also, included are oxidation and reduction reactions, including enzyme-catalyzed oxidation and reduction reactions. Certain exemplary pharmaceutical compositions and pharmaceutically acceptable derivatives will be discussed in more detail herein below.

The term "linker," as used herein, refers to a chemical moiety utilized to attach one part of a compound of interest to another part of the compound. Exemplary linkers are described herein.

Unless indicated otherwise, the terms defined below have the following meanings:

"Compound": The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 120:8565, 1998; incorporated herein by reference). In certain other preferred embodiments, natural-product-like small molecules are utilized.

"Natural Product-Like Compound": As used herein, the term "natural product-like compound" refers to compounds that are similar to complex natural products which nature has selected through evolution. Typically, these compounds contain one or more stereocenters, a high density and diversity of functionality, and a diverse selection of atoms within one structure. In this context, diversity of functionality can be defined as varying the topology, charge, size, hydrophilicity, hydrophobicity, and reactivity to name a few, of the functional groups present in the compounds. The term, "high density of functionality", as used herein, can preferably be used to define any molecule that contains preferably three or more latent or active diversifiable functional moieties. These structural characteristics may additionally render the inventive compounds functionally reminiscent of complex natural products, in that they may interact specifically with a particular biological receptor, and thus may also be functionally natural product-like.

"Metal chelator": As used herein, the term "metal chelator" refers to any molecule or moiety that is is capable of forming a complex (i.e., "chelates") with a metal ion. In certain exemplary embodiments, a metal chelator refers to to any molecule or moiety that "binds" to a metal ion, in solution, making it unavailable for use in chemical/enzymatic reactions. In certain embodiments, the solution comprises aqueous environments under physiological conditions. Examples of metal ions include, but are not limited to, $Ca^{2+}$, $Fe^{3+}$, $Zn^{2+}$, $Na^+$, etc. In certain embodiments, the metal chelator binds $Zn^{2+}$. In certain embodiments, molecules of moieties that precipitate metal ions are not considered to be metal chelators.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g., blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc., administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compounds of the invention can be administered prior to the administration of the other agent, simultaneously with the agent, or after the administration of the agent. Furthermore, the compound of the invention can also be administered in a pro-form which is converted into its active metabolite, or more active metabolite in vivo.

The language "biological activities" of a compound of the invention includes all activities elicited by compound of the inventions in a responsive cell. It includes genomic and non-genomic activities elicited by these compounds.

"Biological composition," "biological sample," or "sample" refer to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "effective amount" includes an amount effective, at dosages and for periods of time necessary, to achieve the desired result, e.g., sufficient to treat a protein degradation disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity, e.g., reduced hypercalcemic activity.

"Inactivating," "inactivation," or "inactivate" "anti-cancer" and "treat protein degradation disorders" as used herein refers to diminishing or eliminating affected cells (e.g. per ml of a treated biological composition). In addition, these terms include reducing or abolishing the protein degradation disorder or the protein degradation disorder. The aforementioned are illustrated in detail in the examples bellow. Preferably the methods of the invention result in at least 50% of the affected cells in the treated preparation are eliminated, preferably at least 70% of the cells are eliminated, more preferably at least 80%, still more preferably at least 90%, still more preferably at least 95%, still more preferably, at least 99%, and even still more preferably, 100% of the affected cells are eliminated. The number of affected cells in a preparation may be measured by cells counts per ml of preparation. Such a measurement may be accomplished by a variety of well known assays well known to a person of ordinary skill in the art.

An "initial period of treatment" and "period of treatment" as used herein may be the time in which it takes to establish a stable and/or therapeutically effective blood serum level of a therapeutic compound of the invention, or the time in which it takes for the subject to clear a substantial portion of the therapeutic, or any period of time selected by the subject or healthcare professional that is relevant to the treatment.

"Therapeutic," as used herein refers to a small molecule, peptide, protein, enzyme antibody, nucleic acid, etc. that is effective to treat or is suspected of being effective to treat a protein degradation disorder.

The term "modulate" refers to increases or decreases in the activity of a cell in response to exposure to a compound of the invention, e.g., the inhibition of proliferation and/or protein degradation of at least a sub-population of cells in an animal such that a desired end result is achieved, e.g., a therapeutic result. In preferred embodiments, this phrase is intended to include protein degradation disorder and/or a protein degradation disorder of cells.

The term "obtaining" is intended to include purchasing, synthesizing or otherwise acquiring the compounds of the invention.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The term "prodrug" includes compounds with moieties that can be metabolized in vivo. Generally, the prodrugs are metabolized in vivo by esterases or by other mechanisms to active drugs. Prodrugs may only become active upon such reaction under biological conditions, or they may have activity in their unreacted forms. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Other examples of prodrugs include derivatives of compounds of any of the formulae disclosed herein that comprise —NO, —NO₂, —ONO, or —ONO₂ moieties. Preferred prodrug moieties are acyl esters. Prodrugs which are converted to active forms through other mechanisms in vivo are also included. The compounds of the invention may be synthesized as pro-drugs that are metabolized by the subject into the compound of the invention.

The language "a prophylactically effective amount" of a compound refers to an amount of a compound of the invention of the formula (I) or otherwise described herein which is effective, upon single or multiple dose administration to the patient, in preventing or treating a protein degradation disorder.

The language "reduced toxicity" is intended to include a reduction in any undesired side effect elicited by a compound of the invention when administered in vivo, e.g., a reduction in the hypercalcemic activity.

The term "subject" and "patient" are used interchangeably herein and include organisms which are capable of suffering from a protein degradation disorder or who could otherwise benefit from the administration of a compound of the invention, such as human and non-human animals. Preferred human animals include human patients suffering from or prone to suffering from a protein degradation disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a protein degradation disorder is meant to include subjects at risk of developing a protein degradation disorder, i.e., subjects suffering from myeloma, subject having a family history of a protein degradation disorder, etc.

The phrases "systemic administration," "administered systemically," "peripheral administration," and "administered peripherally" as used herein includes the administration of a compound of the invention(s), drug or other material, such that it enters the patient's system and, thus, is subject to metabolism and other like processes, for example, subcutaneous administration.

The language "a protein degradation disorder" is a condition or disease, which can be prevented, treated or otherwise ameliorated by administration of one or more compounds of the invention (e.g. is caused, exacerbated or characterized by the presence of aggresomes in the cells or body of a subject). Protein degradation disorders include cellular proliferation disorders and protein deposition disorders. Cellular proliferation disorders include cancer, for example, myeloma. Other cancers include cancers derived from the epithelium. Also included are solid tumors, such as breast, lung and liver. Protein deposition disorders include Wilson's disease, spinocerebellar ataxia, prion disease, Parkinson's disease, Huntington's disease, Familial amytrophic lateral sclerosis, amyloidosis, Alzheimer's disease, Alexander's disease, alcoholic liver disease, cystic fibrosis, or Lewy body dementia.

A protein degradation disorder or includes cancer. Cancers include, for example, epithelial derived cancers, and solid tumors, and cancers involving protein disregulation. Other cancers include multiple myeloma, leukemia, lymphoma, breast cancer, lung cancer and liver cancer.

A protein degradation disorder includes, for example Wilson's disease, spinocerebellar ataxia, prion disease, Parkinson's disease, Huntington's disease, Familial amytrophic lateral sclerosis, amyloidosis, Alzheimer's disease, Alexander's disease, alcoholic liver disease, cystic fibrosis, Pick's disease or Lewy body dementia.

As used herein "suffering from or susceptible to a protein degradation disorder" refers to subjects having or at risk of having such a disorder.

The compounds or other therapeutics of the invention may either directly or indirectly inhibit protein degradation. The compounds or other therapeutics of the invention may directly or indirectly inhibit aggresome formation or activity. The compounds or other therapeutics of the invention may directly or indirectly inhibit proteasome activity. Alternately, the compounds or other therapeutics of the invention may directly or indirectly inhibit aggresome and proteasome activity. The compounds or other therapeutics of the invention may directly or indirectly inhibit HDAC6 activity. Contacting cells or administering the compounds or other therapeutics of the invention to a subject is one method of treating a cell or a subject with susceptible to a protein degradation disorder or inhibiting the occurrence of a protein degradation disorder.

As used herein, "cell from a subject" include bone marrow stromal cell, (BMSC), a peripheral blood mononuclear cell (PBMC), lymphocytes, hair follicles, blood cells, other epithelial cells, bone marrow plasma cells, primary cancer cells, patient derived tumor cells, normal or cancerous hematopoietic stem cells, neural stem cells, solid tumor cells, astrocytes, and the like. "Cultured cell" may include one or more of MM.1S, U266, RPMI8226, DOX40, MM.1R, INA-6, LR5, primary and established cancer cell lines, primary and established normal cell lines.

As used herein, "phenotype of a cell," "phenotype of the subject," or "symptoms of the subject" refer to outward, physical manifestation or characteristic of the cell or subject, e.g., an observable manifestation or observable attribute. The attribute or manifestation may be structural, biochemical, physiological and/or behavioural. The phenotype may be a biological or clinical sequelae in response to a particular treatment or compound. Phenotypes include, anemia, thrombocytopenia, neutropenia, osteolytic lesions, bone pain, immunodeficiency, renal insufficiency, hypercalcemia, aneuploidy of mature plasma cells, percentage of malignant cells, acetylation state of tubulin, apoptosis of mature plasma cells, level of aggresomes in mature plasma cells, HDAC6 ubiquitination in mature plasma cells, HDAC6 association with dynein in mature plasma cells, cellular levels of ubiquintinated proteins in mature plasma cells, level of caspase-8 in mature plasma cells, level of PARP in mature plasma cells, thymidine uptake in mature plasma cells, dilated ER cisternae, aggregation of mature plasma cells, deposits of immunoglobulins in mature plasma cells, acetylation state of non-histone proteins, global ubiquitination state of the cellular proteins, state of cell cycle regulation, necrosis, markers of apoptosis, apoptosis state, Russell body formation, Cystic Fibrosis transmembrane protein receptor state, and modulation of cellular protein deposits, or global acetylation state of cellular and extracellular proteins.

"Modulation of the phenotype," refers to a change or alteration in the observable phenotype. The modulation may be, for example, an increase or decrease in the characteristic, or the appearance or disappearance of a particular phenotype.

"Favorable clinical response," refers to any advantageous or beneficial change in the phenotype of the subject. For example, decreased symptoms or measurable indications of the disease. Favorable clinical responses may also be a total amelioration of the disease state.

"Protein degradation inhibitor" is a compound or other therapeutic that is capable of reducing protein degradation in a cell or subject. Protein degradation inhibitors may, for example inhibit HDAC6. Examples include histone acetylase inhibitors (14, 15), tubacin, bortezomib, velcade, SAHA, R115777 FTI, $^{166}$Holminun-DOTMP, arsenic trioxide, 17-AAG, or compounds described herein. Protein degradation inhibitors may directly or indirectly inhibit HDAC6 enzymatic activity, and without wishing to be bound by any particular scientific theory, to thereby inhibit aggresome mediated protein degradation. Protein degradation inhibitors may also inhibit HSP90, transcription factors, or other chaperone proteins. Protein degradation inhibitors may alternately inhibit the C-terminal acetylation activity of HDAC6, thereby inhibiting aggresome mediated protein degradation. Protein degradation inhibitors may also be aggresome inhibitors. Examples of aggresome inhibitors include tubacin, scriptade, or other compounds described herein. Protein degradation inhibitors may also inhibit, either directly or indirectly, the proteasome. Examples of proteasome inhibitors include bortezomib, MG132, sapojargon, or NPI-0052.

Additional protein degradation inhibitors include peptides derived from HDAC6 sufficient to modulate a phenotype of a cell. For example, peptides derived from the C-terminal peptide of HDAC6. Histone deacetylase inhibitors (HDI) include compounds such as hydroxamates, non-selectively targeting nearly all human HDAC enzymes (14,15).

Determination of a therapeutically effective anti-proliferative amount or a prophylactically effective anti-proliferative amount of the compound of the invention, can be readily made by the physician or veterinarian (the "attending clinician"), as one skilled in the art, by the use of known techniques and by observing results obtained under analogous circumstances. The dosages may be varied depending upon the requirements of the subject in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific disease state; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of protein degradation disorders in animals, e.g., dogs, chickens, and rodents, may also be useful in treatment of the disorders in humans. Those skilled in the art of treating the disorders in humans will know, based upon the data obtained in animal studies, the dosage and route of administration of the compound to humans. In general, the dosage and route of administration in humans is expected to be similar to that in animals.

The identification of those patients who are in need of prophylactic treatment for proliferative disease states is well within the ability and knowledge of one skilled in the art. Certain of the methods for identification of patients which are at risk of developing proliferative disease states which can be treated by the subject method are appreciated in the medical arts, such as family history, the presence of risk factors associated with the development of that disease state in the subject patient. A clinician skilled in the art can readily identify such candidate patients, by the use of, for example, clinical tests, physical examination and medical/family history.

A method of assessing the efficacy of an anti-proliferative treatment in a subject includes determining a pre-treatment phenotype by methods well known in the art and then administering a therapeutically effective amount of a protein degradation inhibitor. After an appropriate period of time after the administration of the compound, e.g., 2 hours, 4 hours, 8 hours, 12 hours, or 72 hours, the phenotype is determined again. The modulation of the phenotype indicates efficacy of an treatment. The phenotype may be determined periodically throughout treatment. For example, the phenotype may be checked every few hours, days or weeks to assess the further efficacy of the treatment. Phenotypes and methods of determining phenotypes are discussed infra. The methods described may be used to screen or select patients that may benefit from treatment with protein degradation inhibitors.

As used herein, "obtaining a biological sample from a subject," includes obtaining a sample for use in the methods described herein. Biological samples are described herein.

In another aspect, a compound or other therapeutic of the invention is packaged in a therapeutically effective amount with a pharmaceutically acceptable carrier or diluent. The composition may be formulated for treating a subject suffering from or susceptible to a protein degradation disorder, and packaged with instructions to treat a subject suffering from or susceptible to a protein degradation disorder.

In yet another aspect, a method of treating a subject suffering from or susceptible to a protein degradation disorder comprising administering to a subject in need thereof a therapeutically effective amount of protein degradation inhibitor, to thereby treat the subject suffering from or susceptible to a protein degradation disorder. Upon identification of a subject suffering from or susceptible to a protein degradation disorder, for example, myeloma, an protein degradation inhibitor is administered.

Methods of inhibiting protein degradation in a protein degradation disorder, comprise contacting cells or subjects with a protein degradation inhibitor. The contacting may be by addition of the inhibitor to a fluid surrounding the cells, for example, to the growth media in which the cells are living or existing. The contacting may also be by directly contacting the inhibitor to the cells. Alternately, the contacting may be by passage of the inhibitor through a subject, for example, after administration, depending on the route of administration, the inhibitor may travel through the digestive tract or the blood stream or may be applied or administered directly to cells in need of the inhibition.

In another aspect, methods of inhibiting a protein degradation disorder in a subject comprise administering an effective amount of an inhibitor to a subject. The administration may be by any route of administering known in the pharmaceutical arts. The subject may have a protein degradation disorder, may be at risk of developing a protein degradation disorder, or may need prophylactic treatment.

In one aspect, the method of treating a subject with or susceptible to a protein degradation disorder comprises contacting the cell with a protein degradation inhibitor. The contacting may be by addition of the inhibitor to a fluid surrounding the cells, for example, to the growth media in which the cells are living or existing. The contacting may also be by directly contacting the inhibitor to the cells. Alternately, the contacting may be by passage of the inhibitor through a subject, for example, after administration, depending on the route of administration, the inhibitor may travel through the digestive tract or the blood stream or may be applied or administered directly to cells in need of the treatment.

In one aspect, methods of assessing the efficacy of an anti-proliferative treatment in a subject comprise determining one or more pre-treatment phenotypes, administering a therapeutically effective amount of a protein degradation inhibitor to the subject, and determining the one or more phenotypes after an initial period of treatment with an inhibitor, wherein the modulation of the phenotype indicates efficacy of an treatment.

Efficacy of a treatment may be measured for example, as an increase, decrease, appearance or disappearance of a phenotype. Efficacy may also be measured in terms of a reduction of symptoms associated with protein degradation disorder, a stabilization of symptoms, or a cessation of symptoms associated with a protein degradation disorder.

Phenotypes include, biological or clinical sequelae in response to a particular treatment or compound. For example, anemia, thrombocytopenia, neutropenia, osteolytic lesions, bone pain, immunodeficiency, renal insufficiency, hypercalcemia, aneuploidy of mature plasma cells, percentage of malignant cells, acetylation state of tubulin, apoptosis of mature plasma cells, level of aggresomes in mature plasma cells, HDAC6 ubiquitination in mature plasma cells, HDAC6 association with dynein in mature plasma cells, cellular levels of ubiquintinated proteins in mature plasma cells, level of caspase-8 in mature plasma cells, level of PARP in mature plasma cells, thymidine uptake in mature plasma cells, dilated ER cisternae, aggregation of mature plasma cells, deposits of immunoglobulins in mature plasma cells, acetylation state of non-histone proteins, global ubiquitination state of the cellular proteins, state of cell cycle regulation, necrosis, markers of apoptosis, apoptosis state, Russell body formation, Cystic Fibrosis transmembrane protein receptor state, and modulation of cellular protein deposits, or global acetylation state of cellular and extracellular proteins. Phenotypes may be observed or measured, for example, visually, by diagnosis, or by an assay as described herein.

In certain embodiments, a reduction in certain phenotypes descried herein indicates efficacy. However, depending on the mechanism of action of the inhibitor, the phenotype may become more severe for a period of time followed by a decrease. This would also indicate efficacy of treatment.

In one embodiment, the phenotype may be determined one or more times prior to treatment to establish a base-line phenotype. The phenotype may also be determined one or more times during and/or after treatment. The phenotype may alternatively be determined one or more times between treatments.

Compounds of the Invention

In another aspect, the invention provides compounds, e.g., compounds useful in the methods, pharmaceutical compositions, kits, and packaged compositions of the invention. The compounds useful in the invention are inhibitors histone deacetylases and/or tubulin deacetylases. Useful compounds are described in U.S. patent applications, U.S. Ser. No. 60/773,510, filed Feb. 14, 2006; U.S. Ser. No. 60/773,172, filed Feb. 14, 2006; U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference.

Compounds useful in the present invention include compounds of the formula:

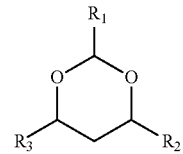

wherein
  $R_1$ is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —$SR_A$; —$SOR_A$; —$SO_2R_A$; —N($R_A$)$_2$; —NHC(O)$R_A$; or —C($R_A$)$_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
  $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —C(=O)$R_B$; —$CO_2R_B$; —CN; —SCN; —$SR_B$; —$SOR_B$; —$SO_2R_B$; —$NO_2$; —N($R_B$)$_2$; —NHC(O)$R_B$; or —C($R_B$)$_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and
  $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —C(=O)$R_C$; —$CO_2R_C$; —CN; —SCN; —$SR_C$; —$SOR_C$; —$SO_2R_C$; —$NO_2$; —N($R_C$)$_2$;

—NHC(O)$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable salts and derivatives thereof. In general, $R_1$ comprises a metal chelating functional group (e.g., hydroxyamic acids, thiols, carboxlic acids, ortho-aminoanilides, etc.). The metal chelating group is thought to bind the active site $Zn^{+2}$ ion of deacetylase enzymes. In certain embodiments, $R_2$ is a substituted or unsubstituted heteroaliphatic moiety (e.g., a heteroaliphatic moiety substituted with a heteroaryl ring, which may be optionally substituted). In certain embodiments, $R_3$ is a substituted or unsubstituted aromatic ring system (e.g., a substituted or unsubstituted phenyl).

Many compounds described above have been previously disclosed in U.S. patent applications, U.S. Ser. No. 60/289, 850, filed May 9, 2001; U.S. Ser. No. 10/144,316, filed May 9, 2002; and U.S. Ser. No. 10/621,276, filed Jul. 17, 2003; each of which is incorporated herein by reference. The present invention includes specific compounds and subclasses of compounds within this class. These subclasses and specific compounds within the class have been found to be particularly useful in the treatment of multiple myeloma by inhibiting HDAC6 known to play a role in the degradation of proteins by the aggresome. Methods of treating cancer (e.g., multiple myeloma, breast cancer, non-Hodgkin's lymphoma, ovarian cancer, acute myelogenous leukemia), protein degradation disorders (e.g., multiple myeloma, neurodegenerative disorders), protein deposition disorders (e.g., neurogenerative disorders), and proliferative disorders (e.g., diabetic retinopathy, inflammatory diseases, angiogenesis, infectious diseases) as well as pharmaceutical compositions and kits for treatment of these disorders using the inventive compounds are also provided. The present invention also provides new synthetic methods for preparing compounds of the invention.

In certain embodiments, the compound is of one of the formulae below with the stereochemistry as shown:

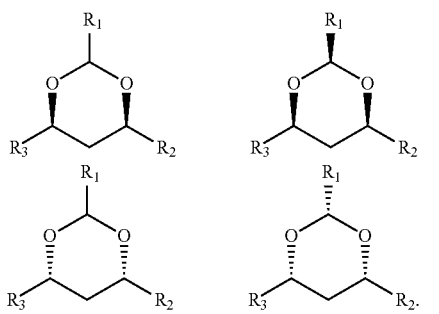

In certain embodiments, $R_3$ is a substituted or unsubstituted aryl moiety. In certain embodiments, $R_3$ is a substituted or unsubstituted heteroaromatic moiety. In certain embodiments, $R_3$ is a monocyclic moiety. In other embodiments, $R_3$ is a bicyclic moiety. In yet other embodiments, $R_3$ is a tricyclic moiety. In yet other embodiments, $R_3$ is a polycyclic moiety. In certain embodiments, $R_3$ is a substituted or unsubstituted five- or six-membered aromatic or heteroaromatic moiety. In certain embodiments, $R_3$ is a substituted or unsubstituted six-membered aromatic or heteroaromatic moiety. In certain embodiments, $R_3$ is a substituted or unsubstituted six-membered aromatic moiety. In certain embodiments, $R_3$ is a substituted or unsubstituted six-membered heteroaromatic moiety. In certain embodiments, $R_3$ is a substituted or unsubstituted non-aromatic carbocyclic or heterocyclic moiety.

In certain embodiments, the invention provides compounds of the formula:

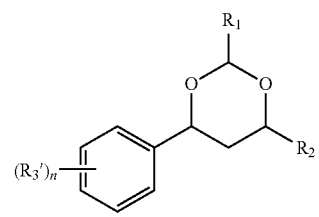

wherein $R_1$ and $R_2$ are defined as above;

n is an integer between 1 and 5, inclusive; and each occurrence of $R_3'$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —C(=O)$R_C$; —$CO_2R_C$; —CN; —SCN; —$SR_C$; —$SOR_C$; —$SO_2R_C$; —$NO_2$; —N($R_C$)$_2$; —NHC(O)$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, n is 0, and the phenyl ring is unsubstituted.

In other embodiments, n is 1, and the compounds are one of the formulae:

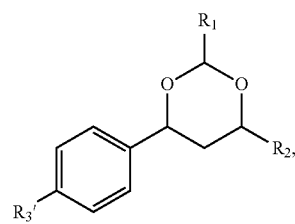

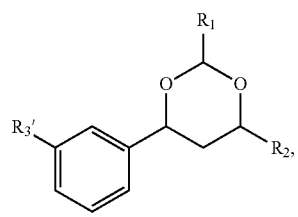

or

-continued

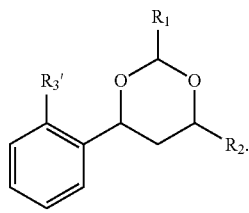

In certain embodiments, the para-substitution pattern is preferred. In other embodiments, the meta-substitution pattern is preferred. And in yet other embodiments, the ortho-substitution pattern is preferred. In certain embodiments, $R_3$ is not

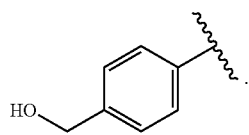

In other embodiments, n is 2. Compounds of the invention include compounds of one of the formulae:

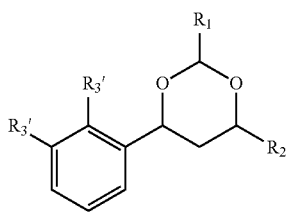

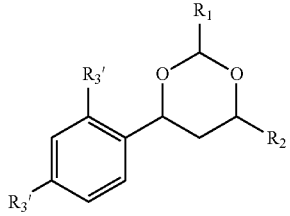

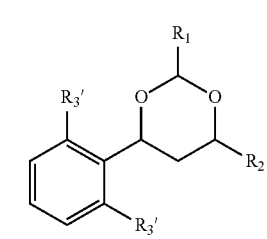

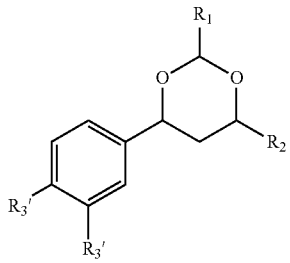

-continued

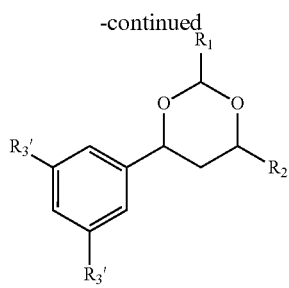

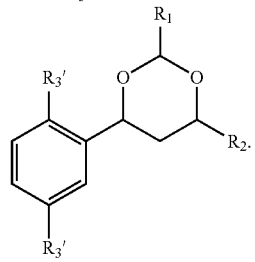

In other embodiments, n is 3. In still other embodiments, n is 4, and in other embodiments, n is 5.

In certain embodiments, $R_3'$ is halogen, hydroxyl, protected hydroxyl, alkoxy, amino, alkylamino, dialkylamino, —$NO_2$, $C_1$-$C_6$ alkyl, $C_1$-$C_6$ alkenyl, $C_1$-$C_6$ alkynyl, or acyl. In certain embodiments, $R_3'$ is —$NO_2$. In certain embodiments, $R_3'$ is —$CH_2OH$. In certain embodiments, $R_3'$ is —$NH_2$. In certain embodiments, $R_3'$ is —H. In other embodiments, $R_3'$ is —OH. In other embodiments, $R_3'$ is —CN. In yet other embodiments, $R_3'$ is —SCN. In still other embodiments, $R_3'$ is acyl. In certain embodiments, $R_3'$ is acetyl. In other embodiments, $R_3'$ is —F. In other embodiments, $R_3'$ is —Cl. In other embodiments, $R_3'$ is —Br. In other embodiments, $R_3'$ is —I. In other embodiments, $R_3'$ is methyl, ethyl, n-propyl, iso-propyl, n-butyl, tert-butyl, or iso-butyl. In certain embodiments, $R_3'$ is vinyl. In certain embodiments, $R_3'$ is halogen-substituted alkyl (e.g., trifluoromethyl). In certain embodiments, $R_3'$ is methoxy, ethyoxy, propoxy, butoxy, or pentoxy.

In certain compounds of this class, $R_2$ is a substituted or unsubstituted aliphatic group. In other embodiments, $R_2$ is a substituted or unsubstituted heteroaliphatic group. In certain embodiments, $R_2$ is a heteroaliphatic group substituted with an aryl or heteroaryl group, which may optionally be substituted. In certain embodiments, $R_2$ is a heteroaliphatic group substituted with a heteroaryl group, which is optionally substituted. In certain embodiments, $R_2$ is a heteroaliphatic group substituted with a heteroaryl group, which is substituted.

In certain embodiments, $R_2$ is of the formula:

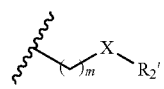

wherein m is an integer between 0 and 8, inclusive; preferably, between 1 and 6, inclusive;

X is O, S, $CH_2$, NH, or $NR_2'$; and $R_2'$ is aliphatic, heteroaliphatic, acyl, substituted or unsubstituted aryl, or substituted or unsubstituted heteroaryl.

In certain embodiments, m is 1, 2 or 3. In certain embodiments, m is 1. In certain embodiments, X is O. In other embodiments, X is S. In certain embodiments, X is NH. In other embodiments, X is CH$_2$. In certain embodiments, R$_2$' is C$_1$-C$_6$ alkyl. In certain embodiments, R$_2$' is a substituted heteroaryl moiety. In other embodiments, R$_2$' is an unsubstituted heteroaryl moiety. In certain particular embodiments, R$_2$' is a substituted oxazolyl moiety. In other embodiments, R$_2$' is a substituted thiazolyl moiety. In yet other embodiments, R$_2$' is a substituted imidazolyl moiety. In certain embodiments, R$_2$ is

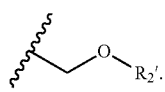

In other embodiments, R$_2$ is

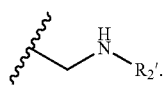

In yet other embodiments, R$_2$ is

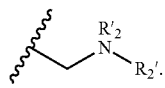

wherein the two R$_2$' moieties may together form a heterocyclic group. In yet other embodiments, R$_2$ is

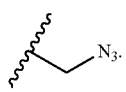

In yet other embodiments, R$_2$ is

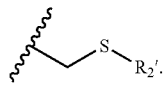

In yet other embodiments, R$_2$ is

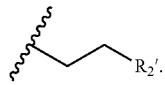

In certain embodiments, R$_2$ is

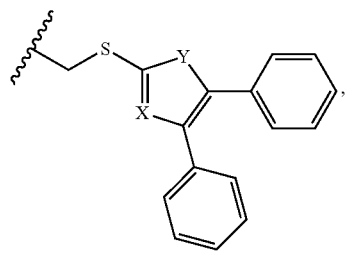

wherein X is N and Y is NH, S, or O. In certain embodiments, R$_2$ is selected from one of the following:

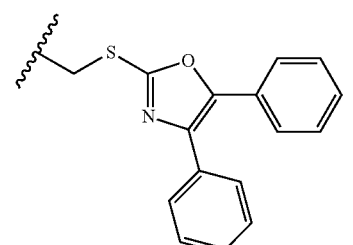

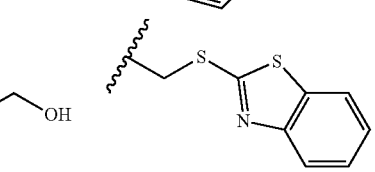

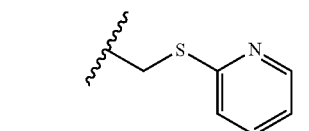

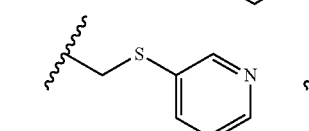

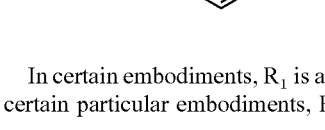

In certain embodiments, R$_1$ is a substituted phenyl ring. In certain particular embodiments, R$_1$ is of the formula:

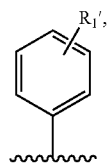

wherein R$_1$' is

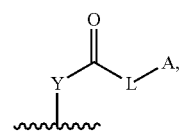

wherein Y is NH or O; L is a linker moiety; and A comprises a functional group that inhibits histone or tubulin deacetylase.

In certain embodiments, $R_1$ is of the formula:

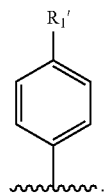

In other embodiments, $R_1$ is of the formula:

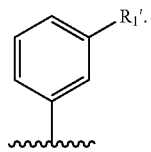

In certain embodiments, Y is NH. In other embodiments, Y is O. In certain embodiments, L is a substituted or unsubstituted, cyclic or acyclic, branched or unbranched aliphatic moiety; a substituted or unsubstituted, cyclic or acyclic, branched or unbranched heteroaliphatic moiety; a substituted or unsubstituted aryl moiety; a substituted or unsubstituted heteroaryl moiety. In certain embodiments, L is a substituted or unsubstituted, cyclic or acyclic, branched or unbranched aliphatic moiety. In certain embodiments, L is $C_1$-$C_{20}$ alkylidene, preferably $C_1$ to $C_{12}$ alkylidene, more preferably $C_4$-$C_7$ alkylidene. In certain embodiments, L is $C_1$-$C_{20}$ alkenylidene, preferably $C_1$ to $C_{12}$ alkenylidene, more preferably $C_4$-$C_7$ alkenylidene. In certain embodiments, L is $C_1$-$C_{20}$ alkynylidene, preferably $C_1$ to $C_{12}$ alkynylidene, more preferably $C_4$-$C_7$ alkynylidene. In certain embodiments, L is a a substituted or unsubstituted, cyclic or acyclic, branched or unbranched heteroaliphatic moiety. In certain embodiments, L comprises a cyclic ring system, wherein the rings may be aryl, heteroaryl, non-aromatic carbocyclic, or non-aromatic heterocyclic. In still other embodiments, L comprises a substituted or unsubstituted heteroaryl moiety. In certain particular embodiments, L comprises a phenyl ring. In certain embodiments, L comprises multiple phenyl rings (e.g., one, two, three, or four phenyl rings).

In certain embodiments, L is

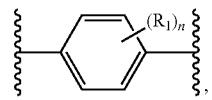

wherein n is an integer between 1 and 4, inclusive; preferably, between 1 and 3, inclusive; more preferably, 1 or 2; and $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —N($R_A$)$_2$; —NH$R_A$; —NHC(O)$R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, L is

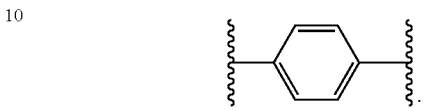

In certain embodiments, L is

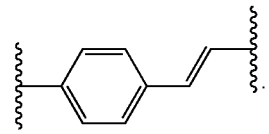

In certain embodiments, L is an unbranched, unsubstituted, acyclic alkyl chain. In certain embodiments, L is

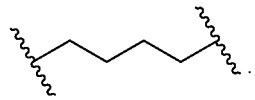 [SMILES: *CCCC*]

In other embodiments, L is

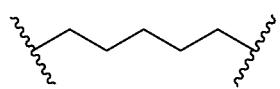

In certain other embodiments, L is

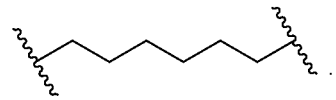 [SMILES: *CCCCCC*]

In other embodiments, L is

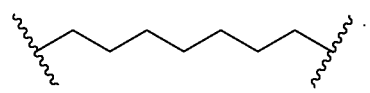 [SMILES: *CCCCCCC*]

In yet other embodiments, L is

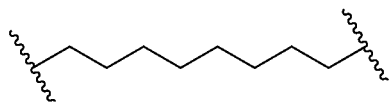

In certain embodiments, L is a substituted, acyclic aliphatic chain. In certain embodiments, L is

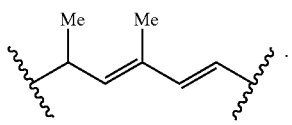 [SMILES: */C=C/C(C)=C/C(*)C]

In certain embodiments, L is an unbranched, unsubstituted, acyclic heteroaliphatic chain. In certain particular embodiments, L is

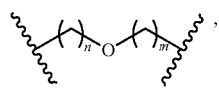

wherein n is an integer between 0 and 10, inclusive; preferably, between 0 and 5, inclusive; and m is an integer between 0 and 10, inclusive; preferably, between 0 and 5, inclusive. In certain particular embodiments, L is

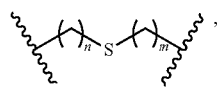

wherein n is an integer between 0 and 10, inclusive; preferably, between 0 and 5, inclusive; and m is an integer between 0 and 10, inclusive; preferably, between 0 and 5, inclusive. In certain particular embodiments, L is

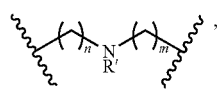

wherein n is an integer between 0 and 10, inclusive; preferably, between 0 and 5, inclusive; m is an integer between 0 and 10, inclusive; preferably, between 0 and 5, inclusive; and R' is hydrogen, $C_1$-$C_6$ aliphatic, heteroaliphatic, aryl, heteroaryl, or acyl. In certain particular embodiments, L is

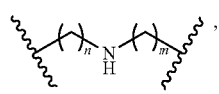

wherein n is an integer between 0 and 10, inclusive; preferably, between 0 and 5, inclusive; and m is an integer between 0 and 10, inclusive; preferably, between 0 and 5, inclusive. In certain embodiments, A comprises a metal chelating functional group. For example, A comprises a $Zn^{2+}$ chelating group. In certain embodiments, A comprises a functional group selected group consisting of:

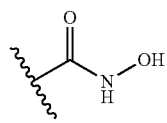

-continued

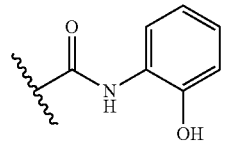

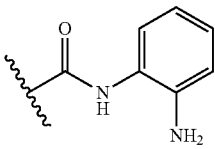
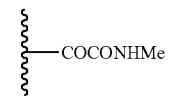

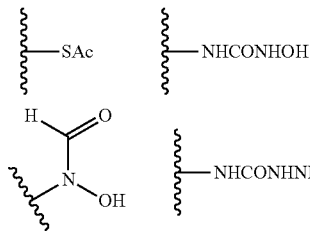
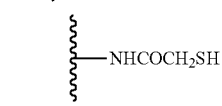

In certain embodiments, A comprises hydroxamic acid

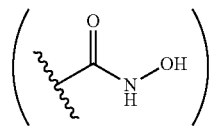

or a salt thereof. In other embodiments, A comprises the formula:

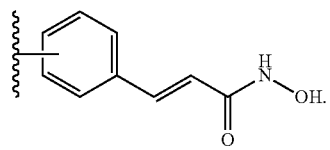

In certain particular embodiments, A comprises the formula:

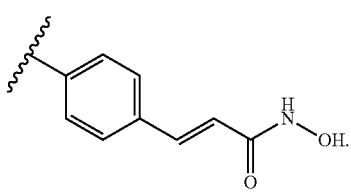 [SMILES: *c1ccc(/C=C/C(=O)NO)cc1]

In other embodiments, A comprises a carboxylic acid (—$CO_2H$). In other embodiments, A comprises an o-amino-anilide

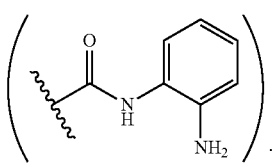

In other embodiments, A comprises an o-hydroxyanilide

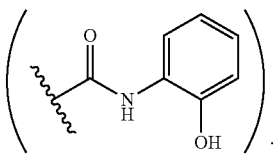

In yet other embodiments, A comprises a thiol (—SH). In certain embodiments, $R_1'$ is

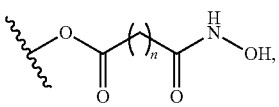

wherein n is an integer between 0 and 15, inclusive; preferably, between 0 and 10, inclusive; more preferably, between 1 and 8, inclusive; even more preferably, 4, 5, 6, 7, or 8. In certain embodiments, $R_1'$ is

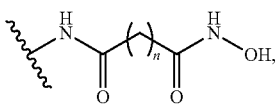

wherein n is an integer between 0 and 15, inclusive; preferably, between 0 and 10, inclusive; more preferably, between 1 and 8, inclusive; even more preferably, 4, 5, 6, 7, or 8. In certain embodiments, $R_1'$ is

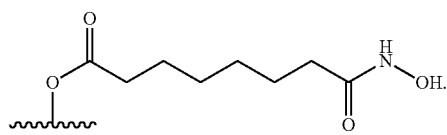 [SMILES: *OC(=O)CCCCCCC(=O)NO]

In other particular embodiments, $R_1'$ is

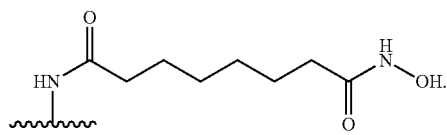 [SMILES: *NC(=O)CCCCCCC(=O)NO]

Certain compounds useful in the present invention include compounds of the formula:

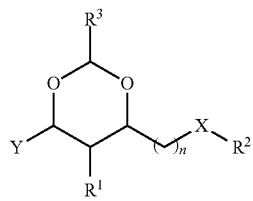

and pharmaceutically acceptable derivatives thereof;
wherein $R^1$ is hydrogen, or an aliphatic, alicyclic, heteroaliphatic, heterocyclic, aromatic or heteroaromatic moiety;

n is 1-5;

$R^2$ is hydrogen, a protecting group, or an aliphatic, alicyclic, heteroaliphatic, heterocyclic, aromatic or heteroaromatic moiety;

X is —O—, —C($R^{2A}$)$_2$—, —S—, or —N$R^{2A}$—, wherein $R^{2A}$ is hydrogen, a protecting group, or an aliphatic, alicyclic, heteroaliphatic, heterocyclic, aromatic or heteroaromatic moiety;

or wherein two or more occurrences of $R^2$ and $R^{2A}$, taken together, form an alicyclic or heterocyclic moiety, or an aryl or heteroaryl moiety;

$R^3$ is an aliphatic, alicyclic, heteroaliphatic, heterocyclic, aromatic or heteroaromatic moiety; and Y is hydrogen or an aliphatic, alicyclic, heteroaliphatic, heterocyclic, aromatic or heteroaromatic moiety.

In certain embodiments, a compound according to the invention can be represented by formula:

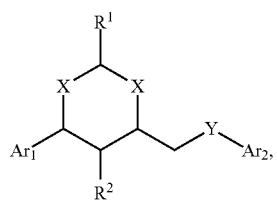

wherein
each X is independently O, S, CH$_2$, or NR$^3$;
Y is O, S, CH$_2$, or NR$^4$;
Ar$_1$ and Ar$_2$ are each independently an aryl group;
R$^1$ is a lower alkyl group or an aryl group;
R$^2$ is hydrogen, a lower alkyl group or an aryl group; and
R$^3$ and R$^4$ are each independently hydrogen, a lower alkyl group, an aryl group, an alkylcarbonyl, an alkoxycarbonyl group, or an aminocarbonyl group. In certain preferred embodiments, X is for each occurrence O, S, or CH$_2$, more preferably O or S, and still more preferably O. In certain preferred embodiments, Y is S. In certain preferred embodiments, Ar$_1$ is phenyl or substituted phenyl, particularly 4-hydromethylphenyl. In certain preferred embodiments, Ar$_2$ is heteroaryl, more preferably optionally substituted oxazolyl, still more preferably phenyl-substituted oxazolyl, and most preferably 4,5-diphenyl-oxazol-2-yl. In certain preferred embodiments, R$^1$ is phenyl or substituted phenyl, more preferably 4-aminosubstituted phenyl or 4-amidosubstituted phenyl; in more preferred embodiments, R$^1$ is a phenyl group substituted at the 4-position with an amido group bearing an alkylene moiety in which the alkylene chain has between four and eight carbon atoms (more preferably 6 carbon atoms) in the alkylene chain, and the alkylene chain preferably bears a terminal hydroxamate group (—NHOH). In certain preferred embodiments, $R_2$ is hydrogen.
Exemplary compounds include compounds of the formulae:
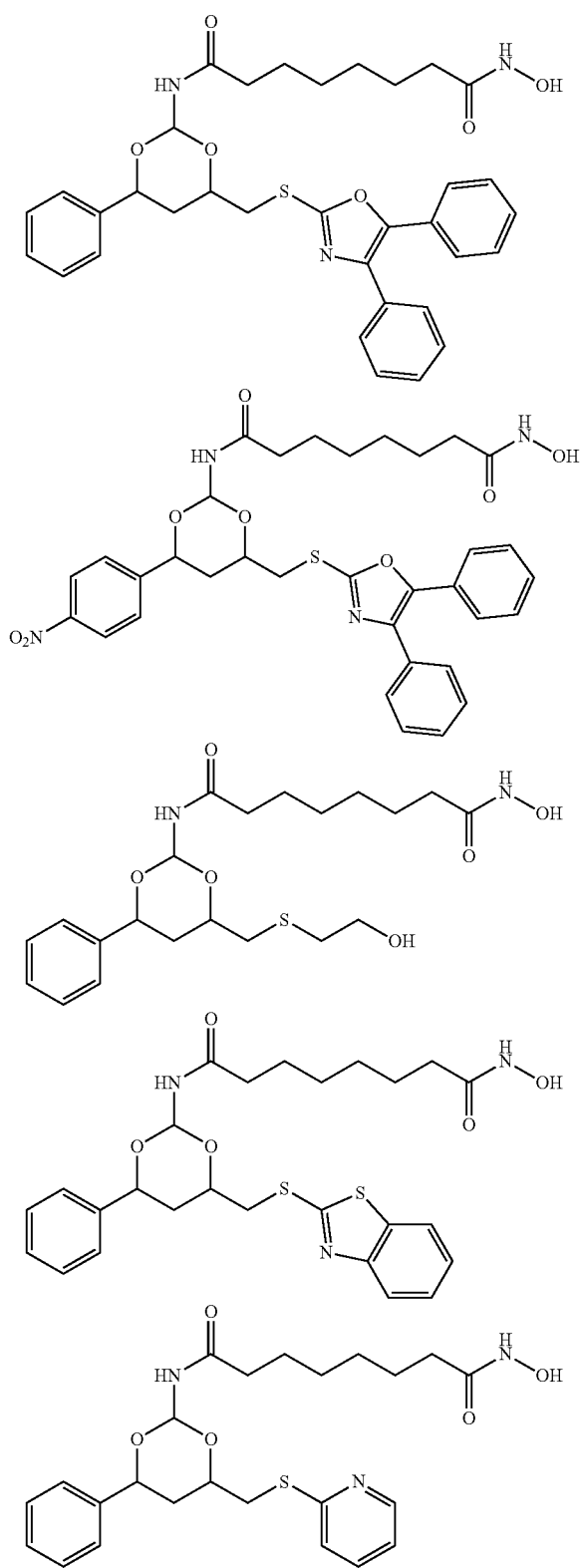
-continued
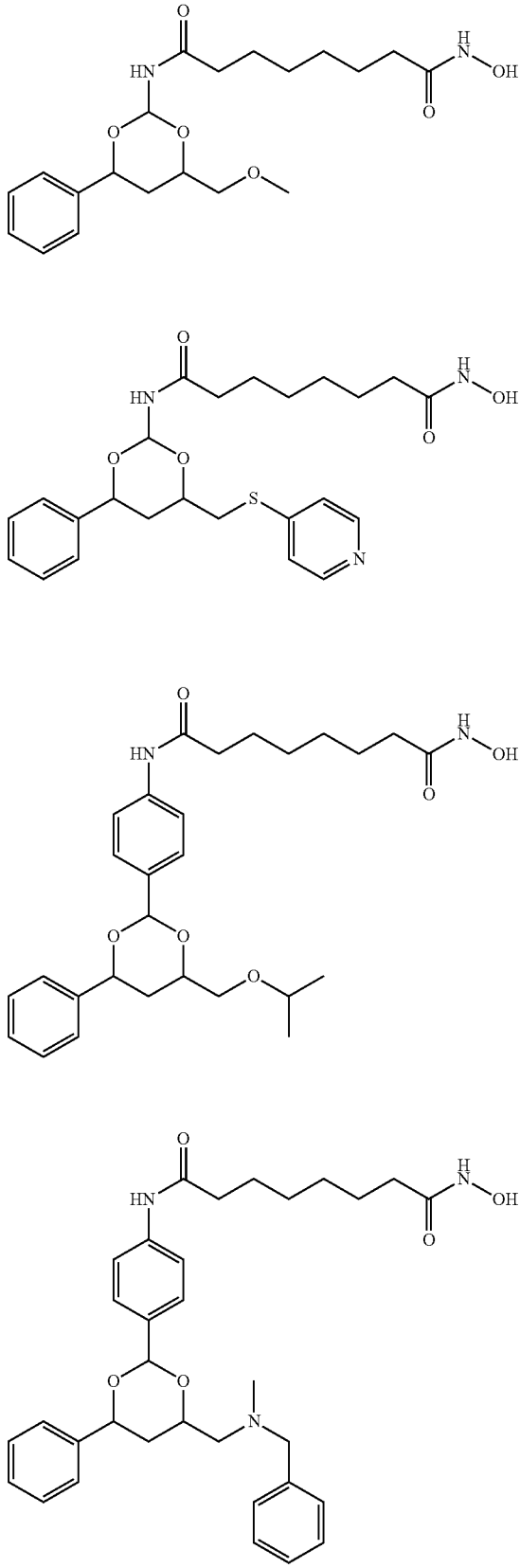

51
-continued

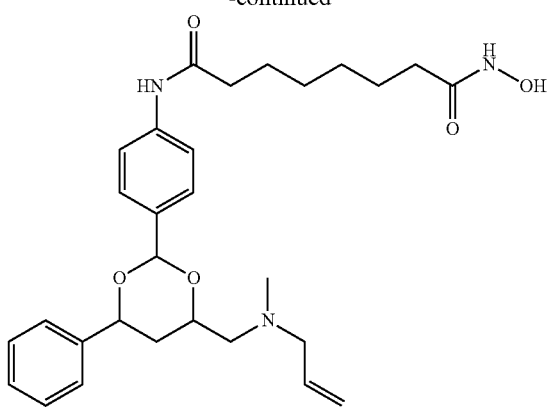

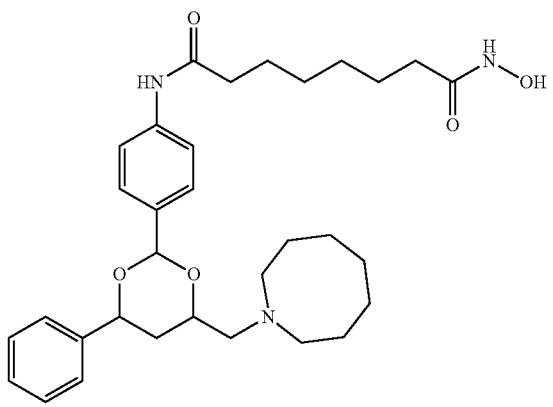

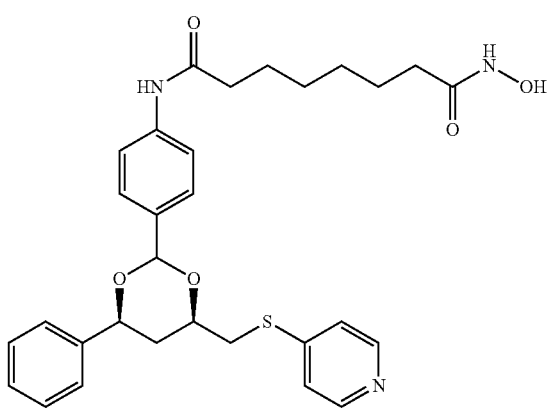

52
-continued

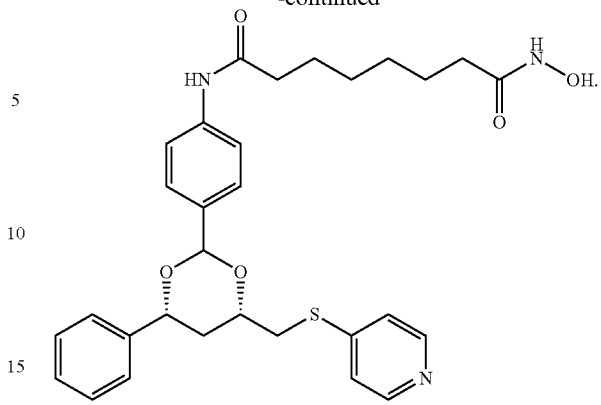

In certain embodiments, the compounds is of the formula:

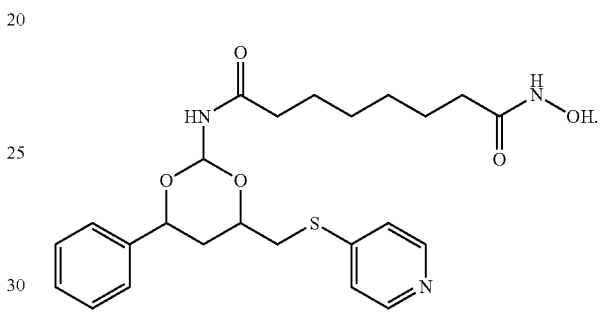

In certain embodiments, the compound is tubacin:

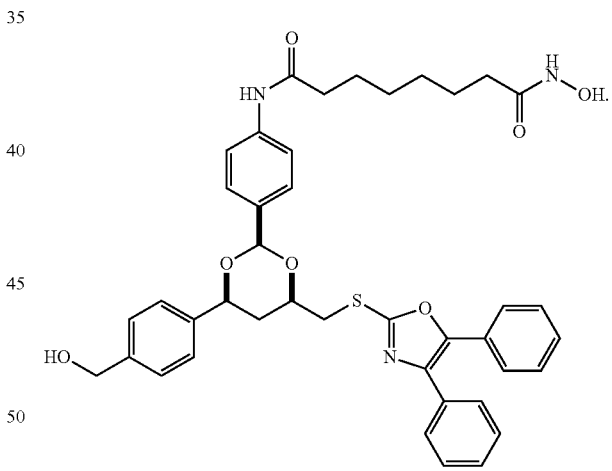

In preferred embodiments, a compound useful in the invention has one or more of the following properties: the compound is a protein degradation inhibitor; the compound is capable of inhibiting at least one histone deacetylase; the compound is capable of inhibiting HDAC6; the compound is a selective HDAC6 inhibitor; the compound binds to the poly-ubiquitin binding domain of HDAC6; the compound is capable of inducing apoptosis in cancer cells (especially multiple myeloma cells, non-Hodgkin's lymphoma (NML) cells, breast cancer cells, acute myelogeous leukemia (AML) cells); and/or the compound is capable of inhibiting aggresome formation.

Compounds useful in at least some of the methods, pharmaceutical compositions, kits and packaged compositions of the invention can be identified, e.g., according to any of the screening methods described herein.

In certain preferred embodiments, a compound of the invention comprises a metal binding moiety, preferably a zinc-binding moiety such as a hydroxamate. As noted above, certain hydroxamates are potent inhibitors of HDAC6 activity; without wishing to be bound by theory, it is believed that the potency of these hydroxamates is due, at least in part, to the ability of the compounds to bind zinc. In preferred embodiments, a compound of the invention includes at least one portion or region which can confer selectivity for a biological target implicated in the aggresome pathway, e.g., a biological target having tubulin deacetylase (TDAC) or HDAC activity, e.g., HDAC6. Thus, in certain preferred embodiments, a compound includes a zinc-binding moiety spaced from other portions of the molecule which are responsible for binding to the biological target. For example, a compound of the invention may include a linker arm or other spacing moiety capable of presenting the zinc-binding moiety in a favored orientation when another portion (or portions) of the molecule is bound to a biological target such as HDAC6. Without being bound by theory, it is believed that steric 'bulk' in the capping region of a compound can contribute to TDAC specificity, although such bulk may not be required in all cases. In addition, without being bound by theory, it is believed that allosteric site inhibition contributes to TDAC activity of certain compounds of the invention.

In certain embodiments, a compound useful in at least some of the methods, pharmaceutical compositions, kits and packaged compositions of the invention is a 1,3-dioxane HDAC inhibitor compound disclosed in U.S. Patent Publication No. US2004/0072849, which is hereby incorporated by reference in its entirety. Related compounds are described in Sternson S M et al., *Org Lett.* 2001 Dec. 27; 3(26):4239-42; Haggarty S J et al., *Chem Biol.* 2003 May; 10(5):383-96; Haggarty S J et al., *Proc Natl Acad Sci USA.* 2003 Apr. 15; 100(8):4389-94. Epub 2003 Apr. 3; and Haggarty S J et al., *Comb Chem High Throughput Screen.* 2004 November; 7(7):669-76; the contents of each of these references is hereby incorporated by reference in its entirety.

Additional compounds useful in at least some of the methods, compositions, kits, and packaged compositions of the invention include NVP-LAQ824 (a cinnamic hydroxamate having the structure shown below):

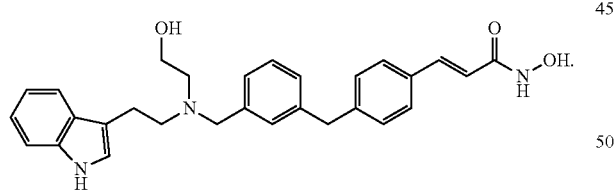

Additional compounds useful in at least some of the methods, compositions, kits, and packaged compositions of the invention include those shown below. Each of the compounds includes a hydroxamate moiety (including O-ethers of hydroxamates and cyclic hydroxamates).

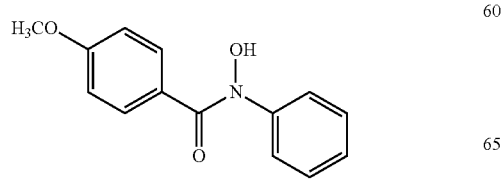

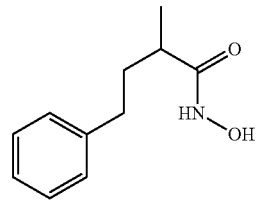

N-Hydroxy-4-methoxy-N-phenyl-benzamide N-Hydroxy-2-methyl-4-phenyl-butyramide

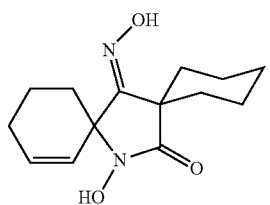 [SMILES: O=C1N(O)C2(C=CCCC2)/C(=N/O)C12CCCCC2]

14-Hydroxy-14-aza-dispiro[5.1.5.2]-pentadec-9-ene-7,15-dione 7-oxime

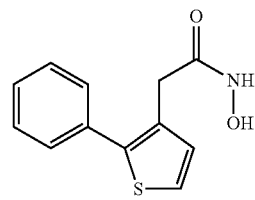 [SMILES: O=C(Cc1ccsc1-c1ccccc1)NO]

N-Hydroxy-2-(2-phenyl-thiophen-3-yl)-acetamide

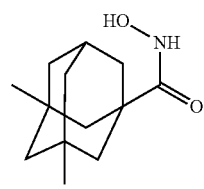 [SMILES: CC12CC3CC(C)(C1)CC(C(=O)NO)(C3)C2]

3,5-Dimethyl-adamantane-1-carboxylic acid hydroxyamide

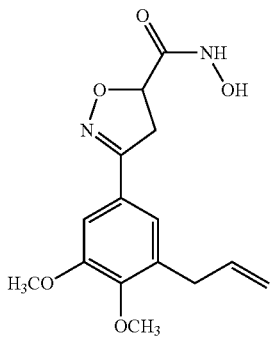 [SMILES: C=CCc1cc(C2=NOC(C(=O)NO)C2)cc(OC)c1OC]

3-(3-Allyl-4,5-dimethoxy-phenyl)-4,5-dihydro-isoxazole-5-carboxylic acid hydroxyamide

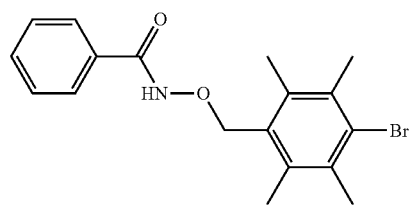 [SMILES: Cc1c(C)c(CONC(=O)c2ccccc2)c(C)c(C)c1Br]

N-(4-Bromo-2,3,5,6-tetramethyl-benzyloxy)-benzamide

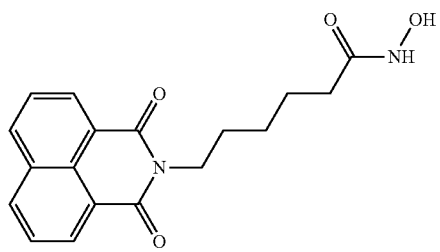 [SMILES: O=C(CCCCCN1C(=O)c2cccc3cccc(c23)C1=O)NO]

6-(1,3-Dioxo-1H,3H-benzo[de]isoquinolin-2-yl)-hexanoic acid hydroxyamide

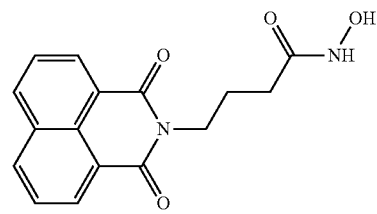 [SMILES: O=C(CCCN1C(=O)c2cccc3cccc(c23)C1=O)NO]

4-(1,3-Dioxo-1H,3H-benzo[de]isoquinolin-2-yl)-N-hydroxy-butyramide

The compounds of this invention include the compounds themselves, as well as any salt (preferably pharmaceutically acceptable salt), solvate, clathrate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Synthesis of Compounds

As described above, the present invention provides novel compounds. The synthesis of many of the compounds described herein has been described in previously filed U.S. patent applications, U.S. Ser. No. 60/289,850, filed May 9, 2001; U.S. Ser. No. 10/144,316, filed May 9, 2002; and U.S. Ser. No. 10/621,276, filed Jul. 17, 2003; each of which is incorporated herein by reference. As would be appreciated by one of skill in this art, the various reactions and synthetic schemes described in these patent applications may be used in preparing the inventive compounds.

Figure 55:
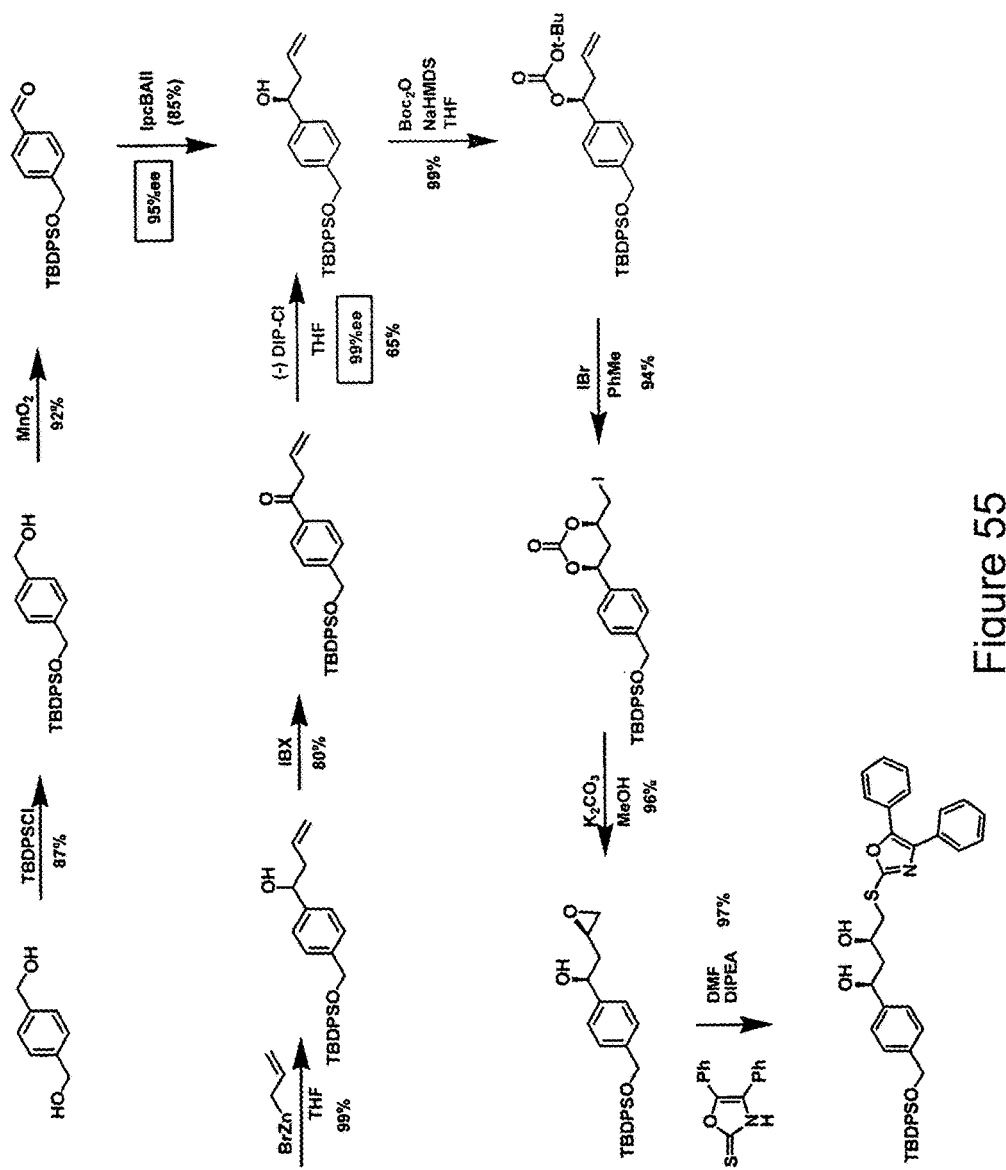
FIG. 55 shows the total synthesis of tubacin.
Figure 55:
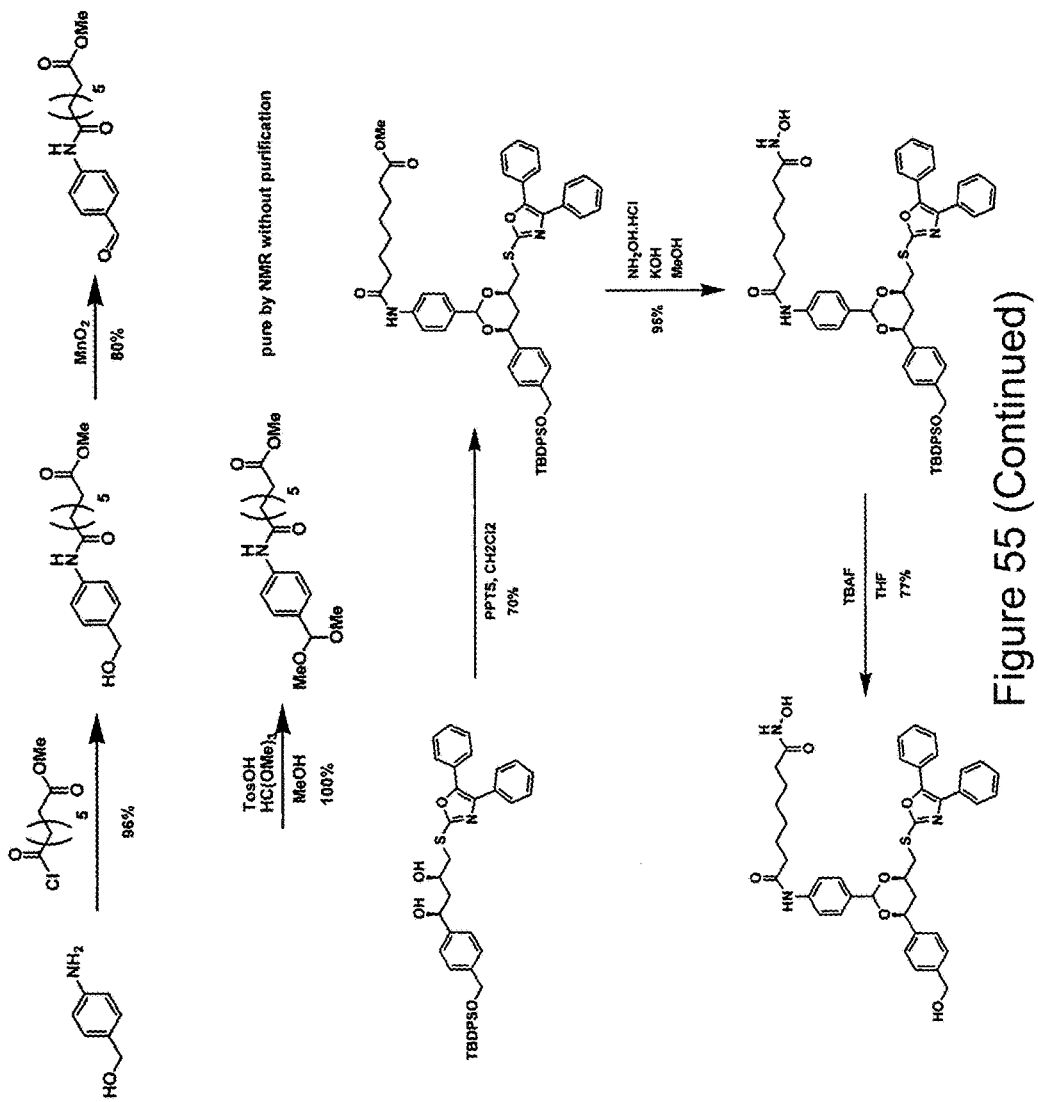
Figure 56:
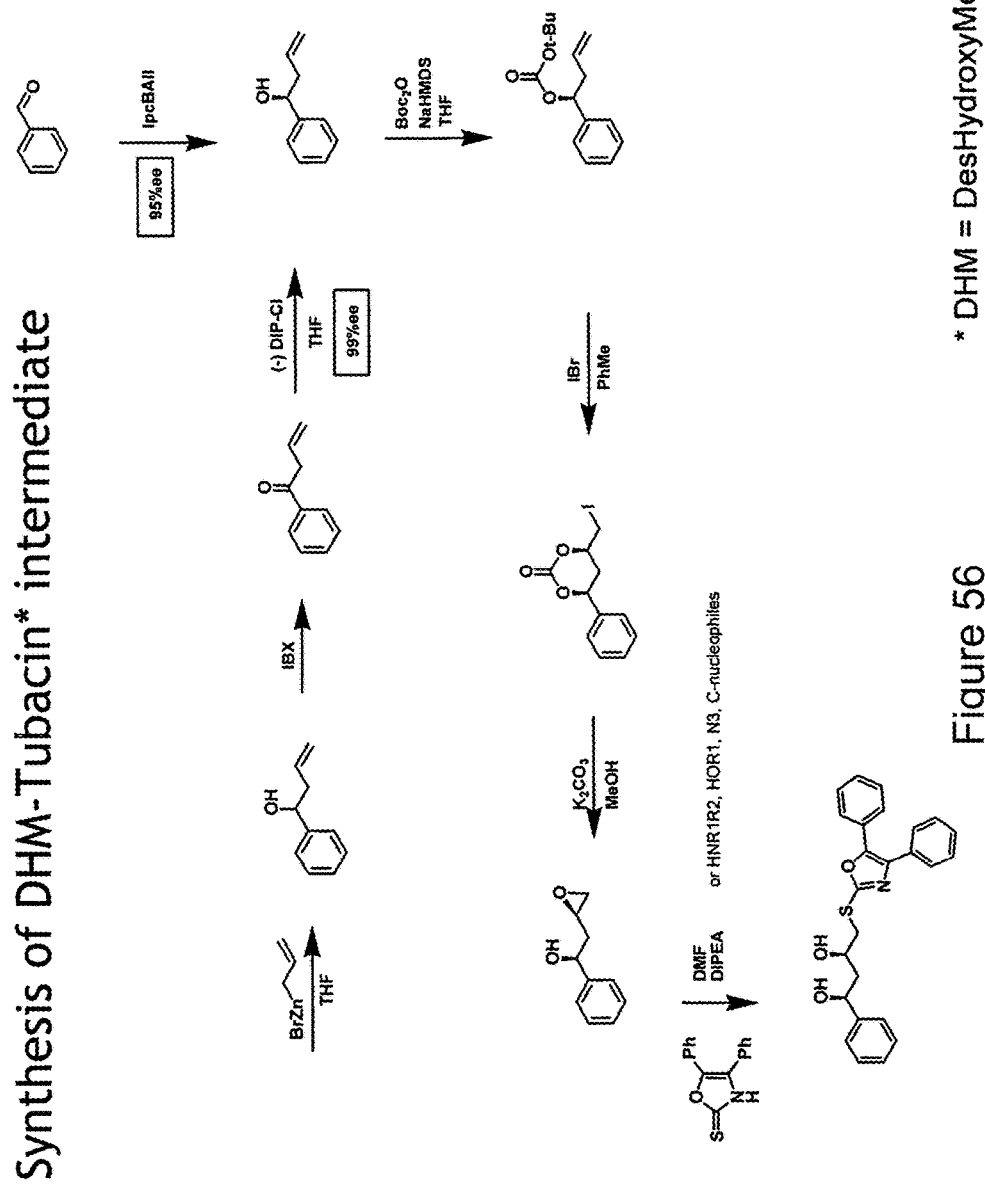
FIG. 56 is a synthetic scheme for preparing an intermediate useful in the synthesis of des(hydroxymethyl)-tubacin. Other aldehydes may be used to begin this synthesis thereby allowing for a great deal of diversity at this site.
Figure 57:
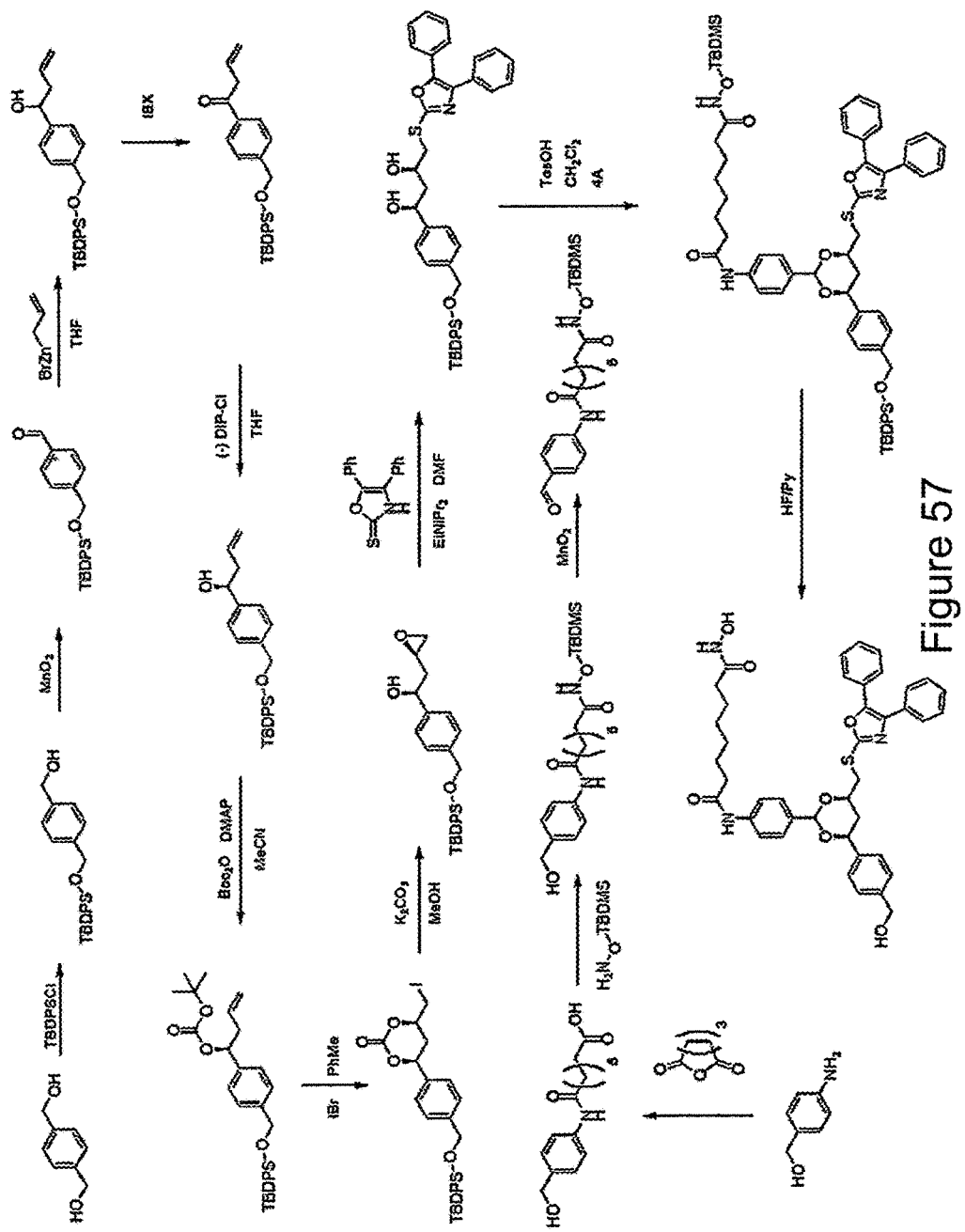
FIG. 57 shows another exemplary synthesis of tubacin.
Figure 58:
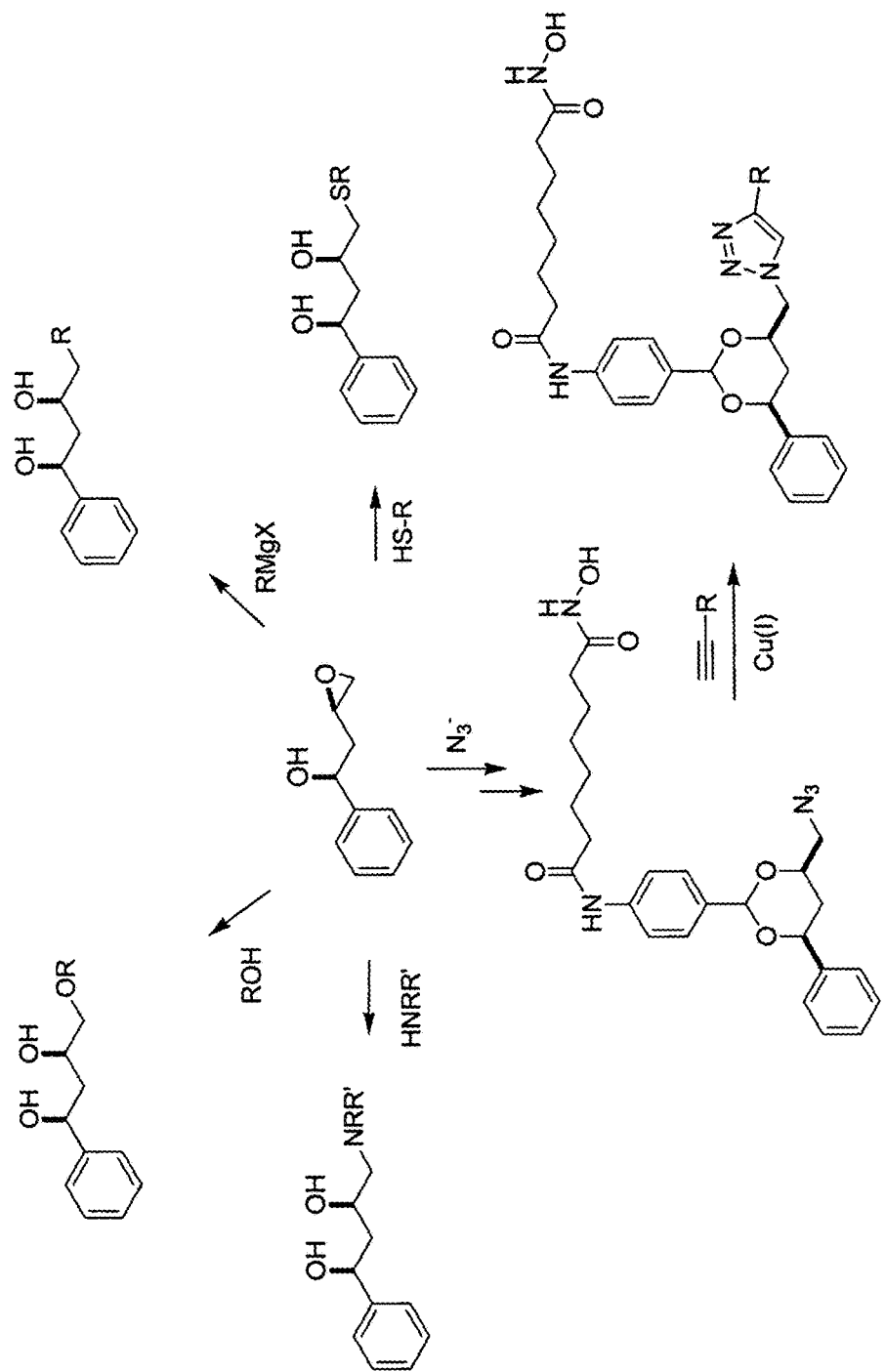
FIG. 58 shows exemplary epoxide-opening reactions useful in preparing various analogs of the inventive compounds. The scheme illustrates the use of various nucleophiles to open the epoxide group to create the diol functionality later capped to create the tubacin structure.

A methodology for preparing the inventive compounds is shown in FIG. 55.

This synthesis provides for a greater diversity of substituents at certain positions of the 1,3-dioxane core structure. In certain embodiments, the synthesis provides for a greater variety of substituents at $R_3$.

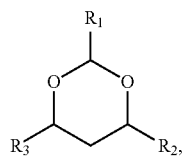

It will be appreciated that for compounds of the formula a method for the synthesis of the core structure is provided, one method comprising steps of:
providing an epoxy alcohol having the structure:

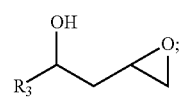

reacting the epoxy alcohol with a reagent having the structure $R_B XH$ under suitable conditions to generate a diol having the core structure:

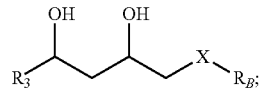

reacting the diol with a reagent having the structure $R_1 CH(OMe)_2$ under suitable conditions to generate a scaffold having the core structure:

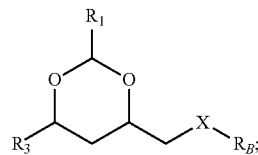

wherein $R_1$ is a substituted or unsubstituted aromatic or heteroaromatic moiety (e.g., an aryl ring substituted with a metal chelating moiety);

$R_B$ is hydrogen, a protecting group, or an aliphatic, alicyclic, heteroaliphatic, heterocyclic, aromatic or heteroaromatic moiety;

X is —O—, —C(R')$_2$—, —S—, or —NR'—, wherein R' is hydrogen, a protecting group, or an aliphatic, alicyclic, heteroaliphatic, heterocyclic, aromatic or heteroaromatic moiety; and $R^3$ is an aliphatic, alicyclic, heteroaliphatic, heterocyclic, aromatic or heteroaromatic moiety.

In certain embodiments, $R_3$ is aliphatic. In certain embodiments, $R_3$ is heteroaliphatic. In certain embodiments, $R_3$ is heterocyclic. In certain embodiments, R3 is carbocyclic. In certain embodiments, $R_3$ is aromatic. In other embodiments, $R_3$ is heteroaromatic. As would be appreciated by one of skill in the art, various substituents at $R_3$ can be introduced into the synthesis by using a different adehyde as the starting material in the synthesis. An examples of this is seen in FIG. 3 where benzaldehyde is used as the starting material. Various substituted benzaldehyde could also be used in the illustrated synthesis as well as aliphatic aldehydes, non-cyclic aldehydes, or non-aromatic aldehydes.

In certain exemplary embodiments, the epoxy alcohol has the structure:

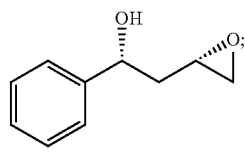 [SMILES: O[C@H](C[C@H]1CO1)c1ccccc1]

the diol has the structure:
wherein X is S or O;

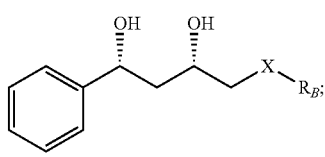

and the core scaffold has the structure:

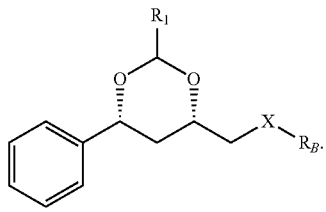

In certain other exemplary embodiments, the epoxy alcohol has the structure:

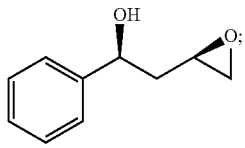 [SMILES: O[C@@H](C[C@@H]1CO1)c1ccccc1]

the diol has the structure:

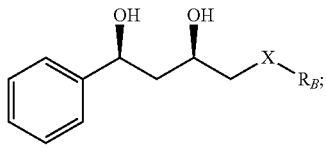

wherein X is S or O;
and the core scaffold has the structure:

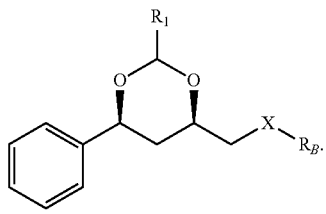

Uses of Compounds of the Invention

As described herein below, it has now surprisingly been found that the compounds of the invention and analogs can treat and prevent protein degradation disorders, especially myleoma. Thus, in one embodiment, the invention also provides methods for treating a subject for a protein degradation disorder, by administering to the subject an effective amount of a compound described herein. The compounds may inhibit protein degradation via the aggresome or the aggresome and the proteasome pathways.

Subjects may be identified as having or being susceptible to a protein degradation disorder by a health care professional or by self-identification by the subject.

The invention also provides methods of treating a cell exhibiting symptoms of a protein degradation disorder comprising administering a therapeutically effective amount of a protein degradation inhibitor to the cell. The cells include one or more of a cell from a subject or a cultured cell. The cells may be removed or isolated from a subject. Useful cells from a subject include one or more of a bone marrow stromal cell, (BMSC), a peripheral blood mononuclear cell (PBMC), lymphocytes, hair follicles, blood cells, other epithelial cells, bone marrow plasma cells, primary cancer cells, patient derived tumor cells, normal or cancerous hematopoietic stem cells, neural stem cells, solid tumor cells, astrocytes, and the like. Cultured cells include one or more of MM.1S, U266, RPMI8226, DOX40, MM.1R, INA-6, LR5, primary and established cancer cell lines, primary and established normal cell lines. The treated cells may be a pure population of cells or may be mixed with other cell types, for example other blood cells, feeder cells, or bone marrow cells. The cultured cells may be pure populations or they may be mixed with other cells. They may be mixed with other cultured cells or with cells from a subject. The cultured cells alternately be mixed with feeder cells or bone marrow cells.

The invention also provides methods for treating a subject suffering from or susceptible to multiple myeloma comprising administering to a subject in need thereof a therapeutically effective amount of a protein degradation inhibitor, to thereby treat the subject suffering from or susceptible to multiple myeloma. Multiple myeloma may be diagnosed by, for example, the detection of an M-protein in the serum or urine, the detection of more than 10% plasma cells on a bone marrow examination, the detection of lytic bone lesions or generalized osteoporosis in skeletal x-rays, and/or the presence of soft tissue plasmacytomas. In certain embodiments, an HDAC inhibitor is combined with a proteasome inhibitor in the treatment of multiple myeloma. In certain embodiments, the HDAC inhibitor is a compound of the invention. In certain embodiments, the proteasome inhibitor is bortezomib (VELCADE®).

The invention also provides methods for treating a subject suffering from or susceptible to solid tumors comprising administering to a subject in need thereof a therapeutically effective amount of a protein degradation inhibitor, to thereby treat the subject suffering from or susceptible to a solid tumor. Solid tumors that are particularly susceptible to treatment with protein degradation inhibitors include breast cancer, lung cancer, colon cancer, and prostate cancer. In certain embodiments, an HDAC inhibitor is combined with a proteasome inhibitor in the treatment of these cancers. In certain embodiments, the HDAC inhibitor is a compound of the invention. In certain embodiments, the proteasome inhibitor is bortezomib (VELCADE®).

The invention provides methods for assessing the efficacy of a protein degradation disorder treatment in a subject, comprising determining one or more pre-treatment phenotypes, administering a therapeutically effective amount of a protein degradation inhibitor to the subject, and determining the one or more phenotypes after an initial period of treatment with the protein degradation inhibitor, wherein the modulation of the one or more phenotypes indicates efficacy of a protein degradation inhibitor treatment. The subject may be pre-diagnosed with a protein degradation disorder, or the method may further comprise diagnosing the subject with a protein degradation disorder.

"After an initial period of treatment" or after an appropriate period of time after the administration of the protein degradation inhibitor, e.g., 2 hours, 4 hours, 8 hours, 12 hours, or 72 hours, weeks, or months, one or more of the proportions, levels, and/or cellular localization may be determined again. The modulation of one ore more of the phenotypes may indicate efficacy of protein degradation inhibitor. One or more of the phenotypes may be determined periodically throughout treatment. For example, one or more of the phenotypes may be checked every few hours, days or weeks to assess the further efficacy of the treatment. The method described may be used to screen or select patients that may benefit from treatment with a protein degradation inhibitor.

Provided herein are methods of monitoring the progress of a subject being treated with an aggresome inhibitor. The methods comprise determining one or more pre-treatment phenotypes; administering a therapeutically effective amount of an aggresome inhibitor to the subject; and determining one or more phenotypes after an initial period of treatment with the aggresome inhibitor, wherein the modulation of one or more of the phenotypes indicates efficacy of aggresome inhibition treatment.

Methods are also provided for selecting a subject with a protein degradation disorder for treatment with a protein degradation inhibitor. The selection methods comprise determining one or more pre-treatment phenotypes, administering a therapeutically effective amount of a protein degradation inhibitor to the subject; and determining the one or more phenotypes after an initial period of treatment with the protein degradation inhibitor wherein the modulation of the one or more phenotype is an indication that the disorder is likely to have a favorable clinical response to treatment with a protein degradation inhibitor.

Useful in the methods described herein as protein degradation inhibitors are one or more of histone acetylase inhibitors (Mitsiades et al. Transcriptional signature of histone deacetylase inhibition in multiple myeloma: biological and clinical implications. Proc Natl Acad Sci USA. 2004; 101:540-545; Rosato R R, Grant S. Histone deacetylase inhibitors in clinical development. Expert Opin Investig Drugs. 2004; 13:21-38; each of which is incorporated herein by reference), tubacin, bortezomib, velcade, SAHA, R115777 FTI, [166]Holminun-DOTMP, arsenic trioxide, 17-AAG, MG132, sapojargon, NPI-0052, or other compounds described herein.

The protein degradation inhibitors of the invention may inhibit the activity of cellular proteins, (e.g., enzymes), for example, suitable protein degradation inhibitors may inhibit the activity of HDAC6, for example, HDAC6 enzymatic activity. The inhibition of HDAC6 enzymatic activity may in turn inhibit aggresome mediated protein degradation. Suitable protein degradation inhibitors may also inhibit, for example, the C-terminal acetylation activity of HDAC6, thereby inhibiting aggresome mediated protein degradation. Other suitable protein degradation inhibitors may inhibit the activity of the aggresome.

In certain embodiments, the inhibition of HDAC6 by the inventive methods and compositions leads to the acetylation of HSP90. The acetylation of HSP90 renders this protein less active against a number of it client proteins and therefore increase protein stress in the cell. This is particularly important in cancers such as breast and prostate cancer. In these cancers, the acetylation of HSP90 lead to diminished activity of steroid-binding receptors because glucocorticoid receptors require HSP90 function to engage glucocorticoids. HSP90 inhibition has been found to diminish the glucocorticoid responsiveness of glucocorticoid receptor-containing cells. Therefore, the administration of HDAC6 inhibitors leads to the hyperacetylation of HSP90 leading to decreased sensitivity to estrogen in breast cancer cells and decreased sensitivity to androgens in prostate cancer cells.

Suitable aggresome inhibitors include tubacin, scriptade, or the compounds described herein.

Protein degradation inhibitors of the invention may also inhibit proteasome activity. Suitable proteasome inhibitors include one or more of histone acetylase inhibitors (14, 15), tubacin, bortezomib, velcade, SAHA, R115777 FTI, 166 Holminun DOTMP, arsenic trioxide, 17-AAG, MG132, sapojargon, NPI-0052, or the compound of Formula I, derivatives of the compounds of Formula I.

Additional suitable protein degradation inhibitors include peptide inhibitors, for example, a peptides derived from HDAC6, HSP 90, proteins in the aggresome pathway, both up-stream and down-stream. For example, the C-terminal portion of HDAC6, including the Buz domain.

The protein degradation inhibitors of the invention are capable of modulating one or more phenotypes of a cell. The phenotype may be a biological or clinical sequalae in response to a particular treatment or compound. Phenotypes include, anemia, thrombocytopenia, neutropenia, osteolytic lesions, bone pain, immunodeficiency, renal insufficiency, hypercalcemia, aneuploidy of mature plasma cells, percentage of malignant cells, acetylation state of tubulin, apoptosis of mature plasma cells, level of aggresomes, level of aggresomes in mature plasma cells, HDAC6 ubiquitination, HDAC6 ubiquitination in mature plasma cells, HDAC6 association with dynein in mature plasma cells, cellular levels of ubiquintinated proteins in mature plasma cells, level of caspase-8 in mature plasma cells, level of PARP in mature plasma cells, thymidine uptake in mature plasma cells, dilated ER cisternae, aggregation of mature plasma cells, deposits of immunoglobulins in mature plasma cells, acetylation state of non-histone proteins, global ubiquitination state of the cellular proteins, state of cell cycle regulation, necrosis, markers of apoptosis, apoptosis state, Russell body formation, Cystic Fibrosis transmembrane protein receptor state, and modulation of cellular protein deposits, or global acetylation state of cellular and extracellular proteins.

A decrease in one or more of anemia, level of aggresomes, thrombocytopenia, neutropenia, osteolytic lesions, bone pain, immunodeficiency, renal insufficiency, hypercalcemia, aneuploidy of mature plasma cells, percentage of malignant cells, thymidine uptake in mature plasma cells, level of full length caspase-8 in mature plasma cells, level of full length PARP in mature plasma cells, or aggregation of mature plasma cells, indicates that the treatment is efficacious.

An increase in acetylation state of tubulin, HDAC6 ubiquitination in mature plasma cells, level of cleaved form of caspase-8, level of cleaved form of PARP, necrosis, acetylation state of non-histone proteins, cellular ubiquitination levels, apoptosis, markers of apoptosis, cell cycle deregulation, or deposits of immunoglobulins in mature plasma cells indicates that the treatment is efficacious.

Phenotypes may be determined by many different methods know in the art. For example, phenotypes of a subject, e.g., anemia, thrombocytopenia, neutropenia, osteolytic lesions, bone pain, immunodeficiency, renal insufficiency, and hypercalcemia, may be determined by diagnostic methods known in the art for diagnosing these conditions. The phenotype aneuploidy of mature plasma cells may be determined by cytogenetic methods. The percentage of malignant cells may be determined, for example, by histological staining, flow cytometry, FISH, PCR, radiographic techniques, MRI, CT scan, metabolic methods, and the like. Acetylation state of tubulin, apoptosis of mature plasma cells, level of aggresomes in mature plasma cells, HDAC6 ubiquitination in mature plasma cells, HDAC6 association with dynein in mature plasma cells, cellular levels of ubiquintinated proteins in mature plasma cells, level of caspase-8 in mature plasma cells, level of the cleaved form of caspase-8, level of PARP in mature plasma cells, level of cleaved form of PARP, and thymidine uptake in mature plasma cells may be determined by biochemical methods, for example, immunoprecipitation, Western blotting, ELISA, immunohistochemistry, mass spectrometry, or a combination of these and other methods.

According the methods of the invention, phenotypes of samples may be determined at any point before treatment, after a suspected diagnosis of a protein degradation disorder, after treatment, and during treatment. The methods may be employed one or more times on sample from a subject during any of these time periods or any other time period.

Methods of the invention may further comprise determining the subject's phenotype after a second period of treatment with the protein degradation inhibitor. The second period of treatment may of the same length as the first period or initial period of treatment of may be longer or shorter than the first or initial period of treatment. The determination as the second period of treatment may be on a second biological sample obtained from the subject.

Subjects or cells being treated with protein degradation inhibitors may be further administered a therapeutically effective amount of one or more additional protein degradation inhibitors. The additional inhibitor may be an aggresome inhibitor or a proteasome inhibitor. The additional inhibitor, may be, for example, bortezomib, tubacin, histone acetylase inhibitors, tubacin, bortezomib (VELCADE®), SAHA, R115777 FTI, [166]Holminun-DOTMP, arsenic trioxide, 17-AAG, or the compound of Formula I, derivatives of the compounds of Formula I.

A subject or cell may be co-administered one or more of a chemotherapeutic agent, radiation agent, hormonal agent, biological agent or an anti-inflammatory agent to the subject while being treated for a protein degradation disorder. Chemotherapeutic agents may include tamoxifen, trastuzamab, raloxifene, doxorubicin, fluorouracil/5-fu, pamidronate disodium, anastrozole, exemestane, cyclophos-phamide, epirubicin, letrozole, toremifene, fulvestrant, fluoxymesterone, trastuzumab, methotrexate, megastrol acetate, docetaxel, paclitaxel, testolactone, aziridine, vinblastine, capecitabine, goselerin acetate, zoledronic acid, taxol, vinblastine, and/or vincristine. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

While a subject or cell is being treated with a protein degradation inhibitor, the cell or subject may be monitored.

Methods of the invention may further comprise comparing one or more of the pre-treatment or post-treatment phenotypes to a standard phenotype. The standard phenotype is the corresponding phenotype in a reference cell or population of cells. Reference cells are one or more of the following, cells from a person or subject that is not suspected of having a protein degradation disorder, cells from the subject, cultured cells, cultured cells from the subject, or cells from the subject pre-treatment. Cells from the subject may include, for example, a bone marrow stromal cell, (BMSC), a peripheral blood mononuclear cell (PBMC), lymphocytes, hair follicles, blood cells, other epithelial cells, bone marrow plasma cells, primary cancer cells, patient derived tumor cells, normal or cancerous hematopoietic stem cells, neural stem cells, solid tumor cells, astrocytes, and the like.

Methods of the invention also include methods of inhibiting aggresome mediated protein degradation in a cell or subject comprising contacting the cell with an aggresome inhibitor. In one embodiment, the aggresome protein degradation is mediated by HDAC6. The method may further comprise inhibiting proteasome protein degradation in the cell or subject. For example, by the administration of bortezomib and tubacin.

Pharmaceutical Compositions

The invention also provides a pharmaceutical composition, comprising an effective amount of a compound of the invention of formula I, formula II, or otherwise described herein and a pharmaceutically acceptable carrier. In a further embodiment, the effective amount is effective to treat a protein degradation disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious hypercalcemia. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

Screening Assays

In pursuit of potency selective inhibitors (e.g., effective in the nanomolar range) of protein degradation, and in particular of HDAC6, the invention provides novel screening methods. In one embodiment, the screening method is a quantitative, cellular, image-based screen of cancer cells.

Screening methods of the invention include a quantitative, high-throughput, image-based screen of cancer cells. The cells may be grown, for example in multi-well plates or chips, for example 384-well plate formats or in chips, such as the BioTrove OpenArray™ Chips (BioTrove, Woburn, Mass.). The cells may be grown and treated in these wells and plates. The are treated with a small molecule library, peptide library, nucleic acid library. Some of the libraries may be biased for HDAC inhibition as discussed herein. Other libraries may be biased toward inhibition of other aggresome or proteasome inhibition targets. Once treated, the cells may be monitored by phenotype as discussed herein. For example, tubulin and histone acetylation state-specific antibodies may be used and recognized by corresponding fluorescent secondary antibodies or may be directly labeled and detected if they bind. Wells or through-holes are then scored in an unbiased fashion. This may be done, for example, by an automated Axon 5000A epifluorescence microscope. Scoring takes into account, for example, the amount of fluorescence, compared with controls, the relative amount of fluorescence relative to a reference, or the amount of fluorescence. Controls may be used for reference. For example, as a control for tubacin, trichostatin, and DMSO may be used as controls. Molecules have subsequently been prioritized following assessment for direct cytotoxicity and synergy with bortezomib in the RPMI-8226 myeloma cell line.

A tubulin-selective sub-library can includes molecules derived from diversity-oriented synthetic pathways. For example, the libraries of compounds described in Sternson S M et al., *Org Lett.* 2001 Dec. 27; 3(26):4239-42; Haggarty S J et al., *Chem Biol.* 2003 May; 10(5):383-96; Haggarty S J et al., *Proc Natl Acad Sci USA.* 2003 Apr. 15; 100(8): 4389-94. Epub 2003 Apr. 3; and Haggarty S J et al., *Comb Chem High Throughput Screen.* 2004 November; 7(7):669-76 can be screened to identify additional active compounds.

Method for identifying a candidate compounds to inhibit protein degradation in a cell comprise contacting a cell exhibiting aggresome formation with a candidate compound, and determining a phenotype of the cell, wherein modulation of the phenotype is indicative of the efficacy of the compound. Phenotypes of cells may be determined as described herein, for example by image-based multidimensional screening. The cell types used in the screening assays may include myeloma patient cells, myeloma cell lines, primary cell cultures of myeloma cell line. Cell cultures, primary cultures, or patient cells may be co-cultured with stromal cells or other cells. The contacting may be by adding the candidate compound to the media, directly to the cells, or as a fluid flowing over the cell, e.g., in a lateral flow or a planar flow patch clamp device. One of skill in the art would be able to identify other appropriate methods having the benefit of this disclosure.

Candidate molecules may be one or more of a small molecule, a peptide, or a nucleic acid. The nucleic acids may be, for example, an RNA or DNA molecule, e.g., mRNA, RNAi, siRNA or an oligo.

Suitable peptides may include peptides derived from HDAC6, dynenin, Ubiquitin, or chaperones. For example, peptides derived from the C-terminus of HDAC6, (amino acids 439-503), amino acids 500-790 of HDAC 6, amino acids 781-931 of HDAC6, or the amino acids 1-460. Other suitable peptides include the dynein-binding domain of HDAC6 identified by by Yao (aa 439-503); the C-terminal TDAC domain (aa 500-790), the ubiquitin-binding BUZ domain (aa 781-931); or the N-terminal 460 amino acids.

Suitable small molecules include natural and synthetic products. The molecules may be contained in a library; libraries of compounds can be obtained commercially (e.g., from ChemBridge, San Diego, Calif., or may be prepared by known methods (e.g., as described in herein).

Other screening methods for evaluating a test compound comprise contacting an cell exhibiting aggresome formation with a test compound, and evaluating the cell following contact, wherein a correlation of a modulation of one of more phenotypes to a reference value is an indication that the test compound may be useful as a protein degradation disorder treatment.

The method may further comprise determining a phenotype of the cell after an initial period of treatment with the protein degradation inhibitor. The initial period of treatment may be the time in which it takes to establish a stable and/or therapeutically effective blood serum level of a therapeutic compound of the invention, or the time in which it takes for the subject to clear a substantial portion of the therapeutic, or any period of time selected by the subject or healthcare professional that is relevant to the treatment.

This embodiment of the invention is well suited to screen chemical libraries for molecules which modulate, e.g., inhibit protein degradation in a cell, tissue or subject, or modulate a phenotype as described herein of a cell, tissue or subject. The chemical libraries can be peptide libraries, peptidomimetic libraries, chemically synthesized libraries, recombinant, e.g., phage display libraries, and in vitro translation-based libraries, other non-peptide synthetic organic libraries, etc.

Libraries screened using the methods of the present invention can comprise a variety of types of compounds. Examples of libraries that can be screened in accordance with the methods of the invention include, but are not limited to, peptides; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as γ-amino phosphoric acids and γ-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a preferred embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptides; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pa.; Martek Biosciences, Columbia, Md.; etc.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multistep solid phase synthesis (Egner et al., 1995, J.Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

Immunofluorscence Assay for Identifying HDAC and TDAC Inhibitors

The present invention provides an immunofluorescence-based assay for identifying test agents with HDAC and/or TDAC inhibitory activity. The inventive assay is based on the use of specific antibodies for acetylated tubulin and acetylated lysine (i.e., a marker for acetylated histones). The assay is particularly useful in identifying agents that specifically inhibit HDAC versus TDAC or vice versa. As described above, any type of agent, including small molecules, polymers, biomolecules, proteins, peptides, polynucleotides, etc., may be screened using the inventive assay. In certain embodiments, small molecules are screened. In certain particular embodiments, the small molecules are tubacin-like or are tubacin derivatives. In certain embodiments, the small molecules are compounds of the present invention. The test agents may also be small molecules purchased, prepared through traditional synthetic techniques, prepared through combinatorial chemistry techniques, or obtained from historical chemical collections. In certain embodiments, the test agents are biomolecules. In other embodiments, the test agents are proteins or peptides. In yet other embodiments, the test agents are polynucleotides. In certain embodiments, the test agents are polymers.

The assay involves contacting cells with a specific concentration of the test agent under specific conditions. The specific conditions include type of media, concentration of agent, solvent agent is dissolved or suspended in, pH, temperature, time of incubation, etc. There particular parameters may be determined by the operator or scientist conducting the assay as would be appreciated by one of skill in this art. After a determined time of incubation with the test compound, the cells are treated with a first primary antibody directed against acetylated tubulin and a second primary antibody directed against acetylated lysine. The cells are then contacted with two secondary antibodies specific for each of the primary antibodies and identifiable by a unique signal. In certain embodiments, the unique signals are unique fluorsecence signals. However, chemiluminescence, phosphorescence, colorimetric, enzymatic reaction products, or other reporters may also be used. The signal from each of the secondary antibodies is measured and optionally quantitated to determine the amount of TDAC and HDAC inhibition under the specified conditions with the test agent. Optionally, the extent of inhibition is determined relative to a control in which no test agent was added. In certain embodiments, the secondary antibody is left out and the primary antibodies are uniquely labeled for identification and optionally quantification.

Any type of cell may be used in the inventive assay. The cells may be from any species. For example, bacterial cells, yeast cells, mammalian cells, murine cells, rat cells, primate cells, or human cells may be used. In certain embodiments, the cells are human cells which may be derived from any tissue or organ system or be at any stage of development. The cells may be derived from skin, hair, nerve, muscle, bone, digestive tract, genitourinary tract, blood vessels, bone marrow, heart, lung, liver, pancreas, stomach, colon, kidneys, bladder, testes, ovaries, uterus, cervix, spleen, endocrine system, brain, spinal cord, eye, etc. The cells may be stem cell, embryonic stem cells, fetal cells, progenitor cells, etc. In certain embodiments, the cells are human cancer cells lines. Any type of cancer cell may be used. Certain exemplary cell lines include multiple myeloma, non-Hodgkin's lymphoma, acute myelogenous leukemia (AML), breast cancer, ovarian cancer, prostate cancer, lung cancer, colon cancer, leukemia, lymphoma, skin cancer, brain cancer, cervical cancer, stomach cancer, bone cancer, etc. Specific cell lines include MM.1S, U266, RPMI8226, DOX40, MM.1R, INA-6, LR5, etc.

The cells are typically plated in multi-well tissue culture plates (e.g. 384 well plates) and allowed to adhere to the plate before the test agent at a specified concentration is added. Multiple concentrations for each test agent may be tested to establish a dose-response curve to allow the calculation of $IC_{50}$ values. The test agent is allowed to incubate with the cells under physioligical conditions for 1-24 hours, preferably 4-16 hours. Afterwards, the cells are fixed, blocked, and washed. The treated cells are incubated with the primary antibodies-one specific for acetylated tubulin and the other for acetylated lysine. The antibodies may be monoclonal or polyclonal. In certain embodiments, the antibodies are obtained from a commercial source. The primary antibodies are then tagged with a fluorescent secondary antibody. The plates are imaged, and the fluorescence signal from each of the secondary antibodies is optionally quantitated. As would be appreciated by one of skill in the art, the cells may be stained for other markers, such as other proteins, nucleic acid content, DNA content, RNA content, organelles, etc.

The data gathered may then be used to calculate dose-response curves, to calculate $IC_{50}$ values, to establish structure-function relationships, to calculate the ratio of HDAC to TDAC inhibition, to determine the specificity for HDAC or TDAC, etc.

The inventive assay is particularly amenable for use in high-throughput systems using multi-well plates, fluid handling robots, plate imagers, and computers and software developed for high-throughput screening. In certain embodiments, at least 100 test conditions (e.g., test agent, concentration of test agent, type of cell, temperature, length of incubation with test agent, pH, media, etc.) are assayed in parallel. In other embodiments, at least 300 test conditions are assayed in parallel. In yet other embodiments, at least 500 test conditions are assayed in parallel. In still other embodiments, at least 1000 test conditions are assayed in parallel.

Compounds identified to be HDAC and/or TDAC inhibitors using the inventive assay are considered part of the invention. In certain embodiments, the assay is used to identify specific inhibitors of HDAC. In other embodiments, the assay is used to identify specific inhibitors of TDAC.

Kits

The invention provides kits for treating a protein degradation disorder in a subject. The kits may comprise one or more compound of the invention, (e.g., tubacin, a compound of Formula I) or pharmaceutically acceptable esters, salts, and prodrugs thereof, and instructions for use. The instructions for use may include dosages, administration routes, patient educational information, expiration date, storage conditions, indications, and the like.

The compounds of the present invention can be provided in therapeutically effective amounts in the kits with pharmaceutically acceptable carriers or they may be provided in bulk amounts with pharmaceutically acceptable carriers.

The invention also provides packaged composition comprising therapeutically effective amounts of an a protein degradation inhibitor and a pharmaceutically acceptable carrier or diluent. The packaged composition is formulated for treating a subject suffering from or susceptible to a protein degradation disorder, and packaged with instructions to treat a subject suffering from or susceptible to a protein degradation disorder.

The invention also provides kits for screening for protein degradation inhibitors. The kits may include control composition, for example, tubacin and niltubicin for reference. The kits may also include, reagents, for example, test compounds, buffers, media (e.g., cell growth media), cells, etc. Test compounds may include known compounds or newly discovered compounds, for example, combinatorial libraries of compounds.

Kits for assessing the efficacy of a protein degradation disorder treatment are also provided. The kits may include reagents for determining one or more of the phenotypes described herein (e.g., reagents for the determining of the aceylation state of tubulin), instructions for use, and instruments for collecting subject samples.

One or more of the kit of the invention may be packaged together, for example, a kit for assessing the efficacy of a protein degradation treatment may be package with a kit for treating a protein degradation disorder.

EXAMPLES

Experimental Procedures
Bone Marrow Stromal Cell (BMSC) Cultures.

BM specimens were obtained from patients with MM. Mononuclear cells (MNCs) separated by Ficoll-Hipaque density sedimentation was used to established long-term BM cultures. When an adherent cell monolayer had developed, cells were harvested in Hank's Buffered Saline Solution containing 0.25% trypsin and 0.02% EDTA, washed, and collected by centrifugation.
Cell Lines, Patients BM Plasma Cells and BM Stromal Cell (SCs).

Dex-sensitive (MM.1S) and resistant (MM.1R) human MM cell lines were kindly provided by Dr. Steven Rosen (Northwestern University, Chicago, Ill.). RPMI8226 and U266 human MM cell lines were obtained from American Type Culture Collection (Rockville, Md.). IL-6 dependent INA-6 cell line was kindly provided by Dr M Gramatzki (Erlangen, Germany). Melphalan-resistant RPMI-LR5 and doxorubicin-resistant RPMI-Dox40 cell lines were provided by Dr William Dalton (Lee Moffitt Cancer Center, Tampa, Fla.). All MM cell lines were cultured in RPMI-1640 containing 10% fetal bovine serum (FBS, Sigma Chemical Co., St. Louis, Mo.), 2 µM L-glutamine, 100 U/ml penicillin, and 100 µg/ml streptomycin (GIBCO, Grand Island, N.Y.). INA-6 cells were maintained with addition of IL-6 (1 ng/ml). MM patient plasma cells were purified from bone marrow (BM) aspirates by negative selection using an antibody cocktail (RosetteSep Separation System, StemCell Technologies, Vancouver, Canada), as previously described (31). The purity of MM cells was >90%, as confirmed by flow cytometric analysis using anti-CD138 Ab (BD Pharmingen, San Diego, Calif.). Mononuclear cells (MNCs) separated by Ficoll-Hipaque density sedimentation from BM aspirates were also used to establish long-term BM stromal cells (BMSCs), as previously described (28, 43). All experiments with patient samples were performed according to the protocol approved by the Institutional Review Board.
Inhibitors.

The peptide boronate proteasome inhibitor bortezomib was provided by Millennium Pharmaceuticals (Cambridge, Mass.). HDAC6 specific inhibitor tubacin and its non-active derivative niltubacin are obtained from Broad Institute of Harvard University (18) and Massachusetts Institute of Technology. Both inhibitors were dissolved in DMSO and stored at −20° C. until use.
DNA Synthesis.

Proliferation was measured by $^3$H-thymidine uptake. Briefly, MM cells ($3 \times 10^4$ cells/well) were incubated in 96-well culture plates in the presence of media, Velcade and/or Tubacin for 48 h at 37° C. DNA synthesis was measured by [$^3$H]-thymidine ([$^3$H]-TdR, Perkin Elmer, Boston, Mass.) uptake. Cells were pulsed with [$^3$H]TdR (0.5 µCi/well) during the last 8 h of 48 h cultures. All experiments were performed in triplicate.
Growth Inhibition Assay.

The inhibitory effect of bortezomib and/or tubacin on MM cell growth was assessed by measuring 3-(4,5-dimethylthiazol-2-yl)-2,5-diphenyl tetrazolium bromide (MTT) dye absorbance, as described previously (33). Cells from 48 h cultures were pulsed with 10 µl of 5 mg/ml MTT to each well for the last 4 h of 48 h cultures, followed by 100 µl isopropanol containing 0.04N HCl. Absorbance was measured at 570 nm using a spectrophotometer (Molecular Devices Corp., Sunnyvale Calif.). All experiments were performed in quadruplicate.
Western Blotting.

MM cells were cultured with Velcade and/or Tubacin; harvested; washed; and lysed using lysis buffer: 50 mM Tris-HCl (pH 7.4), 150 mM NaCl, 1% NP-40, 5 mM EDTA, 5 mM NaF, 2 mM $Na_3VO_4$, 1 mM PMSF, 5 µg/ml leupeptine, and 5 µg/ml aprotinin. Cell lysates were subjected to SDS-PAGE, transferred to PVDF membrane (Bio-Rad Laboratories, Hercules, Calif.), and immunoblotted with Abs against specific proteins.
Flow Cytometric Analysis.

For cell cycle analysis, MM cells cultured for 24 h in Velcade (5 µM) and/or Tubacin (5 µM) were harvested, washed with phosphate-buffered saline (PBS), fixed with 70% ethanol, and treated with 10 µg/ml of RNase (Roche Diagnostics Corp., Indianapolis, Ind.). Cells were then stained with propidium iodine (PI, Sigma) (5 µg/ml) and cell cycle profile was determined using program M software on an Epics flow cytometer (Coulter Immunology, Hialeah, Fla.) (44).
Effect of Velcade and Tubacin on Paracrine MM Cell Growth in the BM.

To evaluate growth stimulation and signaling in MM cells adherent to BMSCs, $3 \times 10^4$ MM.1S cells were cultured in BMSC coated 96-well plates for 48 h, in the presence of Velcade and/or Tubacin. DNA synthesis was measured as described above.
Immunoblotting.

Cells cultured with tubacin and/or bortezomib were harvested; washed, and lysed using lysis buffer: 50 mM Tris-HCl (pH 7.4), 150 mM NaCl, 1% NP-40, 5 mM EDTA, 5 mM NaF, 1 mM $Na_3VO_4$, 1 mM PMSF, 5 µg/ml leupeptine, and 5 µg/ml aprotinin. Whole cell lysates were subjected to SDS-PAGE, transferred to nitrocellulose membrane (Bio-Rad Laboratories, Hercules, Calif.), and immunoblotted with specific Abs (31). Western blotting was done using anti-HDAC6, acetylated lysine, acetylated histone H3, acetylated histone H4, ubiquitin (Ub), phospho-SAPK (JNK), caspase-8 caspase-9, caspase-3, and PARP Abs (Cell Signaling, Beverly, Mass.); with anti-α-tubulin Ab (Santa Cruz Biotechnology, Santa Cruz, Calif.); as well as with anti-dynein Ab (Sigma, Saint Louis, Mo.). For immunoprecipitation, whole cell lysates were incubated with anti-Ub or dynein Abs overnight at 4° C., and then incubated with protein A/G PLUS-Agarose (Santa Cruz Biotechnology) for 2 h at 4° C., as in our prior study (31). Immunoprecipitates were then subjected to Western blotting for detection of HDAC6 and dynein.
Transient Transfection of HDAC6 siRNA.

MM.1S cells were transiently transfected with HDAC6 siRNA (Dharmacon Inc., Lafayette, Colo.) using "Cell Line Nucleofecto™ Kit V," according to manufacturer's (Amaxa Biosystems, Gaithersburg, Md.) instructions (33). Following transfection, MM.1S cells were subjected to Western blotting and MTT assay, in the presence or absence of bortezomib.
Growth of MM Cells Adherent to BMSCs.

To evaluate the effect of combined tubacin and bortezomib treatment on growth of MM cells adherent to BMSCs, MM.1S and RPMI8226 cells were cultured for 24 h in BMSC coated 96-well plates, in the presence or absence of tubacin and/or bortezomib. After treatment, DNA synthesis was measured by [$^3$H]-thymidine (Perkin Elmer, Boston Mass.) uptake, as previously described (44). All experiments were performed in quadruplicate.

Statistical Analysis.

Statistical significance of differences observed in drug-treated versus control cultures was determined using the Wilcoxon signed-ranks test. The minimal level of significance was $p<0.05$. The interaction between tubacin and bortezomib was analyzed by isobologram analysis using the CalcuSyn software program (Biosoft, Ferguson, Mo.) to determine whether the combination was additive or synergistic, as previously described (45).

Example 1

Tubacin Specifically Induces Acetylation of α-Tubulin in MM Cell Lines.

The baseline expression of HDAC6 was examined in several MM cell lines. Although MM.1S, U266, INA-6, RPMI8226, and RPMI-LR5 MM cell lines constitutively express HDAC6, only low levels of HDAC6 are evident in RPMI-Dox-40 cells (FIG. 1A). Since tubacin induces acetylation of α-tubulin in A549 human lung cancer cell line by specific inhibition of HDAC6 activity (40), the effect of tubacin was examined on acetylation of α-tubulin in MM.1S and RPMI8226 MM cells. As shown in FIG. 1B, tubacin significantly induces aceylation of α-tubulin in a dose-dependent fashion in both MM.1S and RPMI8226 cells, without alteration of protein expression; importantly, no other acetylated proteins were recognized by Western blotting. Similar results were observed in INA-6 and RPMI-Dox40 cells (data not shown). The dose-dependent effect of tubacin was assessed, and show that tubacin (5 μM) induces peak acetylation of α-tubulin in RPMI8226 cells at 12 h (FIG. 1C). Importantly, expression of HDAC6 is not altered by tubacin treatment (data not shown).

Histone acetylation has been associated with development of malignancies (46, 47); conversely, inhibitors of histone deacetylase represent a promising new treatment strategy (48). It has been demonstrated that both second generation of a hybrid polar compound SAHA (49) and novel hydroxamic acid derivative NVP-LAQ824 (50) mediate anti-MM activity. Since these agents non-selectively inhibit HDACs, the effect of SAHA on acetylation of lysine in MM.1S and RPMI8226 cells was also examined. In contrast to tubacin, which specifically induces acetylation of α-tubulin (FIG. 1B, IC), SAHA triggers more potent acetylation of lysine on histone H3 and H4 than α-tubulin (FIG. 1D). These results demonstrate that HDAC6 is constitutively expressed in MM cell lines and that tubacin specifically induces acetylation of α-tubulin, confirming the specific inhibitory effect of tubacin on HDAC6 activity in MM cells.

Example 2

Tubacin Inhibits MM Cell Growth.

Based upon the specific inhibitory effect of tubacin on HDAC6, next examined was the cytotoxicity of tubacin against drug-sensitive (MM.1S, U266, INA-6, and RPMI8226) and -resistant (RPMI-LR5 and RPMI-Dox40) MM cell lines. These cells were treated with tubacin (1.25-20 μM) for 48 h (FIG. 2A) and 72 h (FIG. 2B), and cytotoxicity was assessed by MTT assay, as describe. Tubacin significantly inhibits both drug-sensitive and -resistant MM cell growth, with $IC_{50}$ 5-20 μM at 72 h. The most sensitive and resistant cell lines are RPMI8226 and MM.1R cells, respectively (FIG. 2B). Importantly, no cytotoxicity in PBMCs is induced by tubacin (FIG. 2C). These results indicate that tubacin sensitivity is independent of resistance to conventional chemotherapeutic agents (dexamethasone, melphalan and doxorubicin) and suggest a favorable therapeutic index in tumor cells versus normal cells. It was shown that HDAC inhibitors SAHA and NVP-LAQ824 trigger MM cell death via caspase-dependent apoptosis, it was studied whether tubacin-induced cytotoxicity is also mediated via apoptosis. In MM.1S and RPMI8226 cells treated with tubacin (10 μM) for 0-24 h, time-dependent caspase-8/PARP cleavage is induced (FIG. 2D), confirming our MTT results. These data strongly suggest that tubacin-induced cytotoxicity in MM cells is mediated via caspase-dependent apoptosis.

Example 3

Tubacin Inhibits Interaction of HDAC6 with Dynein; when Combined with Bortezomib, it Induces Accumulation of Ubiquitinated Proteins.

Figure 3A:
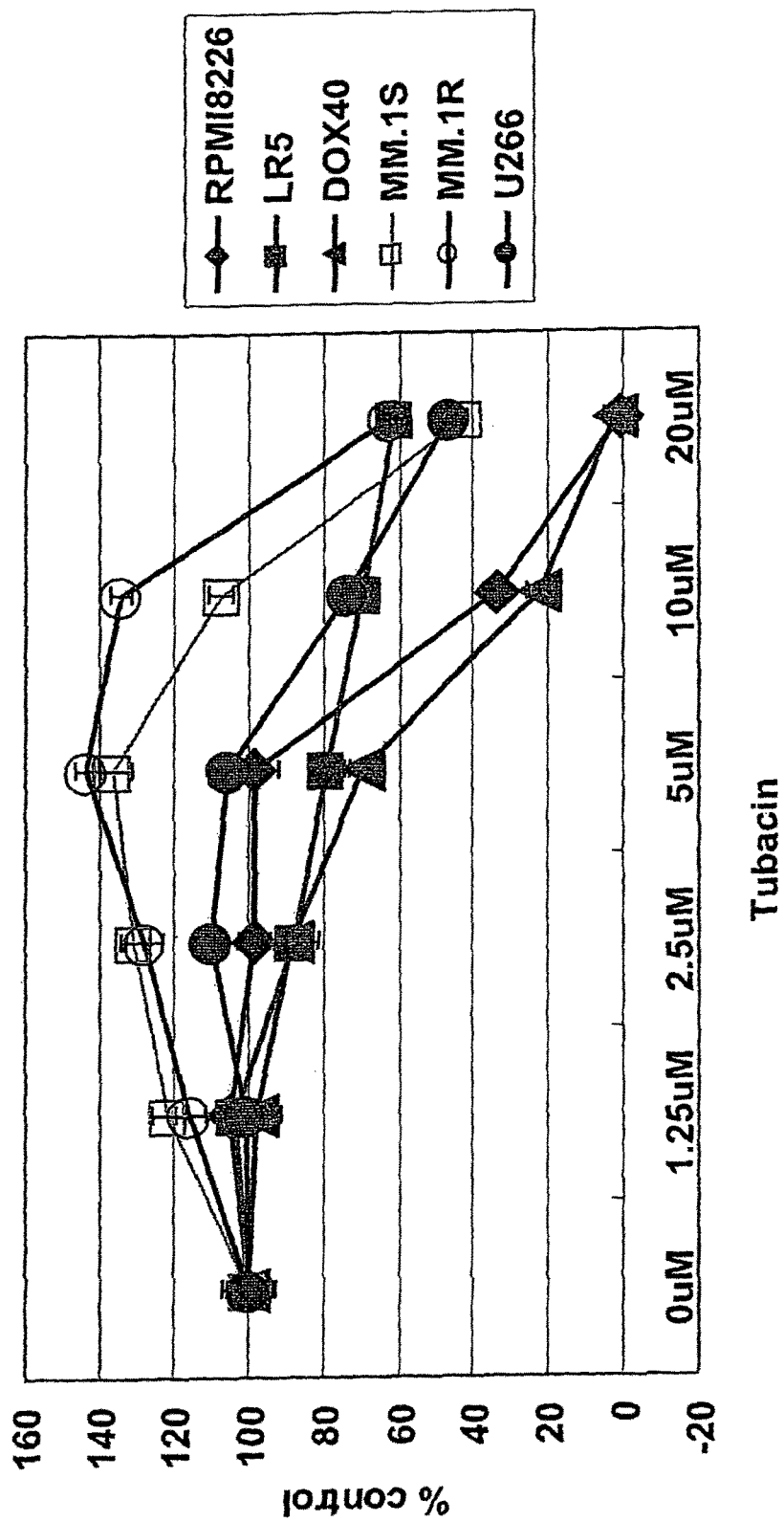
FIGS. 3A to 3B show the growth inhibitory effect of tubacin in MM cell lines. MM cell lines were cultured with tubacin (1.25-20 µM) for 48 h. The growth inhibitory effect of tubacin was assessed by both MTT assay (FIG. 3A) and $^3$H-thymidine uptake (FIG. 3B).

To overcome bortezomib resistance in MM, novel therapeutic options are urgently needed. Based upon our preclinical studies showing that bortezomib inhibits DNA repair (29, 31), combined treatment of bortezomib has been shown to sensitize or overcome resistance to DNA damaging agents (ie, melphalan and doxorubicin) (29). It has also been shown that hsp-27 expression is associated with bortezomib resistance (30, 51); conversely, p38MAPK inhibitors can down-regulate hsp-27 in bortezomib resistant MM cell lines and patient cells, and overcome bortezomib resistance. Recent studies have demonstrated that polyubiquitinated proteins are degraded via both proteasome and aggresome pathways (FIG. 3A).

Figure 3B:
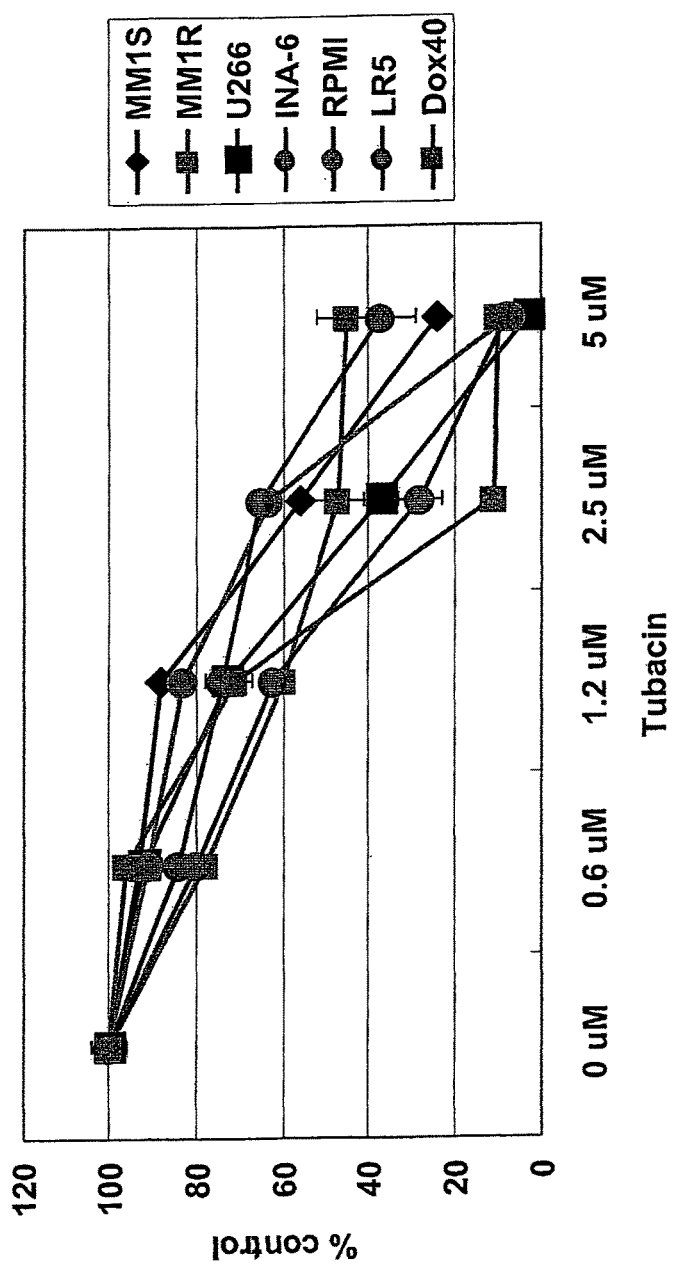

HDAC6 constitutively binds both polyubiquitinated misfolded proteins and dynein, thereby recruiting misfolded protein cargo to dynein motors for transport to aggresomes along microtubules (39). It was examined whether inhibition of HDAC6 activity by tubacin alters the interaction of HDAC6 with Ub and/or dynein. HDAC6 is consistently co-immunoprecipitated with polyubiquitinated proteins in MM.1S cells (FIG. 3B) and dynein (FIG. 3C). After treatment with tubacin (2.5 μM and 5 μM for 8 h), co-immunoprecipitation of HDAC6 with dynein is markedly inhibited in a dose-dependent fashion, whereas co-immunoprecipitation between HDAC6 and ubiquitinated proteins is unaffected (FIG. 3B). Next examined was the impact of tubacin on polyubiquitination of proteins. As expected, polyubiquitinated proteins significantly accumulate in tubacin-treated RPMI8226 cells; however, no significant change was recognized in treated MM.1S cells (FIG. 3D), suggesting compensatory proteasomal degradation of polyubiquitinated proteins. These results also indicate that degradation of polyubiquitinqted protein in RPMI8226 cells is more dependent on aggresomes than proteasomes, consistent with MTT data demonstrating that RPMI8228 cells are more sensitive to tubacin than MM.1S cells (FIG. 2A, 2B). Importantly, combined tubacin (5 μM) and bortezomib (5 nM) dramatically augments accumulation of polyubiquitinated proteins in both MM.1S and RPMI8226 cells, compared to either agent alone (FIG. 3E). These results further indicate that degradation of polyubiquitinated occurs in both proteasomes and aggresomes; therefore, inhibiting both pathways induces significant accumulation of polyubiquitinated proteins in MM cells.

Example 4

Synergistic Anti-MM Activity of Tubacin with Bortezomib is Mediated Via JNK-Caspase Activation.

Figure 4:
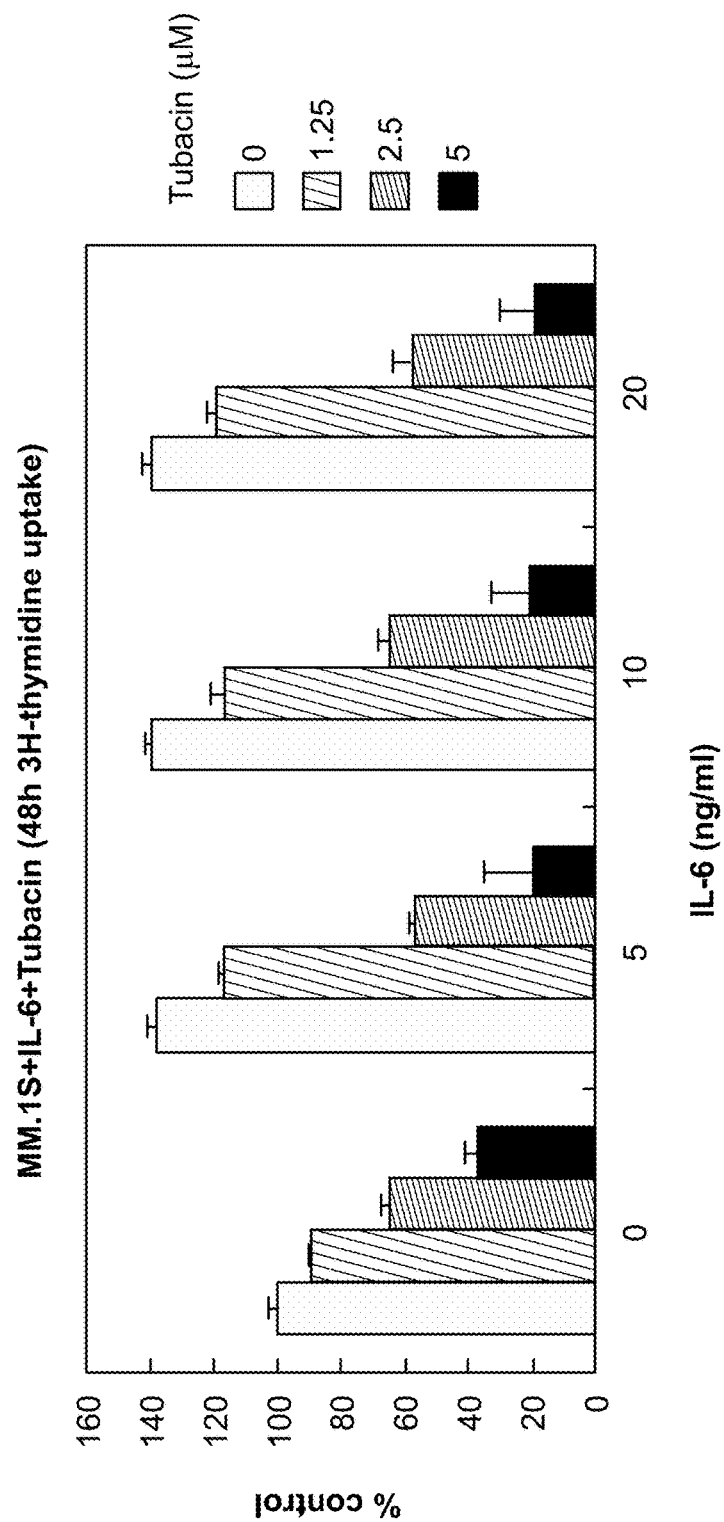
FIG. 4 demonstrates that IL-6 does not overcome the effect of tubacin. MM.1S cells were cultured with tubacin (1.25-5 µM) in the presence (5-20 ng/ml) or absence of IL-6 for 48 h. DNA synthesis was measured by $^3$H-thymidine uptake.

Having shown significant accumulation of polyubiquitinated proteins after combined treatment with tubacin and bortezomib, examined was whether combination treatment could also induce significant cytotoxicity in MM cells. As expected, tubacin synergistically enhances bortezomib-induced cytotoxicity in both MM.1S and RPMI8226 cells. For example, 5 nM and 10 nM bortezomib trigger 26% and 66% RPM18226 cell death, respectively, which is increased to 87% and 91%, respectively, when combined with 5 µM tubacin (FIG. 4A). To analyze the mechanism whereby this combination treatment mediates synergistic anti-MM toxicity, next performed cell cycle profiling in MM.1S cells. Tubacin (5 µM) alone does not alter cell cycle profile, whereas bortezomib (5 nM) alone triggers increased (14.2% to 39.5%) G2M phase MM.1S cells, as in our previous studies (4); importantly, the combination of tubacin and bortezomib triggers significantly increased (5.6% to 30 4%) sub-G0/G1 phase cells, suggesting that combination treatment triggers apoptotic cell death (FIG. 4B). Further examined was expression of $p21^{Cip1}$. Consistent to cell cycle profile, tubacin does not trigger induction of $p21^{Cip1}$. Importantly, tubacin inhibits induction of $p21^{Cip1}$ induced by bortezomib (FIG. 4C).

Since accumulation of polyubiquitinated proteins induces a cell stress response, next examined whether this combination treatment of MM.1S cells triggers activation of JNK (also known as stress-activated protein kinase), a hallmark of cell stress response, followed by caspase cleavage, as described in our previous studies (9, 22). Tubacin alone does not trigger phosphorylation of JNK or caspase/PRAP cleavage, and bortezomib alone induces only modest phosphorylation of JNK as well as caspase-9, -8, -3 and PARP cleavage (FIG. 4C). Of great interest, combined tubacin and bortezomib treatment markedly augments both JNK phosphorylation and caspase/PARP cleavage in MM.1S cells (FIG. 4C), consistent with cytotoxicity assays (FIG. 4A). Other cell stress response-related proteins (ie, hsp-70 and Grp78) are also induced by this combination treatment (data not shown). These results indicate that tubacin inhibits the G2 phase arrest induced by bortezomib, thereby facilitating apoptosis mediated via stress-induced JNK activation, followed by caspase/PARP cleavage.

To identify the specific role of HDAC6 inhibition mediating synergistic MM cell cytotoxicity with bortezomib, MM.1S cells were transiently transfected with HDAC6 siRNA, as previously described. HDAC6 protein expression is significantly downregulated by transfection (FIG. 4D); importantly, bortezomib significantly increases cytotoxicity in transfectants in a dose-dependent fashion (FIG. 4E). In contrast niltubacin, an inactive carboxylic acid tubacin analog, does not affect either acetylation of α-tubulin (FIG. 4F) or enhance cytotoxicity in MM.1S cells induced by bortezomib (FIG. 4G). Similar results were observed in RPMI8226 cells (data not shown). These results show that inhibition of HDAC6 specifically augments bortezomib-induced cytotoxicity in MM.

Example 5

Tubacin Combined with Bortezomib Demonstrates Significant Cytotoxicity in MM Patient Plasma Cells.

Figure 5:
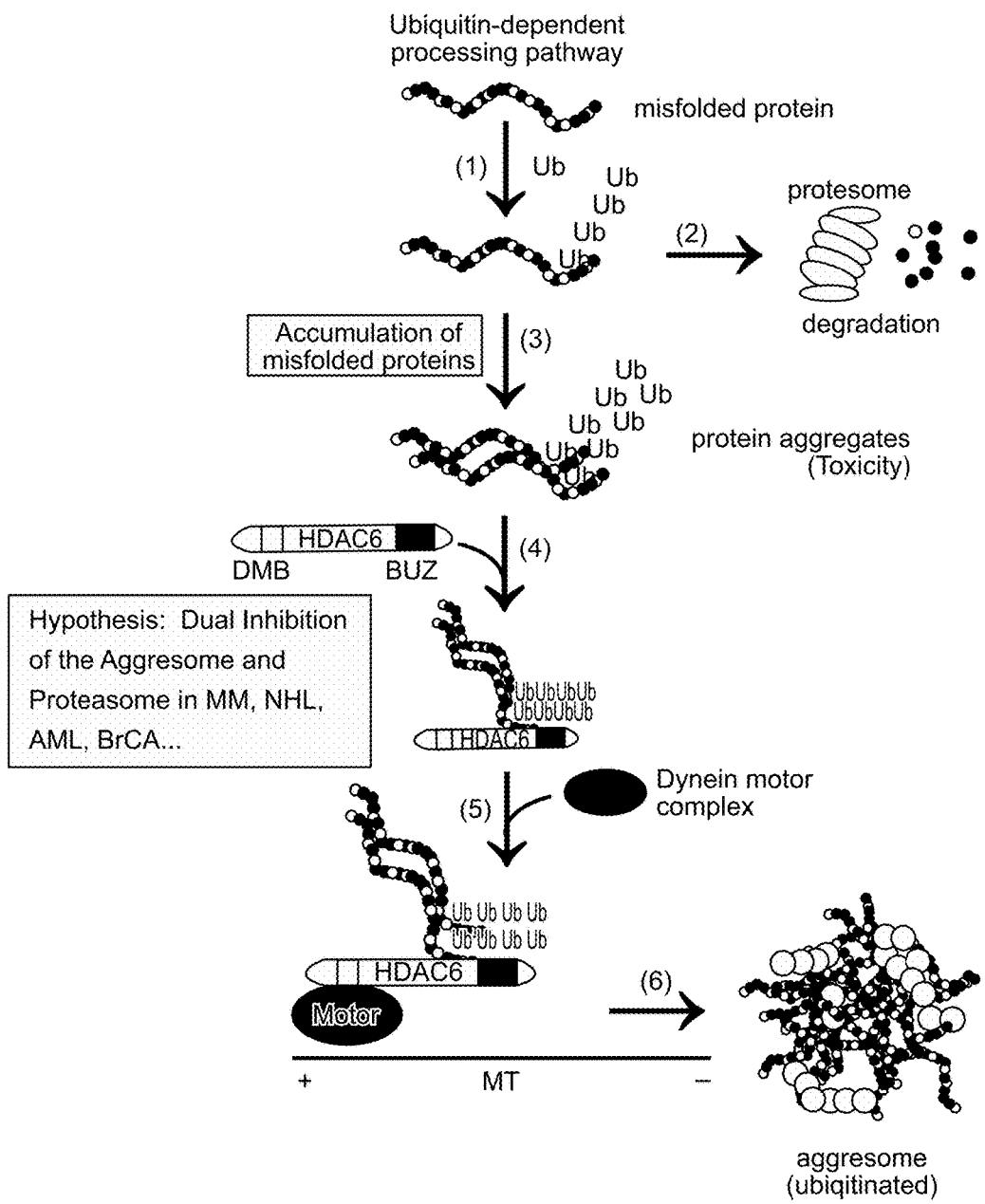
FIG. 5 graphically depicts protein degradation pathways and the scientific rationale for combining VELCADE with tubacin in the treatment of protein degradation disorders. There are two pathways which degrade misfolded/unfolded proteins which are ubiquitinated. The former is the proteasome pathway, and the latter is the aggresome pathway, which requires HDAC 6 activity. Therefore inhibition of both pathways by specific inhibitors bortezomib (VELCADE®) and tubacin induced accumulation of cytotoxic misfolded/unfolded proteins.

Having show significant cytotoxicity of combined treatment of tubacin and bortezomib in MM cell lines, further examined was the effect of the combination in isolated CD138-positive MM patient plasma cells from BM (BMPCs). These BMPCs were cultured for 24 h with or without tubacin (5 µM), in the presence or absence of bortezomib (5 nM and 10 nM). Consistent with MM cell line data, cytotoxicity in BMPCs induced by bortezomib is markedly augmented by tubacin (FIGS. 5A, 5B, and 5C); importantly, no toxicity is recognized in normal PBMCs similarly treated (FIG. 5D).

We next examined the mechanism whereby combined tubacin with bortezomib specifically induces cytotoxicity in MM patient plasma cells, but not in PBMCs. Both PBMCs and BMPCs obtained from the same MM patient were treated for 12 h with tubacin (5 µM). Constitutive expression of HDAC6 is relatively higher in BMPCs than PBMC; importantly, acetylation of t-tubulin is markedly enhanced by tubacin in BMPCs, but not in PBMCs (FIG. 5E). Ongoing studies are further delineating the molecular mechanisms of this observation.

Example 6

Tubacin Combined with Bortezomib Inhibits Paracrine MM Cell Growth.

Figure 6A:
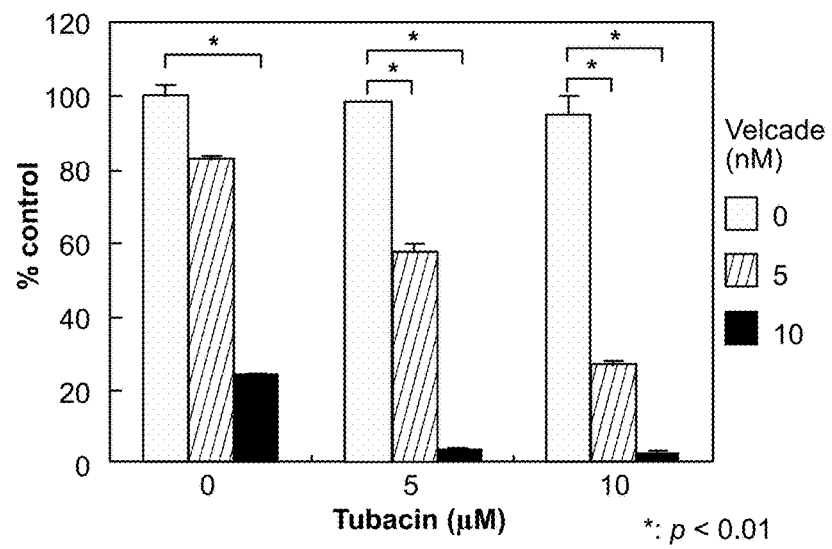
FIGS. 6A to 6B show that tubacin significantly enhances Velcade-induced cytotoxicity in MM cell lines. MM.1S (FIG. 6A) and RPMI8226 (FIG. 6B) cells were cultured with Velcade (5 and 10 nM) in the presence (5 and 10 µM) or absence of tubacin for 24 h. Cytotoxicity was assessed by MTT assay.
Figure 6B:
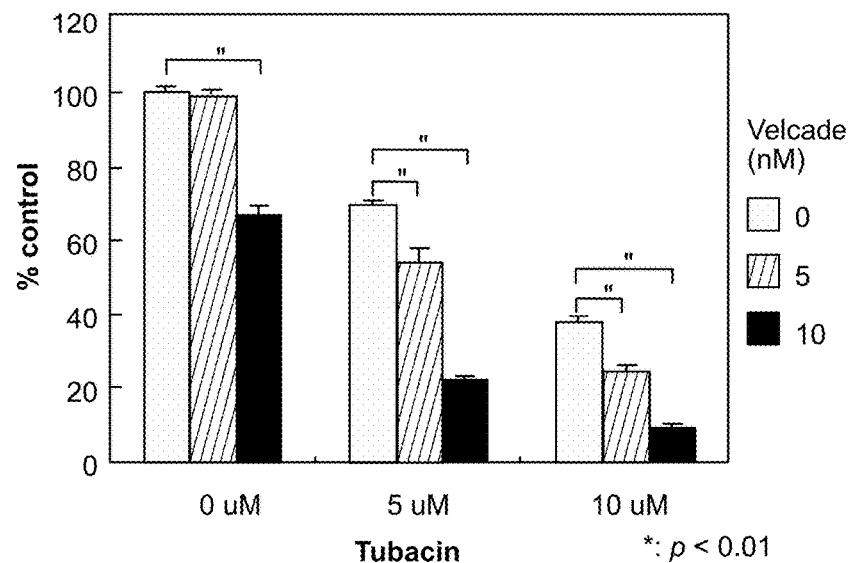
Figure 8:
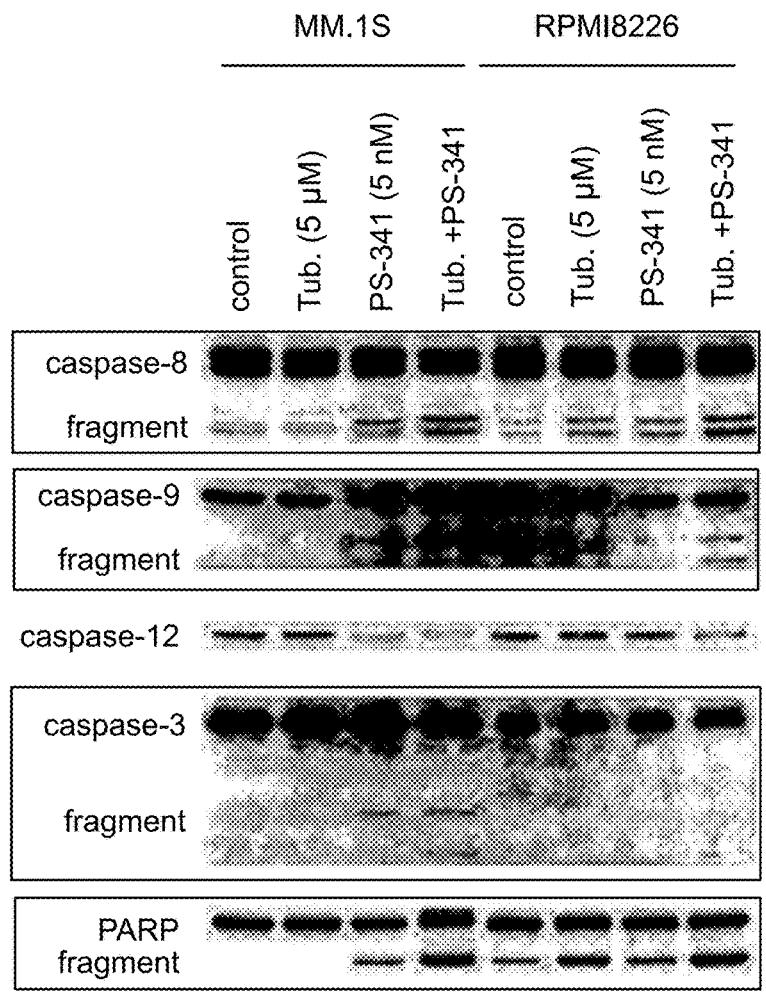
FIG. 8 demonstrates that caspase and PARP cleavage is induced by the combination of Velcade with tubacin. MM.1S and RPMI8226 cells were cultured with Velcade (5 nM) in the presence (5 µM) or absence of tubacin for 24 h. Caspase-8/9/3 and PARP cleavage were assessed by Western blotting using specific antibodies.
Figure 9:
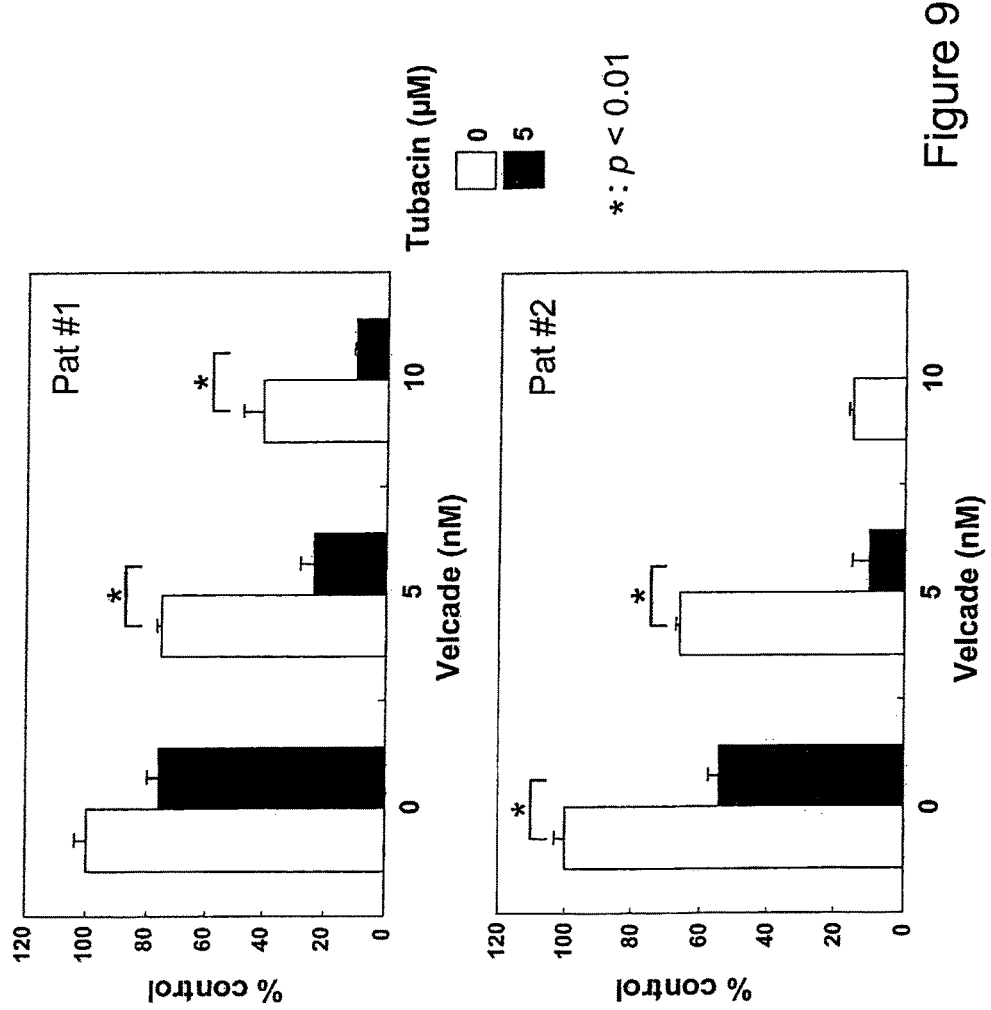
FIG. 9 shows that tubacin significantly enhances Velcade-induced cytotoxicity in MM patient tumor cells. Purified tumor cells from MM patients were cultured with Velcade (5 and 10 nM) in the presence (5 µM) or absence of tubacin for 24 h. Cytotoxicity was assessed by MTT assay.
Figure 10:
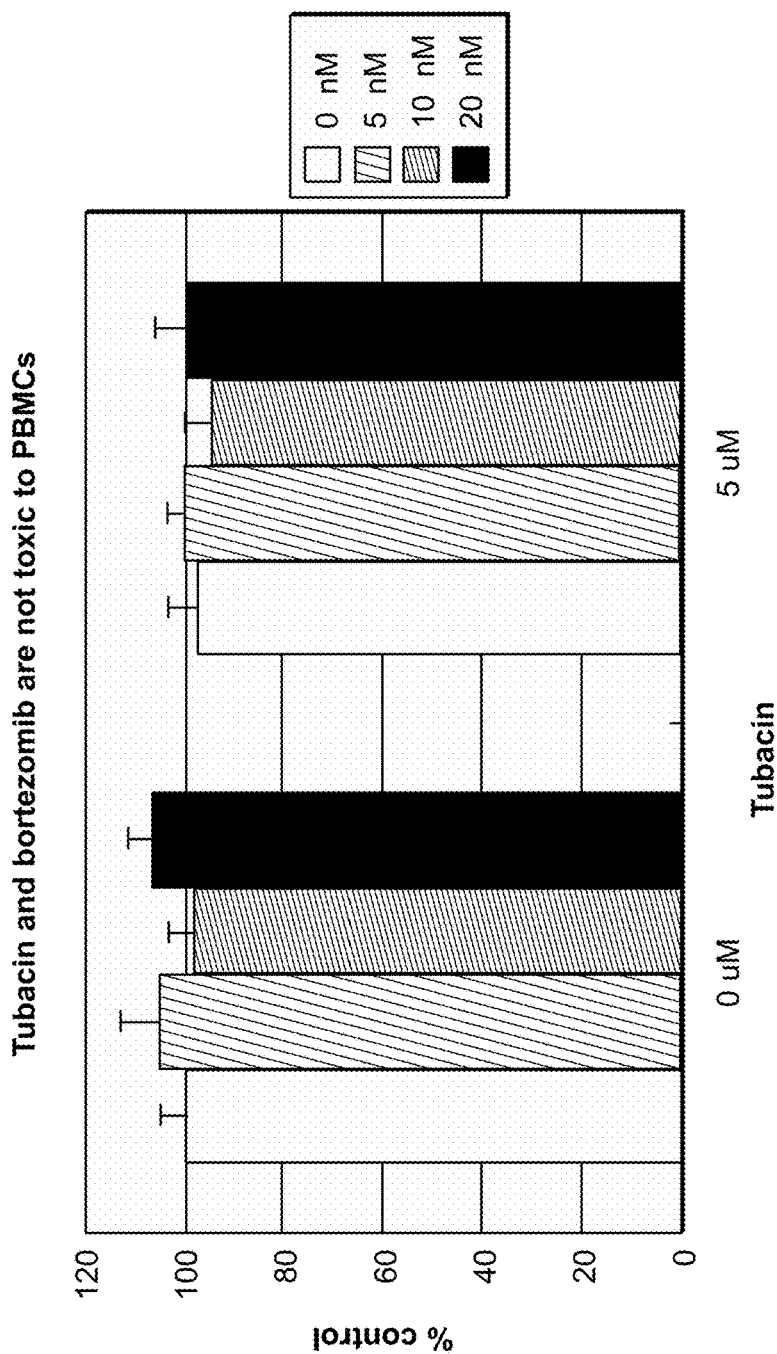
FIG. 10 demonstrates that the combination treatment of Velcade with Tubacin does not trigger cytotoxicity in normal peripheral blood mononuclear cells (PBMCs). PBMCs from 3 normal volunteers were cultured with Velcade (5-20 nM) in the presence (5 µM) or absence of tubacin for 24 h. Cytotoxicity was assessed by MTT assay.
Figure 11:
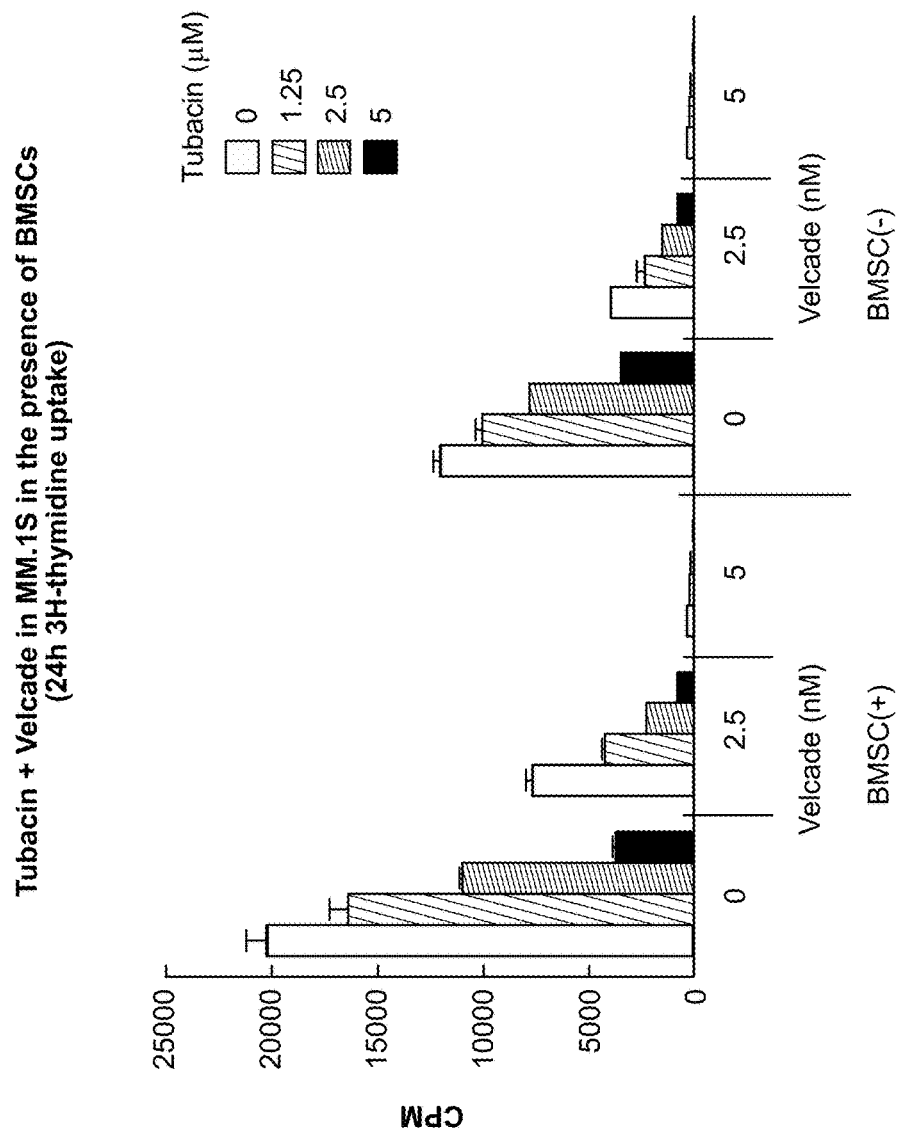
FIG. 11 shows that tubacin inhibits MM.1S cell growth in the bone marrow microenvironment. MM.1S cells were cultured with tubacin (1.25-5 µM) in the presence (2.5 and 5 nM) or absence of Velcade, with or without bone marrow stromal cells (BMSCs) for 24 h. Cell growth was assessed by $^3$H-thymidine uptake.
Figure 12A:
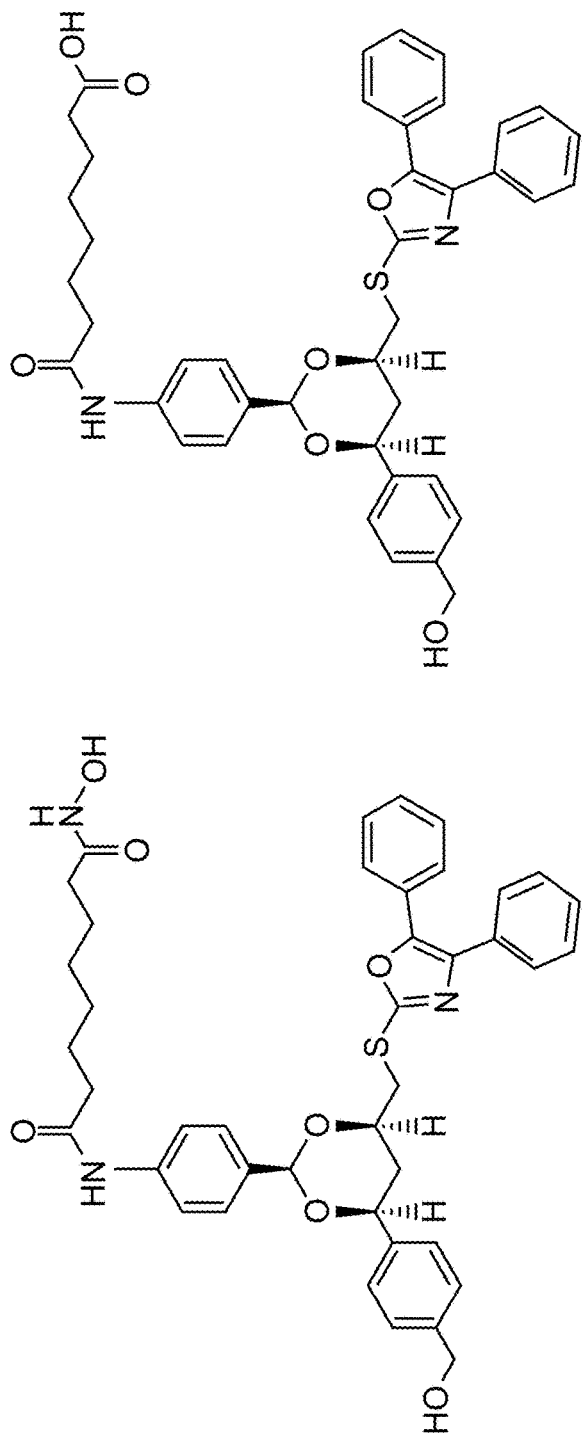
FIGS. 12A to 12E demonstrate that tubacin specifically induces acetylation of α-tubulin in MM cells.
Figure 12B:
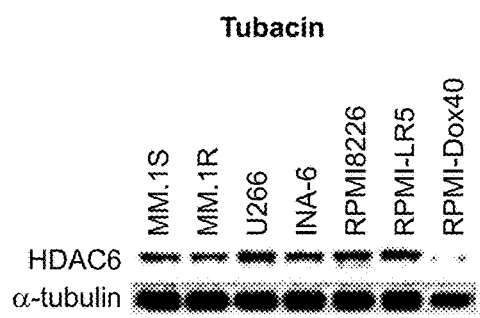
Figure 12C:
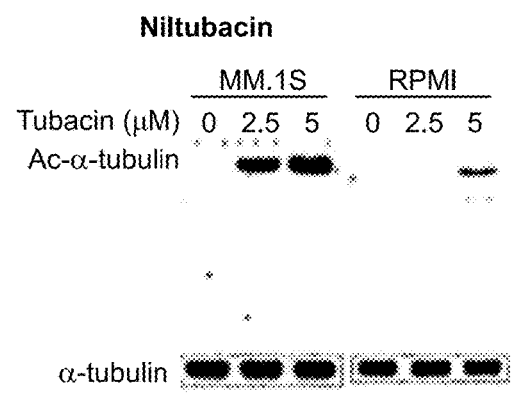
Figure 12D:
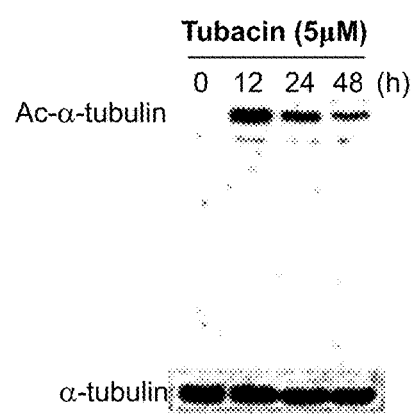
Figure 12E:
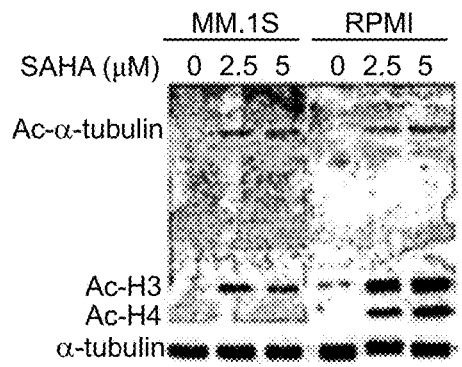
Figure 13B:
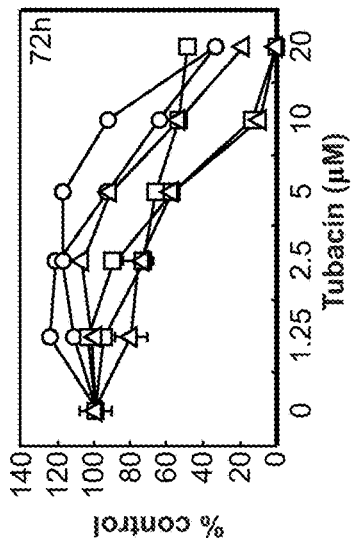
FIGS. 13A to 13D demonstrate that tubacin induces cytotoxicity via activation of caspases. MM.1S (●), MM.1R (●), U266 (▲), RPMI8226 (▲), RPMI-LR5 (■) and RPMI-Dox40 (■) cells were cultured in the presence of tubacin (1.25-20 µM) for 48 h (FIG. 13A) and 72 h (FIG. 13B).
Figure 13A:
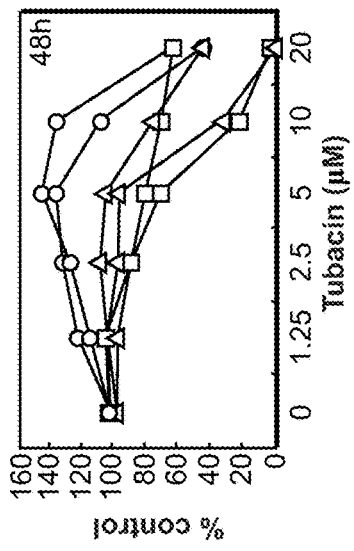
Figure 13D:
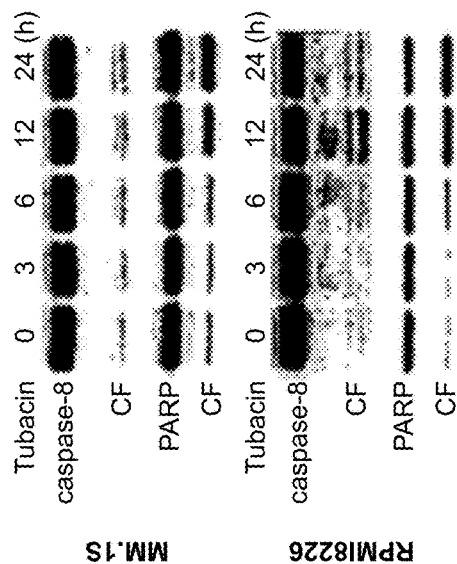
Figure 13C:
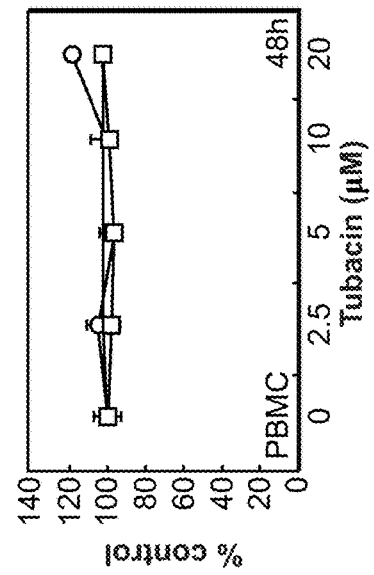
Figure 14D:
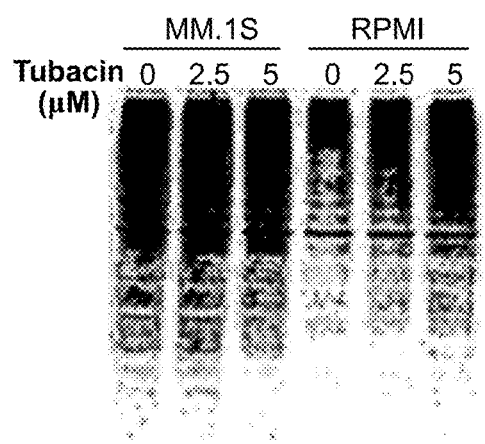
Figure 14E:
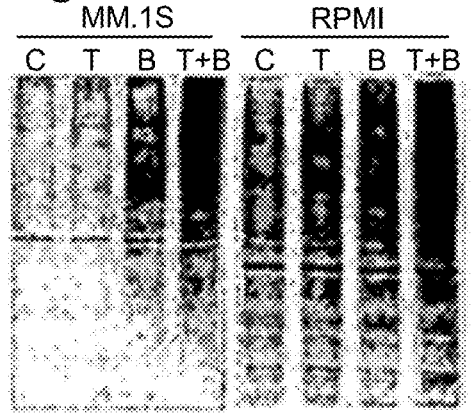
Figure 15A:
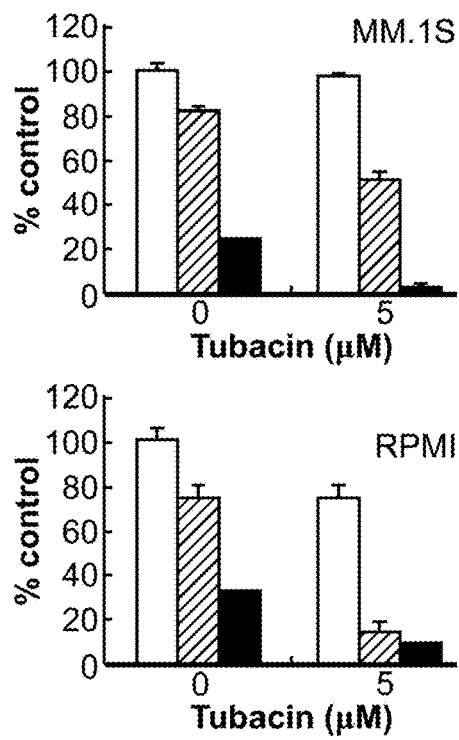
FIGS. 15A to 15G demonstrate that tubacin and bortezomib induce synergistic anti-tumor activity in MM cell lines.
Figure 15B:
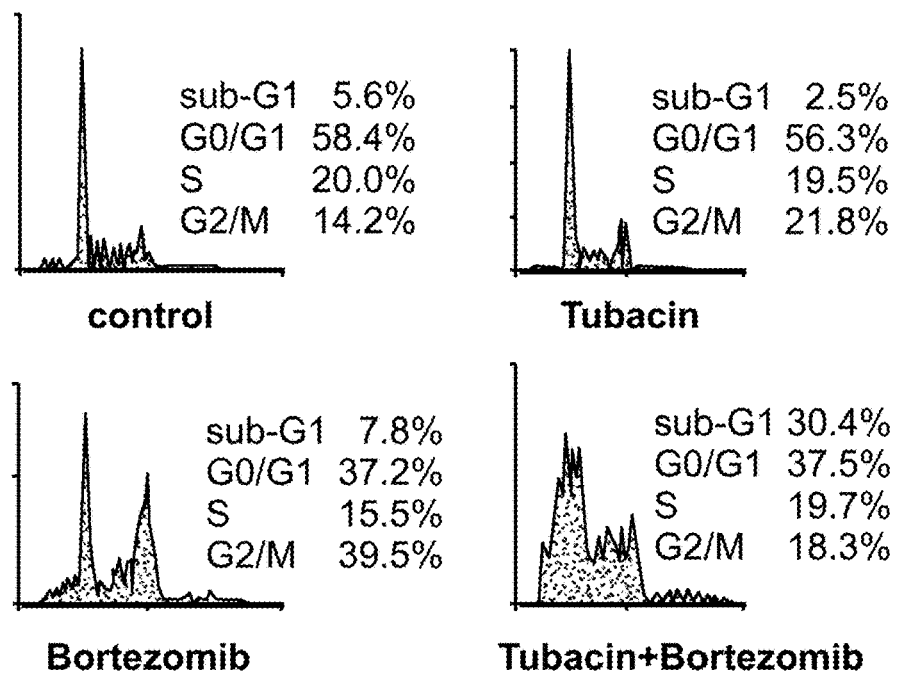
Figure 15C:
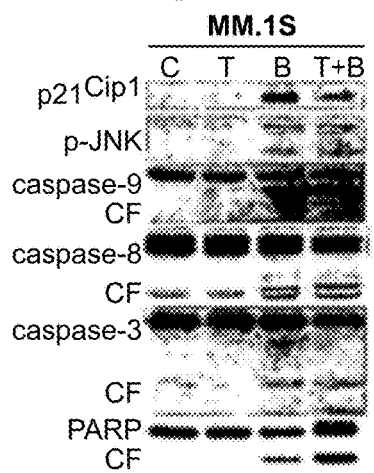
Figure 15D:
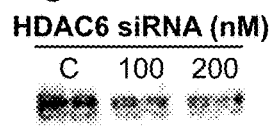
Figure 15E:
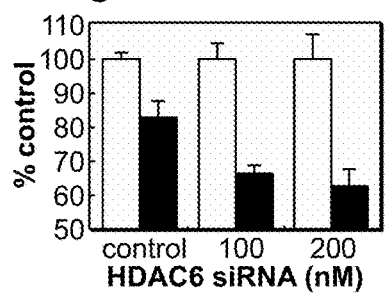
Figure 15F:
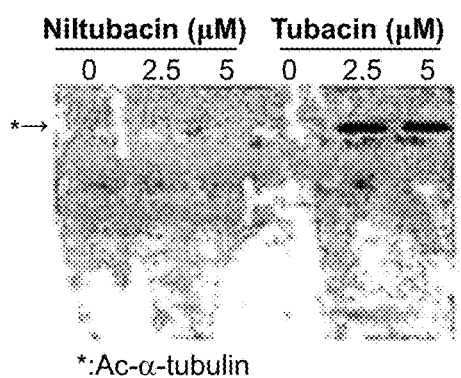
Figure 15G:
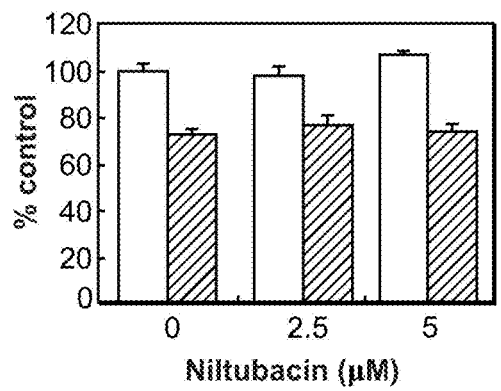
Figure 16A:
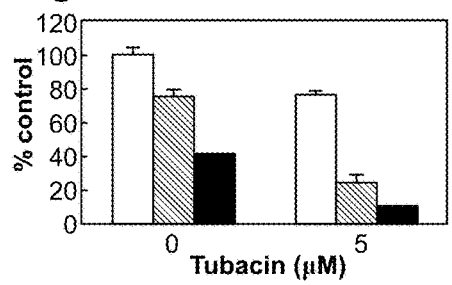
FIGS. 16A to 16E demonstrate that tubacin synergistically enhances bortezomib-induced cytotoxicity in patient MM cells without cytotoxicity to PBMCs. BMPCs (FIGS. 16A, 16B, and 16C) and PBMCs (FIG. 16D) from 3 MM patients were cultured in the presence or absence of tubacin (5 µM) in control media (Q) as well as with 10 nM (■) or 20 nM (■) bortezomib for 24 h; cytotoxicity was assessed by MTT assay.
Figure 16B:
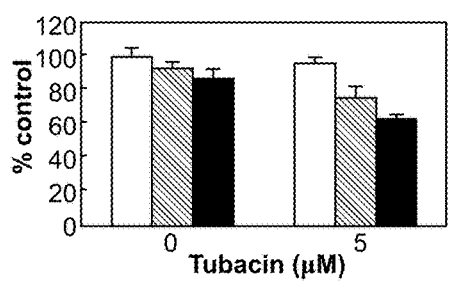
Figure 16C:
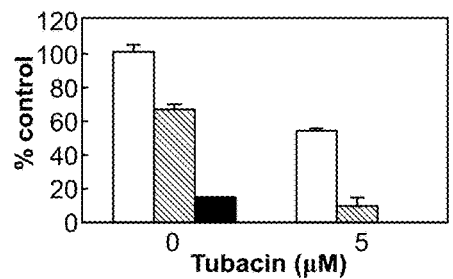
Figure 16D:
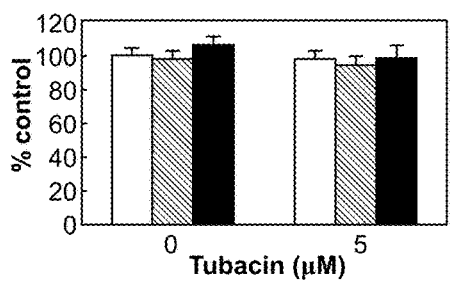
Figure 16E:
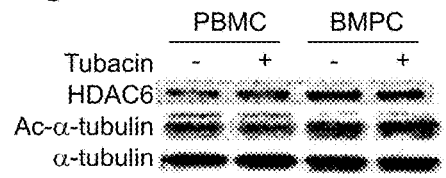
Figure 17A:
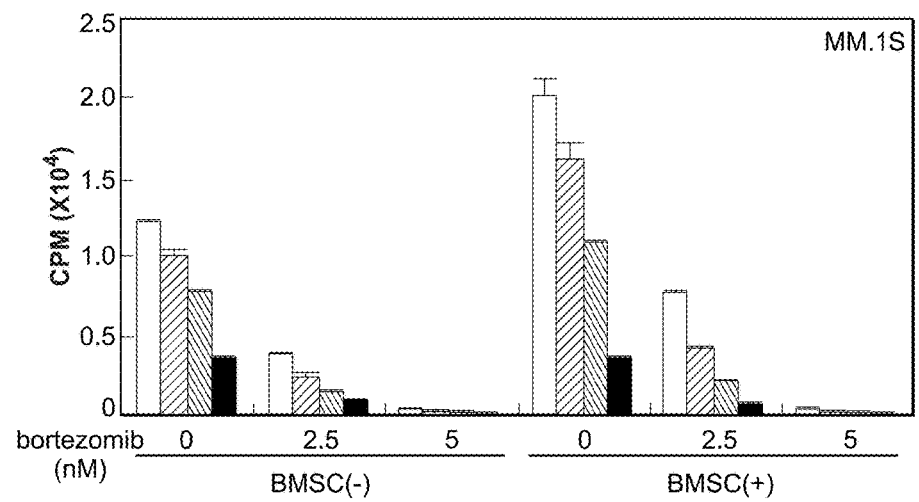
FIGS. 17A to 17B demonstrate that tubacin inhibits paracrine MM cell growth. MM.1S (FIG. 17A) and RPMI8226 (FIG. 17B) cells were cultured for 24 h in BMSC-coated or non-coated plates in control media (□); as well as with 1.25 µM (■), 2.5 µM (■), or 5 µM (■) tubacin, in the presence or absence of bortezomib (2.5 nM, 5 nM). DNA synthesis was assessed by [$^3$H]-thymidine uptake; data represent mean (±SD) of quadruplicate cultures.
Figure 17B:
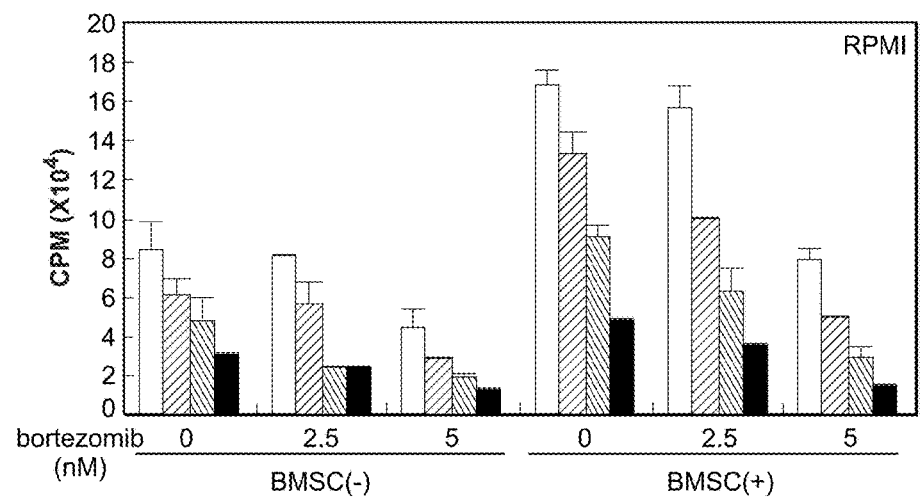
Figure 18:
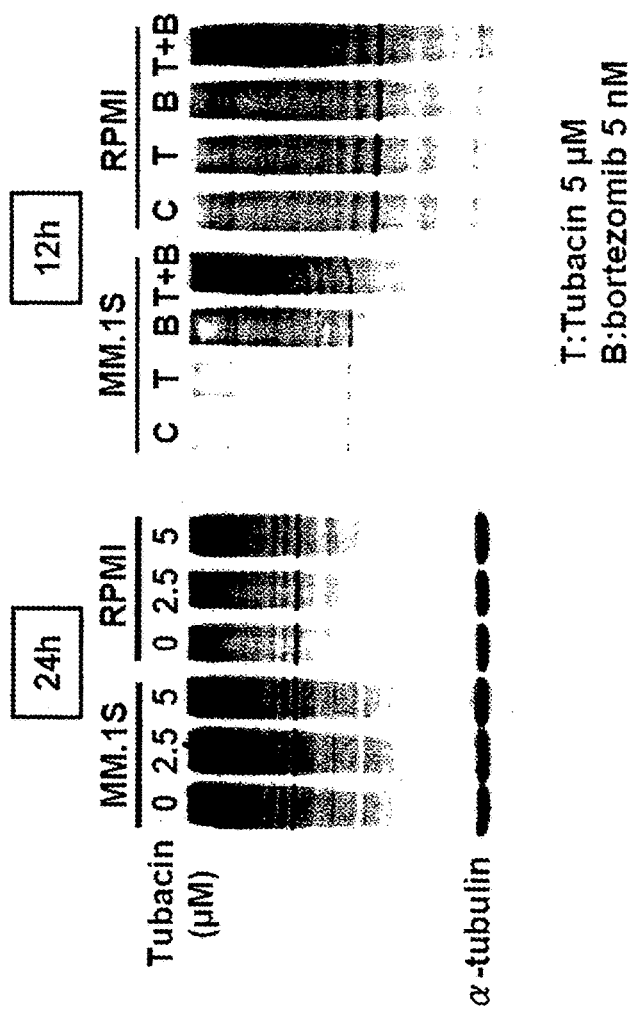
FIG. 18 demonstrates that tubacin alone, bortezomib alone, and combinations of tubacin and bortezomib are potent inhibitors of protein catabolism in MM.1S cells and RPMI cells.
Figure 19:
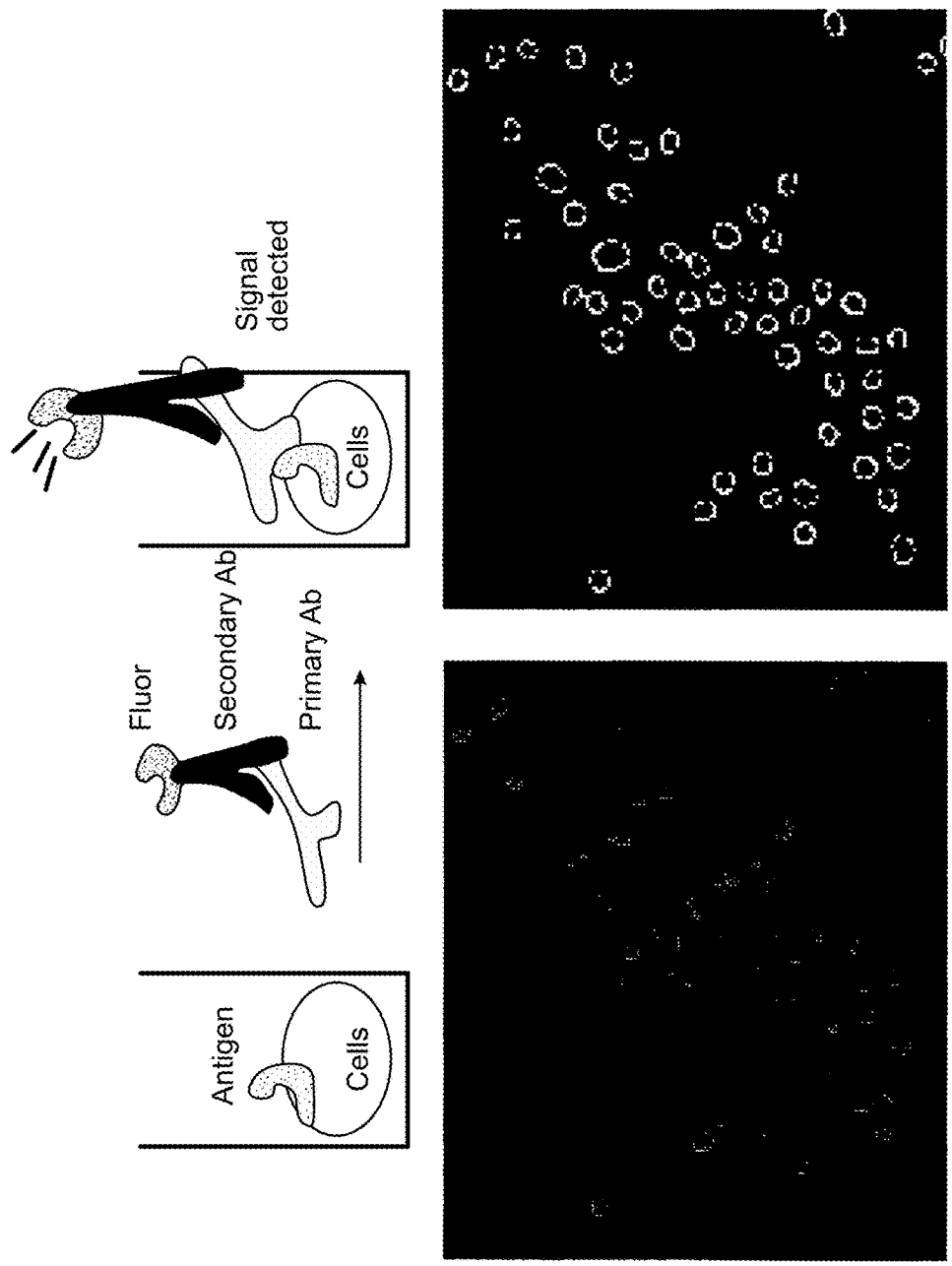
FIG. 19 shows a schematic of the high-throughput immunofluorescence quantitative assay for acetylated tubulin with resulting images.
Figure 20:
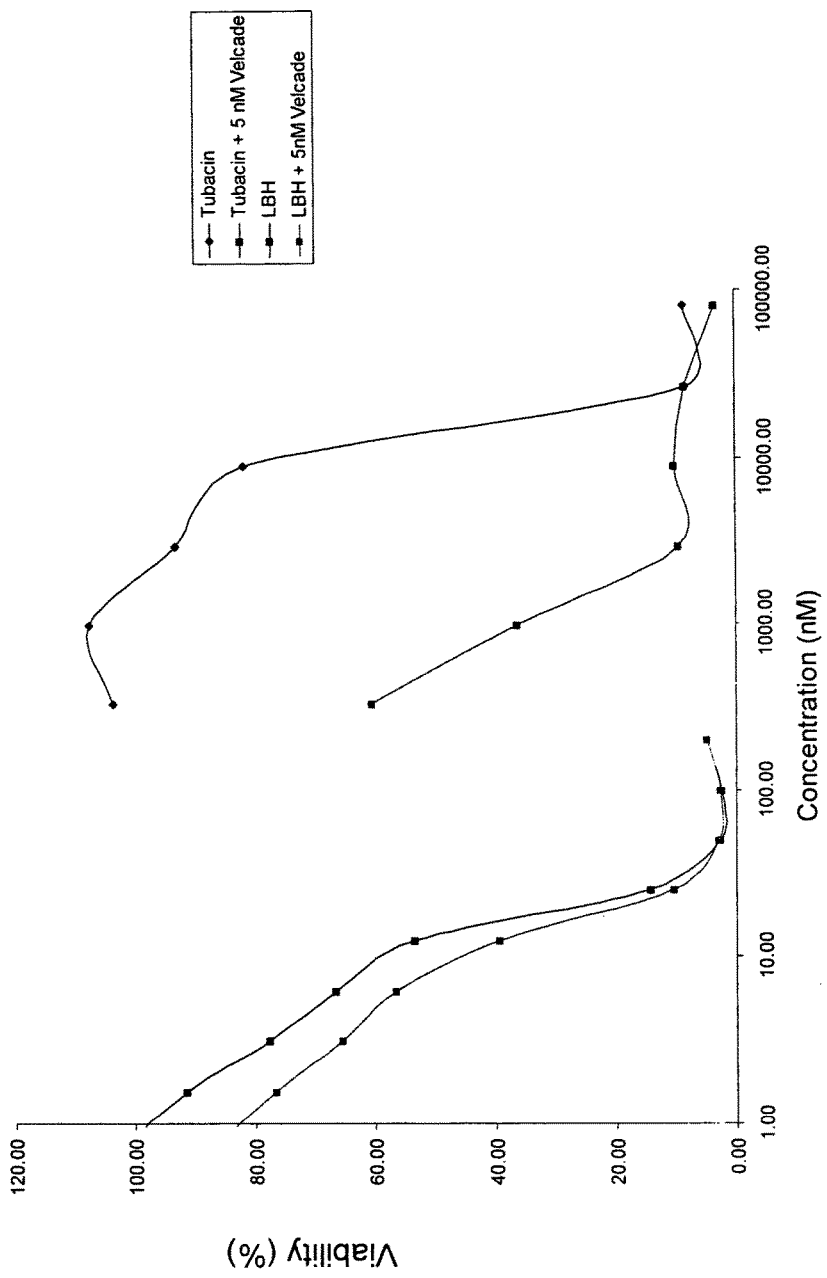
FIG. 20 shows the toxicity and synergy of Tubacin and LBH589 with Bortezomib in MM.1S cells.
Figure 21:
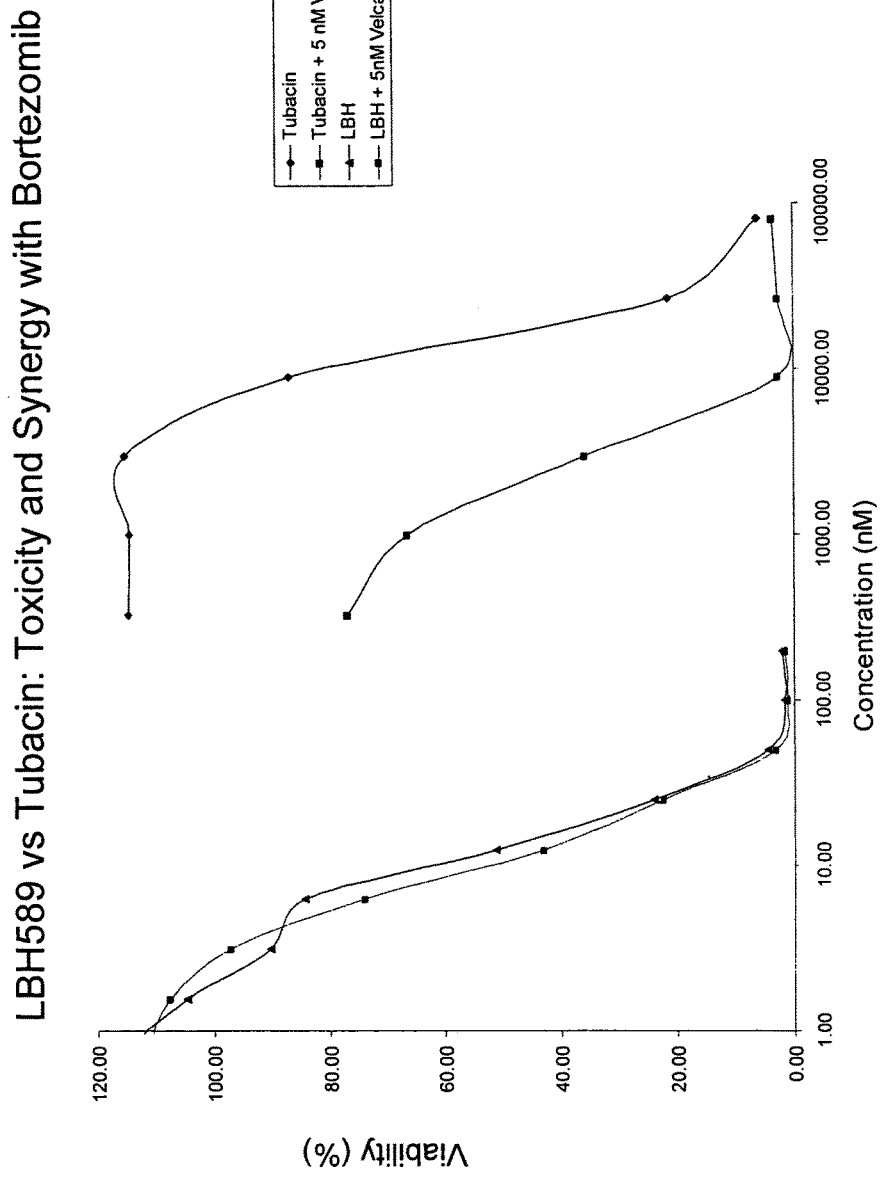
FIG. 21 shows the toxicity and synergy of Tubacin and LBH589 with Bortezomib with RPMI-8226 cells.
Figure 22:
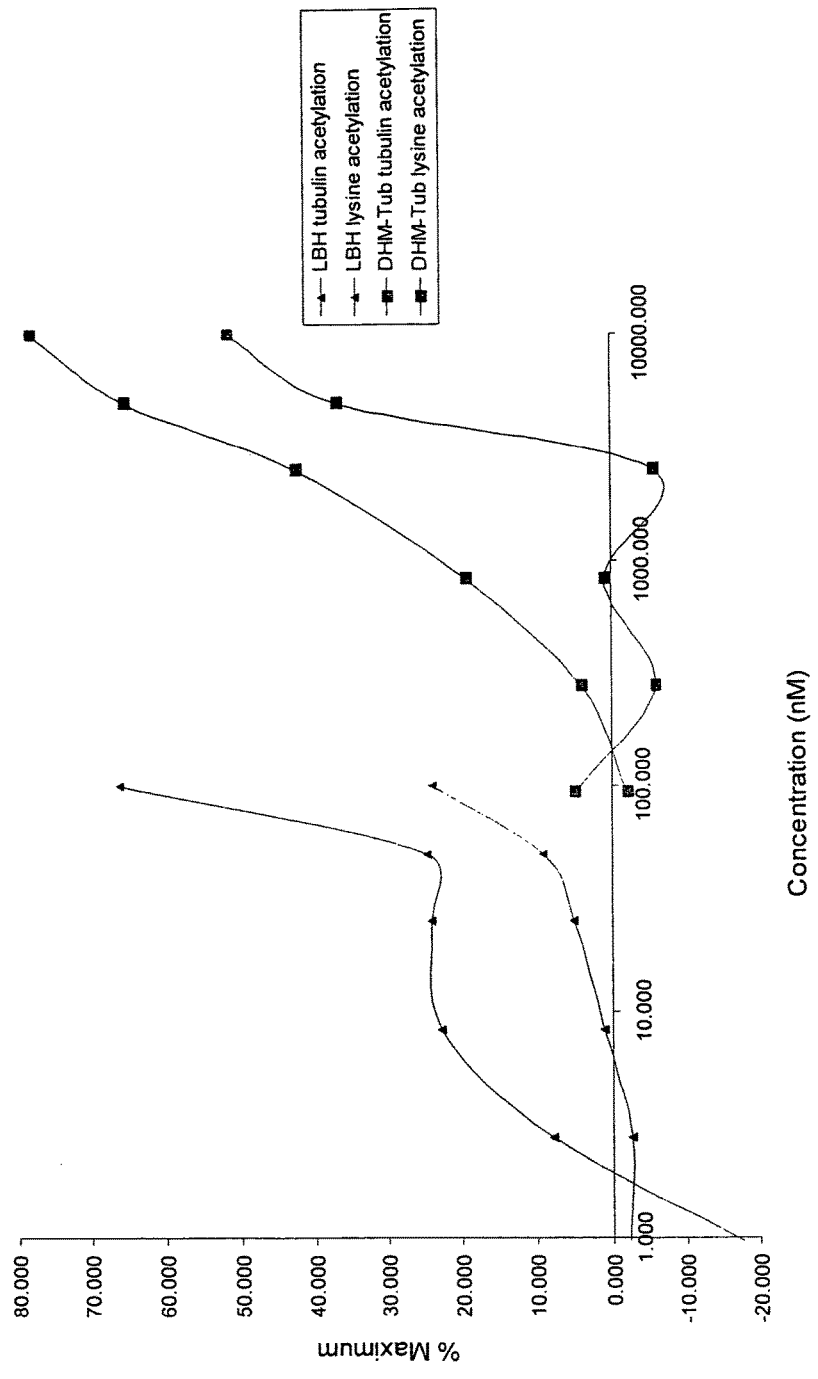
FIG. 22 shows the effects of LBH589 and Tubacin on acetylated tubulin versus acetylated lysine using the cytoblot assay.
Figure 23:
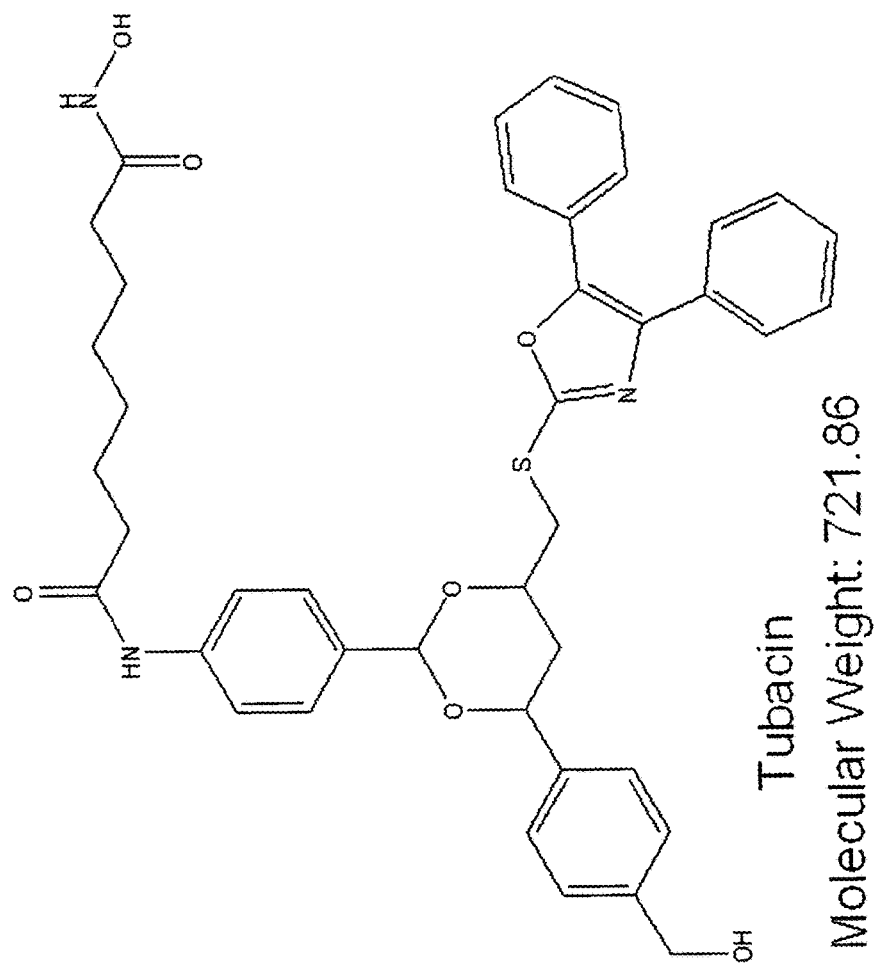
FIG. 23 shows the chemical structure of Tubacin.
Figure 25:
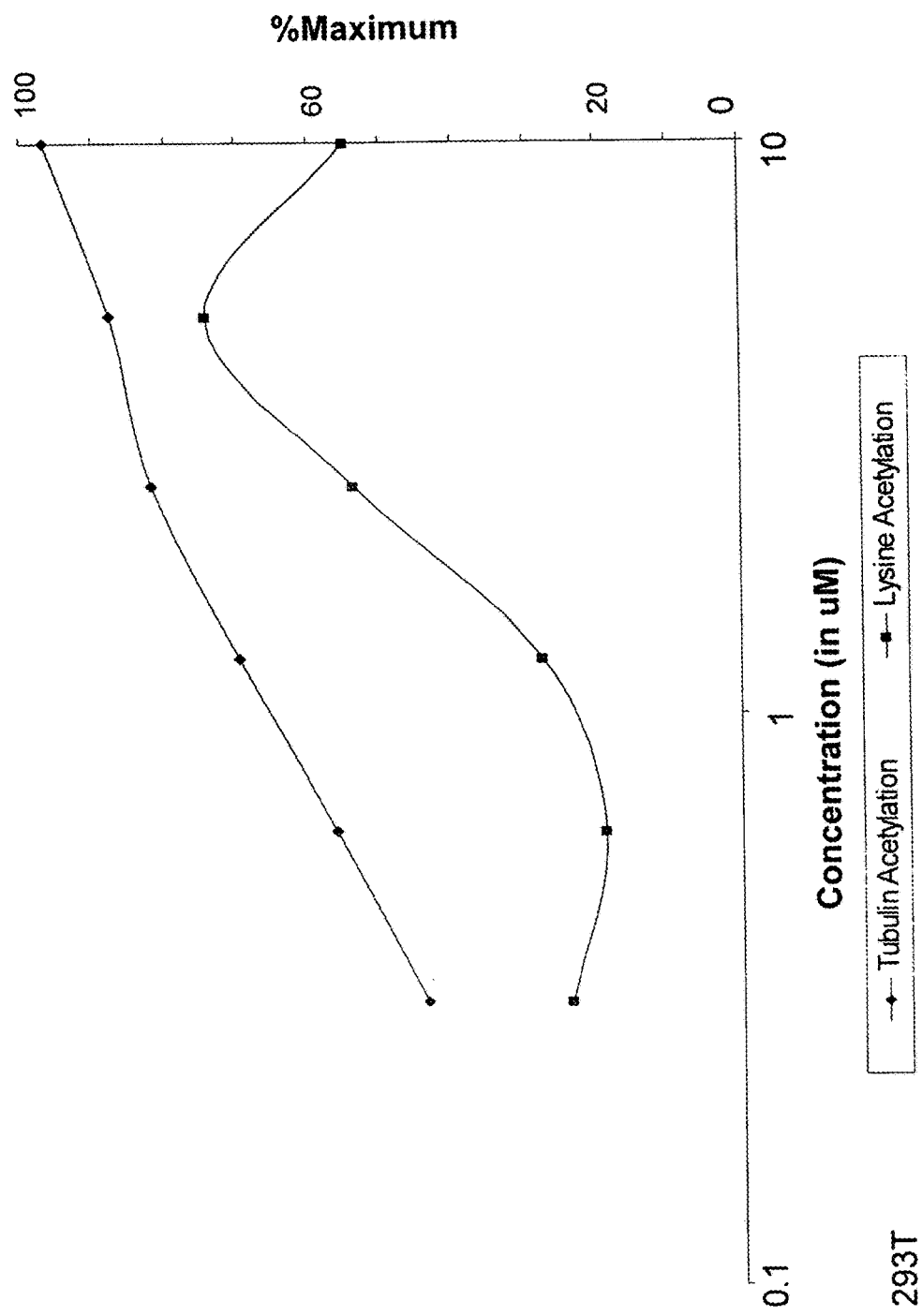
FIG. 25 demonstrates the specificity of Tubacin for tubulin acetylation versus lysine acetylation.
Figure 26:
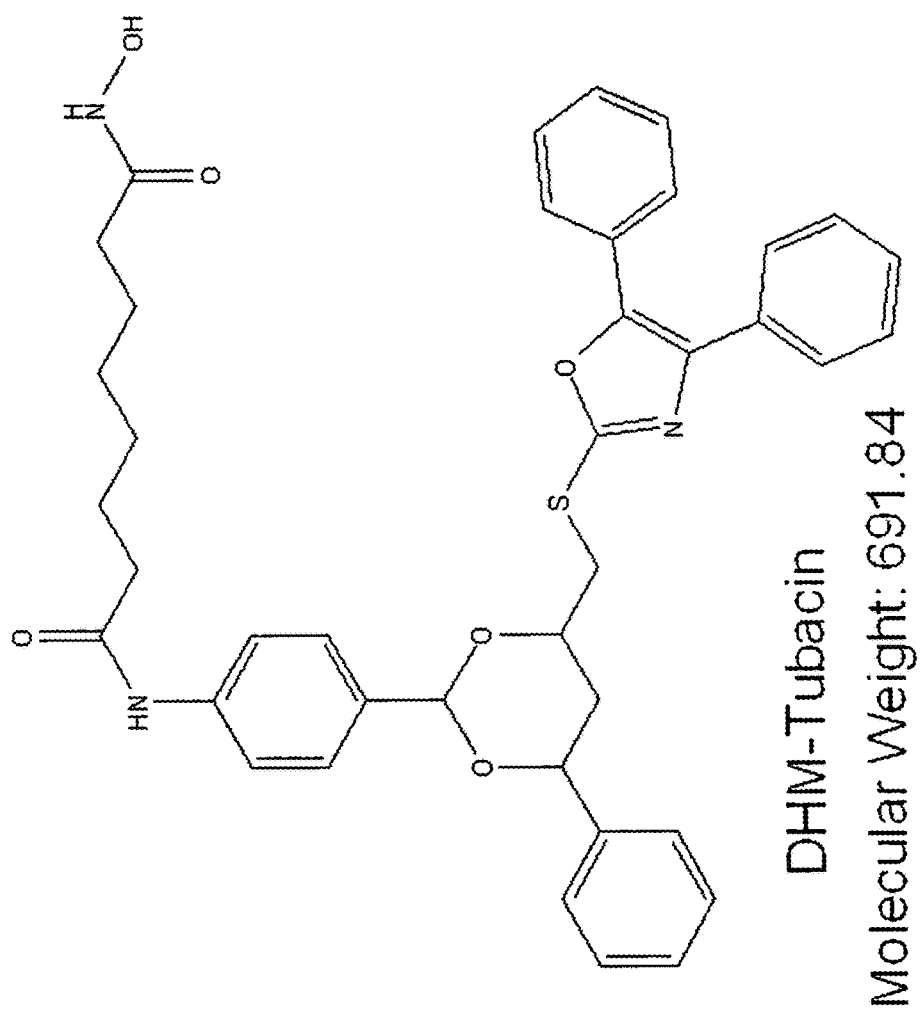
FIG. 26 shows the chemical structure of des(hydromethyl)-Tubacin (DHM-Tubacin). The hydroxymethyl substituent off the phenyl ring in Tubacin has been removed.
Figure 28:
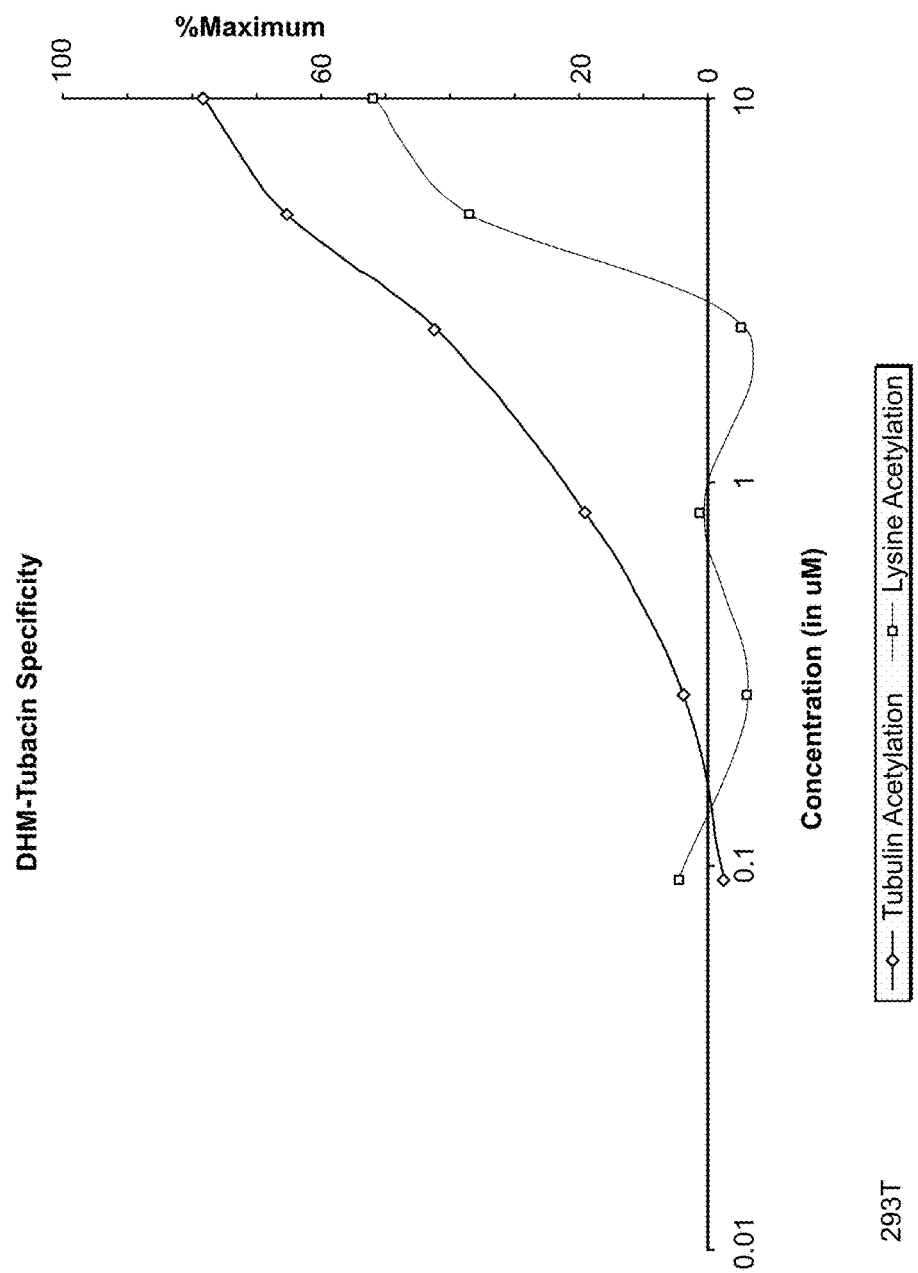
FIG. 28 demonstrates the specificity of DHM-Tubacin for tubulin acetylation versus lysine acetylation.
Figure 29:
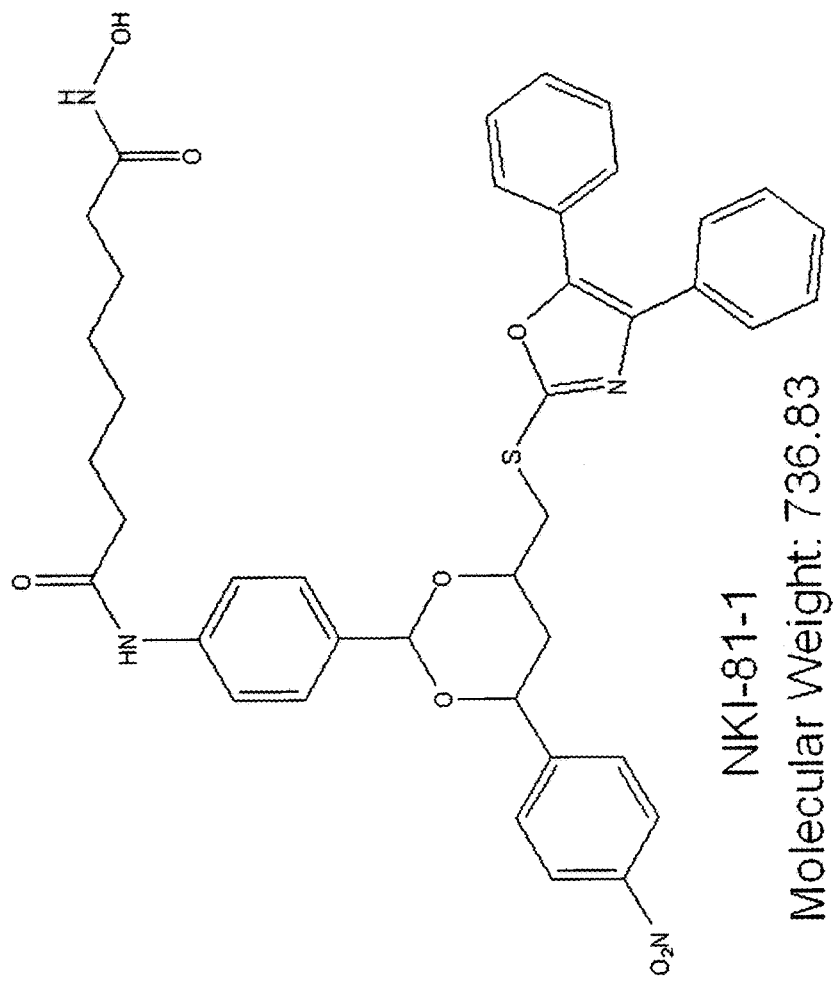
FIG. 29 shows the chemical structure of NKI-81-1.
Figure 30A:
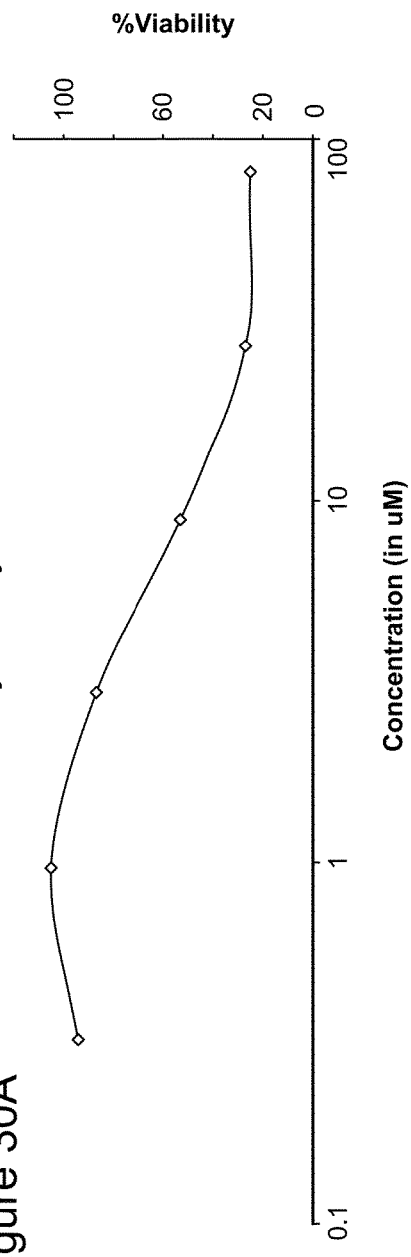
FIGS. 30A to 30B show the synergy between NKI-81-1 and Velcade in myeloma cell lines (FIG. 30A) MM.1S, and (FIG. 30B) RPMI cells.
Figure 30B:
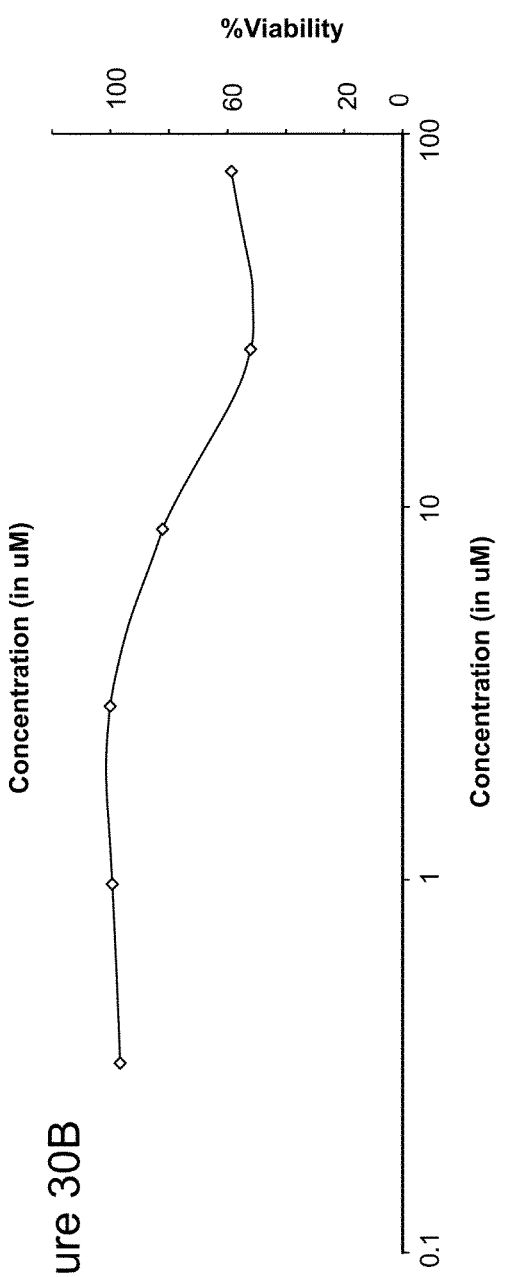
Figure 31:
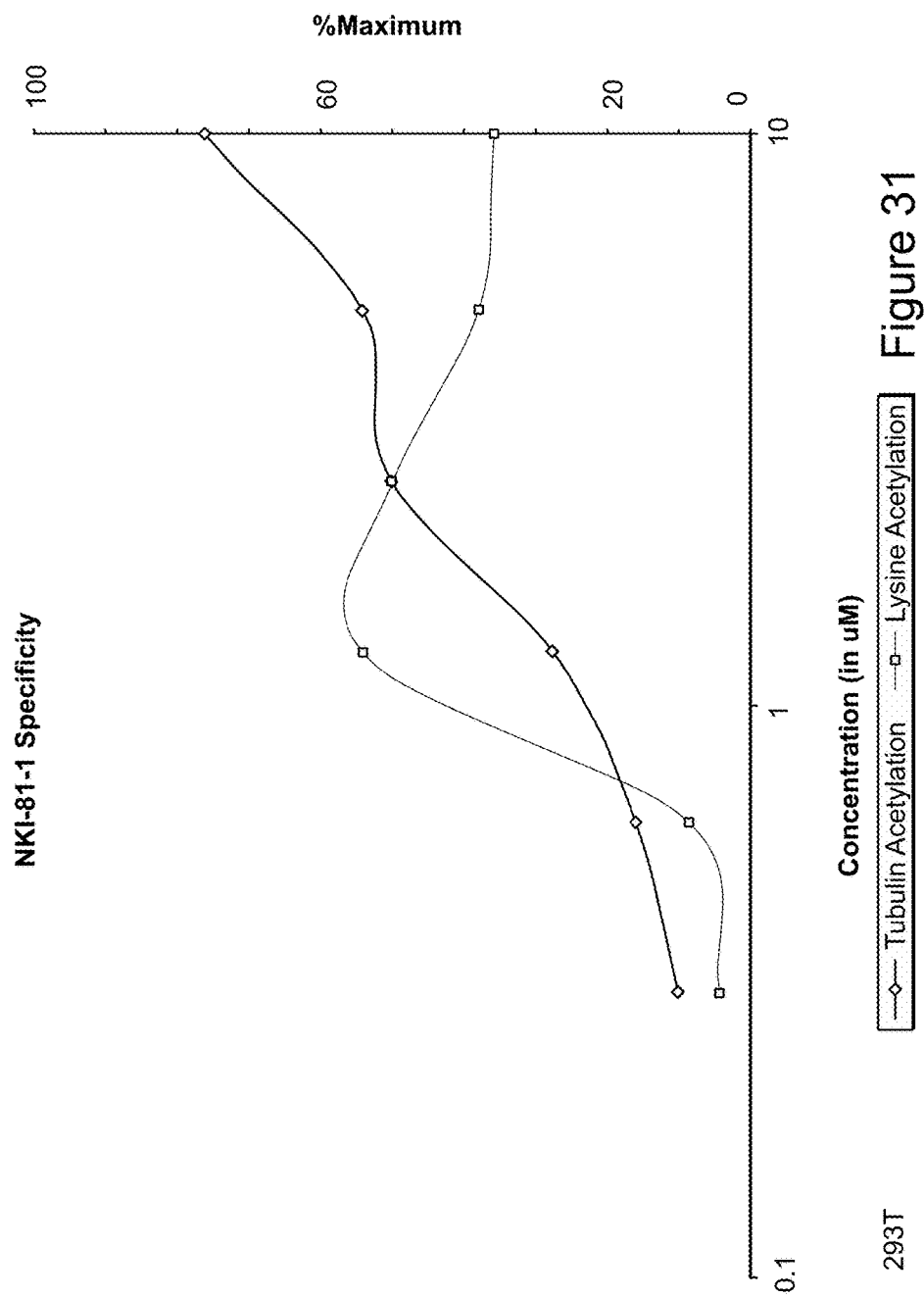
FIG. 31 demonstrates the specificity of NKI-81-1 for tubulin acetylation versus lysine acetylation.
Figure 32:
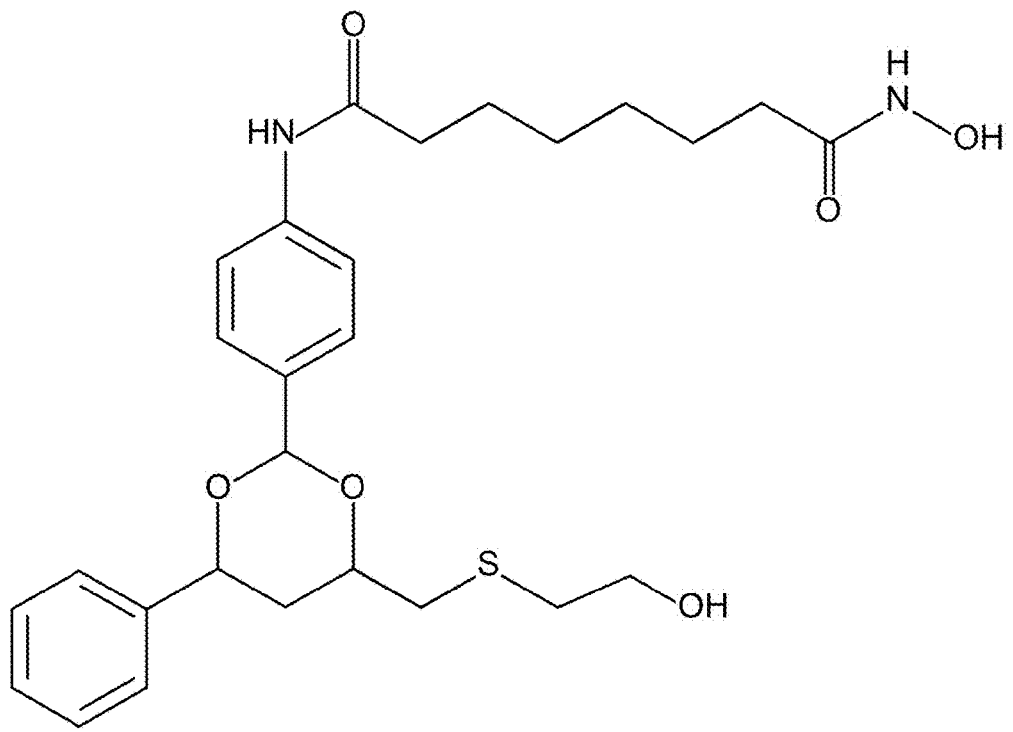
FIG. 32 shows the chemical structure for NKI-94-1.
Figure 33A:
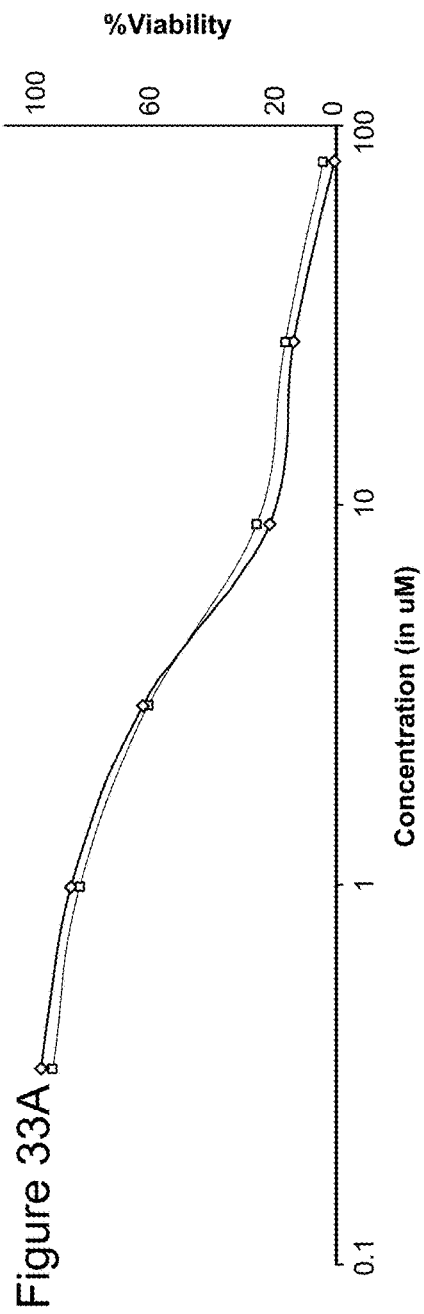
FIGS. 33A to 33B show the synergy between NKI-94-1 and Velcade in myeloma cell lines (FIG. 33A) MM.1S, and (FIG. 33B) RPMI cells.
Figure 33B:
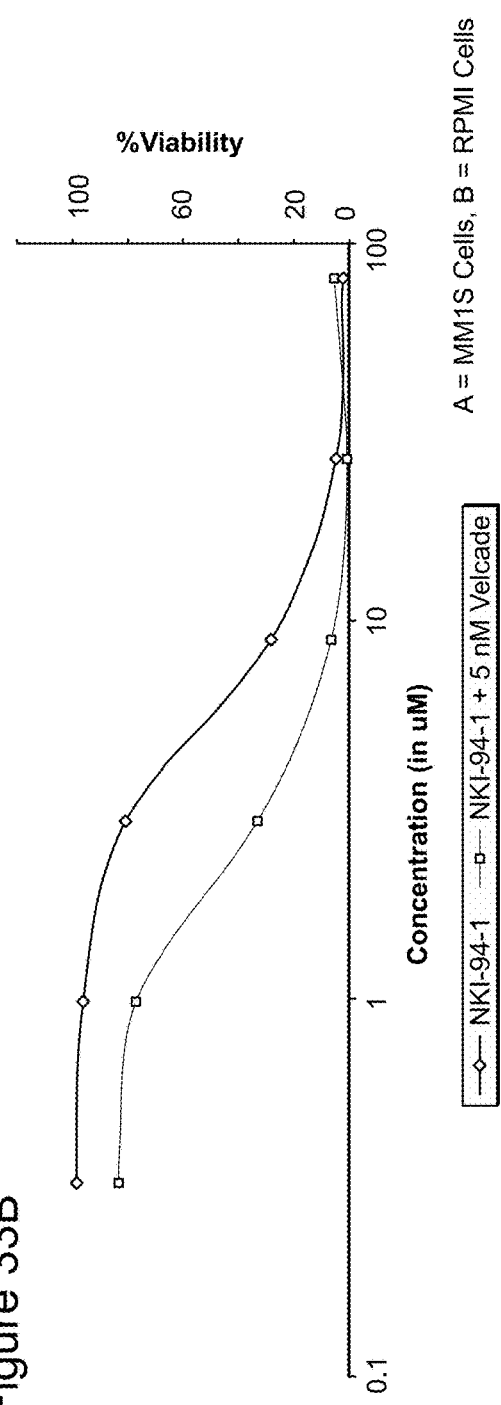
Figure 34:
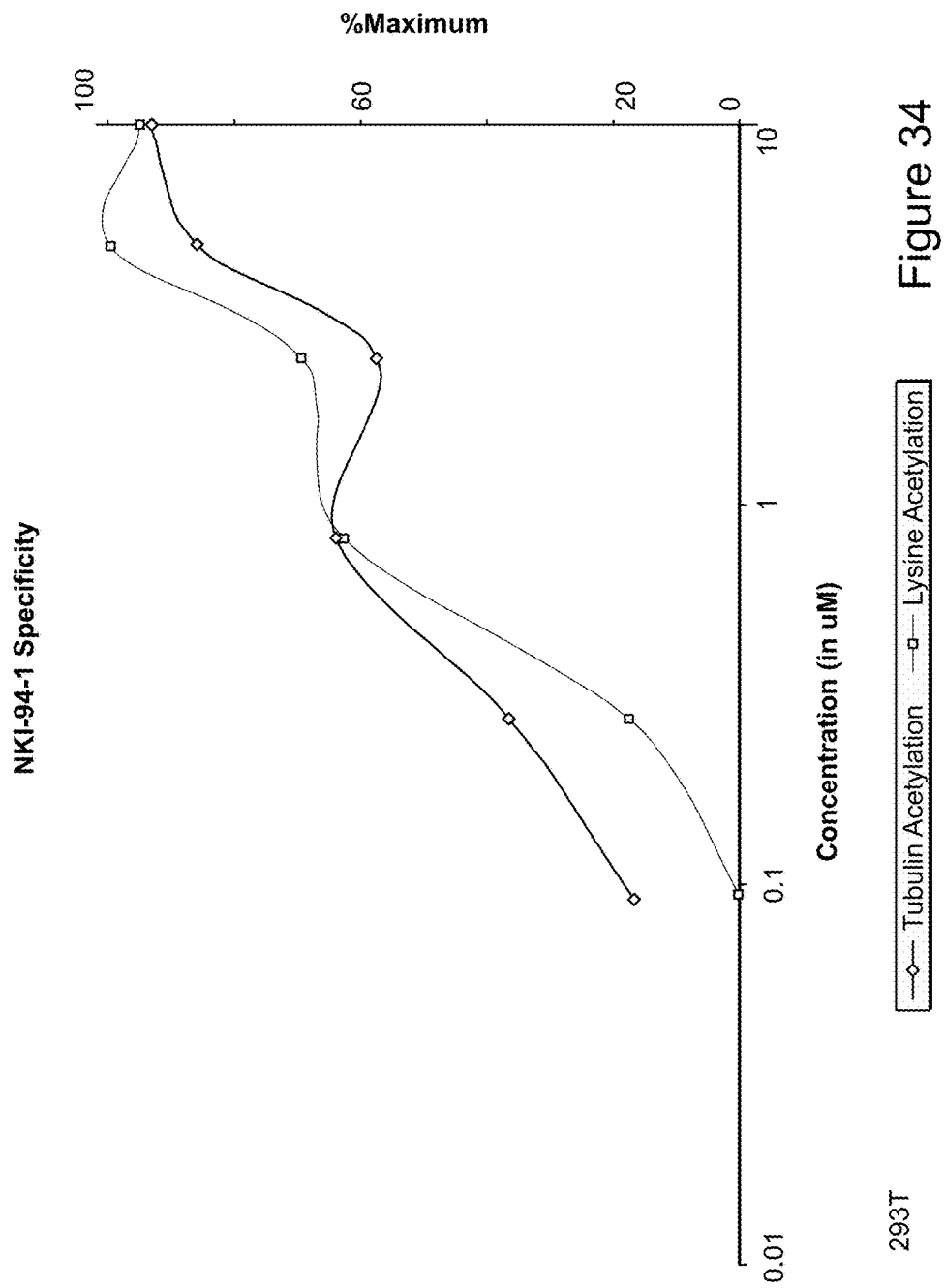
FIG. 34 demonstrates the specificity of NKI-94-1 for tubulin acetylation versus lysine acetylation.
Figure 35:
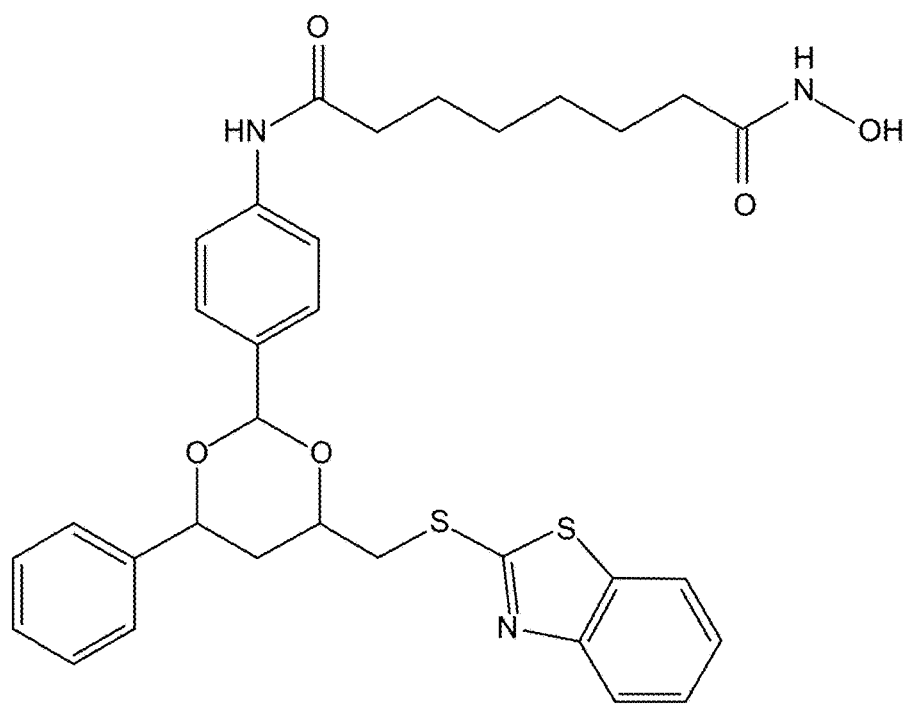
FIG. 35 shows the chemical structure for NKI-59-1.
Figure 36A:
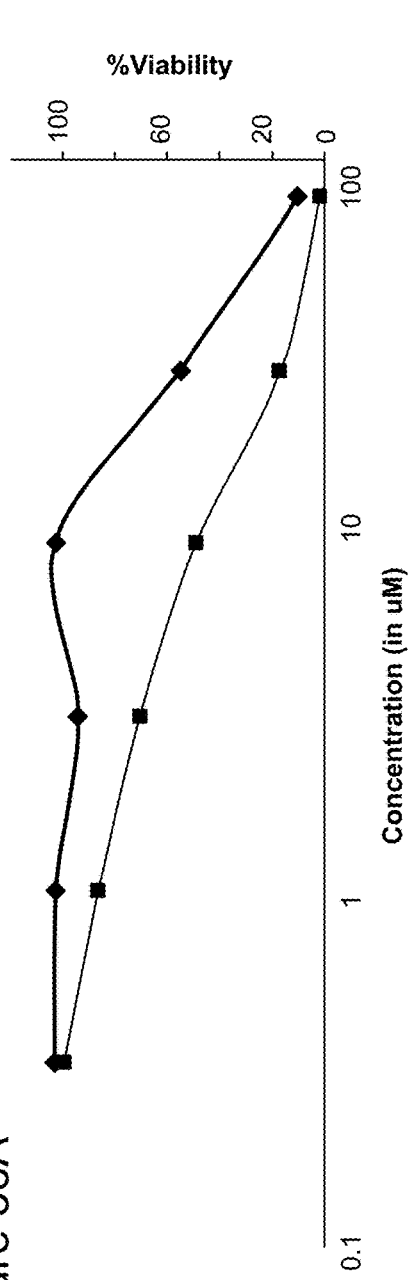
FIGS. 36A to 36B show the synergy between NKI-59-1 and Velcade in myeloma cell lines (FIG. 36A) MM.1S, and (FIG. 36B) RPMI cells.
Figure 36B:
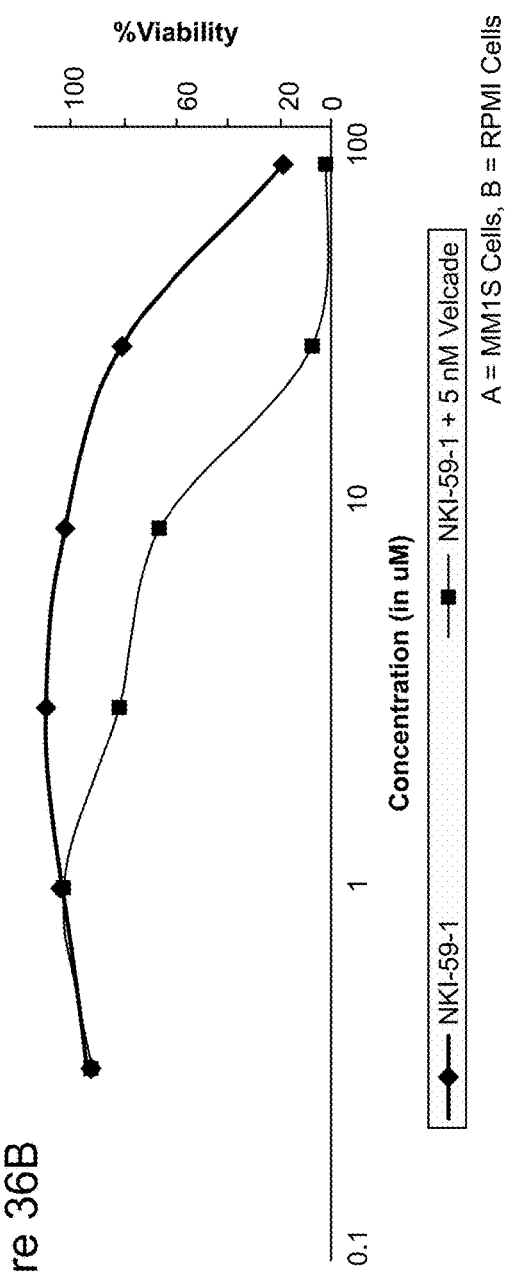
Figure 37:
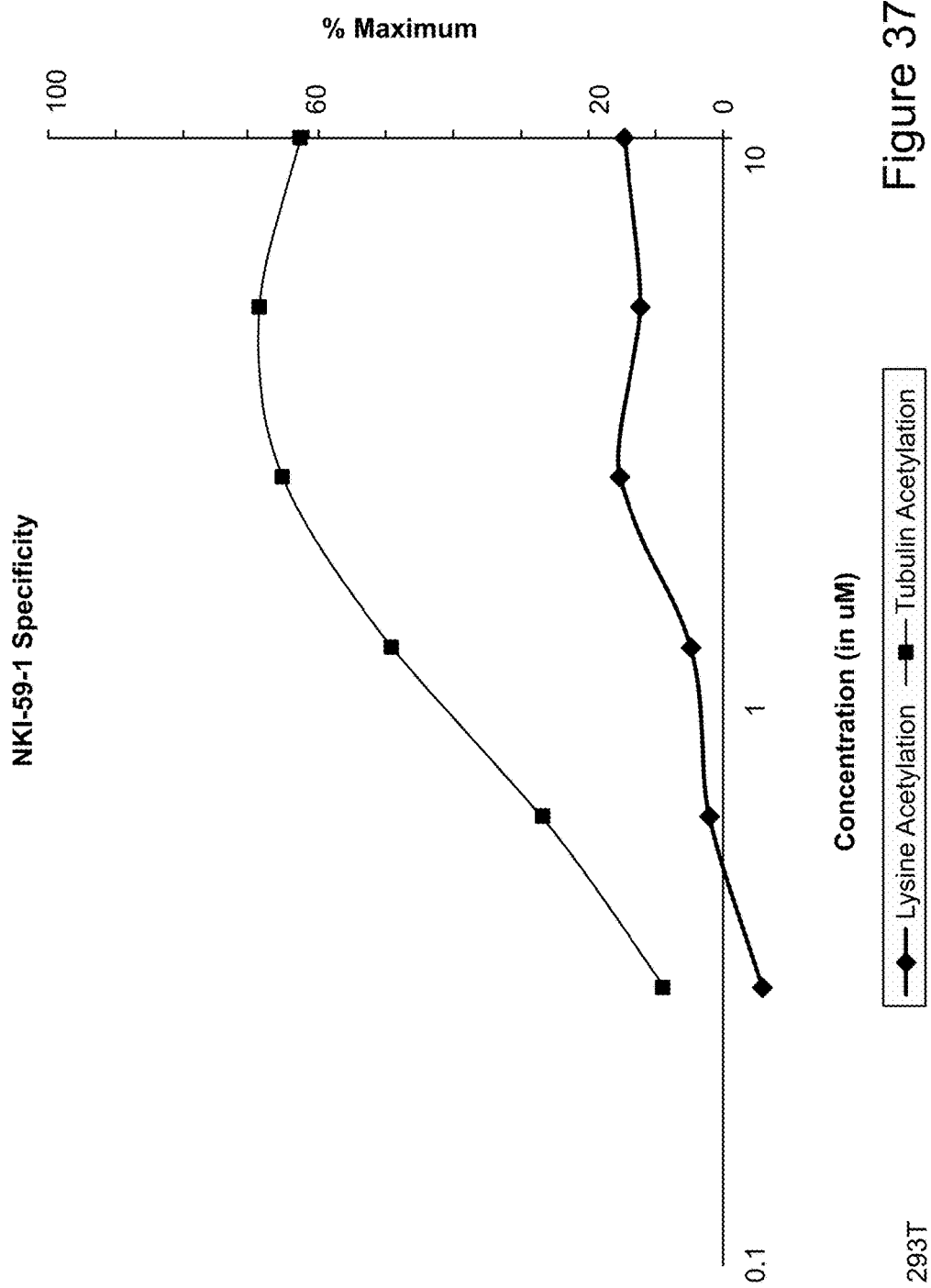
FIG. 37 demonstrates the specificity of NKI-59-1 for tubulin acetylation versus lysine acetylation.
Figure 38:
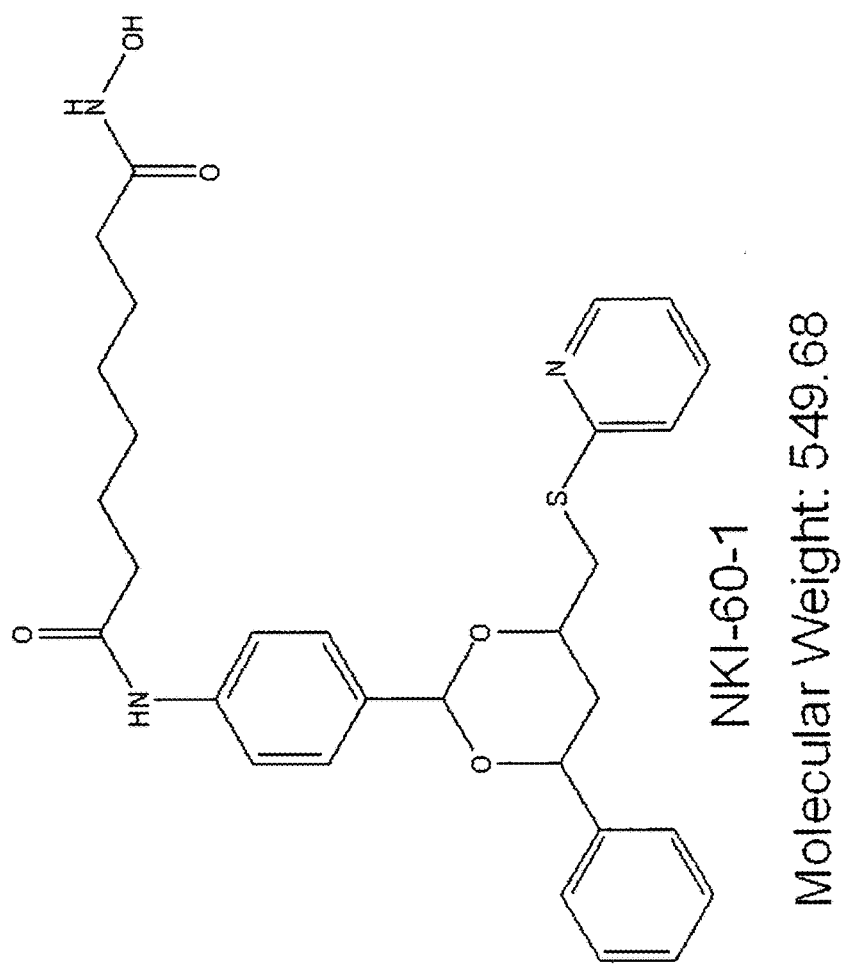
FIG. 38 shows the chemical structure for NKI-60-1.
Figure 40:
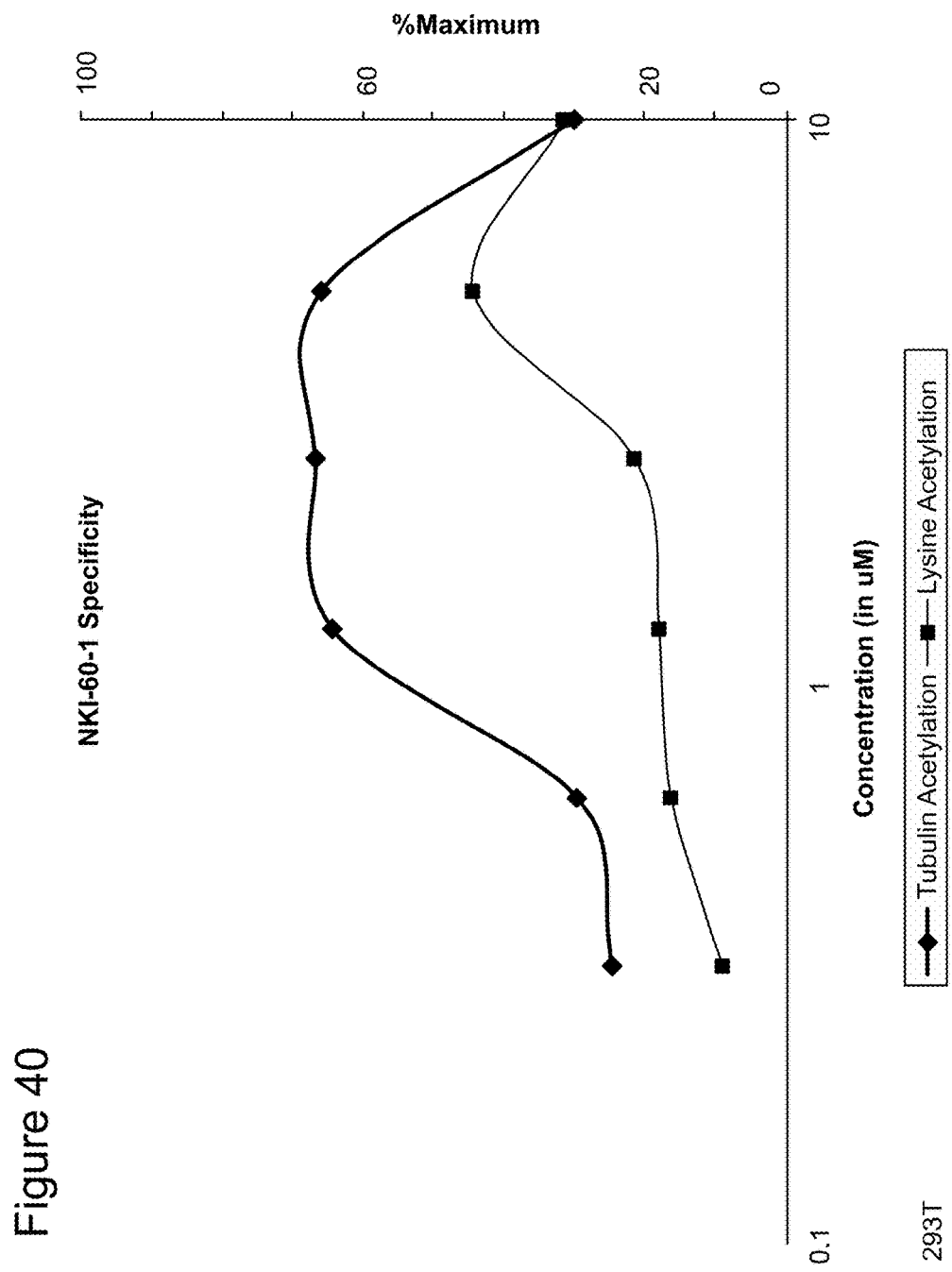
FIG. 40 demonstrates the specificity of NKI-60-1 for tubulin acetylation versus lysine acetylation.
Figure 41:
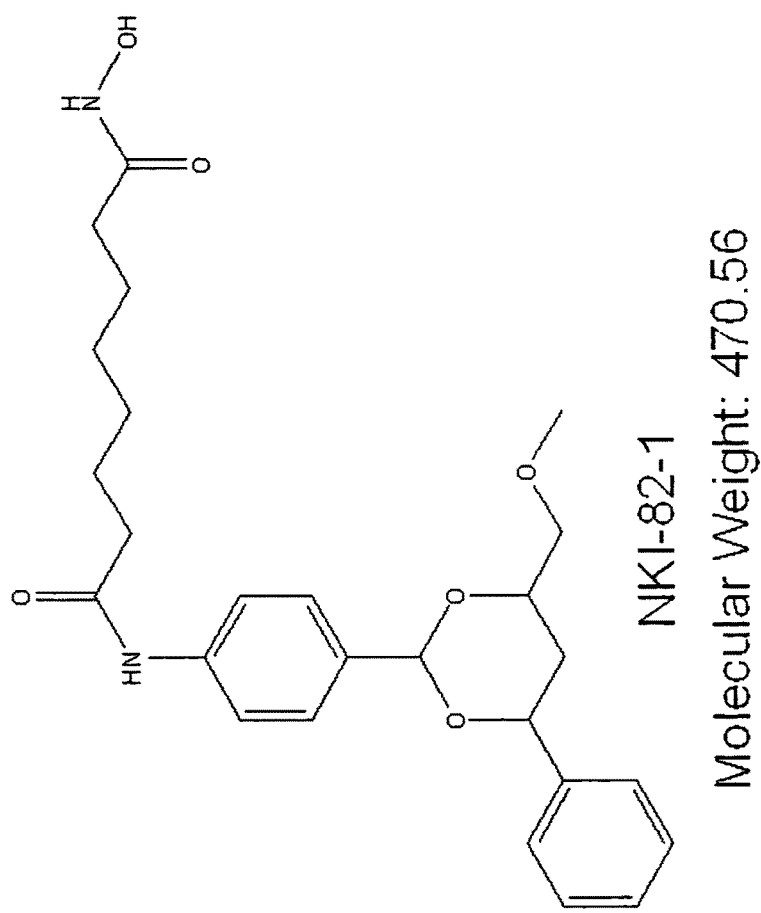
FIG. 41 shows the chemical structure for NKI-82-1.
Figure 42A:
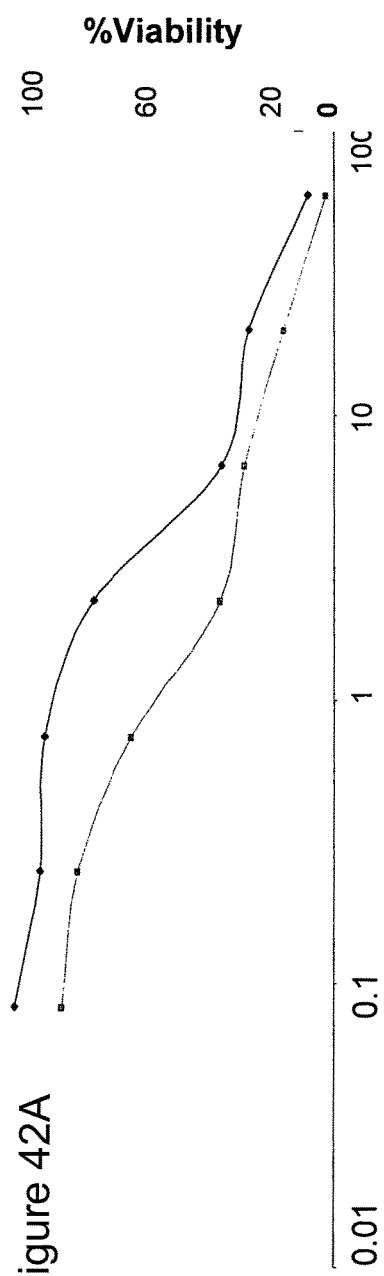
FIGS. 42A to 42B show the synergy between NKI-82-1 and Velcade in myeloma cell lines (FIG. 42A) MM.1S, and (FIG. 42B) RPMI cells.
Figure 42B:
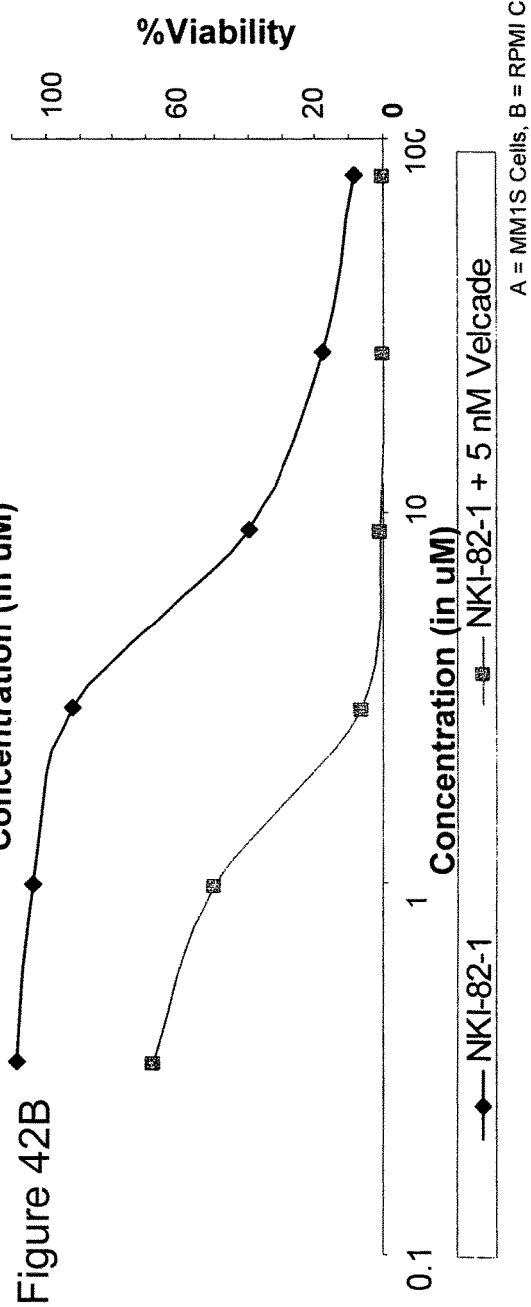
Figure 43:
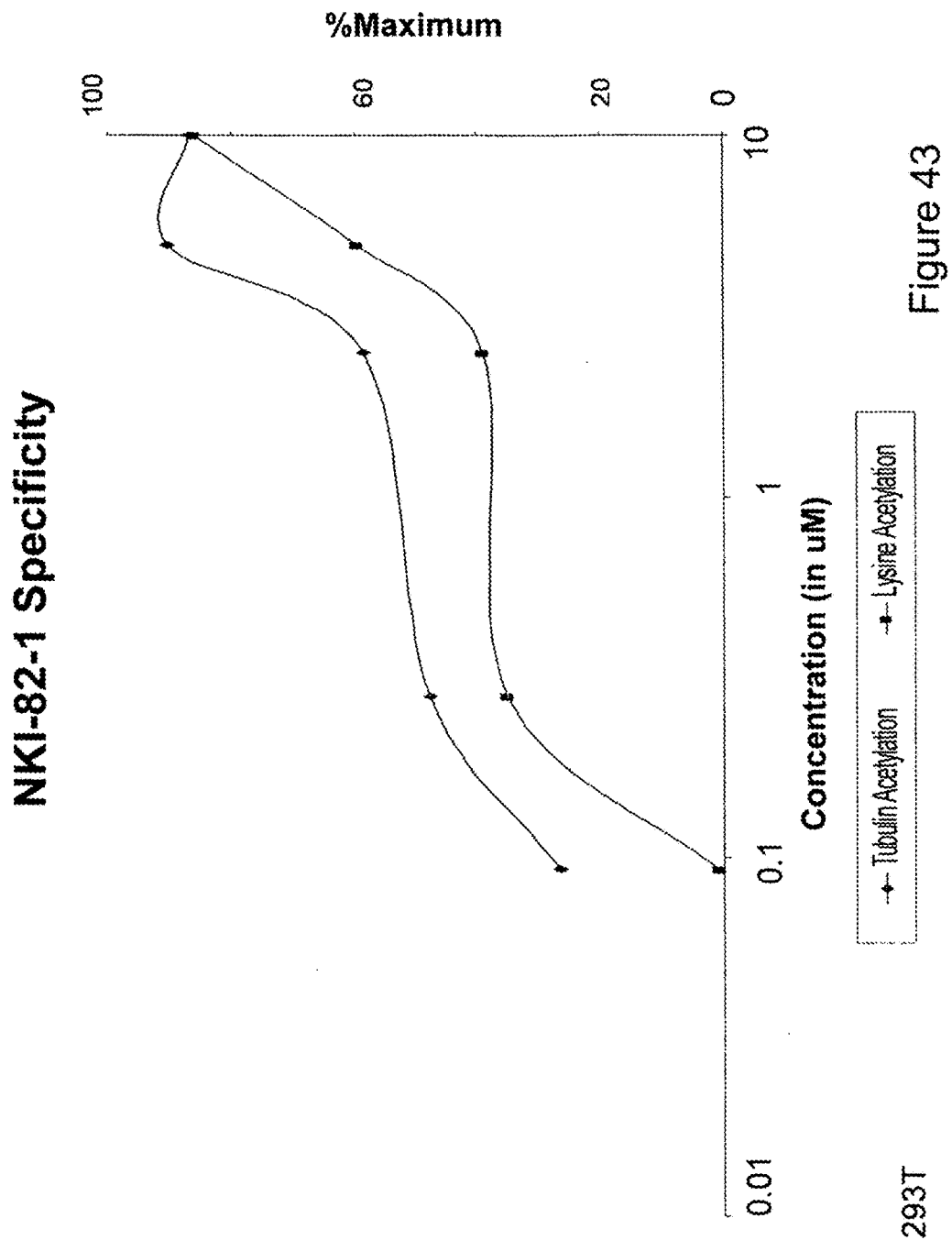
FIG. 43 demonstrates the specificity of NKI-82-1 for tubulin acetylation versus lysine acetylation.
Figure 44:
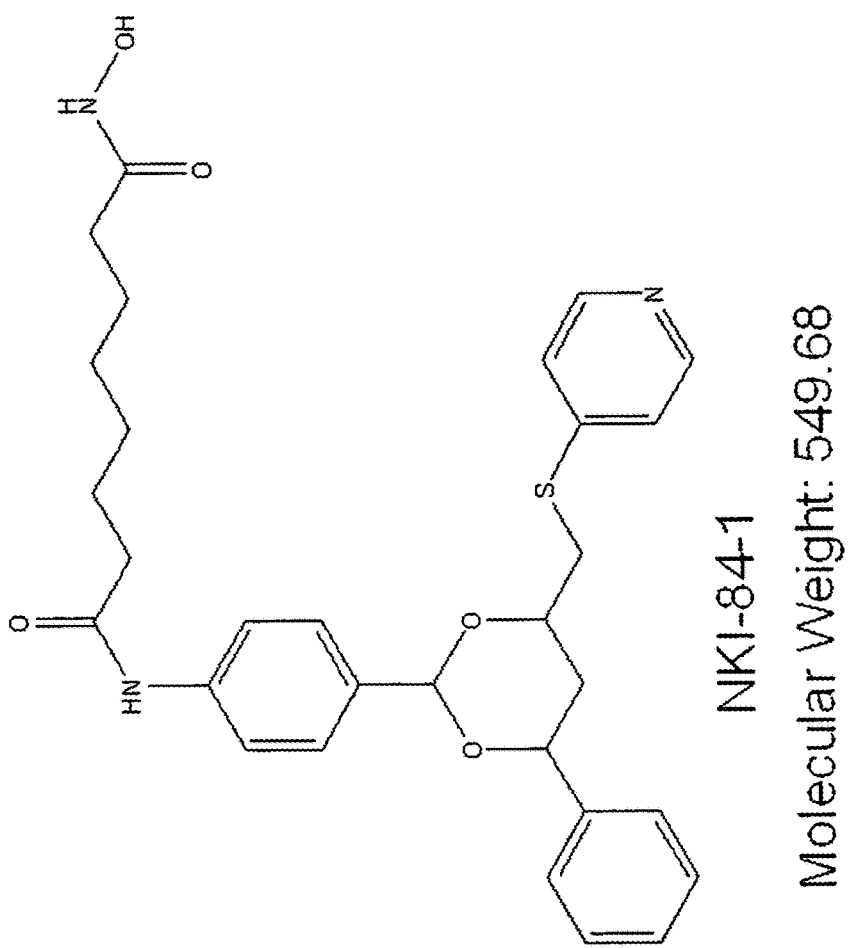
FIG. 44 shows the chemical structure for NKI-84-1.
Figure 47:
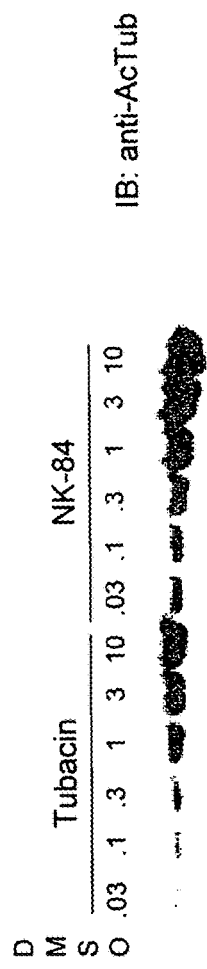
FIG. 47 shows the effect of Tubacin and NKI-84-1 on tubulin acetylation in RPMI-8226 cells.
Figure 48:
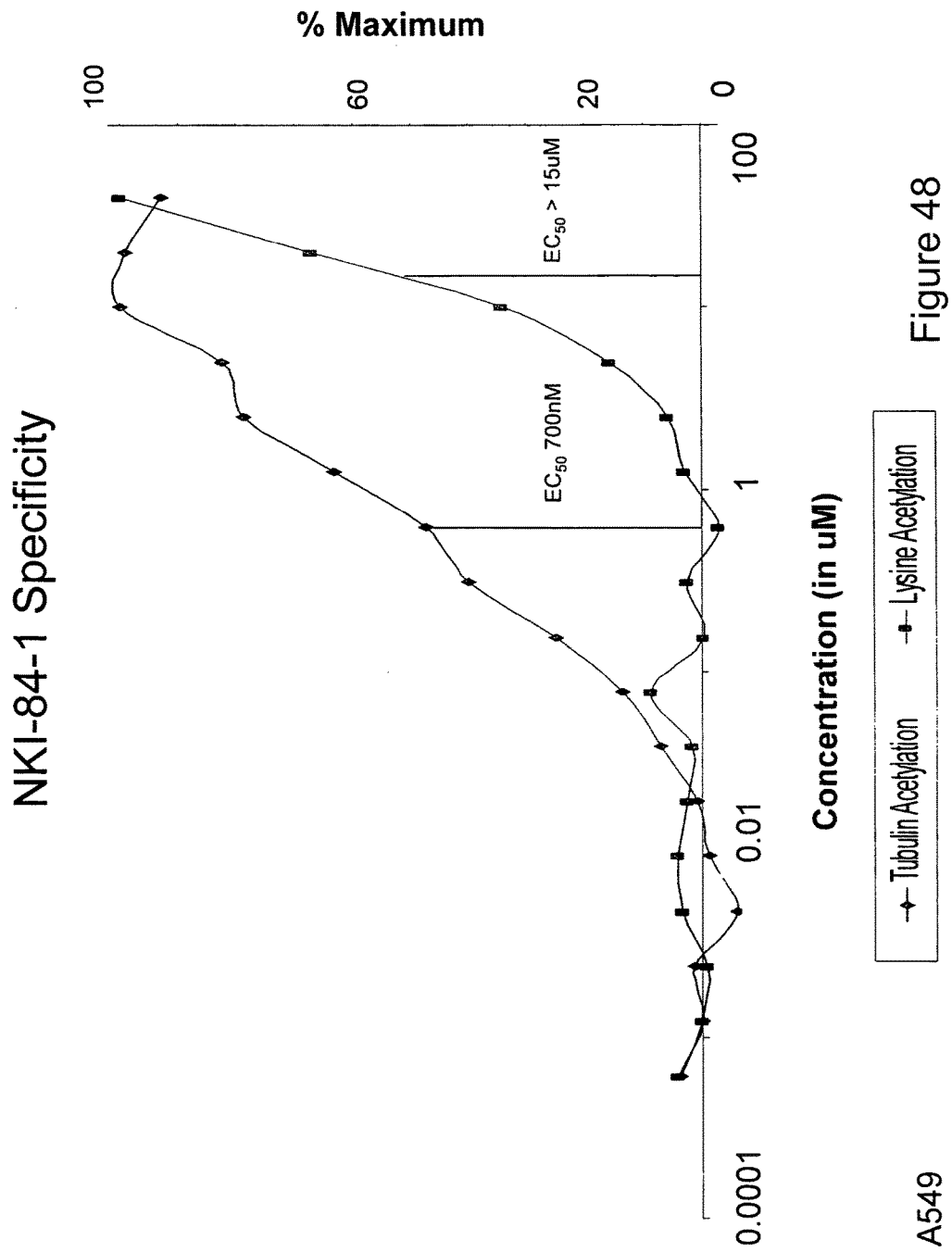
FIG. 48 demonstrates the specificity of NKI-84-1 for tubulin acetylation versus lysine acetylation in A549 cells.
Figure 49:
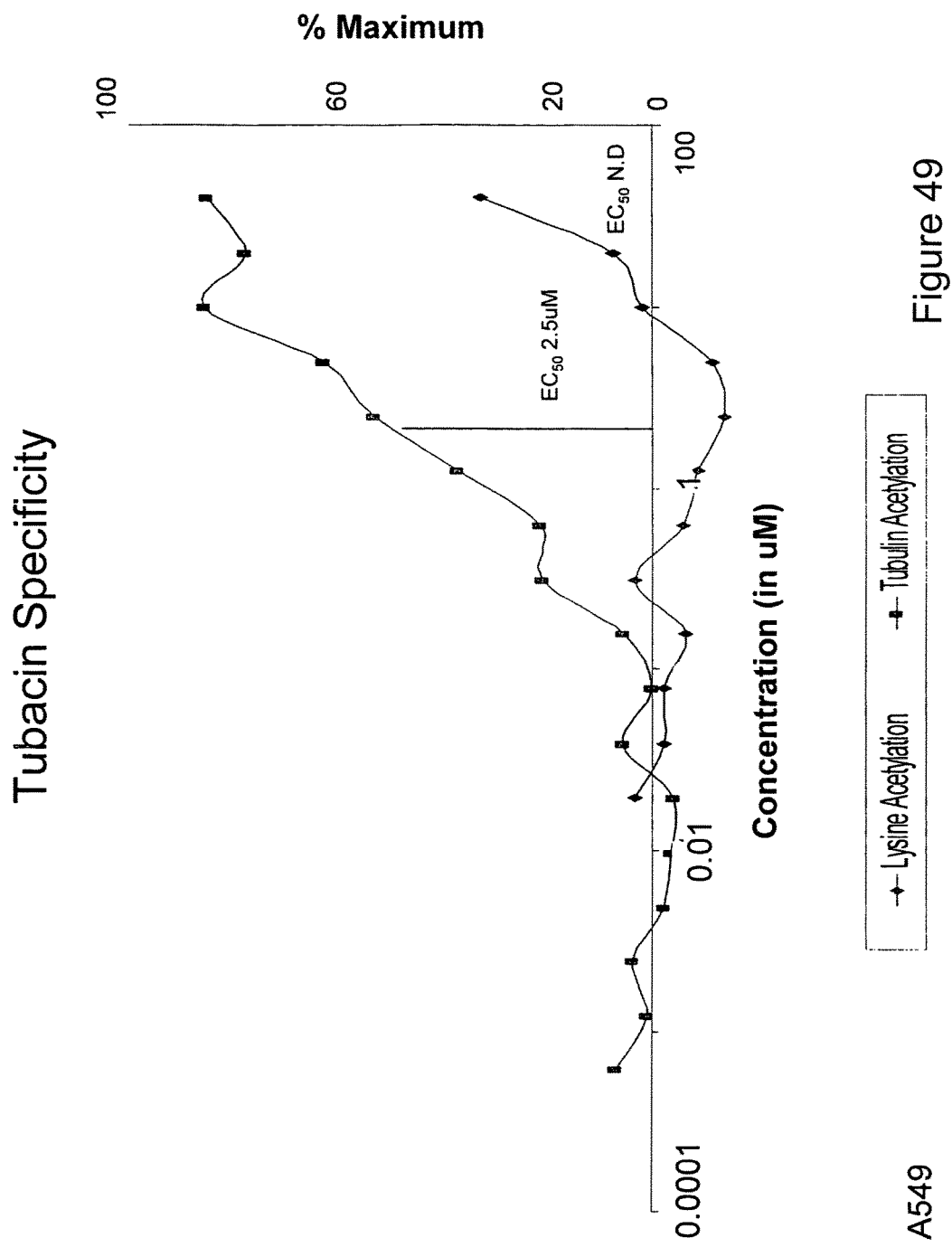
FIG. 49 demonstrates the specificity of Tubacin for tubulin acetylation versus lysine acetylation in A549 cells.
Figure 50:
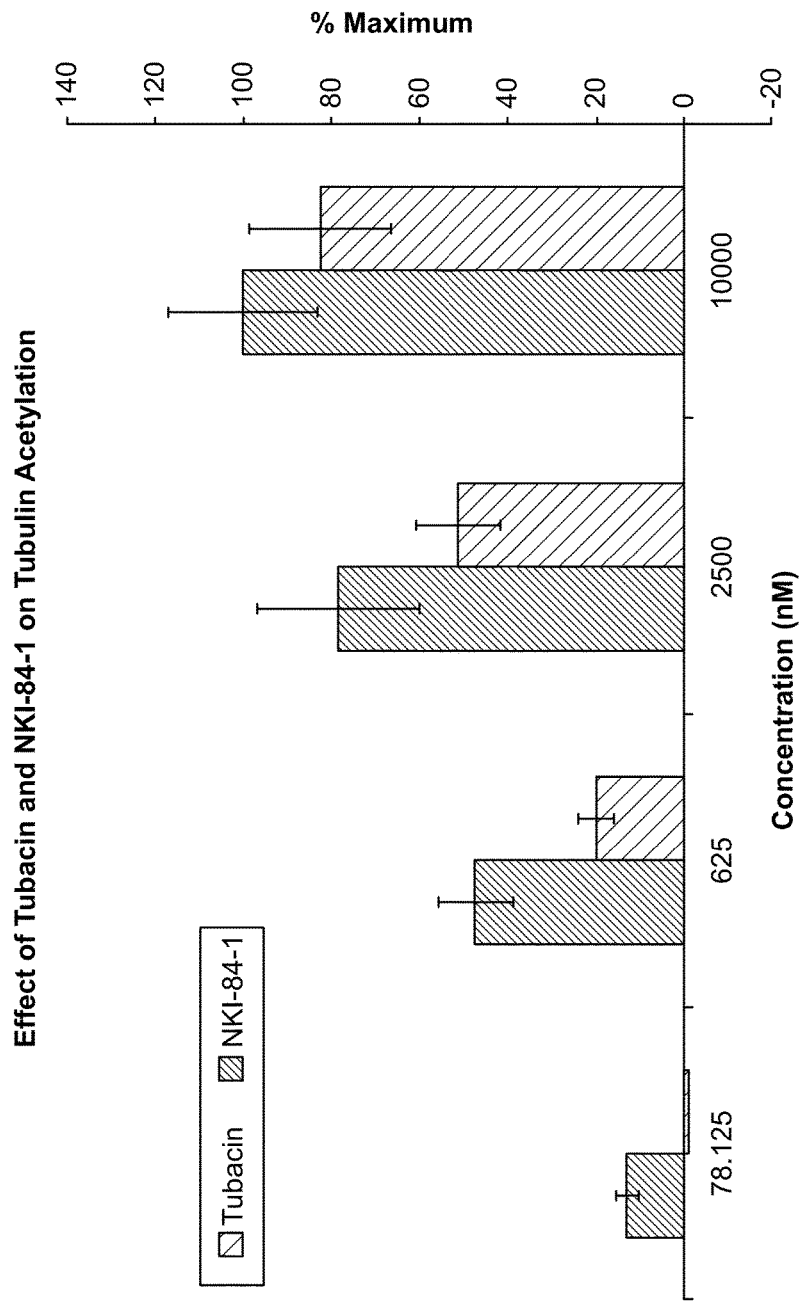
FIG. 50 shows the effect of Tubacin and NKI-84-1 on tubulin acetylation in A549 cells.
Figure 51:
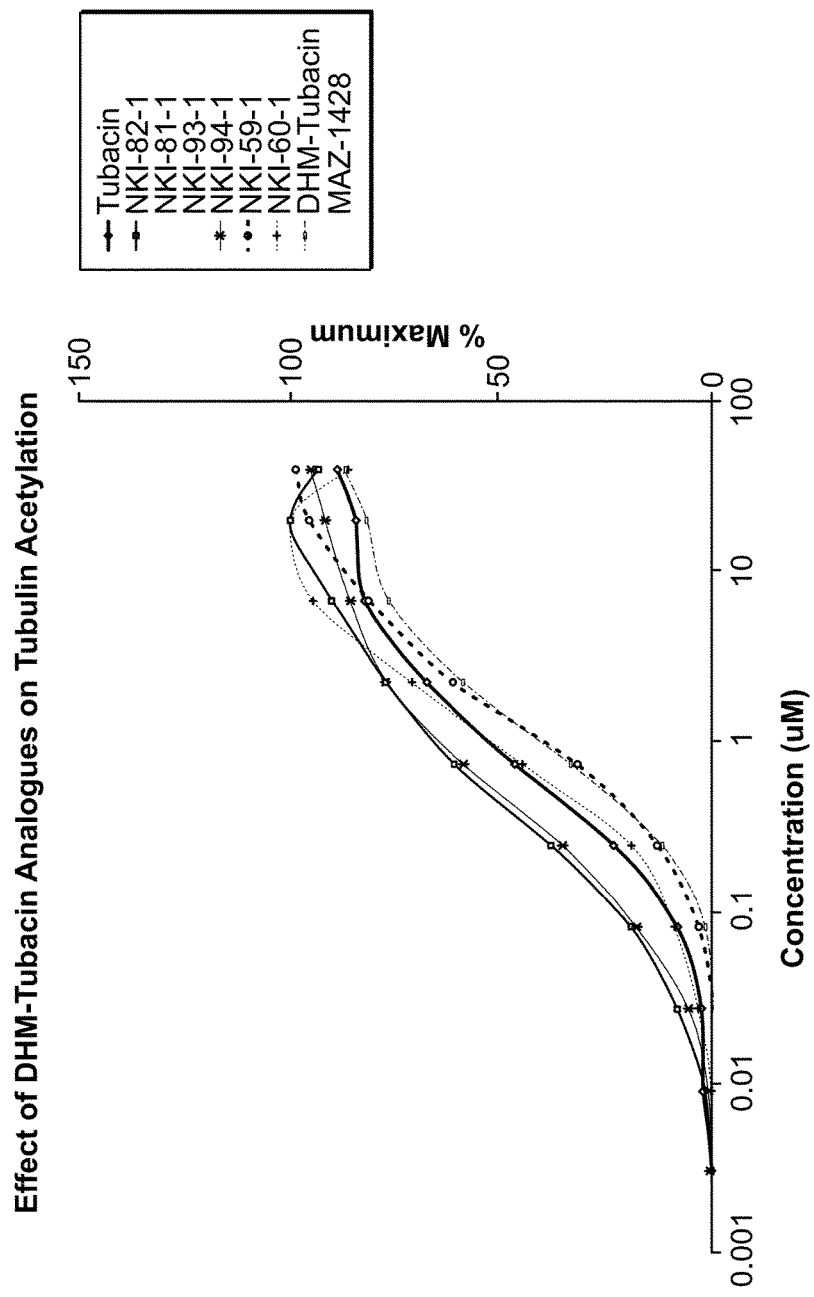
FIG. 51 shows the TDAC inhibitory activity of the compounds-tubacin, NKI-82-1, NKI-81-1, NKI-93-1, NKI-94-1, NKI-59-1, NKI-60-1, DHM-Tubacin, and MAZ-1428.
Figure 52:
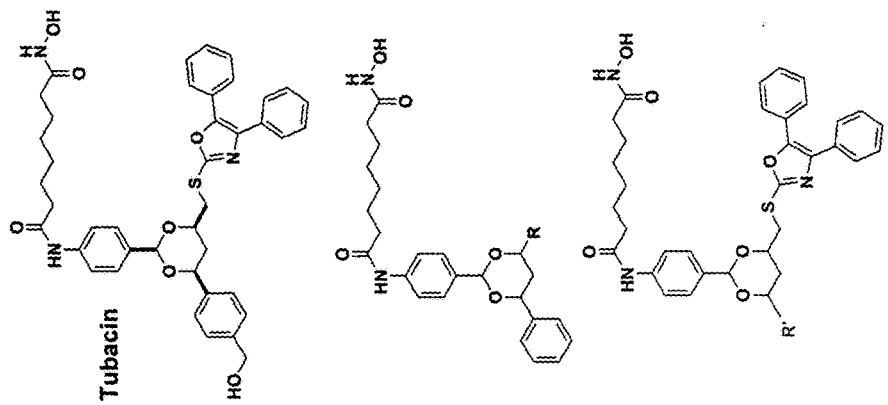
FIG. 52 is a chart showing the HDAC inhibition and TDAC inhibition of the compounds-tubacin, DHM-tubacin, NKI-59-1, NKI-60-1, NKI-82-1, NKI-84-1, NKI-94-1, and NKI-81-1.
Figure 53A:
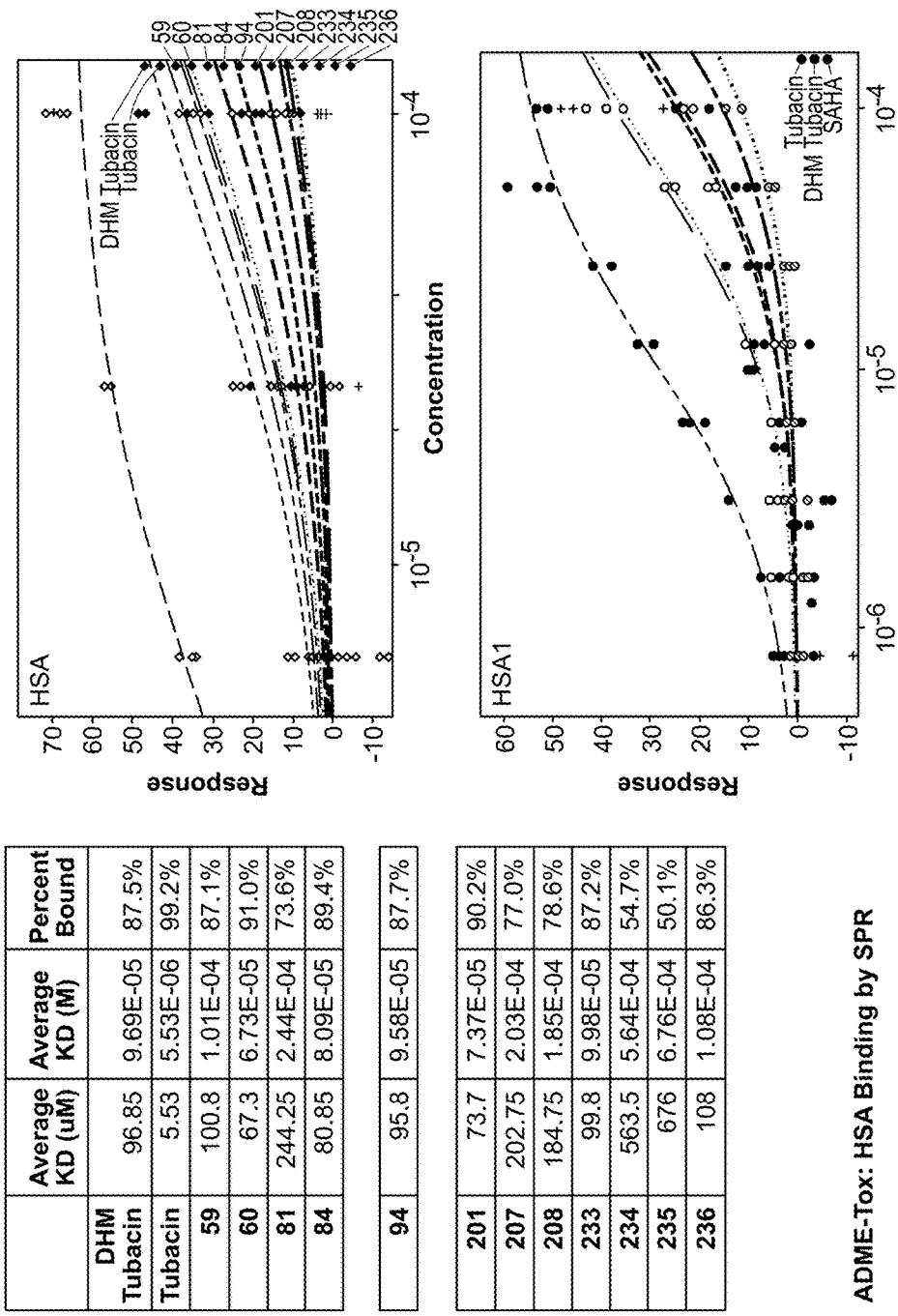
FIGS. 53A to 53B show the binding of various compounds to HAS (FIG. 53A) and the structures of various compounds listed in FIG. 53A, which were not included in previous figures (FIG. 53B).
Figure 53B:
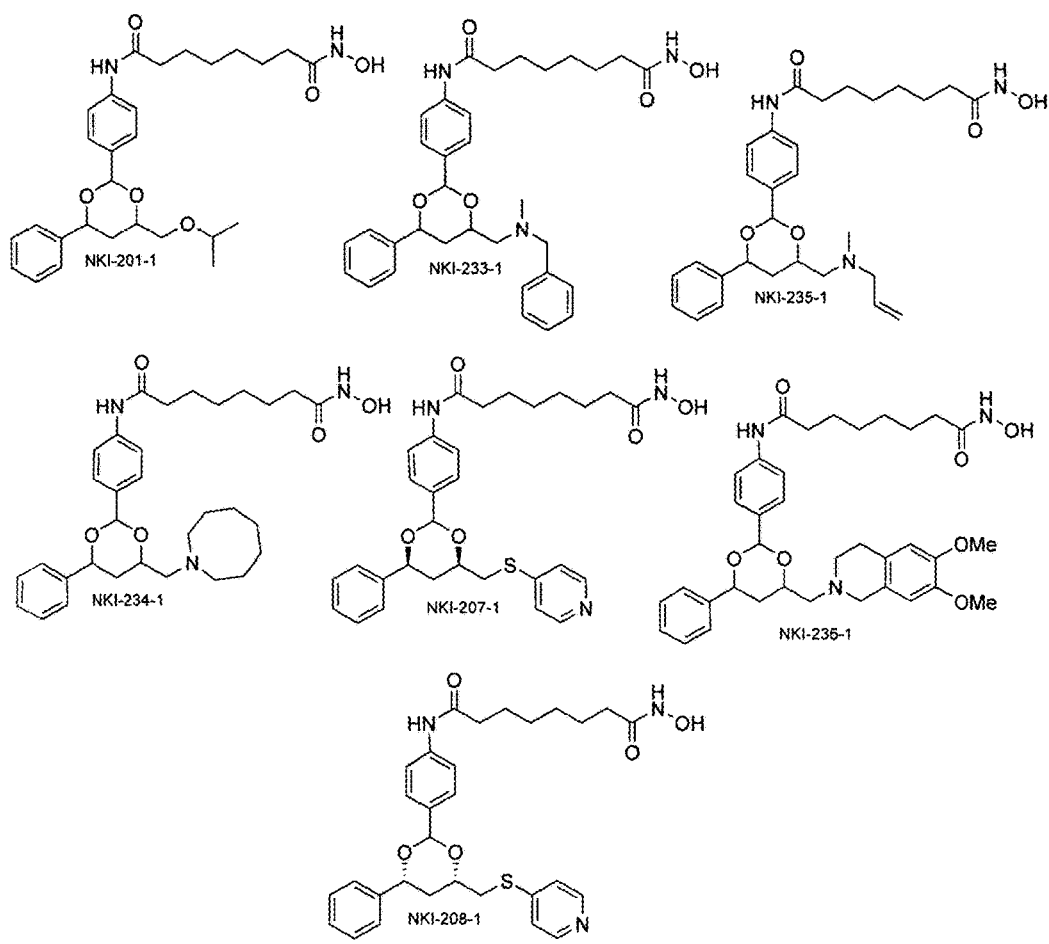
Figure 54:
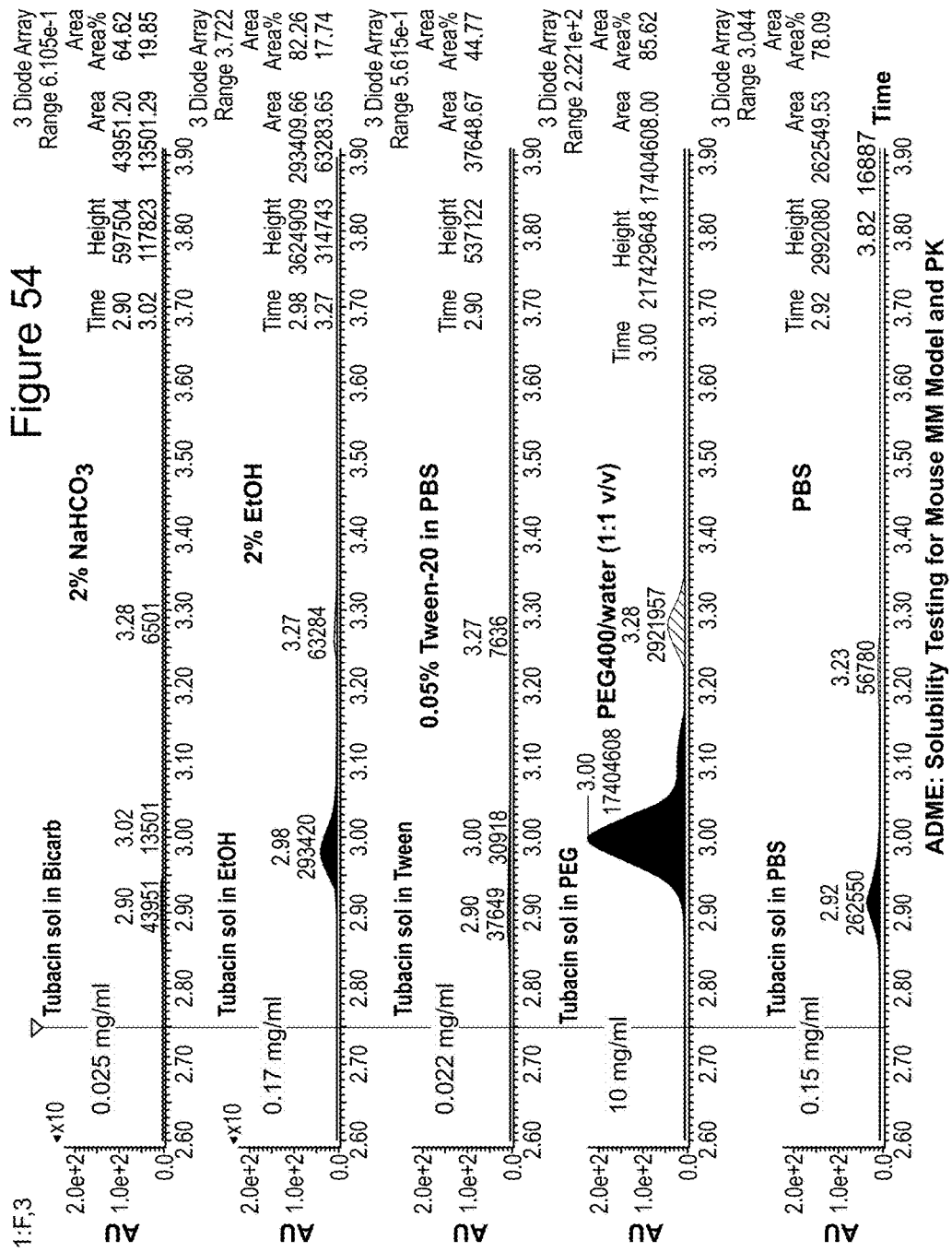
FIG. 54 shows the solubility of tubacin in various solutions for mouse multiple myeloma model and pharmacokinetics.

We have previously shown that the BM microenvironment confers cell growth and drug resistance in MM cells (3, 30, 31), and next studied was the functional sequelae of HDAC6 inhibition in the presence or absence of bortezomib, in MM cells within the BM milieu. MM.1S and RPMI8226 cells were cultured with or without BMSCs, in the presence or absence of tubacin (2.5 and 5M) and/or bortezomib (2.5-10 nM). MM cell adherence to BMSCs triggers increased [$^3$H]-thymidine uptake of both MM.1S cells (1.75, p<0.01) (FIG. 6A) and RPMI8226 cells (2.0 fold, p<0.01) (FIG. 6B). Either tubacin or bortezomib alone inhibits BMSC-induced [$^3$H]-thymidine uptake in a dose-dependent fashion (p<0.01). Importantly, tubacin significantly enhances bortezomib-induced inhibition of [$^3$H]-thymidine uptake in adherent MM.1S (FIG. 6A) and RPMI8226 (FIG. 6B) cells. The viability of BMSCs, assessed by MTT assay, is not altered by combination treatment (data not shown). These data indicate that combined treatment of tubacin with bortezomib triggers synergistic selective anti-tumor activity against MM cells in the BM milieu, thereby overcoming cell adhesion mediated resistance to conventional therapies. In conclusion, these results strongly suggest that dual inhibition of the aggresome and proteasome with tubacin and bortezomib, respectively, synergistically enhances MM cytotoxicity. They provide the framework for clinical trials designed to enhance sensitivity and overcome resistance to bortezomib, thereby improving patient outcome in MM.

Tubacin selectively inhibits the carboxy-terminal domain of HDAC6, causing tubulin hyperacetylation. Notably, tubacin was previously reported to have no effect on histone acetylation, the transcriptional profile, cell cycle, or viability of A549 lung cancer cells.

Tubacin is cytotoxic to myeloma cell lines at concentrations required to exert an effect on tubulin acetylation (FIG. 1a, b). Synergy is observed between tubacin and the potent proteasome inhibitor, bortezomib (Velcade), (FIG. 1c). Remarkably, these molecules in combination have no effect on the viability of peripheral blood mononuclear cells (FIG. 1d). These data suggest a plausible cytotoxic consequence of inhibited protein catabolism warranting further investigation. Preliminary data obtained in the RPMI-8226 cell line demonstrate an increase in cellular ubiquitinated proteins with tubacin (FIG. 2a). Previous experiments with tubacin at comparable concentrations in rat astrocytes and striatal neurons have elicited features suggestive of Russell body formation (FIG. 2b). These data support the hypothesis that HDAC6-mediated aggresome formation is mediated by the carboxy-terminus deacetylase domain and ascribe a mechanism for tubacin cytotoxicity.

Screening methods of the invention include a quantitative, high-throughput, image-based screen of cancer cells treated in 384-well plate format with a small molecule library biased for HDAC inhibition. Tubulin and histone acetylation state-specific antibodies were used and recognized by corresponding fluorescent secondary antibodies. Wells were scored in an unbiased fashion on an automated Axon 5000A epifluorescence microscope, for the ability of cause potent, selective tubulin acetylation. Controls of trichostatin, tubacin and DMSO were used for reference. Molecules have subsequently been prioritized following assessment for direct cytotoxicity and synergy with bortezomib in the RPMI-8226 myeloma cell line.

Tubacin is the first domain-selective HDAC inhibitor, targeting HDAC6. At low micromolar concentrations, tubacin causes tubulin hyperacetylation and marked anti-proliferative, proapoptotic effects against every myeloma cell lines. In addition, tubacin potently sensitizes myeloma cells to subtoxic concentrations of bortezomib. No adverse effect of tubacin on peripheral blood mononuclear cells was noted, with or without bortezomib. Remarkably, the robust cytotoxic effect of tubacin was maintained in all cell lines in the presence of bone marrow stroma, and interleukin-6.

Example 7

Characterization of the Role of the Aggresome in the Protein Catabolism of Malignant Plasma Cells.

Biochemical purification of the aggresome. The aggresome will be isolated biochemically in a panel of classical human cellular models of multiple myeloma. The presence of proteasome subunits in the pericentriolar microtubule organizing complex (MTOC) is determined as discussed below. The expression of HDAC6 in each of these cell lines has already been validated by immunoblotting. Preparation of the centrosomes will be performed as described[20]. Briefly, cells are harvested and treated with cytochalasin D and nocodazole to depolymerize the cytoskeleton and microtubules. After cell lysis and nuclear pelleting, centrosomes are purified by a sucrose gradient and assessed for 20S proteasome content. The effect of proteasome inhibition and protein folding stress on the proteosomal content of the purified aggresome will also be determined.

Fluorescence Microscopic Detection of the Aggresome:

With aggresome formation, intermediate filament reorganization occurs with the formation of a vimentin cap at the centrosome. Aggresome formation is assessed by fluorescence microscopy using antibodies against HDAC6, hsp70 and vimentin. Examination of myeloma cell lines treated with proteasome inhibitors and molecules causing misfolded protein stress will determine if aggresome formation is augmented, as reported previously.

Aggresome Formation in Patient-Derived Myeloma Cells:

The role of the aggresome in protein catabolism in myeloma cells is determined in vivo, the effects of proteasome and HDAC6 inhibition on aggresome formation is assessed in patient-derived myeloma cells. Using an immunofluorescence approach, the structure and composition of the aggresome is characterized as above. The cellular reservoirs of monotypic are examined by immunoglobulins using fluorescence microscopy. The study of bortezomib-sensitive and resistant patient-derived cells will be examined, using peripheral blood mononuclear cell as controls. This analysis may establish the aggresome as a proteolytic hallmark of cancer cell survival, and a determinant of clinical resistance to proteasome inhibition.

Example 8

Determine the Mechanism of HDAC6-Mediated Aggresome Formation.

Structure-Function Analysis of HDAC6:

Characterization of the enzymatic domain relevant for aggresome formation is done by both a genetic and chemical genetic approach using the classical ubiquitinated-protein model (DF508 CFTR)[3] of aggresome formation. One method will be to knock-down wild-type HDAC6 and transfected cells with an HDAC6 protein mutated in both amino- and carboxy-terminal deacetylase domains[9]. Another approach is to knock-down HDAC6 with small, interfering RNA, preferably using separately transfected selective mutants of each enzymatic domain.

Chemical Genetic Analysis of HDAC6:

In DF508 CFTR over-expressing cells, the effect of tubacin on ubiquitinated protein stress and aggresome formation is assessed with appropriate trichostatin and trapoxin controls. Trichostatin is a potent inhibitor of both HDAC6 domains, whereas trapoxin is a potent HDAC inhibitor, which uniquely does not inhibit HDAC6.

Proteomic Analysis of Protein Targets of HDAC6:

The non-histone targets of HDAC6 is determined. Two approaches grounded in chemical genetics and mass spectrometry are used. Adherent cells are treated with tubacin for 24 hours and lysed on culture dishes without disturbing nuclei or microtubules, enriching for cytoplasmic protein targets. An antibody-based purification detection scheme is employed using the acetylated-lysine rabbit polyclonal antibody, which is known to bind numerous cellular proteins with modified lysine residues. Selectively acetylated targets will be determined by mass spectrometry. Cytoplasmic lysates from tubacin-treated cells are prepared as above, and reacted with succinimide, covalently modifying non-acetylated lysine residues. The lysates are treated with purified HDAC6-H216A, which possesses only a functional carboxy-terminal deacetylase domain. The newly deacetylated lysines are then covalently modified with succinimidyl-biotin for streptavidin purification and mass spectrometric detection.

Example 9

Identification of Potent, Selective Inhibitors of HDAC6 Enabling the Investigation of Protein Catabolism and Aggresome Formation in Mouse Models of Multiple Myeloma.

Molecules derived from diversity-oriented synthetic pathways are used in in silico structure-activity relationship modeling to ascertain modular determinants of selectivity, potency and cytotoxicity.

REFERENCES

1. Adams J. The proteasome: a suitable antineoplastic target. Nat Rev Cancer. 2004; 4:349-360
2. Kopito R R. Aggresomes, inclusion bodies and protein aggregation. Trends Cell Biol. 2000; 10:524-530

3. Johnston J A, Ward C L, Kopito R R. Aggresomes: a cellular response to misfolded proteins. J Cell Biol. 1998; 143:1883-1898
4. Junn E, Lee S S, Suhr U T, Mouradian MM. Parkin accumulation in aggresomes due to proteasome impairment. J Biol Chem. 2002; 277:47870-47877
5. Notterpek L, Ryan M C, Tobler A R, Shooter E M. PMP22 accumulation in aggresomes: implications for CMT1A pathology. Neurobiol Dis. 1999; 6:450-460
6. Anton L C, Schubert U, Bacik I, Princiotta M F, Wearsch P A, Gibbs J, Day P M, Realini C, Rechsteiner M C, Bennink J R, Yewdell J W. Intracellular localization of proteasomal degradation of a viral antigen. J Cell Biol. 1999; 146:113-124
7. Garcia-Mata R, Bebok Z, Sorscher E J, Sztul E S. Characterization and dynamics of aggresome formation by a cytosolic GFP-chimera. J Cell Biol. 1999; 146:1239-1254
8. Dul J L, Davis D P, Williamson E K, Stevens F J, Argon Y. Hsp70 and antifibrillogenic peptides promote degradation and inhibit intracellular aggregation of amyloidogenic light chains. J Cell Biol. 2001; 152:705-716
9. Kawaguchi Y, Kovacs J J, McLaurin A, Vance J M, Ito A, Yao T P. The deacetylase HDAC6 regulates aggresome formation and cell viability in response to misfolded protein stress. Cell. 2003; 115:727-738
10. Hideshima T, Richardson P, Chauhan D, Palombella V J, Elliott P J, Adams J, Anderson K C. The proteasome inhibitor PS-341 inhibits growth, induces apoptosis, and overcomes drug resistance in human multiple myeloma cells. Cancer Res. 2001; 61:3071-3076
11. Kopito R R, Sitia R. Aggresomes and Russell bodies. Symptoms of cellular indigestion? EMBO Rep. 2000; 1:225-231
12. Manetto V, Abdul-Karim F W, Perry G, Tabaton M, Autilio-Gambetti L, Gambetti P. Selective presence of ubiquitin in intracellular inclusions. Am J Pathol. 1989; 134:505-513
13. Sullivan M L, Youker R T, Watkins S C, Brodsky J L. Localization of the BiP molecular chaperone with respect to endoplasmic reticulum foci containing the cystic fibrosis transmembrane conductance regulator in yeast. J Histochem Cytochem. 2003; 51:545-548
14. Mitsiades C S, Mitsiades N S, McMullan C J, Poulaki V, Shringarpure R, Hideshima T, Akiyama M, Chauhan D, Munshi N, Gu X, Bailey C, Joseph M, Libermann T A, Richon V M, Marks P A, Anderson K C. Transcriptional signature of histone deacetylase inhibition in multiple myeloma: biological and clinical implications. Proc Natl Acad Sci USA. 2004; 101:540-545
15. Rosato R R, Grant S. Histone deacetylase inhibitors in clinical development. Expert Opin Investig Drugs. 2004; 13:21-38
16. Taunton J, Hassig C A, Schreiber S L. A mammalian histone deacetylase related to the yeast transcriptional regulator Rpd3p. Science. 1996; 272:408-411
17. Grozinger C M, Hassig C A, Schreiber S L. Three proteins define a class of human histone deacetylases related to yeast Hda1p. Proc Natl Acad Sci USA. 1999; 96:4868-4873
18. Haggarty S J, Koeller K M, Wong J C, Grozinger C M, Schreiber S L. Domain-selective small-molecule inhibitor of histone deacetylase 6 (HDAC6)-mediated tubulin deacetylation. Proc Natl Acad Sci USA. 2003; 100:4389-4394
19. Sternson S M, Wong J C, Grozinger C M, Schreiber S L. Synthesis of 7200 small molecules based on a substructural analysis of the histone deacetylase inhibitors trichostatin and trapoxin. Org Lett. 2001; 3:4239-4242
20. Fabunmi R P, Wigley W C, Thomas P J, DeMartino G N. Activity and regulation of the centrosome-associated proteasome. J Biol Chem. 2000; 275:409-413
21. Corcoran L J, Mitchison T J, Liu Q. A novel action of histone deacetylase inhibitors in a protein aggresome disease model. Curr Biol. 2004; 14:488-492
22. Serrador J M, Cabrero J R, Sancho D, Mittelbrunn M, Urzainqui A, Sanchez-Madrid F. HDAC6 deacetylase activity links the tubulin cytoskeleton with immune synapse organization. Immunity. 2004; 20:417-428
23. Gregory, W. M., Richards, M. A. & Malpas, J. S. (1992) *J Clin Oncol* 10, 334-342.
24. Attal, M., Harousseau, J. L., Facon, T., Guilhot, F., Doyen, C., Fuzibet, J. G., Monconduit, M., Hulin, C., Caillot, D., Bouabdallah, R., Voillat, L., Sotto, J. J., Grosbois, B. & Bataille, R. (2003) *N Engl J Med* 349, 2495-2502.
25. Hideshima, T. & Anderson, K. C. (2002) *Nat Rev Cancer* 2, 927-937.
26. Hideshima, T., Richardson, P., Chauhan, D., Palombella, V., Elliott, P., Adams, J. & Anderson, K. C. (2001) *Cancer Res*. 61, 3071-3076.
27. Mitsiades, N., Mitsiades, C. S., Poulaki, V., Chauhan, D., Gu, X., Bailey, C., Joseph, M., Libermann, T. A., Treon, S. P., Munshi, N. C., Richardson, P. G., Hideshima, T. & Anderson, K. C. (2002) *Proc Natl Acad Sci USA* 99, 14374-14379.
28. Hideshima, T., Chauhan, D., Richardson, P., Mitsiades, C., Mitsiades, N., Hayashi, T., Munshi, N., Dang, L., Castro, A., Palombella, V., Adams, J. & Anderson, K. C. (2002) *J Biol Chem* 277, 16639-47.
29. Mitsiades, N., Mitsiades, C. S., Richardson, P. G., Poulaki, V., Tai, Y. T., Chauhan, D., Fanourakis, G., Gu, X., Bailey, C., Joseph, M., Libermann, T. A., Schlossman, R., Munshi, N. C., Hideshima, T. & Anderson, K. C. (2003) *Blood* 101, 2377-80.
30. Chauhan, D., Li, G., Shringarpure, R., Podar, K., Ohtake, Y., Hideshima, T. & Anderson, K. C. (2003) *Cancer Res* 63, 6174-6177.
31. Hideshima, T., Mitsiades, C., Akiyama, M., Hayashi, T., Chauhan, D., Richardson, P., Schlossman, R., Podar, K., Munshi, N. C., Mitsiades, N. & Anderson, K. C. (2003) *Blood* 101, 1530-1534.
32. Hideshima, T., Chauhan, D., Hayashi, T., Akiyama, M., Mitsiades, N., Mitsiades, C., Podar, K., Munshi, N. C., Richardson, P. G. & Anderson, K. C. (2003) *Oncogene* 22, 8386-8393.
33. Hideshima, T., Podar, K., Chauhan, D., Ishitsuka, K., Mitsiades, C., Tai, Y.-Z., Hamasaki, M., Raje, N., Hideshima, H., Schreiner, G., Nguyen, A. N., Navas, T., Munshi, N. C., Richardson, P. G., Higgins, L. S. & Anderson, K. C. (2004) *Oncogene* 23, 8766-8776.
34. Hideshima, T., Chauhan, D., Schlossman, R. L., Richardson, P. R. & Anderson, K. C. (2001) *Oncogene* 20, 4519-4527.
35. Richardson, P. G., Barlogie, B., Berenson, J., Singhal, S., Jagannath, S., Irwin, D., Rajkumar, S. V., Srkalovic, G., Alsina, M., Alexanian, R., Siegel, D., Orlowski, R. Z., Kuter, D., Limentani, S. A., Lee, S., Hideshima, T., Esseltine, D. L., Kauffman, M., Adams, J., Schenkein, D. P. & Anderson, K. C. (2003) *N Engl J Med* 348, 2609-2617.
36. Kopito, R. R. (2000) *Trends Cell Biol* 10, 524-530.
37. Bennett, E. J., Bence, N. F., Jayakumar, R. & Kopito, R. R. (2005) *Mol Cell* 17, 351-365.

38. Garcia-Mata, R., Gao, Y. S. & Sztul, E. (2002) *Traffic* 3, 388-396.
39. Kawaguchi, Y., Kovacs, J. J., McLaurin, A., Vance, J. M., Ito, A. & Yao, T. P. (2003) *Cell* 115, 727-738.
40. Haggarty, S. J., Koeller, K. M., Wong, J. C., Grozinger, C. M. & Schreiber, S. L. (2003) *Proc Natl Acad Sci USA* 100, 4389-4394.
41. Haggarty, S. J., Koeller, K. M., Wong, J. C., Butcher, R. A. & Schreiber, S. L. (2003) *Chem Biol* 10, 383-396.
42. Wong, J. C., Hong, R. & Schreiber, S. L. (2003) *J Am Chem Soc* 125, 5586-5587.
43. Uchiyama, H., Barut, B. A., Mohrbacher, A. F., Chauhan, D. & Anderson, K. C. (1993) *Blood* 82, 3712-20.
44. Hideshima, T., Chauhan, D., Hayashi, T., Podar, K., Akiyama, M., Mitsiades, C., Mitsiades, N., Gong, B., Bonham, L., de Vries, P., Munshi, N., Richardson, P. G., Singer, J. W. & Anderson, K. C. (2003) *Cancer Res* 63, 8428-8436.
45. Raje, N., Kumar, S., Hideshima, T., Ishitsuka, K., Chauhan, D., Mitsiades, C., Podar, K., Le Gouill, S., Richardson, P., Munshi, N. C., Stirling, D. I., Antin, J. H. & Anderson, K. C. (2004) *Blood* in press.
46. Urnov, F. D., Yee, J., Sachs, L., Collingwood, T. N., Bauer, A., Beug, H., Shi, Y. B. & Wolffe, A. P. (2000) *Embo J* 19, 4074-4090.
47. Cress, W. D. & Seto, E. (2000) *J Cell Physiol* 184, 1-16.
48. Marks, P. A., Miller, T. & Richon, V. M. (2003) *Curr Opin Pharmacol* 3, 344-351.
49. Mitsiades, N., Mitsiades, C. S., Richardson, P. G., McMullan, C., Poulaki, V., Fanourakis, G., Schlossman, R., Chauhan, D., Munshi, N. C., Hideshima, T., Richon, V. M., Marks, P. A. & Anderson, K. C. (2003) *Blood* 101, 4055-62.
50. Catley, L., Weisberg, E., Tai, Y. T., Atadja, P., Remiszewski, S., Hideshima, T., Mitsiades, N., Shringarpure, R., LeBlanc, R., Chauhan, D., Munshi, N., Schlossman, R., Richardson, P., Griffin, J. & Anderson, K. C. (2003) *Blood* 102, 2615-2622.
51. Chauhan, D., Li, G., Hideshima, T., Podar, K., Mitsiades, C., Mitsiades, N., Catley, L., Tai, Y. T., Hayashi, T., Shringharpure, R., Burger, R., Munshi, N., Ohtake, Y., Saxena, S. & Anderson, K. C. (2003) *Blood* 102, 3379-3386.
52. Hideshima, T., Richardson, P. & Anderson, K. C. (2003) *Immunol Rev* 194, 164-76.
53. Mitsiades, C. S., Mitsiades, N. S., McMullan, C. J., Poulaki, V., Shringarpure, R., Akiyama, M., Hideshima, T., Chauhan, D., Joseph, M., Libermann, T. A., Garcia-Echeverria, C., Pearson, M. A., Hofmann, F., Anderson, K. C. & Kung, A. L. (2004) *Cancer Cell* 5, 221-230.

The contents of all references, patents, and patent applications cited herein are hereby incorporated by reference in their entirety. The contents of Appendix A (25 pages), attached hereto, are hereby incorporated by reference in their entirety.

Other embodiments are within the following claims.

What is claimed is:

1. A method of treating a subject suffering from ovarian cancer comprising administering to a subject in need thereof a therapeutically effective amount of a proteasome inhibitor and an aggresome inhibitor, wherein the aggresome inhibitor selectively inhibits HDAC6.

2. The method of claim 1, wherein the proteasome inhibitor is selected from the group consisting of bortezomib, MG 132, sapojargon, and NPI-0052.

3. The method of claim 1, wherein the aggresome inhibitor is of the formula:

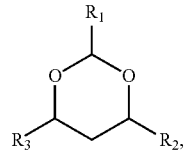

or a pharmaceutically acceptable salt thereof, wherein
$R_1$ is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $—OR_A$; $—C(=O)R_A$; $—CO_2R_A$; $—SR_A$; $—SOR_A$; $—SO_2R_A$; $—N(R_A)_2$; $—NHC(O)R_A$; or $—C(R_A)_3$; wherein each occurrence of $R_A$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety;
$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $—OR_B$; $—C(=O)R_B$; $—CO_2R_B$; $—CN$; $—SCN$; $—SR_B$; $—SOR_B$; $—SO_2R_B$; $—NO_2$; $—N(R_B)_2$; $—NHC(O)R_B$; or $—C(R_B)_3$; wherein each occurrence of $R_B$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety; and
$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $—OR_C$; $—C(=O)R_C$; $—CO_2R_C$; $—CN$; $—SCN$; $—SR_C$; $—SOR_C$; $—SO_2R_C$; $—NO_2$; $—N(R_C)_2$; $—NHC(O)R_C$; or $—C(R_C)_3$; wherein each occurrence of $R_C$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety.

4. The method of claim 1, wherein the aggresome inhibitor is of the formula:

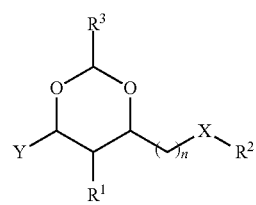

or a pharmaceutically acceptable salt thereof, wherein
- R$^1$ is hydrogen, or an aliphatic, alicyclic, heteroaliphatic, heterocyclic, aromatic or heteroaromatic moiety;
- n is 1-5;
- R$^2$ is hydrogen, a protecting group, or an aliphatic, alicyclic, heteroaliphatic, heterocyclic, aromatic or heteroaromatic moiety;
- X is —O—, —C(R$^{2A}$)$_2$—, —S—, or —NR$^{2A}$—, wherein R$^{2A}$ is hydrogen, a protecting group, or an aliphatic, alicyclic, heteroaliphatic, heterocyclic, aromatic or heteroaromatic moiety;
- or wherein two or more occurrences of R$^2$ and R$^{2A}$, taken together, form an alicyclic or heterocyclic moiety, or an aryl or heteroaryl moiety;
- R$^3$ is an aliphatic, alicyclic, heteroaliphatic, heterocyclic, aromatic, or heteroaromatic moiety; and
- Y is hydrogen or an aliphatic, alicyclic, heteroaliphatic, heterocyclic, aromatic, or heteroaromatic moiety.

5. The method of claim 1, wherein the aggresome inhibitor is selected from the group consisting of:

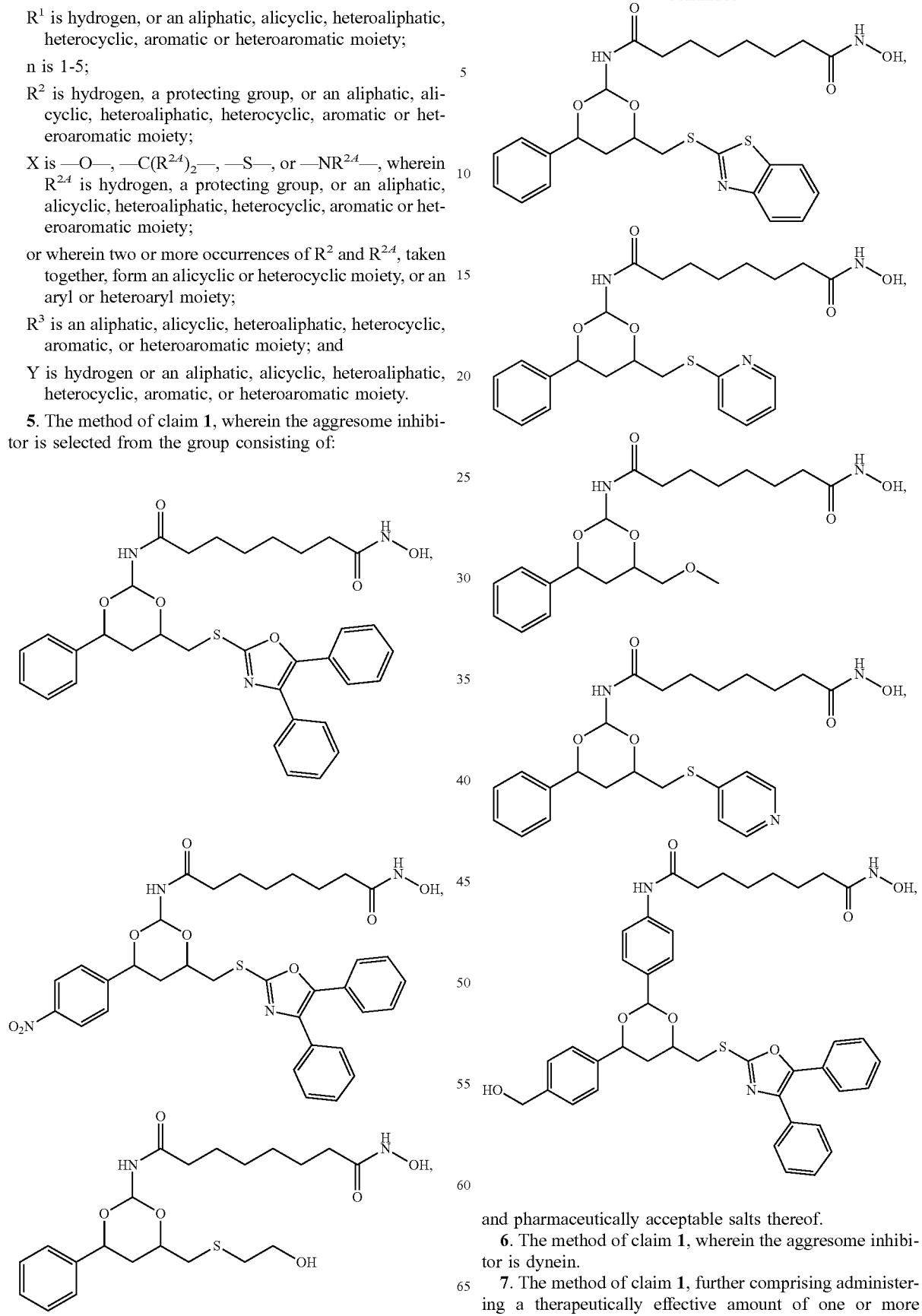

and pharmaceutically acceptable salts thereof.

6. The method of claim 1, wherein the aggresome inhibitor is dynein.

7. The method of claim 1, further comprising administering a therapeutically effective amount of one or more additional protein degradation inhibitors to the subject.

8. The method of claim 7, wherein at least one of the additional protein degradation inhibitors is a proteasome inhibitor.

9. The method of claim 1, further comprising co-administering one or more of a chemotherapeutic agent, radiation agent, hormonal agent, biological agent, or anti-inflammatory agent to the subject.

10. The method of claim 1, wherein the subject is a human.

11. The method of claim 1, wherein the aggresome inhibitor is the following:

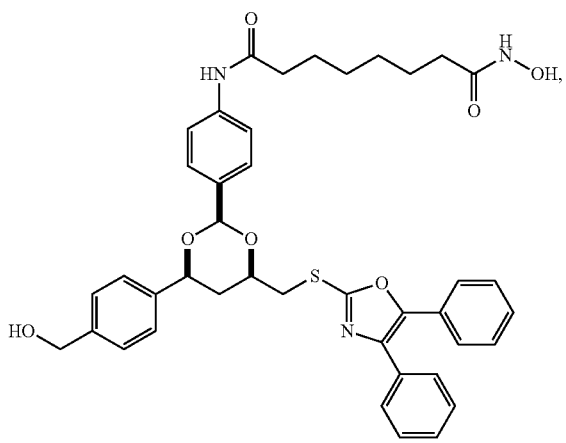

or a pharmaceutically acceptable salt thereof.

12. The method of claim 1, wherein the aggresome inhibitor is of the following formula:

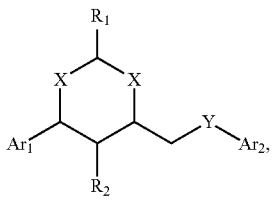

or a pharmaceutically acceptable salt thereof, wherein:
each X is independently O, S, $CH_2$, or $NR_3$;
Y is O, S, $CH_2$, or $NR_4$;
$Ar_1$ and $Ar_2$ are each independently an aryl group;
$R_1$ is a lower alkyl group or an aryl group;
$R_2$ is hydrogen, a lower alkyl group, or an aryl group; and
$R_3$ is hydrogen, a lower alkyl group, an aryl group, an alkylcarbonyl, an alkoxycarbonyl group, or an aminocarbonyl group.

13. The method of claim 12, wherein:
X is for both occurrences O;
Y is S;
$Ar_1$ is phenyl or substituted phenyl;
$Ar_2$ is heteroaryl;
$R_1$ is phenyl or substituted phenyl; and
$R_2$ is hydrogen.

14. The method of claim 12, wherein:
X is for both occurrences O;
Y is S;
$Ar_1$ is phenyl or substituted phenyl;
$Ar_2$ is optionally substituted oxazolyl;
$R_1$ is 4-aminosubstituted phenyl; and
$R_2$ is hydrogen.

15. The method of claim 1, wherein the aggresome inhibitor inhibits the C-terminal aceylation activity of HDAC6, thereby inhibiting aggresome mediated protein degradation.

16. The method of claim 7, wherein at least one of the additional protein degradation inhibitors is an aggresome inhibitor.

17. The method of claim 1, further comprising obtaining a biological sample from a subject.

18. The method of claim 1, further comprising monitoring the treatment or progress of the subject.

19. The method of claim 9, wherein a chemotherapeutic is co-administered.

20. The method of claim 19, wherein the chemotherapeutic agent is tamoxifen, trastuzamab, raloxifene, doxorubicin, fluorouracil/5-fu, pamidronate disodium, anastrozole, exemestane, cyclophosphamide, epirubicin, letrozole, toremifene, fulvestrant, fluoxymesterone, trastuzumab, methotrexate, megastrol acetate, docetaxel, paclitaxel, testolactone, aziridine, vinblastine, capecitabine, goselerin acetate, zoledronic acid, taxol, or vincristine.

* * * * *